US009567526B2

(12) United States Patent
Engel et al.

(10) Patent No.: US 9,567,526 B2
(45) Date of Patent: Feb. 14, 2017

(54) POLYMERIZABLE COMPOUNDS AND THE USE THEREOF IN LIQUID-CRYSTAL DISPLAYS

(71) Applicant: MERCK PATENT GMBH, Darmstadt (DE)

(72) Inventors: Martin Engel, Darmstadt (DE);
Eveline Baron, Darmstadt (DE);
Constanze Brocke, Gross-Gerau (DE);
Helga Haas, Lampertheim (DE);
Stephan Derow, Griesheim (DE);
Christoph Marten, Darmstadt (DE);
Qiong Tong, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 94 days.

(21) Appl. No.: 14/314,470

(22) Filed: Jun. 25, 2014

(65) Prior Publication Data
US 2014/0375943 A1    Dec. 25, 2014

(30) Foreign Application Priority Data
Jun. 25, 2013  (EP) .................... 13003221

(51) Int. Cl.
| | | |
|---|---|---|
| *C07C 69/76* | (2006.01) | |
| *C09K 19/12* | (2006.01) | |
| *C09K 19/44* | (2006.01) | |
| *C09K 19/54* | (2006.01) | |
| *C09K 19/30* | (2006.01) | |
| *G02F 1/1333* | (2006.01) | |
| *C09K 19/04* | (2006.01) | |

(52) U.S. Cl.
CPC ............ *C09K 19/542* (2013.01); *C07C 69/76* (2013.01); *C09K 19/04* (2013.01); *C09K 19/12* (2013.01); *C09K 19/3003* (2013.01); *C09K 19/44* (2013.01); *G02F 1/1333* (2013.01); *C09K 2019/0448* (2013.01); *C09K 2019/0481* (2013.01); *C09K 2019/0485* (2013.01); *C09K 2019/122* (2013.01); *C09K 2019/123* (2013.01); *C09K 2019/301* (2013.01); *C09K 2019/3004* (2013.01); *C09K 2019/3009* (2013.01); *C09K 2019/548* (2013.01)

(58) Field of Classification Search
CPC ......... C09K 19/04; C09K 19/12; C09K 19/44; C09K 19/542; C09K 2019/3004; C09K 2019/3009; C09K 2019/301; C09K 2019/548; C09K 2019/0448; C09K 2019/0481; C09K 2019/0485; C09K 2019/122; C09K 2019/123; C07C 69/76

See application file for complete search history.

(56) References Cited

U.S. PATENT DOCUMENTS

| | | | |
|---|---|---|---|
| 6,613,245 B1 * | 9/2003 | Ohlemacher | ........... C07C 69/92 252/299.62 |
| 2004/0011996 A1 | 1/2004 | Klasen-Memmer | |
| 2005/0101752 A1 * | 5/2005 | Matsumoto | .......... C07D 305/06 526/319 |
| 2009/0103011 A1 * | 4/2009 | Bernatz | ................. C09K 19/12 349/86 |
| 2010/0103366 A1 | 4/2010 | Farrand | |
| 2011/0069241 A1 | 3/2011 | Okada | |
| 2011/0089372 A1 | 4/2011 | Okada | |
| 2011/0092718 A1 | 4/2011 | Enger | |
| 2012/0241664 A1 | 9/2012 | Brill | |
| 2012/0256124 A1 | 10/2012 | Ohgiri | |
| 2014/0117269 A1 | 5/2014 | Brill | |

FOREIGN PATENT DOCUMENTS

| | | |
|---|---|---|
| EP | 1378557 | 1/2004 |
| EP | 2295397 | 3/2011 |
| EP | 2305777 | 4/2011 |
| JP | 07110469 A * | 4/1995 |
| WO | 2013021826 | 2/2013 |

OTHER PUBLICATIONS

CAPLUS 1995:680891.*
Machine English Translation of WO2013/021826. Publication Date: Feb. 14, 2013. Title: Polymerizable Liquid Crystal Composition, and Method for Producing Optically Anisotropic Body. Inventor: Hiroshi Hasebe et al., Applicant: DIC Corporation. Application No. PCT/JP2012/068953. Filing Date: Jul. 26, 2012. (Thomason Innovation).
European Search Report in correspondence EP Application No. 14001791. Date of Complete of the Search: Oct. 21, 2014.

* cited by examiner

*Primary Examiner* — Shean C Wu
(74) *Attorney, Agent, or Firm* — Millen White Zelano & Branigan, PC

(57) ABSTRACT

The present invention relates to polymerizable compounds, to processes and intermediates for the preparation thereof, to liquid-crystal (LC) media comprising them, and to the use of the polymerizable compounds and LC media for optical, electro-optical and electronic purposes, in particular in LC displays, especially in LC displays of the PSA ("polymer sustained alignment") type.

23 Claims, No Drawings

POLYMERIZABLE COMPOUNDS AND THE USE THEREOF IN LIQUID-CRYSTAL DISPLAYS

The present invention relates to polymerizable compounds, to processes and intermediates for the preparation thereof, to liquid-crystal (LC) media comprising them, and to the use of the polymerizable compounds and LC media for optical, electro-optical and electronic purposes, in particular in LC displays, especially in LC displays of the PSA ("polymer sustained alignment") type.

BACKGROUND OF THE INVENTION

The liquid-crystal displays (LC displays) used at present are usually those of the TN ("twisted nematic") type. However, these have the disadvantage of a strong viewing-angle dependence of the contrast.

In addition, so-called VA ("vertically aligned") displays are known which have a broader viewing angle. The LC cell of a VA display contains a layer of an LC medium between two transparent electrodes, where the LC medium usually has a negative value of the dielectric (DC) anisotropy. In the switched-off state, the molecules of the LC layer are aligned perpendicular to the electrode surfaces (homeotropically) or have a tilted homeotropic alignment. On application of an electrical voltage to the two electrodes, a realignment of the LC molecules parallel to the electrode surfaces takes place.

Furthermore, OCB ("optically compensated bend") displays are known which are based on a birefringence effect and have an LC layer with a so-called "bend" alignment and usually positive (DC) anisotropy. On application of an electrical voltage, a realignment of the LC molecules perpendicular to the electrode surfaces takes place. In addition, OCB displays normally contain one or more birefringent optical retardation films in order to prevent undesired transparency to light of the bend cell in the dark state. OCB displays have a broader viewing angle and shorter response times compared with TN displays.

Also known are so-called IPS ("in-plane switching") displays, which contain an LC layer between two substrates, where the two electrodes are arranged on only one of the two substrates and preferably have intermeshed, comb-shaped structures. On application of a voltage to the electrodes, an electric field which has a significant component parallel to the LC layer is thereby generated between them. This causes realignment of the LC molecules in the layer plane.

Furthermore, so-called FFS ("fringe-field switching") displays have been proposed (see, inter alia, S. H. Jung et al., Jpn. J. Appl. Phys., Volume 43, No. 3, 2004, 1028), which likewise contain two electrodes on the same substrate, but, in contrast to IPS displays, only one of these is in the form of an electrode which is structured in a comb-shaped manner, and the other electrode is unstructured. A strong, so-called "fringe field" is thereby generated, i.e. a strong electric field close to the edge of the electrodes, and, throughout the cell, an electric field which has both a strong vertical component and also a strong horizontal component. Both IPS displays and also FFS displays have a low viewing-angle dependence of the contrast.

In VA displays of the more recent type, uniform alignment of the LC molecules is restricted to a plurality of relatively small domains within the LC cell. Disclinations may exist between these domains, also known as tilt domains. VA displays having tilt domains have, compared with conventional VA displays, a greater viewing-angle independence of the contrast and the grey shades. In addition, displays of this type are simpler to produce since additional treatment of the electrode surface for uniform alignment of the molecules in the switched-on state, such as, for example, by rubbing, is no longer necessary. Instead, the preferential direction of the tilt or pretilt angle is controlled by a special design of the electrodes.

In so-called MVA ("multidomain vertical alignment") displays, this is usually achieved by the electrodes having protrusions which cause a local pretilt. As a consequence, the LC molecules are aligned parallel to the electrode surfaces in different directions in different, defined regions of the cell on application of a voltage. "Controlled" switching is thereby achieved, and the formation of interfering disclination lines is prevented. Although this arrangement improves the viewing angle of the display, it results, however, in a reduction in its transparency to light. A further development of MVA uses protrusions on only one electrode side, while the opposite electrode has slits, which improves the transparency to light. The slitted electrodes generate an inhomogeneous electric field in the LC cell on application of a voltage, meaning that controlled switching is still achieved. For further improvement of the transparency to light, the separations between the slits and protrusions can be increased, but this in turn results in a lengthening of the response times. In so-called PVA ("patterned VA") displays, protrusions are rendered completely superfluous in that both electrodes are structured by means of slits on the opposite sides, which results in increased contrast and improved transparency to light, but is technologically difficult and makes the display more sensitive to mechanical influences ("tapping", etc.). For many applications, such as, for example, monitors and especially TV screens, however, a shortening of the response times and an improvement in the contrast and luminance (transmission) of the display are demanded.

A further development are the so-called PS ("polymer sustained") or PSA ("polymer sustained alignment") displays, for which the term "polymer stabilized" is also occasionally used. In these, a small amount (for example 0.3% by weight, typically <1% by weight) of one or more polymerizable, compound(s), preferably polymerizable monomeric compound(s), is added to the LC medium and, after introduction into the LC cell, is polymerized or cross-linked in situ, usually by UV photopolymerization, between the electrodes with or without an applied electrical voltage. The polymerization is carried out at a temperature where the LC medium exhibits a liquid crystal phase, usually at room temperature. The addition of polymerizable mesogenic or liquid-crystalline compounds, also known as reactive mesogens or "RMs", to the LC mixture has proven particularly suitable.

Unless indicated otherwise, the term "PSA" is used below as representative of PS displays and PSA displays.

In the meantime, the PS(A) principle is being used in diverse classical LC displays. Thus, for example, PSA-VA, PSA-OCB, PSA-IPS, PSA-FFS and PSA-TN displays are known. The polymerization of the polymerizable compound(s) preferably takes place with an applied electrical voltage in the case of PSA-VA and PSA-OCB displays, and with or without, preferably without, an applied electrical voltage in the case of PSA-IPS displays. As can be demonstrated in test cells, the PS(A) method results in a pretilt in the cell. In the case of PSA-OCB displays, for example, it is possible for the bend structure to be stabilized so that an offset voltage is unnecessary or can be reduced. In the case of PSA-VA displays, the pretilt has a positive effect on response times. For PSA-VA displays, a standard MVA or PVA pixel and electrode layout can be used. In addition, however, it is also possible, for example, to manage with only one structured electrode side and no protrusions, which significantly simplifies production and at the same time results in very good contrast at the same time as very good transparency to light.

Furthermore, the so-called posi-VA displays ("positive VA") have proven to be a particularly suitable mode. Like in classical VA displays, the initial orientation of the LC molecules in posi-VA displays is homeotropic, i.e. substantially perpendicular to the substrates, in the initial state when no voltage is applied. However, in contrast to classical VA displays, in posi-VA displays LC media with positive dielectric anisotropy are used. Like in the usually used IPS displays, the two electrodes in posi-VA displays are arranged on only one of the two substrates, and preferably exhibit intermeshed and comb-shaped (interdigital) structures. By application of a voltage to the interdigital electrodes, which create an electrical field that is substantially parallel to the layer of the LC medium, the LC molecules are transferred into an orientation that is substantially parallel to the substrates. In posi-VA displays, too, a polymer stabilization (PSA) has proven to be advantageous, i.e. the addition of RMs to the LC medium, which are polymerized in the cell, whereby a significant reduction of the switching times could be realized.

PSA-VA displays are described, for example, in EP 1 170 626 A2, U.S. Pat. Nos. 6,861,107, 7,169,449, US 2004/0191428 A1, US 2006/0066793 A1 and US 2006/0103804 A1. PSA-OCB displays are described, for example, in T.-J-Chen et al., Jpn. J. Appl. Phys. 45, 2006, 2702-2704 and S. H. Kim, L.-C-Chien, Jpn. J. Appl. Phys. 43, 2004, 7643-7647. PSA-IPS displays are described, for example, in U.S. Pat. No. 6,177,972 and Appl. Phys. Lett. 1999, 75(21), 3264. PSA-TN displays are described, for example, in Optics Express 2004, 12(7), 1221.

Like the conventional LC displays described above, PSA displays can be operated as active-matrix or passive-matrix displays. In the case of active-matrix displays, individual pixels are usually addressed by integrated, non-linear active elements, such as, for example, transistors (for example thin-film transistors ("TFTs")), while in the case of passive-matrix displays, individual pixels are usually addressed by the multiplex method, as known from the prior art.

The PSA display may also comprise an alignment layer on one or both of the substrates forming the display cell, wherein the alignment layer is in contact with the LC medium and induces initial alignment of the LC molecules, and wherein the alignment layer is obtained by photoalignment.

In particular for monitor and especially TV applications, optimization of the response times, but also of the contrast and luminance (thus also transmission) of the LC display continues to be demanded. The PSA method can provide crucial advantages here. In particular in the case of PSA-VA, PSA-IPS, PSA-FFS and PSA-posi-VA displays, a shortening of the response times, which correlate with a measurable pretilt in test cells, can be achieved without significant adverse effects on other parameters.

In the prior art, use is made, for example, of polymerizable compounds of the following formula:

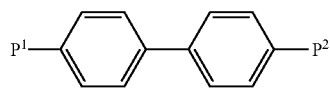

in which P denotes a polymerizable group, usually an acrylate or methacrylate group, as described, for example, in U.S. Pat. No. 7,169,449.

However, the problem arises that not all combinations consisting of LC mixture (also referred to as "LC host mixture" below)+polymerizable component (typically RMs) are suitable for PSA displays since, for example, an inadequate tilt or none at all becomes established or since, for example, the so-called "voltage holding ratio" (VHR or HR) is inadequate for TFT display applications. In addition, it has been found that, on use in PSA displays, the LC mixtures and RMs known from the prior art still have some disadvantages. Thus, not every known RM which is soluble in LC mixtures is suitable for use in PSA displays. In addition, it is often difficult to find a suitable selection criterion for the RM besides direct measurement of the pretilt in the PSA display. The choice of suitable RMs becomes even smaller if polymerization by means of UV light without the addition of photoinitiators is desired, which may be advantageous for certain applications.

In addition, the selected combination of LC host mixture/RM should have the lowest possible rotational viscosity and the best possible electrical properties. In particular, it should have the highest possible VHR. In PSA displays, a high VHR after irradiation with UV light is particularly necessary since UV exposure is a requisite part of the display production process, but also occurs as normal exposure during operation of the finished display.

In particular, it would be desirable to have available novel materials for PSA displays which produce a particularly small pretilt angle. Preferred materials here are those which produce a lower pretilt angle during polymerization for the same exposure time than the materials known to date, and/or through the use of which the (higher) pretilt angle that can be achieved with known materials can already be achieved after a shorter exposure time. The production time ("tact time") of the display could thus be shortened and the costs of the production process reduced.

A further problem in the production of PSA displays is the presence or removal of residual amounts of unpolymerized RMs, in particular after the polymerization step for production of the pretilt angle in the display. For example, unreacted RMs of this type may adversely affect the properties of the display by, for example, polymerizing in an uncontrolled manner during operation after finishing of the display.

Thus, the PSA displays known from the prior art often exhibit the undesired effect of so-called "image sticking" or "image burn", i.e. the image produced in the LC display by temporary addressing of individual pixels still remains visible even after the electric field in these pixels has been switched off or after other pixels have been addressed.

This "image sticking" can occur on the one hand if LC host mixtures having a low VHR are used. The UV component of daylight or the backlighting can cause undesired decomposition reactions of the LC molecules therein and thus initiate the production of ionic or free-radical impurities. These may accumulate, in particular, at the electrodes or the alignment layers, where they may reduce the effective applied voltage. This effect can also be observed in conventional LC displays without a polymer component.

In addition, an additional "image sticking" effect caused by the presence of unpolymerized RMs is often observed in PSA displays. Uncontrolled polymerization of the residual RMs is initiated here by UV light from the environment or by the backlighting. In the switched display areas, this changes the tilt angle after a number of addressing cycles. As a result, a change in transmission in the switched areas may occur, while it remains unchanged in the unswitched areas.

It is therefore desirable for the polymerization of the RMs to proceed as completely as possible during production of the PSA display and for the presence of unpolymerized RMs in the display to be excluded as far as possible or reduced to a minimum. To this end, materials are required which enable highly effective and complete polymerization. In addition, controlled reaction of these residual amounts would be desirable. This would be simpler if the RM polymerized more rapidly and effectively than the materials known to date.

Another problem to be solved is that the RMs of prior art do often have high melting points, and do only show limited solubility in many currently common LC mixtures, and therefore frequently tend to spontaneously crystallize out of the mixture. In addition, the risk of spontaneous polymerization prevents the LC host mixture being warmed in order to dissolve the polymerizable component, meaning that the best possible solubility even at room temperature is necessary. In addition, there is a risk of separation, for example on introduction of the LC medium into the LC display (chromatography effect), which may greatly impair the homogeneity of the display. This is further increased by the fact that the LC media are usually introduced at low temperatures in order to reduce the risk of spontaneous polymerization (see above), which in turn has an adverse effect on the solubility.

Another problem observed in prior art is that LC media for use in PSA displays, including but not limited to displays of the PSA type, do often exhibit high viscosities and, as a consequence, high switching times. In order to reduce the viscosity and switching time of the LC medium, it has been suggested in prior art to add LC compounds with an alkenyl group. However, it was observed that LC media containing alkenyl compounds often show a decrease of the reliability and stability, and a decrease of the VHR especially after exposure to UV radiation. Especially for use in PSA displays this is a considerable disadvantage, because the photo-polymerization of the RMs in the PSA display is usually carried out by exposure to UV radiation, which will then cause a VHR drop in the LC medium.

There is thus still a great demand for PSA displays, in particular of the VA and OCB type, and LC media and polymerizable compounds for use in such displays, which do not exhibit the disadvantages described above or only do so to a small extent and have improved properties. In particular, there is a great demand for PSA displays, and materials for use in PSA displays, which enable a high specific resistance at the same time as a large workingtemperature range, short response times, even at low temperatures, and a low threshold voltage, a low pretilt angle, a multiplicity of grey shades, high contrast and a broad viewing angle, have high values for the "voltage holding ratio" (VHR) after UV exposure, and have low melting points and a high solubility in the LC host mixtures.

The invention is based on the object of providing novel suitable materials, in particular RMs and LC media comprising same, for use in PSA displays, which do not have the disadvantages indicated above or do so to a reduced extent, polymerize as rapidly and completely as possible, enable a low pretilt angle to be established as quickly as possible, reduce or prevent the occurrence of "image sticking" in the display, and preferably at the same time enable very high specific resistance values, high VHR values, low threshold voltages and short response times, and have a high solubility in the LC media which are typically used as host mixtures in PSA displays.

A further object of the invention is the provision of novel RMs, in particular for optical, electro-optical and electronic applications, and of suitable processes and intermediates for the preparation thereof.

In particular, the invention is based on the object of providing polymerizable compounds which produce a greater maximum pretilt after photo-polymerization, which results in the desired pretilt being achieved more quickly and thus in significantly shortened times for production of the LC display, and which are easily processable in an LC mixture.

Upon further study of the specification and appended claims, other objects, aspects and advantages of the invention will become apparent.

These objects have been achieved in accordance with the present invention by materials and processes as described in the present application. In particular, it has been found, surprisingly, that the use of polymerizable compounds of formula I as described hereinafter in PSA displays facilitates a quick polymerization reaction, fast establishment of the desired tilt angles, and a high VHR value of the LC medium after UV photopolymerization. The compounds of formula I are characterized in that they contain a mesogenic group and one or more polymerizable groups P, wherein at least one of the polymerizable groups P is attached to the mesogenic group via the carbonyl function of a carbonyloxy spacer Sp (—CO—O-Sp-P).

It was found that the use of compounds according to the present invention has a significant influence on the polymerization speed, and leads to faster polymerization reaction, compared to polymerizable compounds as reported in prior art, wherein polymerizable groups P are attached to a mesogenic group via an alkyl spacer, or the ether function of an alkoxy spacer, or via the O-atom of an oxycarbonyl spacer Sp (—O—CO-Sp-P).

This has been demonstrated in connection with an LC medium by means of pretilt measurements. In particular, a pretilt has been achieved without the addition of photoinitiator. In addition, the polymerizable compounds according to the present invention exhibit significantly faster generation of the pretilt angle compared with the materials known from the prior art, as has been demonstrated by exposure time-dependent measurements of the pretilt angle.

It has also been demonstrated that LC media comprising polymerizable compounds according to the present invention have a higher VHR value after irradiation with UV light. It has also been demonstrated that the polymerizable compounds according to the present invention are especially suitable for use in LC host mixtures containing mesogenic or LC compounds with an alkenyl group. The use of the polymerizable compounds according to the present invention in such LC host mixtures enables high VHR values.

In addition, the polymerizable compounds according to the invention exhibit a high polymerization rate, causing smaller unreacted residual amounts to remain in the cell. The electro-optical properties of the cell are thus improved, and in addition controlled reaction of these residual amounts becomes simpler. The polymerizable compounds are therefore suitable for creating a high pretilt in PSA type displays.

Also, the polymerizable compounds according to the invention show a low tendency towards crystallization and high solubility in typical commercially available LC host mixtures.

SUMMARY OF THE INVENTION

The invention relates to polymerizable compounds comprising a mesogenic group and one or more, preferably two or more, polymerizable groups, wherein at least one of the polymerizable groups is linked to the mesogenic group via an optionally substituted spacer group, and wherein the optionally substituted spacer group is linked to the mesogenic group via the carbonyl portion of a carbonyloxy group.

The polymerizable compounds preferably contain a mesogenic group substituted by at least one group P-Sp-O—CO—, wherein P is a polymerizable group and Sp is an optionally substituted spacer group. The mesogenic group preferably comprises one or more, aromatic or aliphatic, rings or condensed rings that are optionally substituted, and is preferably selected of formula -$(A^1\text{-}Z^1)_m\text{-}A^2\text{-}$, wherein $A^1$, $A^2$, $Z^1$ and m are as defined in formula I below.

The polymerizable compounds are preferably selected of formula I

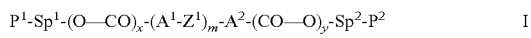

$$P^1\text{-}Sp^1\text{-}(O\text{—}CO)_x\text{-}(A^1\text{-}Z^1)_m\text{-}A^2\text{-}(CO\text{—}O)_y\text{-}Sp^2\text{-}P^2 \qquad I$$

in which the individual radicals have the following meanings $Sp^1$ and $Sp^2$ independently of each other denote a spacer group which is optionally substituted by $P^1\text{-}Sp'\text{-}$, or a single bond, wherein if x is 1 then $Sp^1$ is not single bond and if y is 1 then $Sp^2$ is not a single bond, Sp' is alkylene with 1 to 12, preferably 1 to 6, very preferably 1, 2 or 3, C atoms, $P^1$ and $P^2$ independently of each other denote a polymerizable group, $A^1$, $A^2$ independently of each other, and on each occurrence identically or differently, denote an aryl, heteroaryl, alicyclic or heterocyclic group having 4 to 25 C atoms, which may also contain fused rings, and which is optionally mono- or polysubstituted by L, $Z^1$ denotes, on each occurrence identically or differently, —O—, —S—, —CO—, —CO—O—, —O—CO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_n$—, —CF$_2$CH$_2$—, —CH$_2$CF$_2$—, —(CF$_2$)$_n$—, —CH=CH—, —CF=CF—, —CH=CF—, —CF=CH—, —C≡C—, —CH=CH—CO—O—, —O—CO—CH=CH—, —CH$_2$—CH$_2$—CO—O—, —O—CO—CH$_2$—CH$_2$—, —CR$^{00}$R$^{000}$—, or a single bond, L denotes $P^1$-, $P^1$-Sp$^1$-, $P^1$-Sp$^1$-(O—CO)$_x$—, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl or heteroaryl having 5 to 20 ring atoms, or straight-chain or branched alkyl having 1 to 25, particularly preferably 1 to 10, C atoms, in which, in addition, one or more non-adjacent CH$_2$ groups may each be replaced, independently of one another, by —C(R$^{00}$)=C(R$^{000}$)—, —C≡C—, —N(R$^{00}$)—, —O—, —S—, —CO—, —CO—O—, —O—CO—, or —O—CO—O— in such a way that O and/or S atoms are not linked directly to one another, and in which, in addition, one or more H atoms may each be replaced by F, Cl, CN, $P^1$, $P^1$-Sp$^1$- or $P^1$-Sp$^1$-(O—CO)$_x$—, $R^{00}$ and $R^{000}$ each, independently of one another, denote H or alkyl having 1 to 12 C atoms, $Y^1$ is halogen, $R^x$ denotes $P^1$, $P^1$-Sp$^1$-, $P^1$-(Sp$^1$-O—CO)$_x$—, H, halogen, straight chain, branched or cyclic alkyl having 1 to 25 C atoms, wherein one or more non-adjacent CH$_2$-groups are each optionally replaced by —O—, —S—, —CO—, —CO—O—, —O—CO—, or —O—CO—O— in such a manner that O- and/or S-atoms are not directly connected with each other, and wherein one or more H atoms are optionally replaced by F, Cl, $P^1$-, $P^1$-Sp$^1$- or $P^1$-(Sp$^1$-O—CO)$_x$—, optionally substituted aryl, aryloxy, heteroaryl or heteroaryloxy having 5 to 20 ring atoms, m is 1, 2, 3 or 4, n is 1, 2, 3 or 4, x and y independently of each other, and on each occurrence identically or differently, denote 0 or 1, characterized in that at least one of x and y is 1, The polymerizable compounds according to the present invention preferably do not contain a polymerizable group that is attached to the mesogenic group, or to the rings $A^1$ or $A^2$ in formula I, via a spacer group which is linked to the mesogenic group, or to the rings $A^1$ or $A^2$ in formula I, via the O atom of a carbonyloxy group, (i.e. the mesogenic group and the rings $A^1$ or $A^2$ in formula I do not contain a substituent P-Sp-CO—O—, wherein P is a polymerizable group and Sp is a spacer group).

The invention further relates to use of the polymerizable compound in liquid-crystal (LC) media or LC displays, especially in the LC medium, active layer or alignment layer of an LC display, wherein the LC displays are preferably of the PSA (polymer sustained alignment) type.

The invention further relates to novel methods for preparing compounds of formula I, and to novel intermediates used or obtained in these methods.

The invention furthermore relates to an LC medium comprising one or more polymerizable compounds according to the present invention, preferably selected of formula I and one or more additional compounds, which may also be mesogenic, liquid-crystalline and/or polymerizable.

The invention furthermore relates to an LC medium comprising
  a polymerizable component A) comprising one or more polymerizable compounds according to the present invention, preferably selected of formula I, and
  an liquid-crystalline component B), also referred to below as "LC host mixture", comprising one or more, preferably two or more, low-molecular-weight (monomeric and unpolymerizable) compounds, which are preferably selected from mesogenic or liquid crystalline compounds.

The invention furthermore relates to an LC medium as described above and below, wherein the LC host mixture, or component B, comprises at least one mesogenic or liquid crystalline compound comprising an alkenyl group.

The invention furthermore relates to an LC medium comprising a polymer obtained by polymerization of one or more polymerizable compounds according to the present invention, or by polymerization of a polymerizable component A) as described above, and further comprising one or more additional compounds, which may also be mesogenic, liquid-crystalline and/or polymerizable, or a component B) as described above.

The invention furthermore relates to an LC medium as described above and below, wherein the polymerizable compounds or the polymerizable component A) are polymerized.

The invention furthermore relates to a process for preparing an LC medium as described above and below, comprising the steps of mixing one or more low-molecular-weight liquid-crystalline compounds, or an LC host mixture or a liquid-crystalline component B) as described above and below, with one or more polymerizable compounds according to the present invention, and optionally with further liquid-crystalline compounds and/or additives.

The invention furthermore relates to the use of polymerizable compounds and LC media according to the invention in PSA displays, in particular the use in PSA displays containing an LC medium, for the production of a tilt angle in the LC medium by in-situ polymerization of the polymerizable compound(s) according to the present invention in the PSA display, preferably in an electric or magnetic field.

The invention furthermore relates to an LC display comprising one or more polymerizable compounds or an LC medium according to the invention, in particular a PSA display, particularly preferably a PSA-VA, PSA-OCB, PSA-IPS, PS-FFS, PSA-posi-VA or PSA-TN display.

The invention furthermore relates to an LC display comprising a polymer obtainable by polymerization of one or more polymerizable compounds of formula I or of a polymerizable component A) as described above, or comprising an LC medium according to the invention, in particular a PSA display, particularly preferably a PSA-VA, PSA-OCB, PSA-IPS, PS-FFS, PSA-posi-VA or PSA-TN display.

The invention furthermore relates to an LC display of the PSA type containing an LC cell having two substrates and two electrodes, where at least one substrate is transparent to light and at least one substrate has one or two electrodes, and a layer, located between the substrates, of an LC medium comprising a polymerized component and a low-molecular-weight component, where the polymerized component is obtainable by polymerization of one or more polymerizable compounds between the substrates of the LC cell in the LC medium, preferably while applying an electrical voltage to the electrodes, where at least one of the polymerizable compounds is selected from polymerizable compounds according to the present invention, preferably selected of formula I, as described above and below, and/or wherein the LC medium is an LC medium as described above and below.

The invention furthermore relates to a process for manufacturing an LC display as described above and below, comprising the steps of filling an LC medium, which comprises one or more low-molecular-weight liquid-crystalline compounds or an LC host mixture or a liquid-crystalline component B), as described above and below, and one or more polymerizable compounds according to the present invention, preferably selected or a polymerizable component A) as described above and below, into an LC cell having two substrates and two electrodes as described above and below, and polymerizing the polymerizable compounds, preferably while applying an electrical voltage to the electrodes.

The PSA displays according to the invention have two electrodes, preferably in the form of transparent layers, which are applied to one or both of the substrates which form the LC cell. Either in each case one electrode is applied to each of the two substrates, as, for example, in PSA-VA, PSA-OCB or PSA-TN displays according to the invention, or both electrodes are applied to only one of the two substrates, while the other substrate has no electrode, as, for example, in PSA-posi-VA, PSA-IPS or PSA-FFS displays according to the invention.

DEFINITIONS OF TERMS

As used herein, the terms "tilt" and "tilt angle" mean a tilted alignment of the LC molecules of an LC medium relative to the surfaces of the cell in an LC display (here preferably a PSA display). The tilt angle here denotes the average angle (<90°) between the longitudinal molecular axes of the LC molecules (LC director) and the surface of the plane-parallel outer plates which form the LC cell. A low value for the tilt angle (i.e. a large deviation from the 90° angle) corresponds to a large tilt here. A suitable method for measurement of the tilt angle is given in the examples. Unless indicated otherwise, tilt angle values disclosed above and below relate to this measurement method.

The term "mesogenic group" as used herein is known to the person skilled in the art and described in the literature, and means a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behavior only after mixing with other compounds and/or after polymerization. Typical mesogenic groups are, for example, rigid rod- or disc-shaped units. An overview of the terms and definitions used in connection with mesogenic or LC compounds is given in Pure Appl. Chem. 73(5), 888 (2001) and C. Tschierske, G. Pelzl, S. Diele, Angew. Chem. 2004, 116, 6340-6368.

The term "spacer group", hereinafter also referred to as "Sp", is known to the person skilled in the art and is described in the literature, see, for example, Pure Appl. Chem. 73(5), 888 (2001) and C. Tschierske, G. Pelzl, S. Diele, Angew. Chem. 2004, 116, 6340-6368. As used herein, the terms "spacer group" or "spacer" mean a flexible group, for example an alkylene group, which connects the mesogenic group and the polymerizable group(s) in a polymerizable mesogenic compound.

As used herein, the terms "reactive mesogen" and "RM" mean a compound containing one mesogenic group and one or more functional groups which are suitable for polymerization, the latter also being referred to as "polymerizable group" or "P".

The term "polymerizable compound" as used hereinafter, unless stated otherwise, means a polymerizable monomeric compound.

As used herein, the terms "low-molecular-weight compound" and "unpolymerizable compound" mean compounds, usually monomeric, which contain no functional group that is suitable for polymerization under the usual conditions known to the person skilled in the art, in particular under the conditions used for the polymerization of the polymerizable compounds or RMs as described above and below.

As used herein, the terms "active layer" and "switchable layer" mean a layer in an electrooptical display, for example an LC display, that comprises one or more molecules having structural and optical anisotropy, like for example LC molecules, which change their orientation upon an external stimulus like an electric or magnetic field, resulting in a change of the transmission of the layer for polarized or unpolarized light.

DETAILED DESCRIPTION OF THE INVENTION

Unless stated otherwise, the compounds of formula I are preferably selected from achiral compounds.

Above and below "organic group" denotes a carbon or hydrocarbon group.

"Carbon group" denotes a mono- or polyvalent organic group containing at least one carbon atom, where this either contains no further atoms (such as, for example, —C≡C—) or optionally contains one or more further atoms, such as, for example, N, O, S, P, Si, Se, As, Te or Ge (for example carbonyl, etc.). The term "hydrocarbon group" denotes a carbon group which additionally contains one or more H atoms and optionally one or more heteroatoms, such as, for example, N, O, S, P, Si, Se, As, Te or Ge.

"Halogen" denotes F, Cl, Br or I.

—CO—, —C(═O)— and —C(O)— denote a carbonyl group, i.e.

"Conjugated radical" or "conjugated group" denotes a radical or group which contains principally sp²-hybridized (or possibly also sp-hybridized) carbon atoms, which may also be replaced by corresponding heteroatoms. In the simplest case, this means the alternating presence of double and single bonds. "Principally" in this connection means that naturally (non-randomly) occurring defects which result in conjugation interruptions do not devalue the term "conjugated". Furthermore, the term "conjugated" is likewise used in this application text if, for example, arylamine units or certain heterocycles (i.e. conjugation via N, O, P or S atoms) are located in the radical or group.

A carbon or hydrocarbon group can be a saturated or unsaturated group. Unsaturated groups are, for example, aryl, alkenyl or alkynyl groups. A carbon or hydrocarbon radical having more than 3 C atoms can be straight-chain, branched and/or cyclic and may also contain spiro links or condensed rings.

The terms "alkyl", "aryl", "heteroaryl", etc., also encompass polyvalent groups, for example alkylene, arylene, heteroarylene, etc.

The term "aryl" denotes an aromatic carbon group or a group derived therefrom. The term "heteroaryl" denotes "aryl" as defined above, containing one or more heteroatoms.

Preferred carbon and hydrocarbon groups are optionally substituted alkyl, alkenyl, alkynyl, alkoxy, alkylcarbonyl, alkoxycarbonyl, alkylcarbonyloxy and alkoxycarbonyloxy having 1 to 40, preferably 1 to 25, particularly preferably 1 to 18, C atoms, optionally substituted aryl or aryloxy having 6 to 40, preferably 6 to 25, C atoms, or optionally substituted alkylaryl, arylalkyl, alkylaryloxy, arylalkyloxy, arylcarbonyl, aryloxycarbonyl, aryl carbonyloxy and aryloxycarbonyloxy having 6 to 40, preferably 6 to 25, C atoms.

Further preferred carbon and hydrocarbon groups are $C_1$-$C_{40}$ alkyl, $C_2$-$C_{40}$ alkenyl, $C_2$-$C_{40}$ alkynyl, $C_3$-$C_{40}$ allyl, $C_4$-$C_{40}$ alkyldienyl, $C_4$-$C_{40}$ polyenyl, $C_6$-$C_{40}$ aryl, $C_6$-$C_{40}$ alkylaryl, $C_6$-$C_{40}$ arylalkyl, $C_6$-$C_{40}$ alkylaryloxy, $C_6$-$C_{40}$ arylalkyloxy, $C_2$-$C_{40}$ heteroaryl, $C_4$-$C_{40}$ cycloalkyl, $C_4$-$C_{40}$ cycloalkenyl, etc. Particular preference is given to $C_1$-$C_{22}$ alkyl, $C_2$-$C_{22}$ alkenyl, $C_2$-$C_{22}$ alkynyl, $C_3$-$C_{22}$ allyl, $C_4$-$C_{22}$ alkyldienyl, $C_6$-$C_{12}$ aryl, $C_6$-$C_{20}$ arylalkyl and $C_2$-$C_{20}$ heteroaryl.

Further preferred carbon and hydrocarbon groups are straight-chain, branched or cyclic alkyl radicals having 1 to 40, preferably 1 to 25, C atoms, which are unsubstituted or mono- or polysubstituted by F, Cl, Br, I or CN and in which one or more non-adjacent $CH_2$ groups may each be replaced, independently of one another, by —C($R^x$)═C($R^x$)—, —C≡C—, —N($R^x$)—, —O—, —S—, —CO—, —CO—O—, —O—CO—, —O—CO—O— in such a way that O and/or S atoms are not linked directly to one another.

$R^x$ preferably denotes H, halogen, a straight-chain, branched or cyclic alkyl chain having 1 to 25 C atoms, in which, in addition, one or more non-adjacent C atoms may each be replaced by —O—, —S—, —CO—, —CO—O—, —O—CO—, —O—CO—O— and in which one or more H atoms may each be replaced by fluorine, an optionally substituted aryl or aryloxy group having 6 to 40 C atoms, or an optionally substituted heteroaryl or heteroaryloxy group having 2 to 40 C atoms.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy, n-dodecoxy, etc.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, dodecanyl, trifluoromethyl, perfluoron-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred amino groups are, for example, dimethylamino, methylamino, methylphenylamino, phenylamino, etc.

Aryl and heteroaryl groups can be monocyclic or polycyclic, i.e. they can contain one ring (such as, for example, phenyl) or two or more rings, which may also be fused (such as, for example, naphthyl) or covalently bonded (such as, for example, biphenyl), or contain a combination of fused and linked rings. Heteroaryl groups contain one or more heteroatoms, preferably selected from O, N, S and Se.

Particular preference is given to mono-, bi- or tricyclic aryl groups having 6 to 25 C atoms and mono-, bi- or tricyclic heteroaryl groups having 5 to 25 ring atoms, which optionally contain fused rings and are optionally substituted. Preference is furthermore given to 5-, 6- or 7-membered aryl and heteroaryl groups, in which, in addition, one or more CH groups may each be replaced by N, S or O in such a way that O atoms and/or S atoms are not linked directly to one another.

Preferred aryl groups are, for example, phenyl, biphenyl, terphenyl, [1,1':3',1"]terphenyl-2'-yl, naphthyl, anthracene, binaphthyl, phenanthrene, 9,10-dihydro-phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiadiazothiophene, or combinations of these groups.

The aryl and heteroaryl groups mentioned above and below may also be substituted by alkyl, alkoxy, thioalkyl, fluorine, fluoroalkyl or further aryl or heteroaryl groups.

The (non-aromatic) alicyclic and heterocyclic groups encompass both saturated rings, i.e. those containing exclusively single bonds, and also partially unsaturated rings, i.e. those which may also contain multiple bonds. Heterocyclic rings contain one or more heteroatoms, preferably selected from Si, O, N, S and Se.

The (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 5 to 25 ring atoms, which optionally contain fused rings and are optionally substituted. Preference is furthermore given to 5-, 6-, 7- or 8-membered carbocyclic groups, in which, in addition, one or more C atoms may each be replaced by Si and/or one or more CH groups may each be replaced by N and/or one or more non-adjacent $CH_2$ groups may each be replaced by —O— or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]-pentane-1,3-diyl, bicyclo[2.2.2]octane-1,4-diyl, spiro[3.3]heptane-2,6-diyl, octahydro-4,7-methanoindane-2,5-diyl.

Preferred substituents are, for example, solubility-promoting groups, such as alkyl or alkoxy, electron-withdrawing groups, such as fluorine, nitro or nitrile, or substituents for increasing the glass transition temperature (Tg) in the polymer, in particular bulky groups, such as, for example, t-butyl or optionally substituted aryl groups.

Preferred substituents, also referred to as "L" above and below, are, for example, F, Cl, Br, I, —CN, —$NO_2$, —NCO, —NCS, —OCN, —SCN, —C(=O)N($R^x$)$_2$, —C(=O)$Y^1$, —C(=O)$R^x$, —N($R^x$)$_2$, in which $R^x$ has the meaning indicated above, and $Y^1$ denotes halogen, optionally substituted silyl or aryl having 6 to 40, preferably 6 to 20, C atoms, and straight-chain or branched alkyl, alkoxy, alkylcarbonyl, alkoxycarbonyl, alkylcarbonyloxy or alkoxycarbonyloxy having 1 to 25 C atoms, in which one or more H atoms may optionally be replaced by F or Cl.

"Substituted silyl or aryl" preferably means substituted by halogen, —CN, $R^0$, —$OR^0$, —CO—$R^0$, —CO—O—$R^0$, —O—CO—$R^0$ or —O—CO—O—$R^0$, in which $R^0$ denotes H or alkyl having 1 to 12 C atoms.

Particularly preferred substituents L are, for example, F, Cl, CN, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, furthermore phenyl.

In the compounds wherein r is different from 0, the group

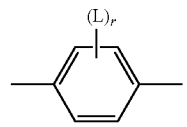

is preferably

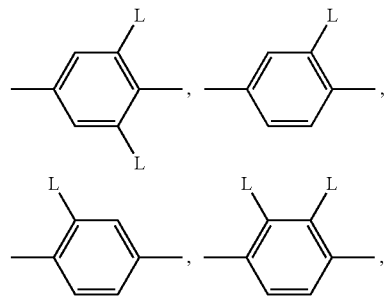

in which L has one of the meanings indicated above.

The polymerizable group (P, $P^1$, $P^2$)) is a group which is suitable for a polymerization reaction, such as, for example, free-radical or ionic chain polymerization, polyaddition or polycondensation, or for a polymer-analogous reaction, for example addition or condensation onto a main polymer chain. Particular preference is given to groups for chain polymerization, in particular those containing a C=C double bond or —C≡C— triple bond, and groups which are suitable for polymerization with ring opening, such as, for example, oxetane or epoxide groups.

Preferred polymerizable groups are selected from the group consisting of $CH_2$=$CW^1$—CO—O—, $CH_2$=$CW^1$—CO—,

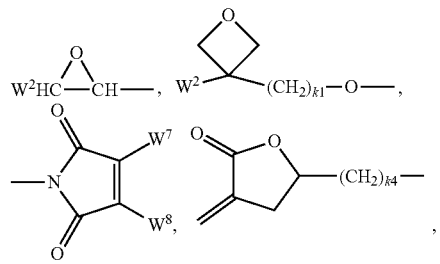

$CH_2$=$CW^2$—(O)$_{k3}$—, $CW^1$=CH—CO—(O)$_{k3}$—, $CW^1$=CH—CO—NH—, $CH_2$=$CW^1$—CO—NH—, $CH_3$—CH=CH—O—, ($CH_2$=CH)$_2$CH—OCO—, ($CH_2$=CH—$CH_2$)$_2$CH—OCO—, ($CH_2$=CH)$_2$CH—O—, ($CH_2$=CH—$CH_2$)$_2$N—, ($CH_2$=CH—$CH_2$)$_2$N—CO—, HO—$CW^2W^3$—, HS—$CW^2W^3$—, $HW^2$N—, HO—$CW^2W^3$—NH—, $CH_2$=$CW^1$—CO—NH—, $CH_2$=CH—(COO)$_{k1}$—Phe-(O)$_{k2}$—, $CH_2$=CH—(CO)$_{k1}$—Phe-(O)$_{k2}$—, Phe-CH=CH—, HOOC—, OCN— and $W^4W^5W^6$Si—, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, which is optionally substituted by one or more non-polymerizable radicals L as defined above, $k_1$, $k_2$ and $k_3$ each, independently of one another, denote 0 or 1, $k_3$ preferably denotes 1, and $k_4$ denotes an integer from 1 to 10.

Particularly preferred polymerizable groups are selected from the group consisting of $CH_2=CW^1-CO-O-$, $CH_2=CW^1-CO-$,

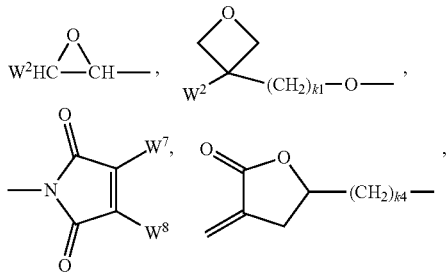

$CH_2=CW^2-O-$, $CH_2=CW^2-$, $CW^1=CH-CO-(O)_{k3}-$, $CW^1=CH-CO-NH-$, $CH_2=CW^1-CO-NH-$, $(CH_2=CH)_2CH-OCO-$, $(CH_2=CH-CH_2)_2CH-OCO-$, $(CH_2=CH)_2CH-O-$, $(CH_2=CH-CH_2)_2N-$, $(CH_2=CH-CH_2)_2N-CO-$, $CH_2=CW^1-CO-NH-$, $CH_2=CH-(COO)_{k1}-Phe-(O)_{k2}-$, $CH_2=CH-(CO)_{k1}-Phe-(O)_{k2}-$, Phe-CH=CH- and $W^4W^5W^6Si-$, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, $k_1$, $k_2$ and $k_3$ each, independently of one another, denote 0 or 1, $k_3$ preferably denotes 1, and $k_4$ denotes an integer from 1 to 10.

Very particularly preferred polymerizable groups are selected from the group consisting of $CH_2=CW^1-CO-O-$, in particular $CH_2=CH-CO-O-$, $CH_2=C(CH_3)-CO-O-$ and $CH_2=CF-CO-O-$, furthermore $CH_2=CH-O-$, $(CH_2=CH)_2CH-O-CO-$, $(CH_2=CH)_2CH-O-$,

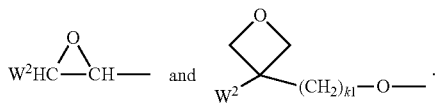

Further very particularly preferred polymerizable groups are selected from the group consisting of vinyl, vinyloxy, acrylate, methacrylate, fluoroacrylate, chloroacrylate, oxetane and epoxide groups, and particularly preferably denote an acrylate, methacrylate or oxetane group.

The spacer groups Sp, $Sp^1$ and $Sp^2$ are preferably selected of the formula Sp"-X", wherein Sp" is linked to the polymerizable group (so that e.g. the radical P-Sp-, $P^1$-$Sp^1$- or $P^2$-$Sp^2$- is of the formula P-Sp"-X" or $P^{1/2}$-Sp"-X"-, respectively), wherein Sp" and X" have the following meanings:
Sp" denotes straight-chain or branched alkylene having 1 to 20, preferably 1 to 15, C atoms, which is optionally mono- or polysubstituted by F, Cl, Br, I, CN or $P^1$-Sp'-, and in which, in addition, one or more non-adjacent $CH_2$ groups may each be replaced, independently of one another, by —O—, —S—, —NH—, —N($R^0$)—, —Si($R^{00}R^{000}$)—, —CO—, —CO—O—, —O—CO—, —O—CO—O—, —S—CO—, —CO—S—, —N($R^{00}$)—CO—O—, —O—CO—N($R^{00}$)—, —N($R^{00}$)—CO—N($R^{00}$)—, —CH=CH— or —C≡C— in such a way that O and/or S atoms are not linked directly to one another,
X" denotes —O—, —S—, —CO—, —CO—O—, —O—CO—, —O—CO—O—, —CO—N($R^{00}$)—, —N($R^{00}$)—CO—, —N($R^{00}$)—CO—N($R^{00}$)—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^2$=CY$^3$—, —C≡C—, —CH=CH—CO—O—, —O—CO—CH=CH— or a single bond, wherein X" denotes a single bond if it is adjacent to an ester group (O—CO or CO—O) in formula I,
$R^0$, $R^{00}$ and $R^{000}$ each, independently of one another, denote H or alkyl having 1 to 12 C atoms,
$Y^2$ and $Y^3$ each, independently of one another, denote H, F, Cl or CN, and
$P^1$ and $Sp^1$ are as defined in formula I.
X" is preferably —O—, —S—, —CO—, —COO—, —OCO—, —O—COO—, —CO—NR$^0$—, —NR$^0$—CO—, —NR$^0$—CO—NR$^0$— or a single bond, very preferably —O— or a single bond.

Preferred spacer groups Sp, $Sp^1$, $Sp^2$ and Sp"-X"— include, without limitation, —(CH$_2$)$_{p1}$—, —(CH$_2$)$_{p2}$—O—(CH$_2$)$_{p3}$—, —(CH$_2$)$_{p2}$—S—(CH$_2$)$_{p3}$—, —(CH$_2$)$_{p2}$—NH—(CH$_2$)$_{p3}$—, —(CH$_2$)$_{p1}$—O—, —O—(CH$_2$)$_{p1}$—, or

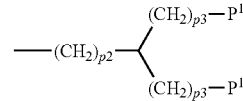

wherein p1 is an integer from 1 to 12, preferably from 1 to 6, and p2 and p3 are, independently of each other, an integer from 1 to 6, preferably 1, 2 or 3, provided that, in a group $Sp^1$-(O—CO)$_x$— if x is 1 then $Sp^1$ is not —(CH$_2$)$_{p1}$—O— or —O—(CH$_2$)$_{p1}$—, and in a group —(CO—O)$_y$-$Sp^2$-$P^2$ if y is 1 then $Sp^2$ is not —(CH$_2$)$_{p1}$—O— or —O—(CH$_2$)$_{p1}$—.

A preferred embodiment of the present invention relates to compounds of formula I wherein the spacer groups Sp, $Sp^1$, and $Sp^2$ denote Sp'-X" in which Sp' is selected from straight-chain alkylene as defined above.

Another preferred embodiment of the present invention relates to compounds of formula I containing at least one group P-Sp-, $P^1$-Sp'-, $P^2$-$Sp^2$- or $P^3$-$Sp^3$-, wherein Sp, $Sp^1$, or $Sp^2$, respectively, denote Sp'-X" in which Sp' is branched alkylene that is substituted by a group P as defined above (branched polymerizable groups).

Further preferred are compounds of formula I in which $A^1$, $A^2$ each, independently of one another, denote 1,4-phenylene, 1,3-phenylene-, 1,2-phenylene, naphthalene-1,4-diyl or naphthalene-2,6-diyl, where one or more CH groups in these groups are optionally replaced by N, cyclohexane-1,4-diyl, in which, in addition, one or more non-adjacent $CH_2$ groups are each optionally replaced by O or S, 1,4-cyclohexenylene, bicyclo[1.1.1]pentane-1,3-diyl, bicyclo[2.2.2]octane-1,4-diyl, spiro[3.3]heptane-2,6-diyl, piperidine-1,4-diyl, decahydronaphthalene-2,6-diyl, 1,2,3,4-tetrahydronaphthalene-2,6-diyl, indane-2,5-diyl, octahydro-4,7-methanoindane-2,5-diyl, anthracene-2,7-diyl, fluorene-2,7-diyl, phenanthrene-2,7-diyl or 9,10-dihydrophenanthrene-2,7-diyl, where all these groups are unsubstituted or mono- or polysubstituted by L.

Further preferred compounds of formula I are those in which
- x and y denote 1,
- x is 0 and y is 1,
- m is 1 or 2,
- at least one of $A^1$ and $A^2$ is substituted by a group L denoting $P^1\text{-}Sp^1\text{-}(O\text{—}CO)_x\text{—}$,
- m is 1 or 2 and one or both groups $A^1$ are substituted by a group L denoting $P^1\text{-}Sp^1\text{-}(O\text{—}CO)_x\text{—}$,
- m is 1 or 2 and $A^2$ is substituted by a group L denoting $P^1\text{-}Sp^1\text{-}(O\text{—}CO)_x\text{—}$,
- m is 1 and $A^2$ is substituted by a group L denoting $P^1\text{-}Sp^1\text{-}(O\text{—}CO)_x\text{—}$,
- m is 2 and $A^2$ is substituted by a group L denoting $P^1\text{-}Sp^1\text{-}(O\text{—}CO)_x\text{—}$,
- m is 2 and the central group $A^1$ is substituted by a group L denoting $P^1\text{-}Sp^1\text{-}(O\text{—}CO)_x\text{—}$,
- the sum of all x and y in formula I is 1 (the compounds contain only one group selected from the formulae $P^1\text{-}Sp^1\text{-}O\text{—}CO\text{—}$ and $CO\text{—}O\text{-}Sp^2\text{-}P^2$),
- $P^1$ and $P^2$ are selected from the group consisting of acrylate, methacrylate and oxetane,
- $Sp^1$ and $Sp^2$ are selected from $-(CH_2)_{p1}-$, $-(CH_2)_{p2}-O-(CH_2)_{p3}-$, $-(CH_2)_{p1}-O-$, $-O-(CH_2)_{p1}-$, or

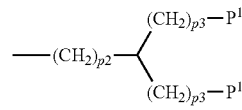

in which p1 is an integer from 1 to 6, preferably 1, 2 or 3, and p2 and p3 are independently of each other 1, 2 or 3,
- at least one group $Sp^1$ or $Sp^2$ denotes $Sp''\text{-}X$ in which $Sp''$ is substituted by a group $P^1\text{-}Sp'\text{-}$ as defined above, wherein preferably Sp' preferably denotes alkylene having 1, 2 or 3 C atoms, and $P^1$ preferably denotes acrylate, methacrylate or oxetane,
- $A^1$ and $A^2$ are selected from the group consisting of 1,4-phenylene, 1,3-phenylene-, 1,2-phenylene, naphthalene-2,6-diyl, phenanthrene-2,7-diyl and 9,10-dihydro-phenanthrene-2,7-diyl, where, in addition, one or two CH groups in these rings are optionally replaced by N, and where these rings are optionally mono- or polysubstituted by L, as described above and below,
- $A^1$ and $A^2$ are selected from the group consisting of 1,4-phenylene, 1,3-phenylene-, 1,2-phenylene, and naphthalene-2,6-diyl,
- $A^1$ and $A^2$ are selected from the group consisting of 1,4-phenylene, 1,3-phenylene- and 1,2-phenylene,
- $Z^1$ in each occurrence is independently selected from the group consisting of —O—, —CO—O—, —OCO—, —OCH$_2$—, —CH$_2$O—, —CF$_2$O—, —OCF$_2$—, —CH$_2$CH$_2$—, —CH=CH—, —CF=CF—, —CH=CF—, —CF=CH—, —C≡C—, and a single bond,
- $Z^1$ is a single bond,
- at least one of $A^1$ and $A^2$ is substituted by a group L that is an unpolymerizable group, preferably selected from F, Cl, —CN and straight-chain or branched alkyl having 1 to 25, particularly preferably 1 to 10, C atoms, in which, in addition, one or more non-adjacent CH$_2$ groups may each be replaced, independently of one another, by —C($R^{00}$)=C($R^{000}$)—, —C≡C—, —N($R^{00}$)—, —O—, —S—, —CO—, —CO—O—, —O—CO—, —O—CO—O— in such a way that O and/or S atoms are not linked directly to one another, and in which, in addition, one or more H atoms may each be replaced by F, Cl, Br, I or CN.

Preferred compounds of formula I are selected from the following subformulae:

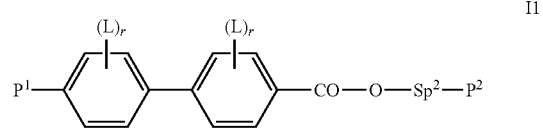

I1

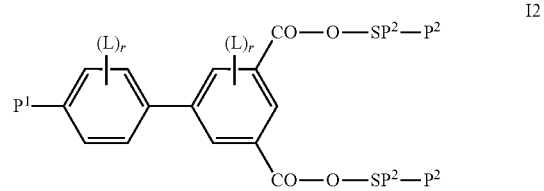

I2

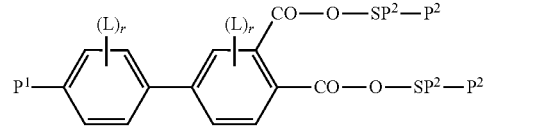

I3

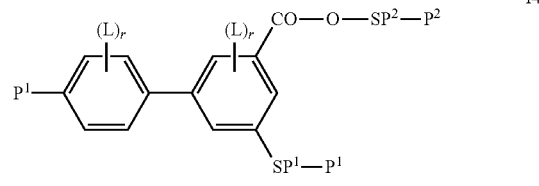

I4

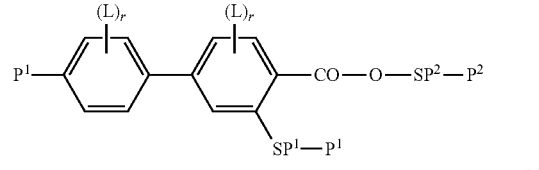

I5

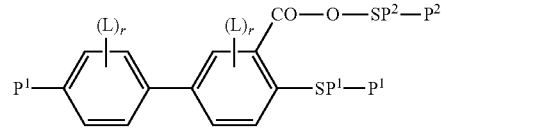

I6

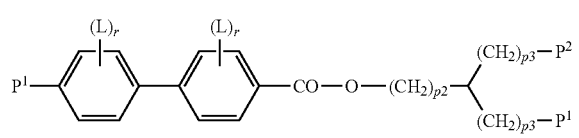

I7

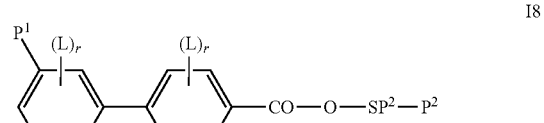

I8

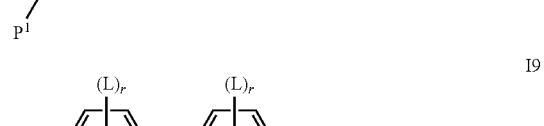

I9

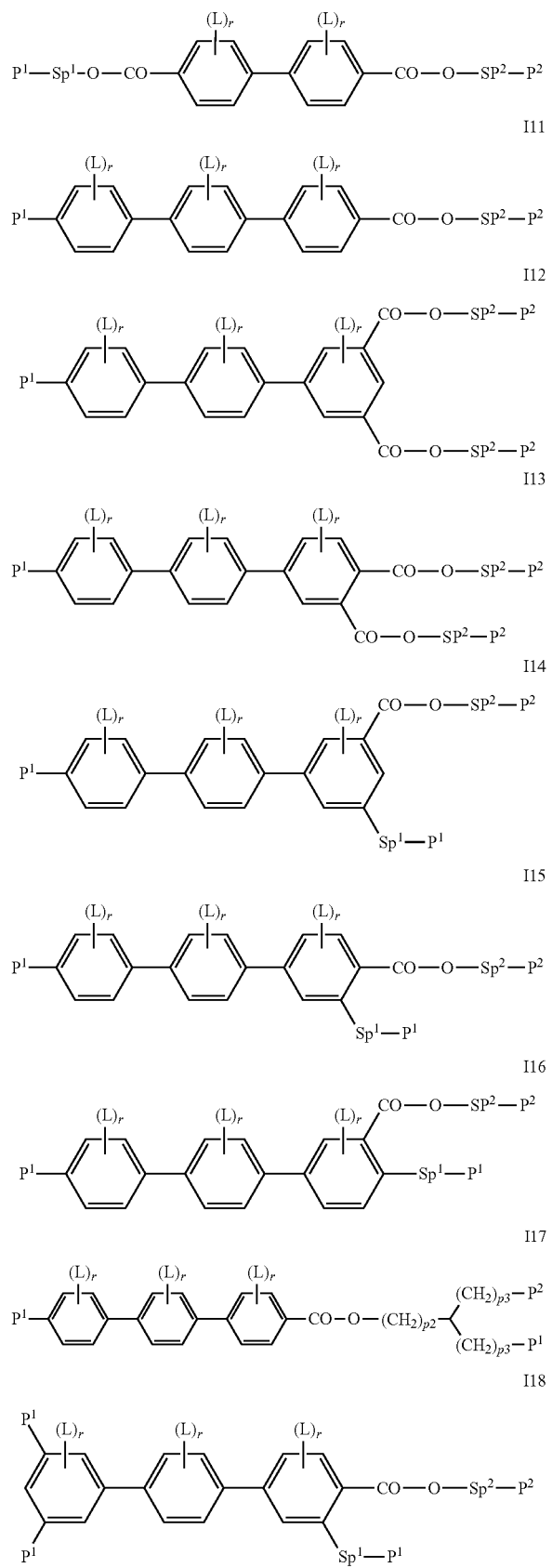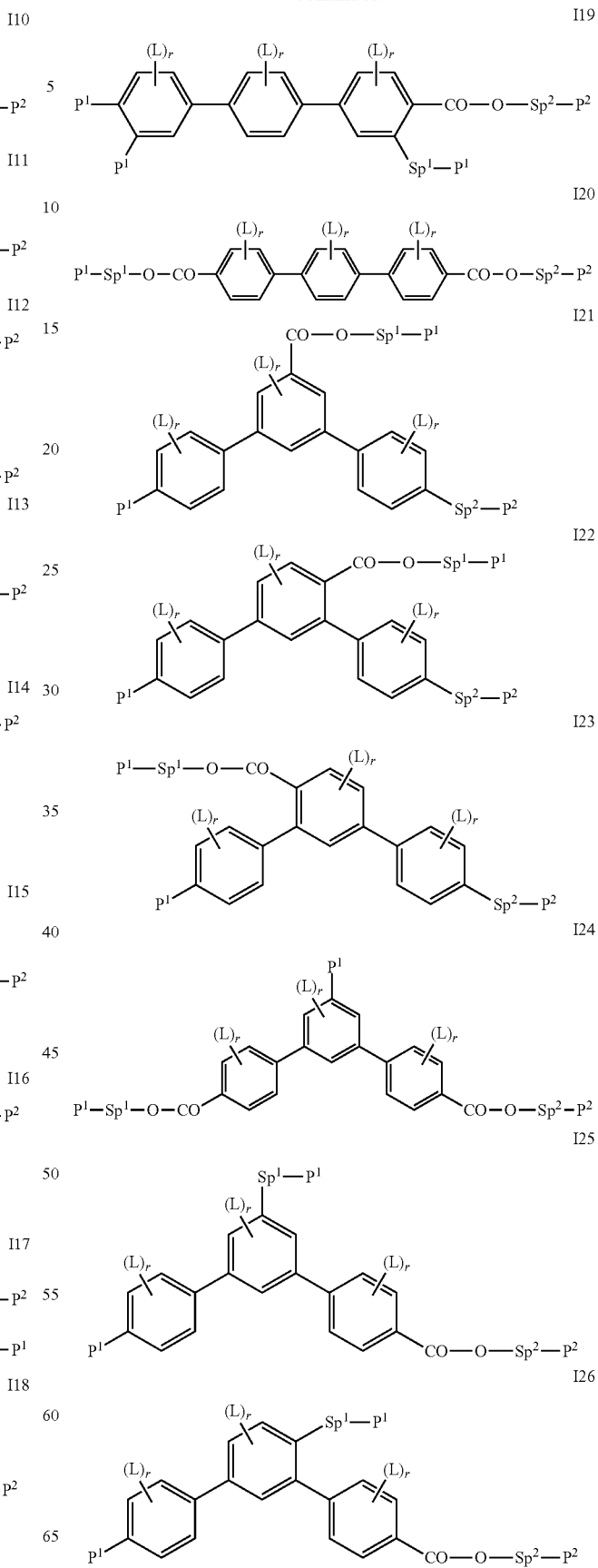

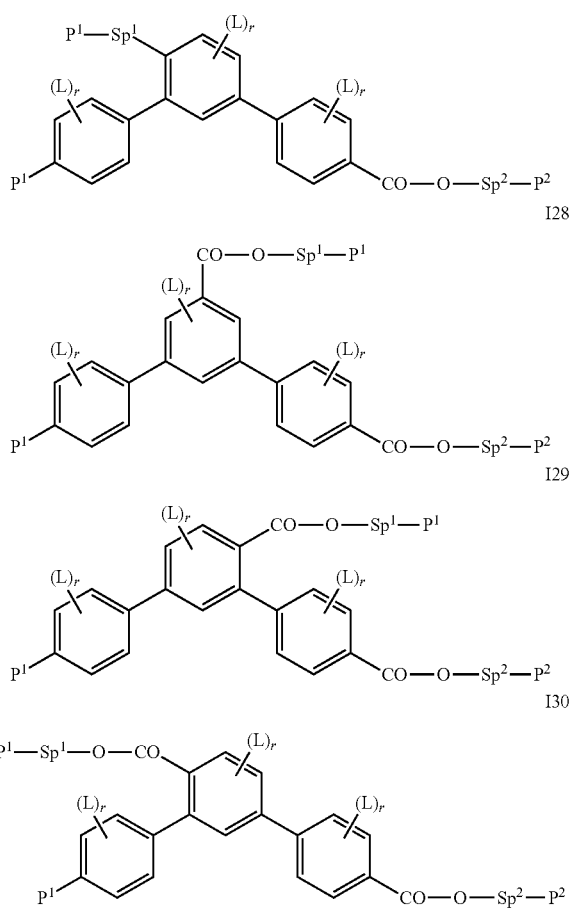
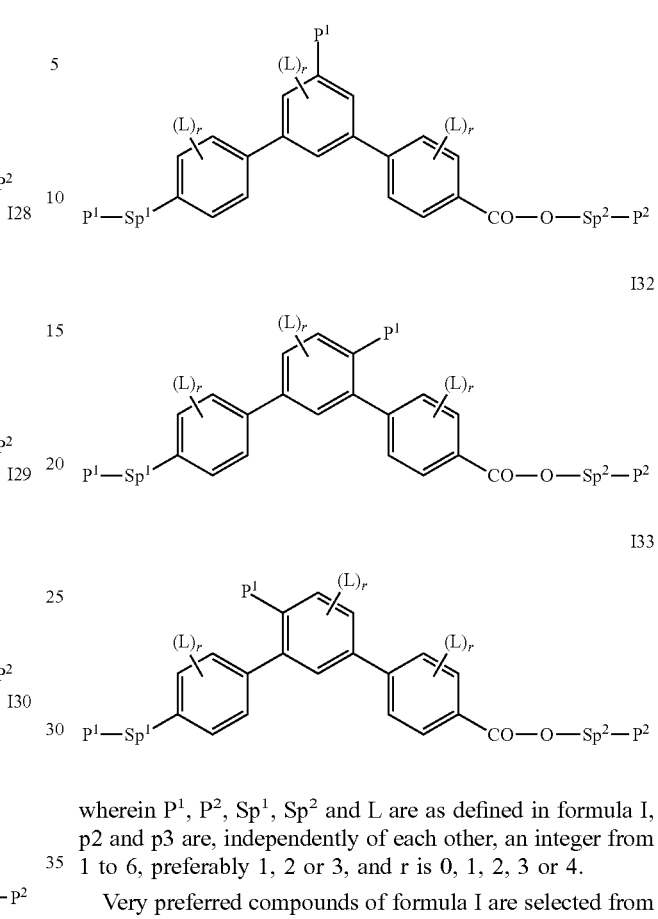
wherein $P^1$, $P^2$, $Sp^1$, $Sp^2$ and L are as defined in formula I, p2 and p3 are, independently of each other, an integer from 1 to 6, preferably 1, 2 or 3, and r is 0, 1, 2, 3 or 4.
Very preferred compounds of formula I are selected from the following subformulae:
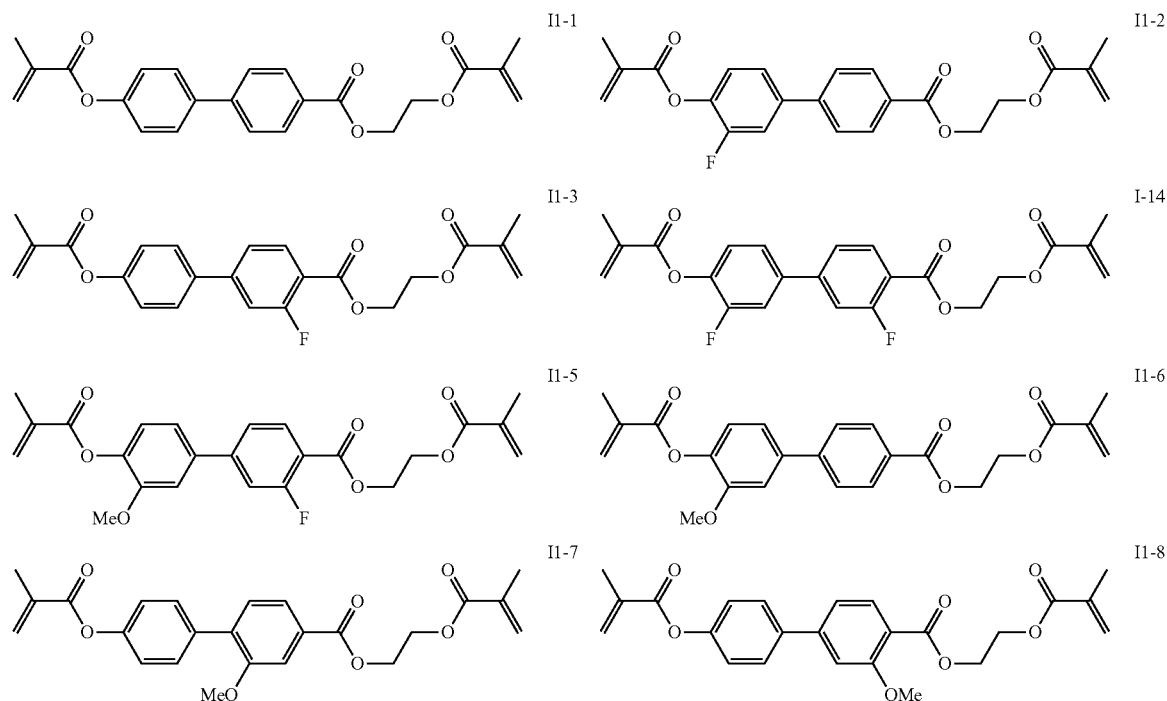

-continued
I1-9
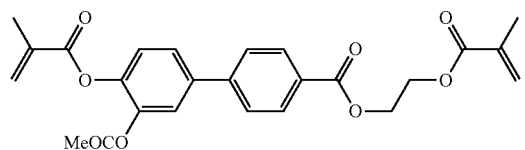
I1-10
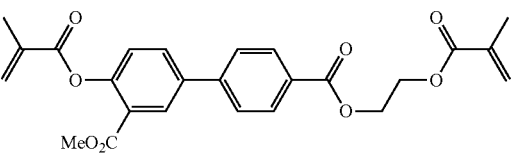
I1-11
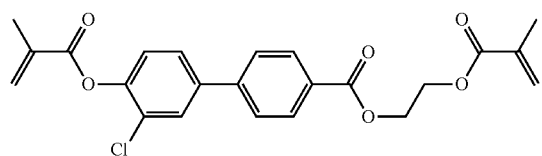
I1-12
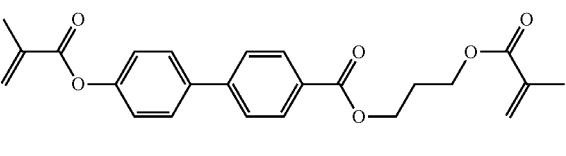
I1-13
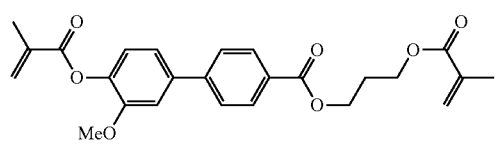
I1-14
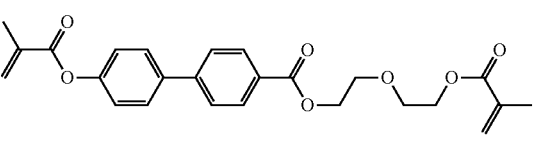
I1-15
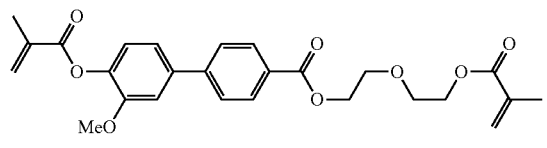
I2-1
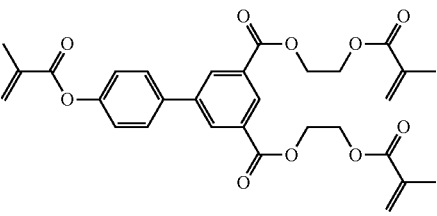
I2-2
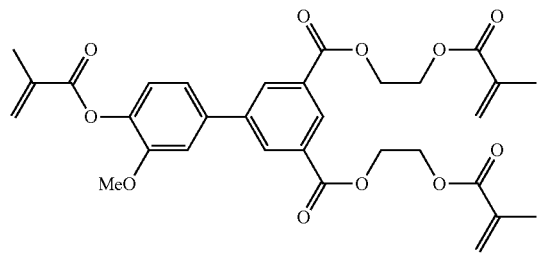
I2-3
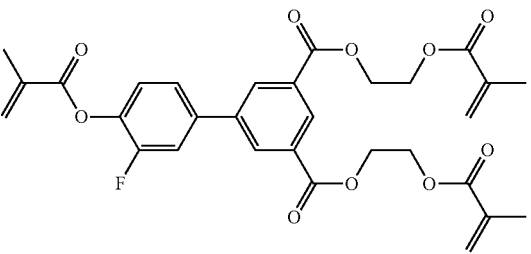
I2-4
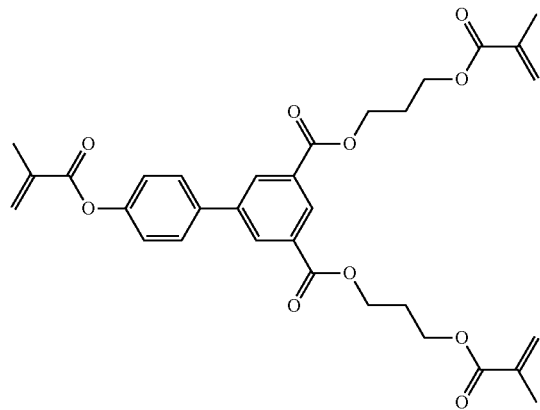
I2-5
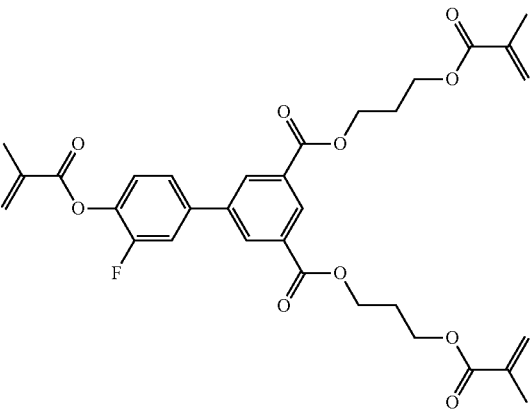

-continued
I2-6
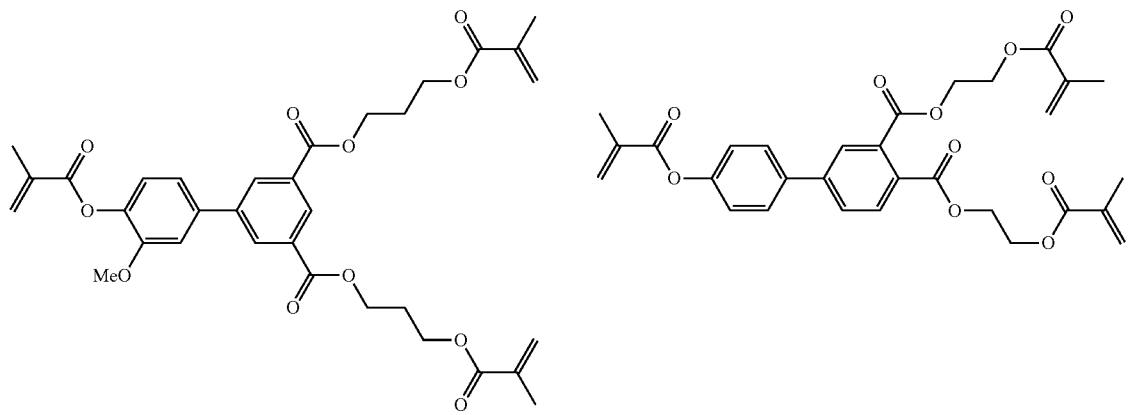
I3-1
I3-2
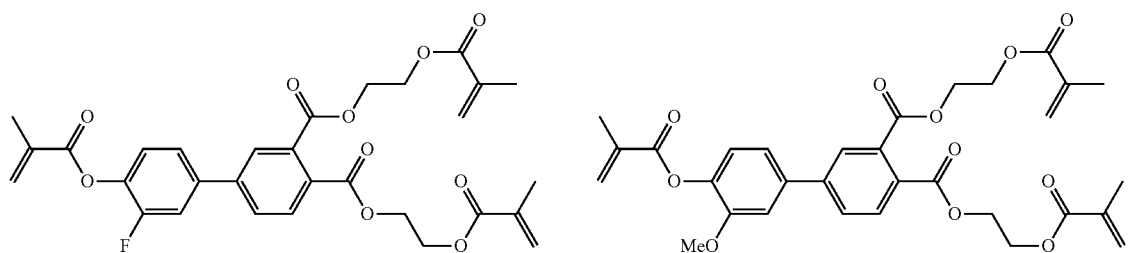
I3-3
I3-4
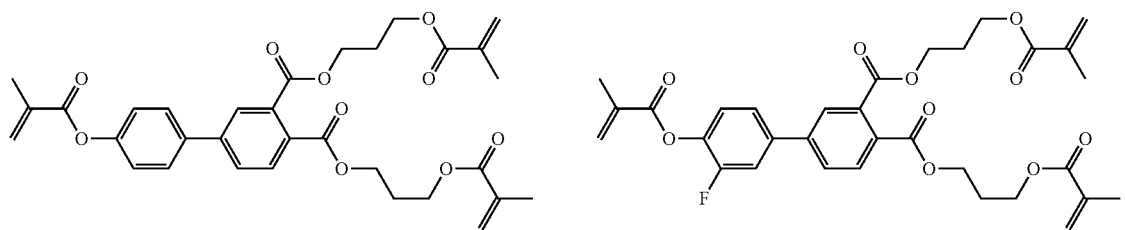
I3-5
I3-6
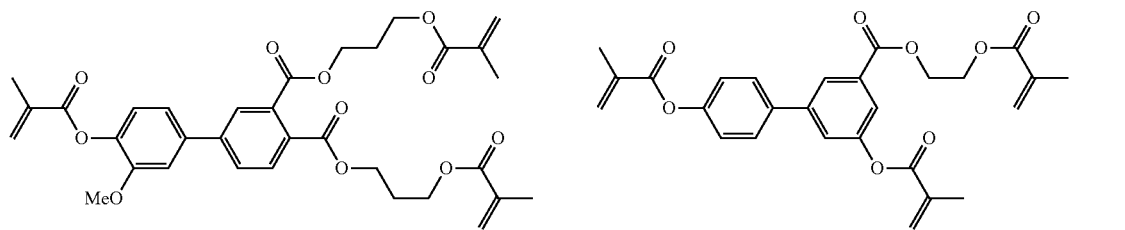
I4-1
I4-2
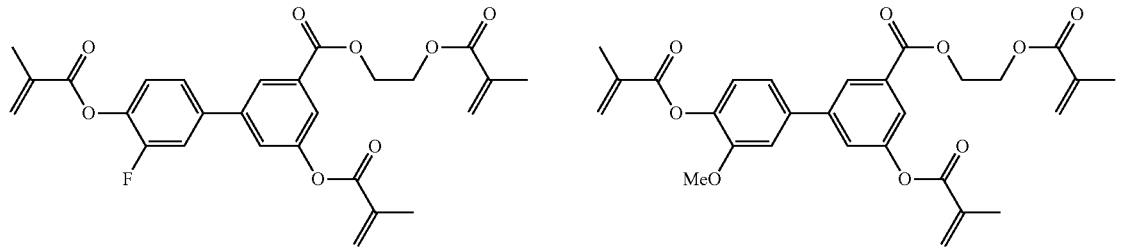
I4-3

-continued
| I4-4 | I4-5 |
|---|---|
| 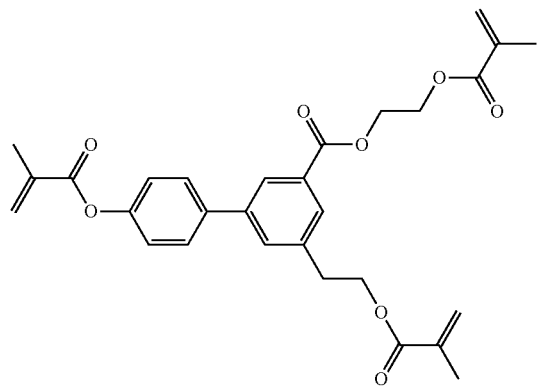 | 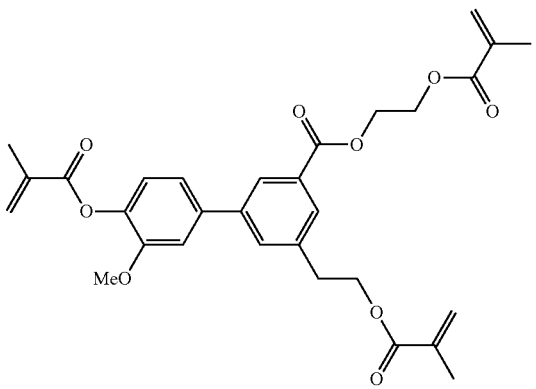 |
| I5-1 | I5-2 |
| 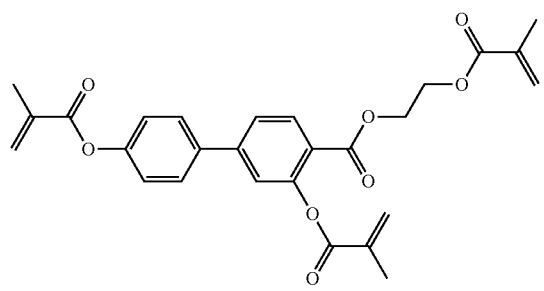 | 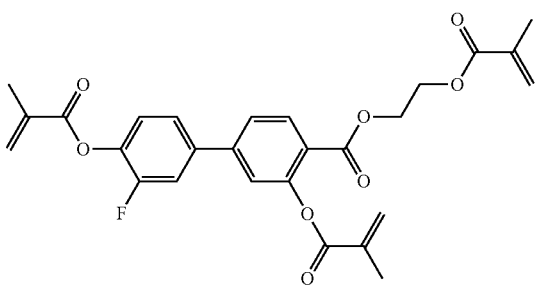 |
| I5-3 | I5-4 |
| 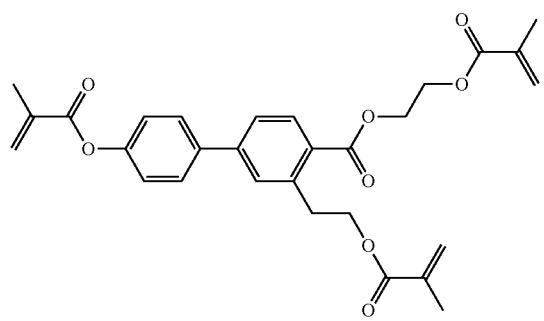 | 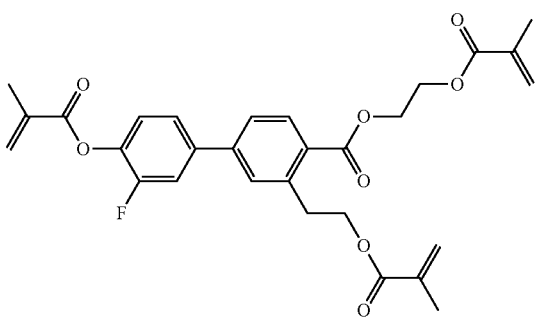 |
| I5-5 | I5-6 |
| 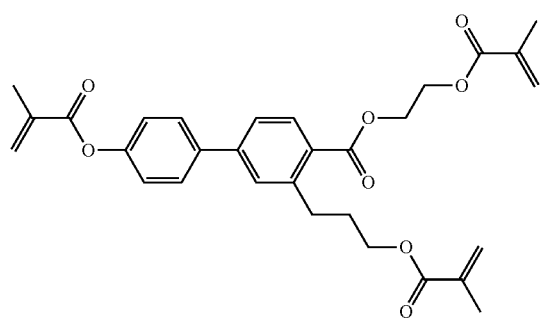 | 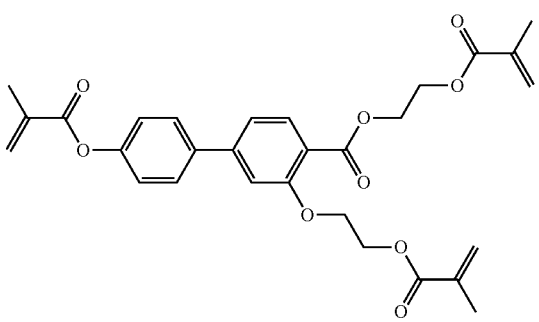 |

-continued
I6-1
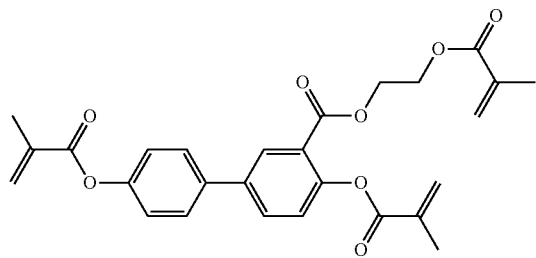
I6-2
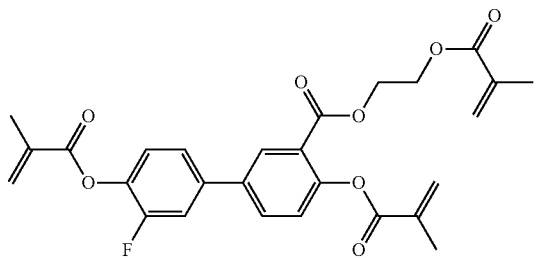
I6-3
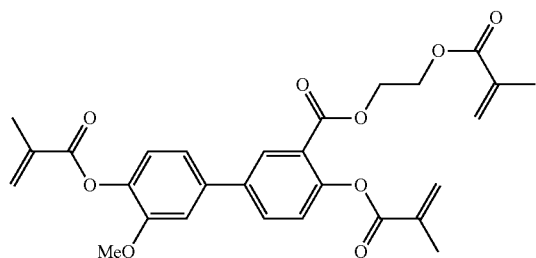
I6-4
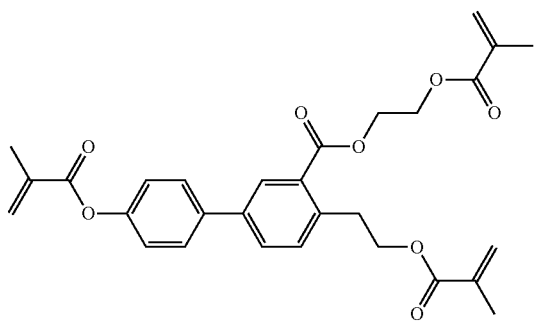
I6-5
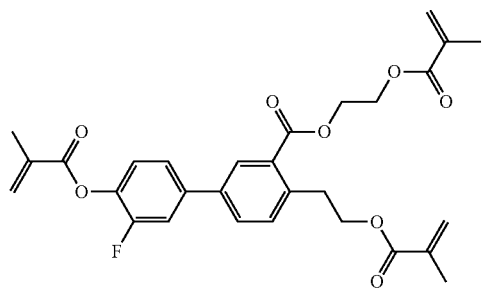
I7-1
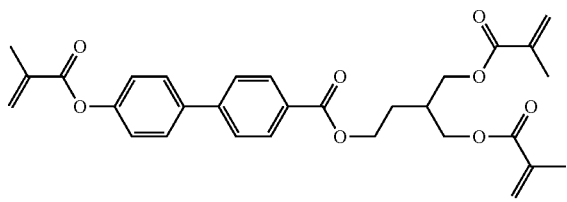
I7-2
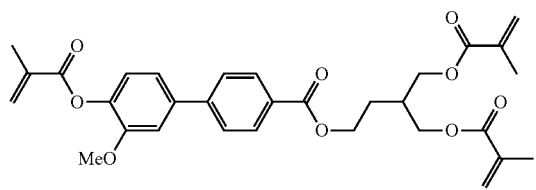
I7-3
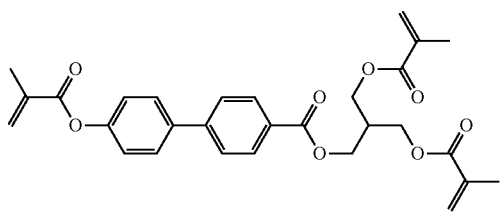
I7-4
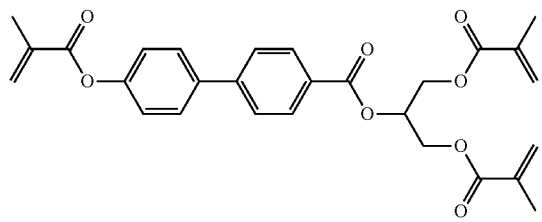
I8-1
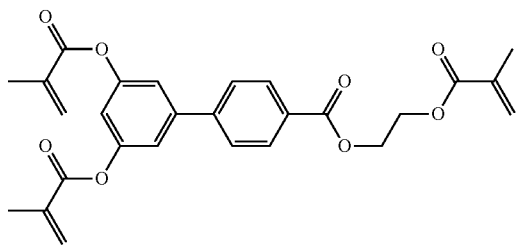

-continued
I8-2
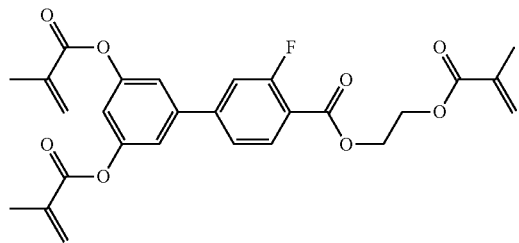
I8-3
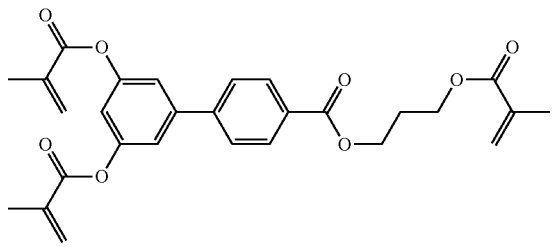
I8-4
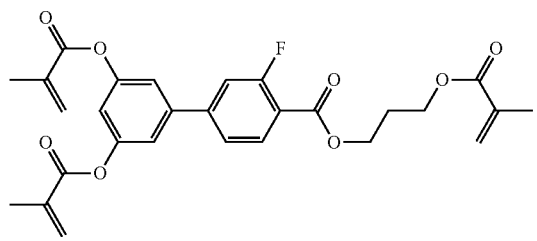
I9-1
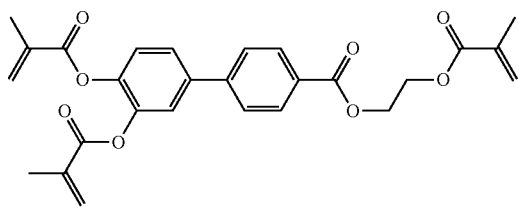
I9-2
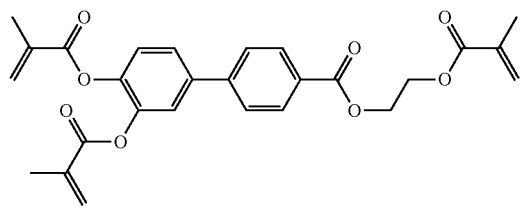
I9-3
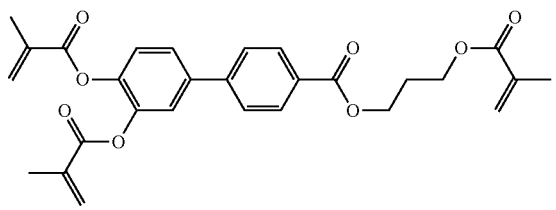
I9-4
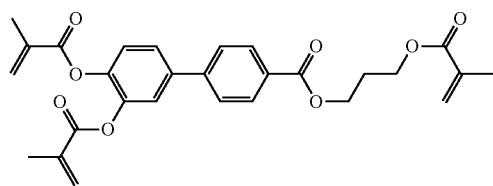
I10-1
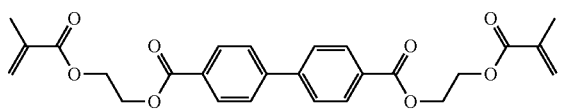
I10-2
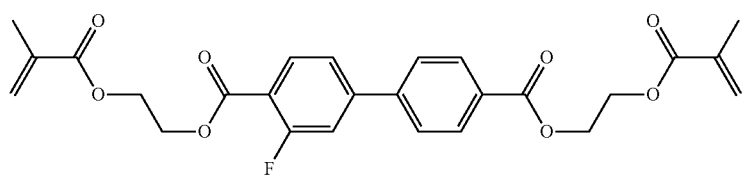
I10-3
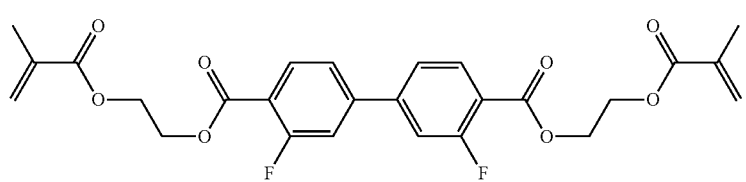
I10-4
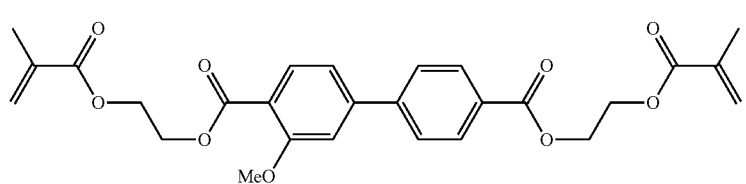

-continued
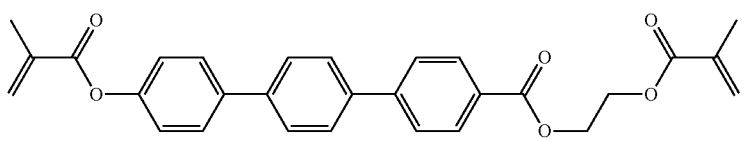
I11-1
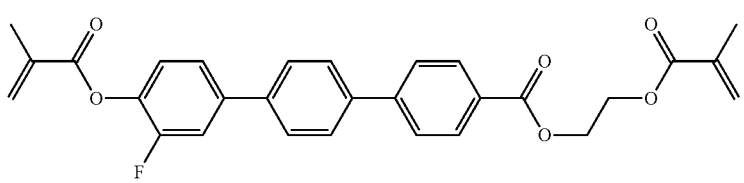
I11-2
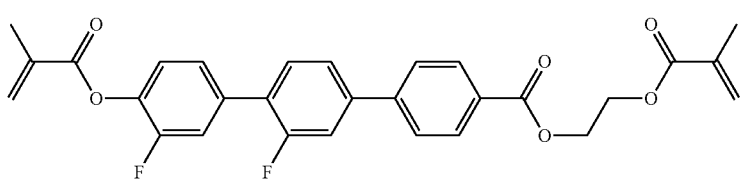
I11-3
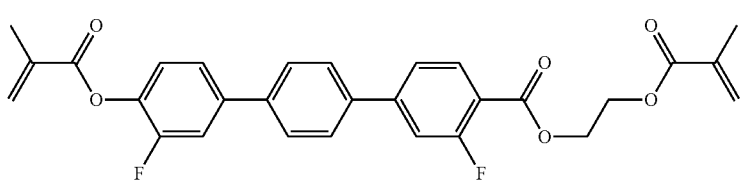
I11-4
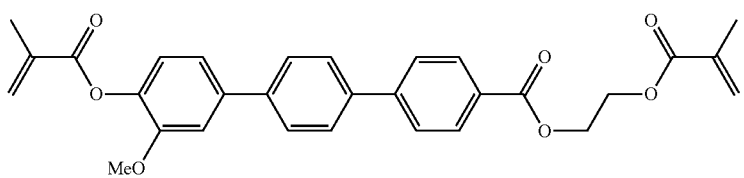
I11-5
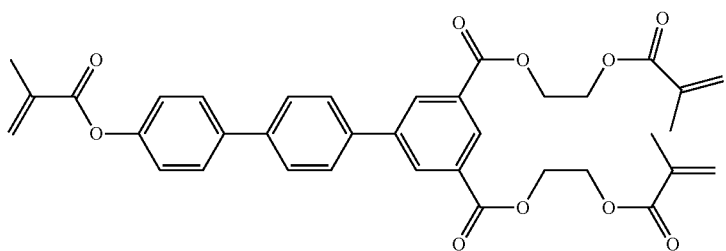
I12-1
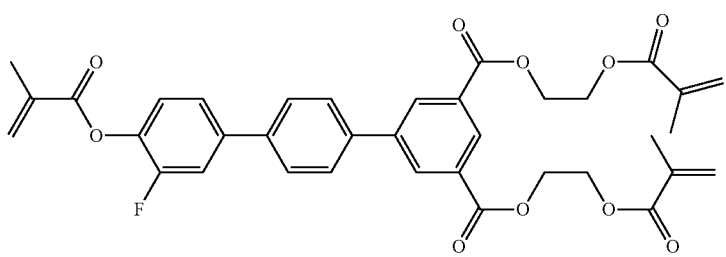
I12-2

I13-1
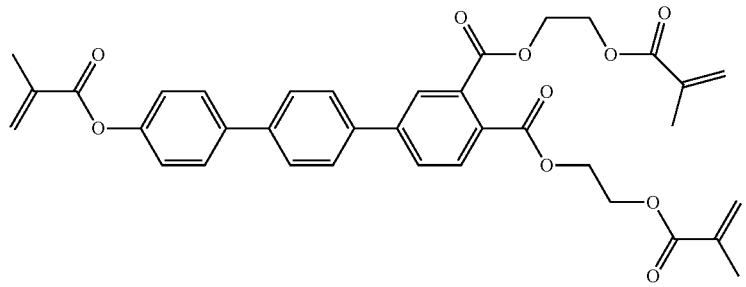
I13-2
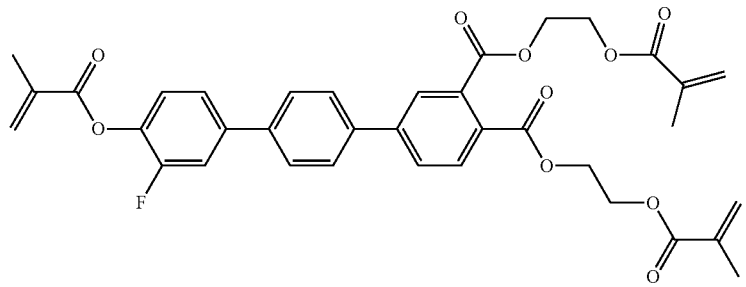
I14-1
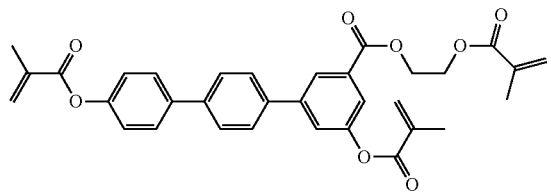
I14-2
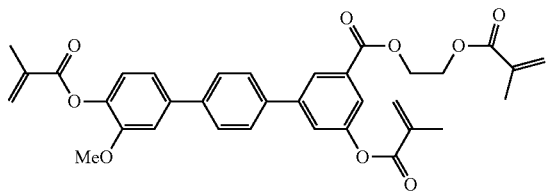
I15-1
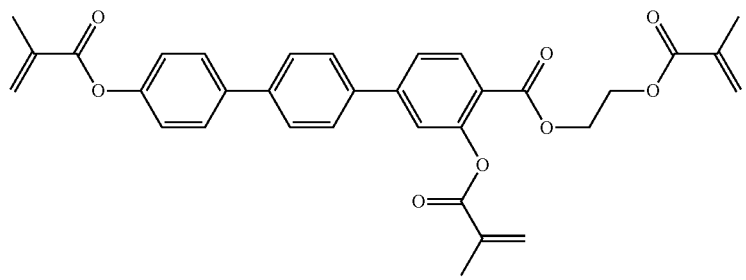
I15-2
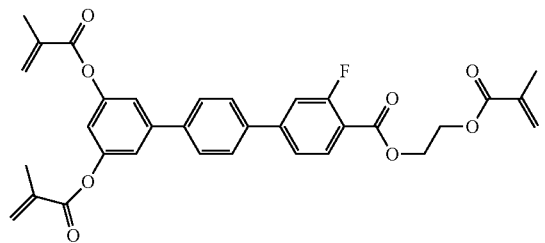
I16-1
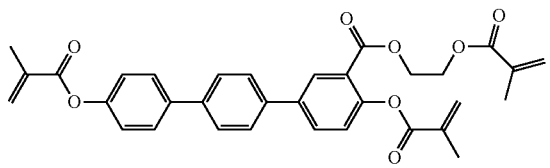
I16-2
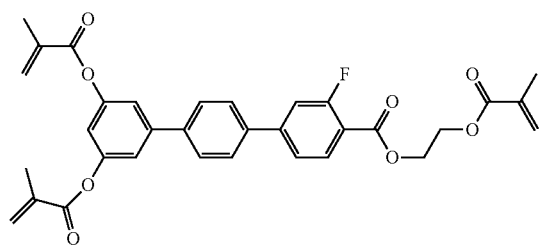
I17-1
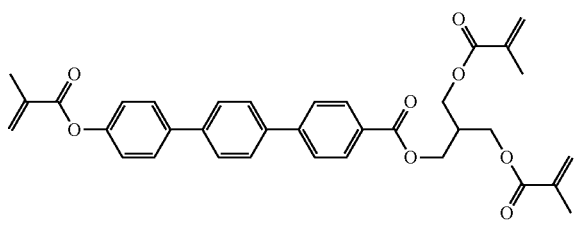

I17-2
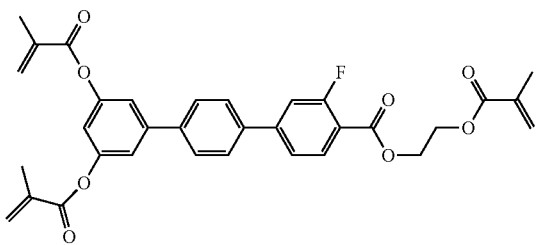
I8-1
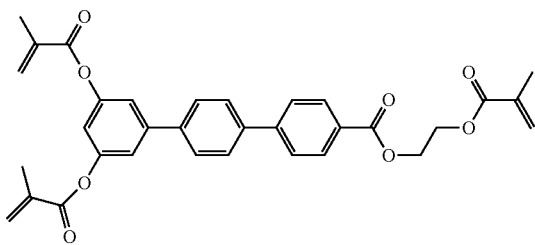
I18-2
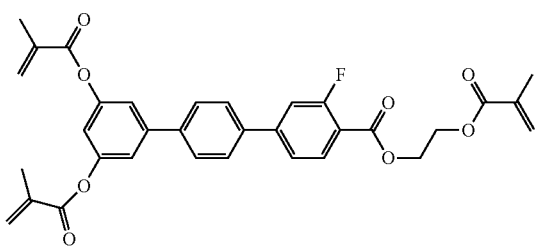
I19-1
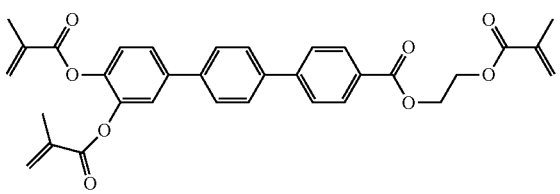
I19-2
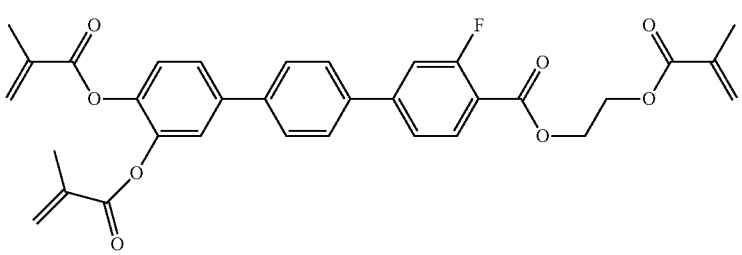
I20-1
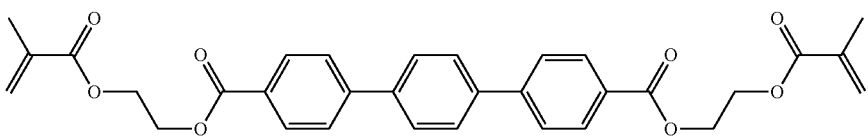
I20-2
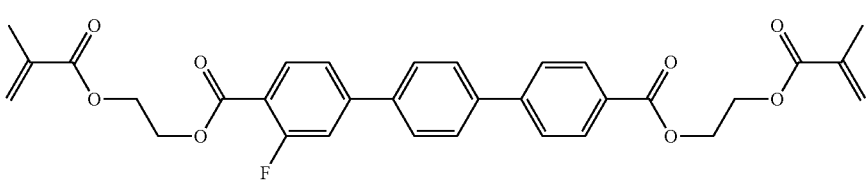
I21-1
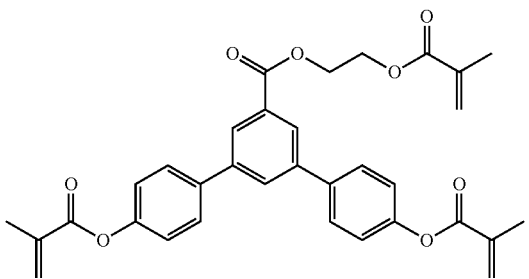
I22-1
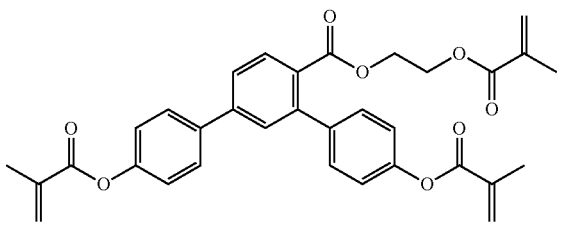

-continued
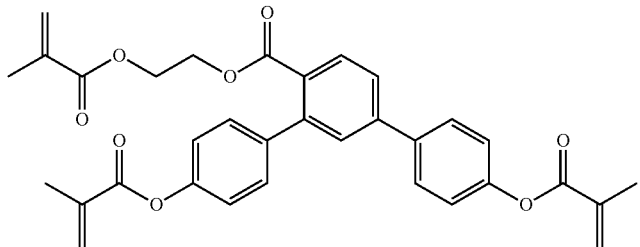
I23-1
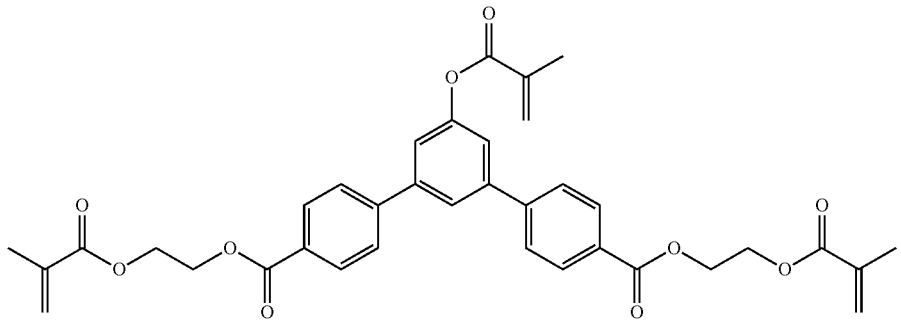
I24-1
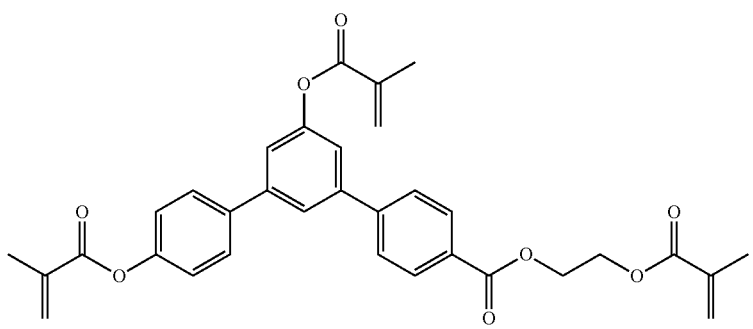
I25-1
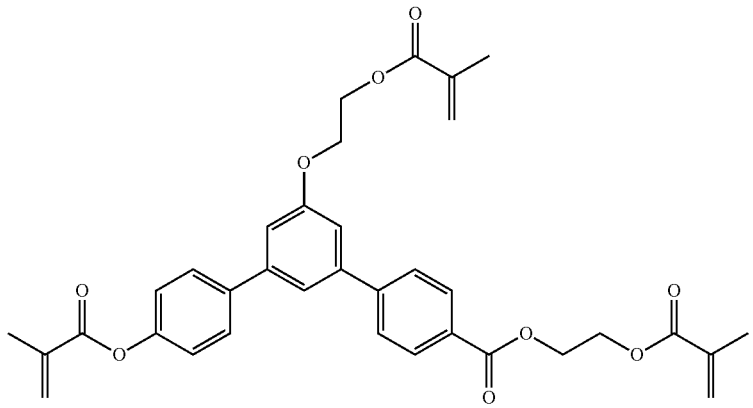
I25-2
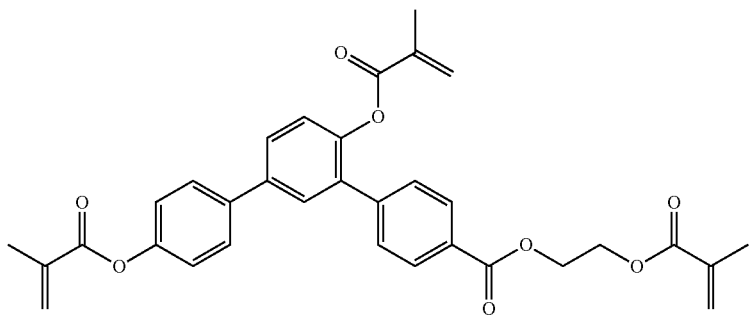
I26-1

-continued
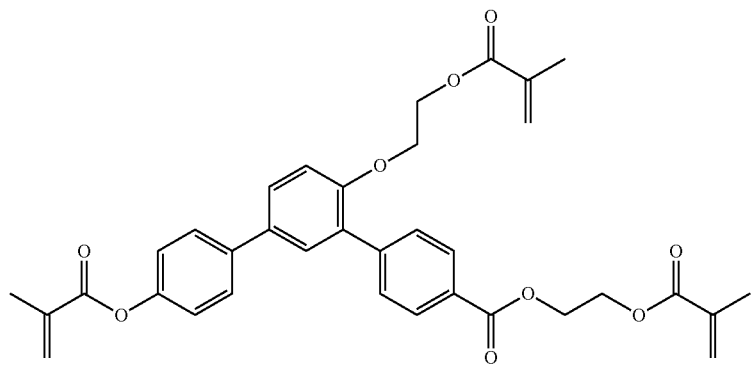
I26-2
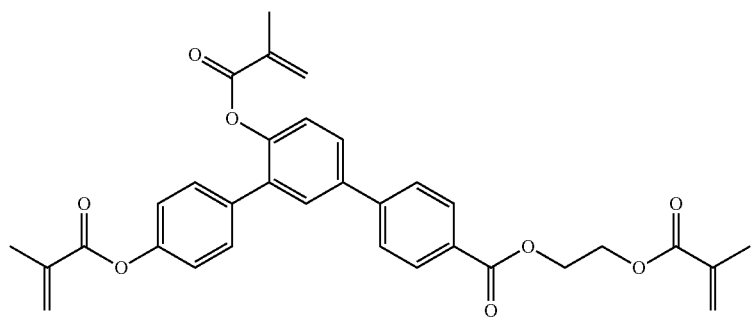
I27-1
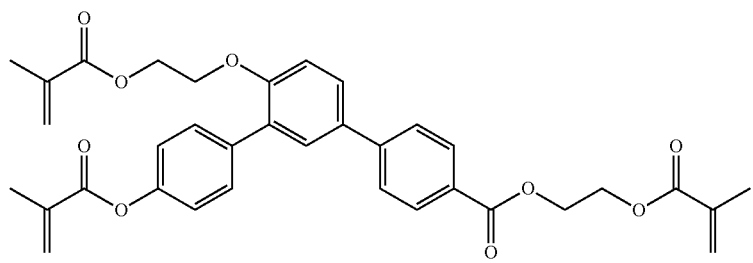
I27-2
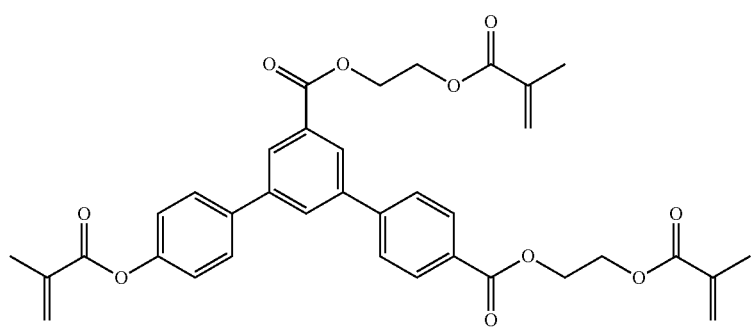
I28-1
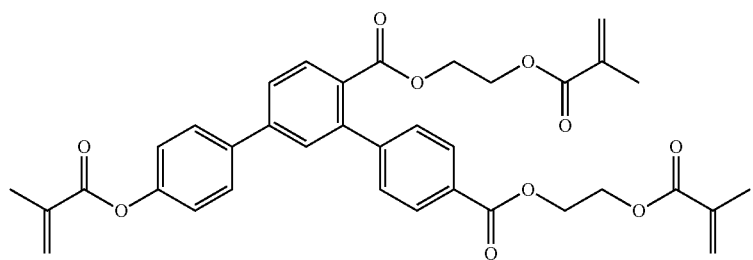
I29-1

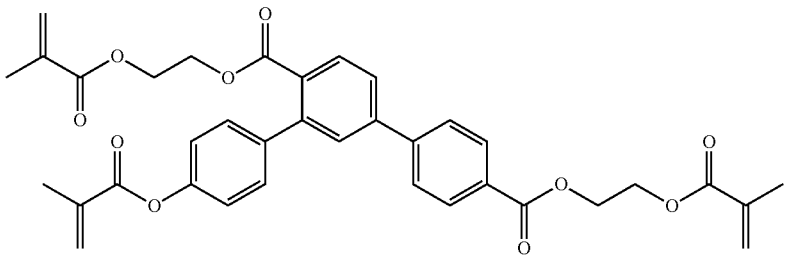

I30-1

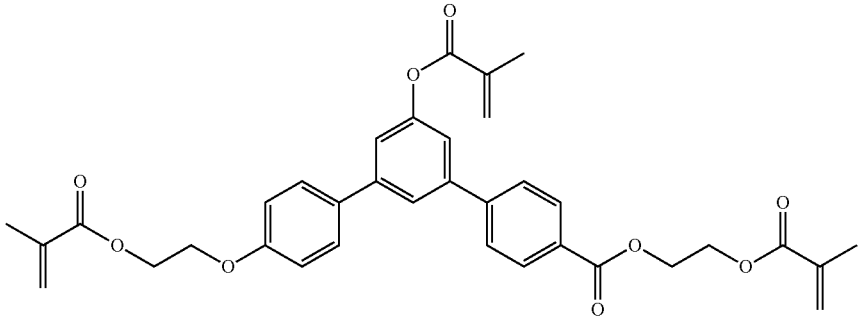

I31-1

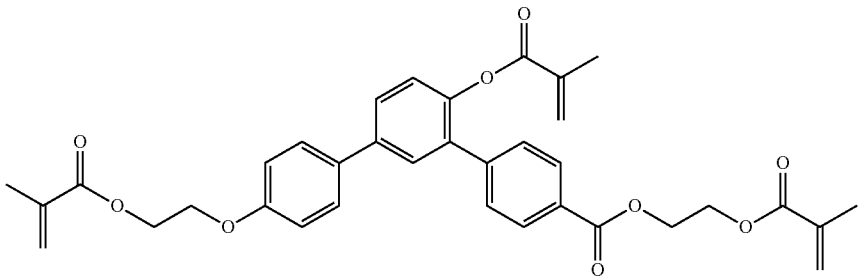

I32-1

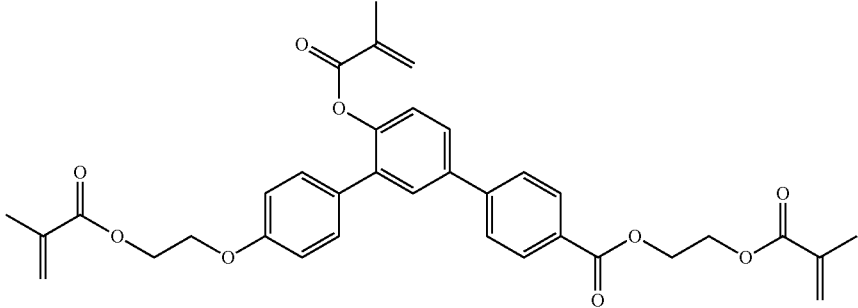

I33-1 wherein "Me" denotes a methyl group, that MeOCO denotes CH$_3$—CO—O— and MeO$_2$C denotes CH$_3$—O—CO.

Further preferred are compounds of subformulae I1-1 to I33-1 as listed above, wherein the methacrylate groups are replaced by acrylate groups.

The invention furthermore relates to novel compounds of formula I and its subformulae I1 to I33 and I1-1 to I33-1 as listed above.

The invention furthermore relates to novel compounds of formula II, which are suitable, and preferably used as, intermediates for the preparation of compounds of the formula I and its subformulae,

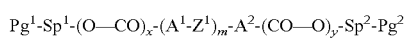
II in which Sp$^1$, Sp$^2$, A$^1$, A$^2$, Z$^1$ and m have the meaning indicated in formula I or above and below, and Pg$^1$ and Pg$^2$ denote independently of each other OH or a protected hydroxyl group or a masked hydroxyl group.

Suitable protected hydroxyl groups Pg$^{1,2}$ are known to the person skilled in the art. Preferred protecting groups for hydroxyl groups are alkyl, alkoxyalkyl, acyl, alkylsilyl, arylsilyl and arylmethyl groups, especially 2-tetrahydropyranyl, methoxymethyl, methoxyethoxymethyl, acetyl, triisopropylsilyl, tert-butyldimethylsilyl or benzyl.

The term "masked hydroxyl group" is understood to mean any functional group that can be chemically converted into a hydroxyl group. Suitable masked hydroxyl groups Pg$^{1,2}$ are known to the person skilled in the art. Preferred "masked hydroxyl groups" are alkene, ether, aldehyde, ketone, ester, Br, Cl, I or epoxides.

Especially preferred compounds of formula II are selected from the above formulae I1 to I33 wherein P$^1$ and P$^2$ are replaced by Pg$^1$ and Pg$^2$, respectively.

The compounds and intermediates of formulae I and II and sub-formulae thereof can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart.

Particularly suitable and preferred processes for the preparation of compounds and intermediates of formulae I and II are depicted by way of example in the following schemes and preferably comprise one or more of the steps described below.

For example, compounds of formula I can be synthesized by esterification or etherification of the intermediates of formula II, wherein $Pg^{1,2}$ denote OH, using corresponding acids, acid derivatives, or halogenated compounds containing a polymerizable group $P^1$.

As exemplarily shown in Scheme 1, acrylic or methacrylic esters (wherein $Sp^{1,2}$, $A^{1-2}$, $Z^1$, m, x and y have the meanings given above, and "Acr" denotes an acrylate or methacrylate group) can be prepared by esterification of the corresponding alcohols with acid derivatives like, for example, (meth)acryloyl chloride or (meth)acrylic anhydride in the presence of a base like pyridine or triethyl amine, and 4-(N,N-dimethylamino)pyridine (DMAP). Alternatively the esters can be prepared by esterification of the alcohols with (meth)acrylic acid in the presence of a dehydrating reagent, for example according to Steglich with dicyclohexylcarbodiimide (DCC), N-(3-dimethylaminopropyl)-N'-ethylcarbodiimide (EDC) or N-(3-dimethylaminopropyl)-N'-ethylcarbodiimide hydrochloride and DMAP.

Scheme 1

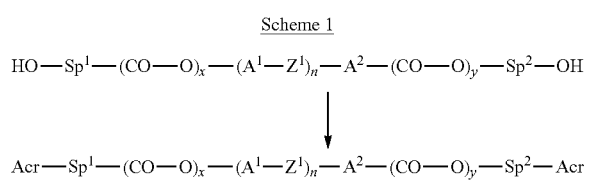

The intermediates of formula II can be synthesized according to or in analogy to known methods that are described in the literature. The synthesis of the compound of formula I, like compound (1), and its intermediate of formula II, like compound (1.3), is exemplarily shown in Scheme 2.

Scheme 2

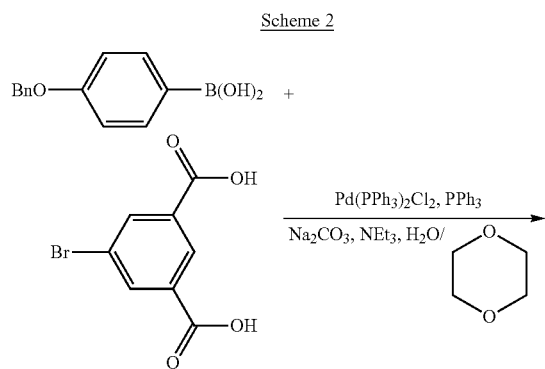

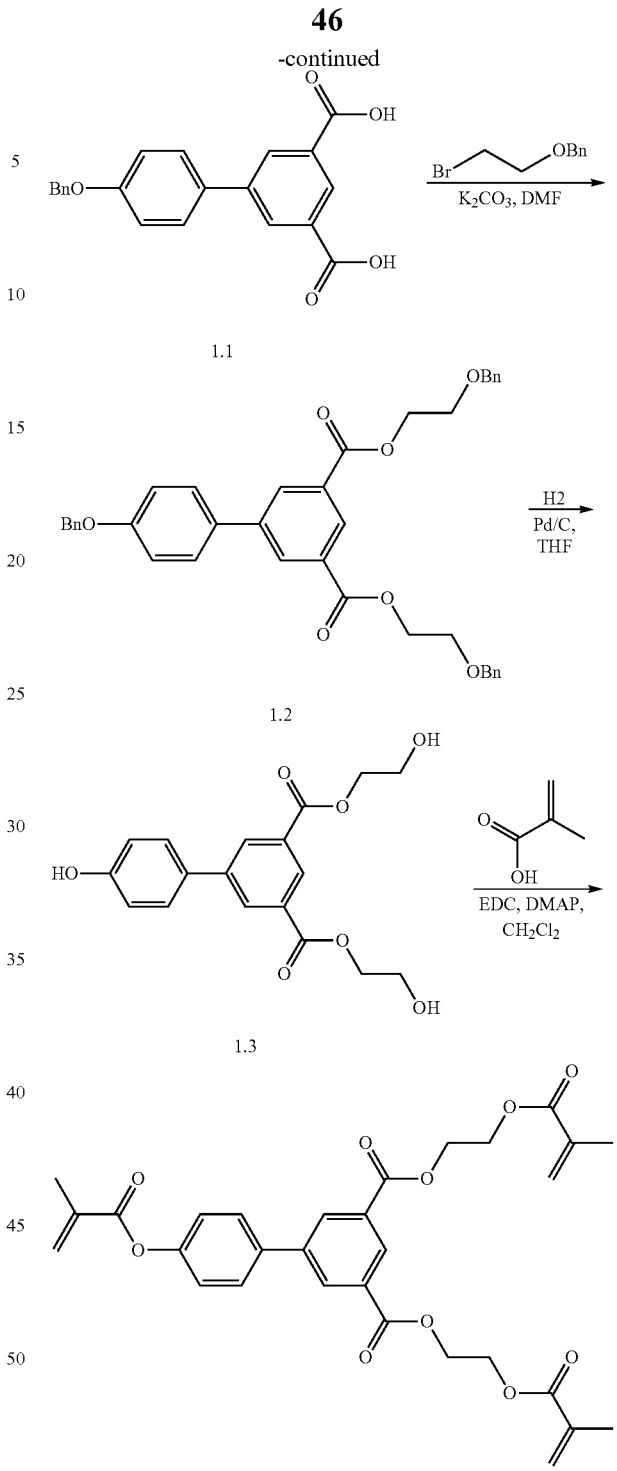

4'-Benzyloxy-biphenyl-3,5-dicarboxylic acid (1.1) is prepared from commercially available [4-(benzyloxy)phenyl]boronic acid and 5-bromoisophthalic acid by aryl-aryl coupling. Esterification with (2-bromoethoxymethyl)-benzene gives compound (1.2). Removal of the benzyl protecting group gives compound (1.3). Esterification with methacrylic acid gives compound (1).

Other compounds of formula I can be prepared in analogy to the method described above.

For the production of PSA displays, the polymerizable compounds are polymerized or crosslinked (if one compound contains two or more polymerizable groups) by in-situ polymerization in the LC medium between the substrates of the LC display with application of a voltage. The polymerization can be carried out in one step. It is also possible firstly to carry out the polymerization with application of a voltage in a first step in order to produce a pretilt angle, and subsequently, in a second polymerization step without an applied voltage, to polymerize or crosslink the compounds which have not reacted in the first step ("end curing").

Suitable and preferred polymerization methods are, for example, thermal or photopolymerization, preferably photopolymerization, in particular UV photopolymerization. One or more initiators can optionally also be added here. Suitable conditions for the polymerization and suitable types and amounts of initiators are known to the person skilled in the art and are described in the literature. Suitable for free-radical polymerization are, for example, the commercially available photoinitiators Irgacure651®, Irgacure184®, Irgacure907®, Irgacure369® or Darocure1173® (Ciba AG). If an initiator is employed, its proportion is preferably 0.001 to 5% by weight, particularly preferably 0.001 to 1% by weight.

The polymerizable compounds according to the invention are also suitable for polymerization without an initiator, which is accompanied by considerable advantages, such, for example, lower material costs and in particular less contamination of the LC medium by possible residual amounts of the initiator or degradation products thereof. The polymerization can thus also be carried out without the addition of an initiator. In a preferred embodiment, the LC medium thus comprises no polymerization initiator.

The polymerizable component A) or the LC medium may also comprise one or more stabilizers in order to prevent undesired spontaneous polymerization of the RMs, for example during storage or transport. Suitable types and amounts of stabilizers are known to the person skilled in the art and are described in the literature. Particularly suitable are, for example, the commercially available stabilizers from the Irganox® series (Ciba AG), such as, for example, Irganox® 1076. If stabilizers are employed, their proportion, based on the total amount of RMs or the polymerizable component A), is preferably 10-500,000 ppm, particularly preferably 50-50,000 ppm.

Preferably the LC medium according to the present invention does essentially consist of one or more polymerizable compounds of formula I and an LC host mixture as described above and below. However, the LC medium or LC host mixture may additionally comprise one or more further components or additives, preferably selected from the list including but not limited to comonomers, chiral dopants, polymerization initiators, inhibitors, stabilizers, surfactants, wetting agents, lubricating agents, dispersing agents, hydrophobing agents, adhesive agents, flow improvers, defoaming agents, deaerators, diluents, reactive diluents, auxiliaries, colorants, dyes, pigments and nanoparticles.

The LC media according to the invention for use in PSA displays preferably comprise from >0 to <5% by weight, particularly preferably from >0 to <1% by weight, very particularly preferably from 0.01 to 0.5% by weight, of polymerizable compounds, in particular polymerizable compounds of the formulae indicated above.

Particular preference is given to LC media comprising one, two or three polymerizable compounds according to the invention.

Preference is furthermore given to LC media in which the polymerizable component (component A) comprises exclusively polymerizable compounds according to the invention.

Preference is furthermore given to LC media in which component B) is an LC compound or an LC mixture which has a nematic liquid-crystal phase.

Preference is furthermore given to achiral polymerizable compounds according to the invention and LC media in which the compounds of component A) and/or B) are selected exclusively from the group consisting of achiral compounds.

Preference is furthermore given to LC media in which the polymerizable component or component A) comprises one or more polymerizable compounds according to the invention containing one polymerizable group (monoreactive) and one or more polymerizable compounds according to the invention containing two or more, preferably two, polymerizable groups (di- or multireactive).

Preference is furthermore given to PSA displays and LC media in which the polymerizable component or component A) comprises exclusively polymerizable compounds according to the invention containing two polymerizable groups (direactive).

The proportion of the polymerizable component or component A) in the LC media according to the invention is preferably from >0 to <5%, particularly preferably from >0 to <1%, very particularly preferably from 0.01 to 0.5%.

The proportion of the liquid-crystalline component or component B) in the LC media according to the invention is preferably from 95 to <100%, particularly preferably from 99 to <100%.

The polymerizable compounds according to the invention can be polymerized individually, but it is also possible to polymerize mixtures which comprise two or more polymerizable compounds according to the invention, or mixtures comprising one or more polymerizable compounds according to the invention and one or more further polymerizable compounds ("co-monomers"), which are preferably mesogenic or liquid-crystalline. In the case of polymerization of such mixtures, copolymers are formed. The invention furthermore relates to the polymerizable mixtures mentioned above and below. The polymerizable compounds and comonomers are mesogenic or non-mesogenic, preferably mesogenic or liquid-crystalline.

Suitable and preferred mesogenic comonomers, particularly for use in PSA displays, are selected, for example, from the following formulae:

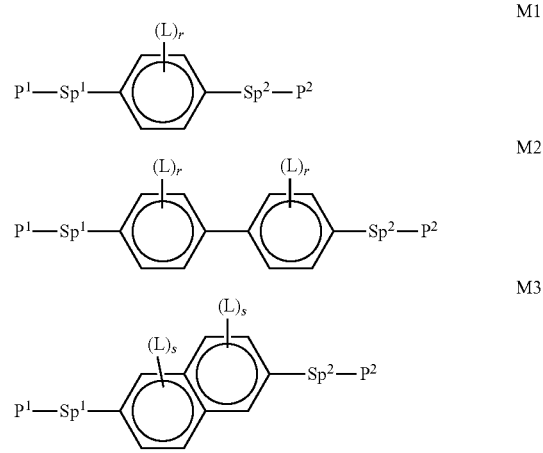

M4
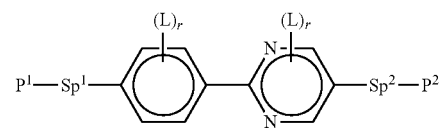
M5
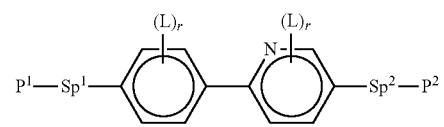
M6
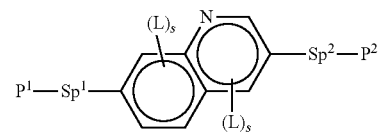
M7
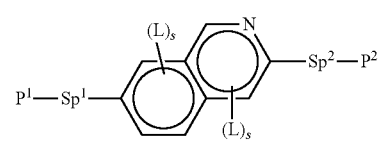
M8
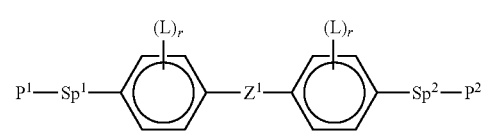
M9
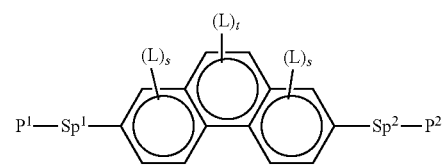
M10
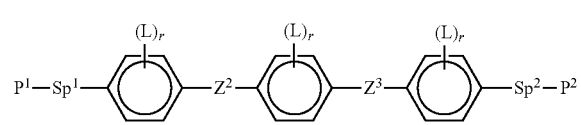
M11
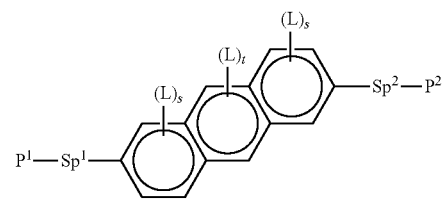
M12
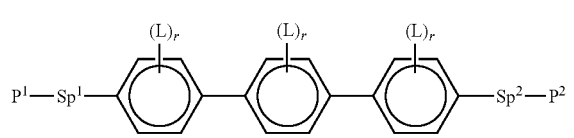
M13
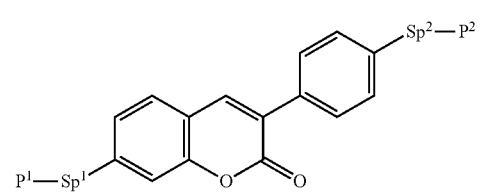
M14
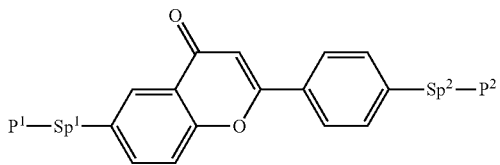
M15
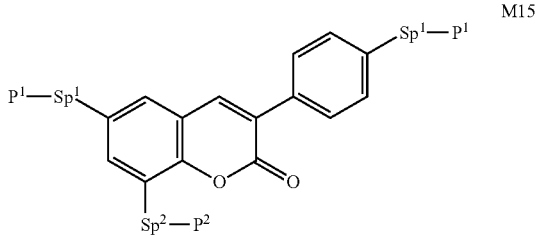
M16
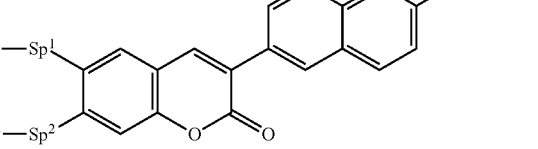
M17
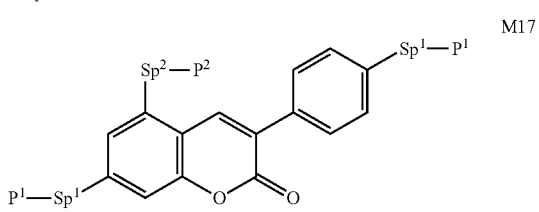
M18
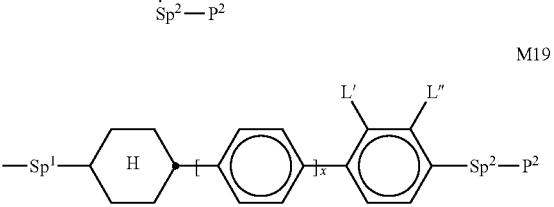
M19
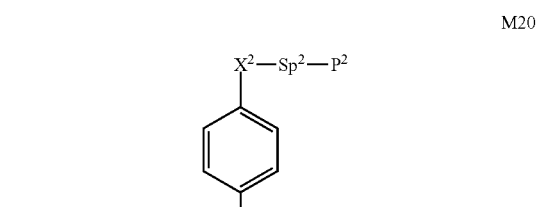
M20
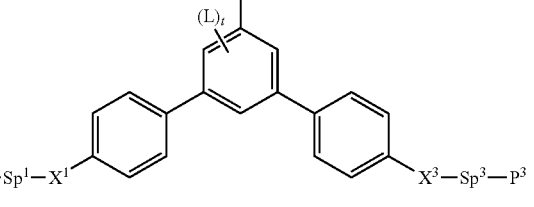

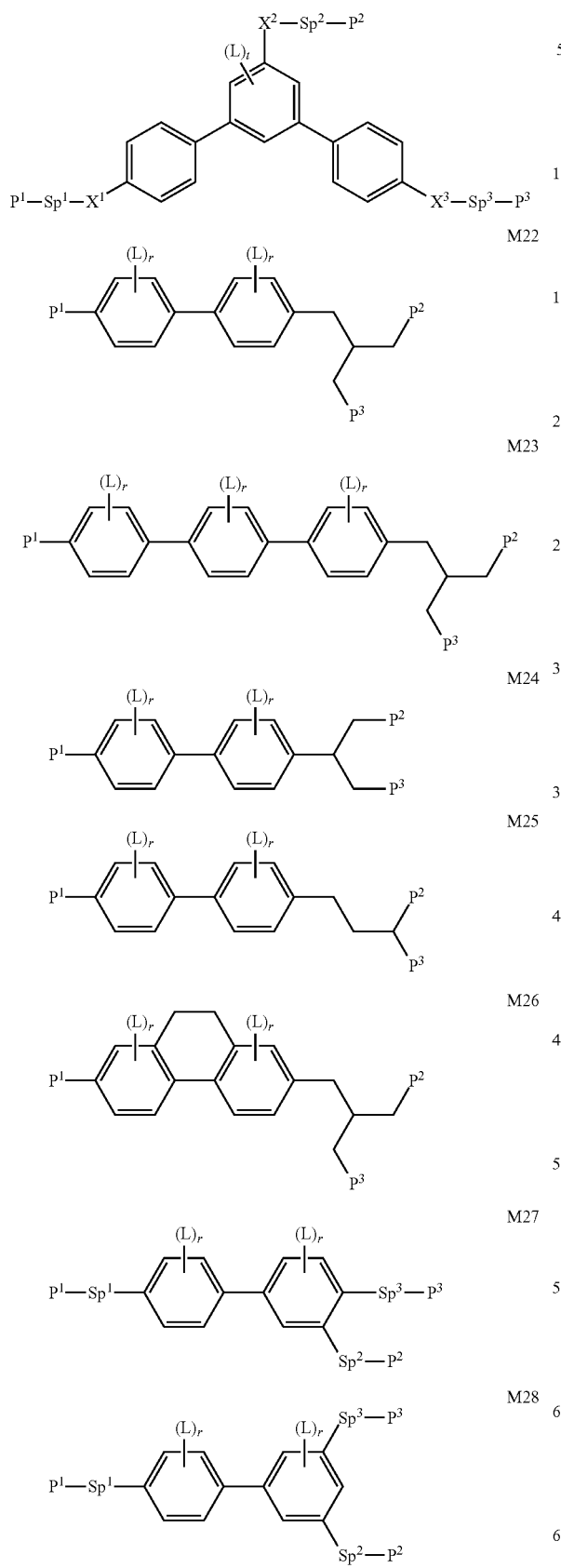
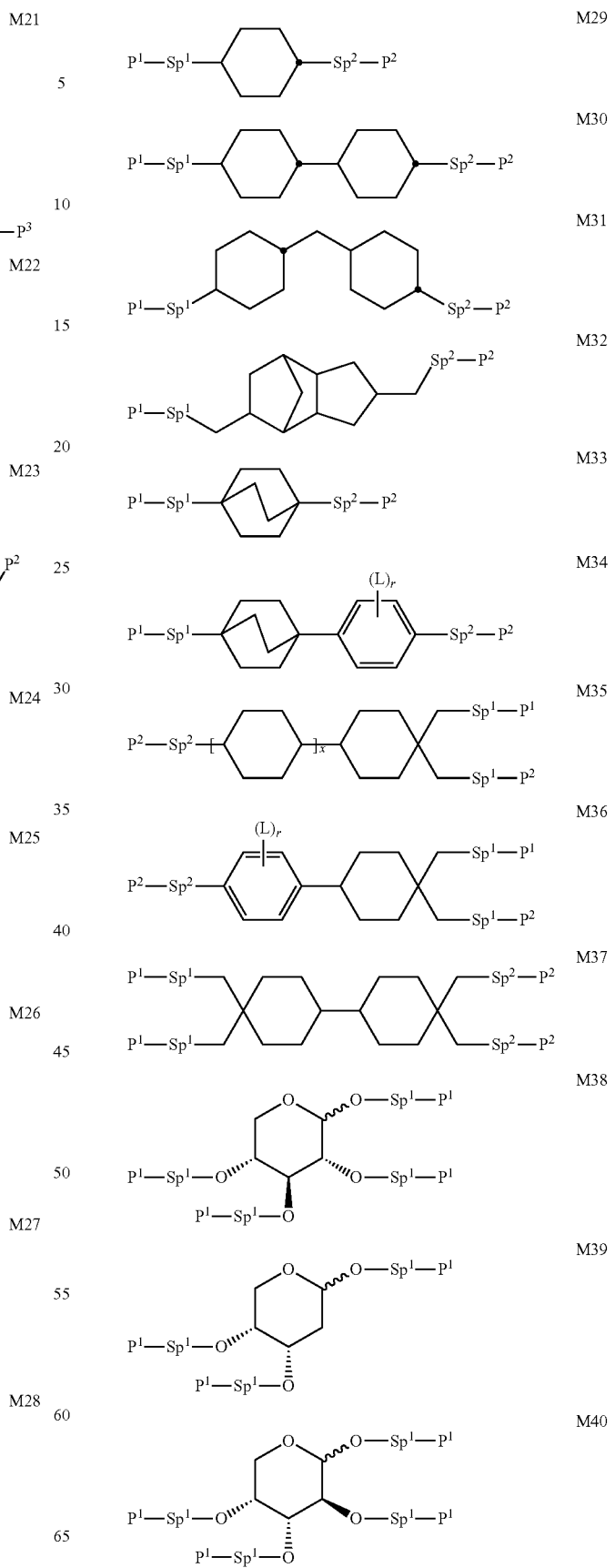

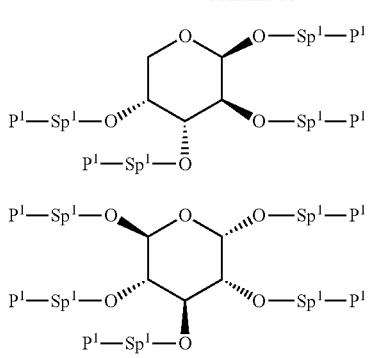

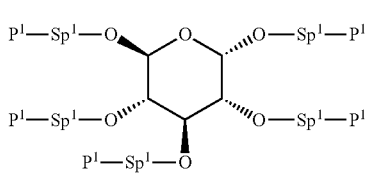

in which the individual radicals have the following meanings:

$P^1$, $P^2$ and $P^3$ each, independently of one another, denote a polymerizable group having one of the meanings indicated above and below for $P^1$, particularly preferably an acrylate, methacrylate, fluoroacrylate, oxetane, vinyl, vinyloxy or epoxide group, $Sp^1$, $Sp^2$ and $Sp^a$ each, independently of one another, denote a single bond or a spacer group having one of the meanings indicated above and below for $Sp^1$, and particularly preferably denote $-(CH_2)_{p1}-$, $-(CH_2)_{p1}-O-$, $-(CH_2)_{p1}-CO-O-$ or $-(CH_2)_{p1}-O-CO-O-$, in which p1 is an integer from 1 to 12, and where the linking to the adjacent ring in the last-mentioned groups takes place via the O atom, where, in addition, one or more of the radicals $P^1$-$Sp^1$-, $P^1$-$Sp^2$- and $P^3$-$Sp^3$- may denote $R^{aa}$, with the proviso that at least one of the radicals $P^1$-$Sp^1$-, $P^2$-$Sp^2$ and $P^3$-$Sp^3$- present is different from $R^{aa}$, $R^{aa}$ denotes H, F, Cl, CN or straight-chain or branched alkyl having 1 to 25 C atoms, in which, in addition, one or more non-adjacent $CH_2$ groups may each be replaced, independently of one another, by $C(R^0)=C(R^{00})-$, $-C\equiv C-$, $-N(R^0)-$, $-O-$, $-S-$, $-CO-$, $-CO-O-$, $-O-CO-$, $-O-CO-O-$ in such a way that O and/or S atoms are not linked directly to one another, and in which, in addition, one or more H atoms may each be replaced by F, Cl, CN or $P^1$-$Sp^1$-, particularly preferably straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms (where the alkenyl and alkynyl radicals have at least two C atoms and the branched radicals have at least three C atoms), $R^0$, $R^{00}$ each, independently of one another and identically or differently on each occurrence, denote H or alkyl having 1 to 12 C atoms, $X^1$, $X^2$ and $X^3$ each, independently of one another, denote $-CO-O-$, $-O-CO-$ or a single bond, $Z^1$ denotes $-O-$, $-CO-$, $-C(R^yR^z)-$ or $-CF_2CF_2-$, $R^y$ and $R^z$ each, independently of one another, denote H, F, $CH_3$ or $CF_3$, $Z^2$ and $Z^3$ each, independently of one another, denote $-CO-O-$, $-O-CO-$, $-CH_2O-$, $-OCH_2-$, $-CF_2O-$, $-OCF_2-$ or $-(CH_2)_n-$, where n is 2, 3 or 4, L on each occurrence, identically or differently, denotes F, Cl, CN or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4, s denotes 0, 1, 2 or 3, t denotes 0, 1 or 2, x denotes 0 or 1.

Especially preferred are compounds of formulae M1 to M28.

In the compounds of formulae M1 to M42

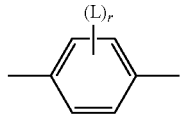

is preferably

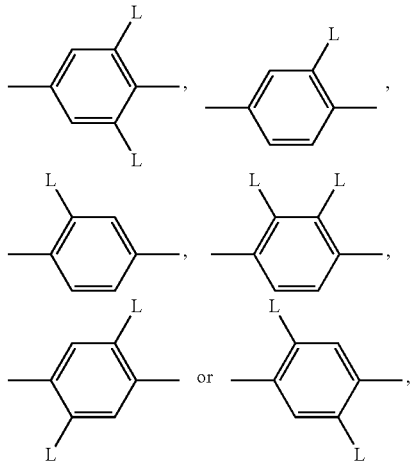

wherein L on each occurrence, identically or differently, has one of the meanings given above or below, and is preferably F, Cl, CN, $NO_2$, $CH_3$, $C_2H_5$, $C(CH_3)_3$, $CH(CH_3)_2$, $CH_2CH(CH_3)C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$ or P-Sp-, very preferably F, Cl, CN, $CH_3$, $C_2H_5$, $OCH_3$, $COCH_3$, $OCF_3$ or P-Sp-, more preferably F, Cl, $CH_3$, $OCH_3$, $COCH_3$ or $OCF_3$, especially F or $CH_3$.

Besides the polymerizable compounds described above, the LC media for use in the LC displays according to the invention comprise an LC mixture ("host mixture") comprising one or more, preferably two or more, low-molecular-weight (i.e. monomeric or unpolymerized) compounds. The latter are stable or unreactive to a polymerization reaction under the conditions used for polymerization of the polymerizable compounds. In principle, any LC mixture which is suitable for use in conventional VA and OCB displays is suitable as host mixture. Suitable LC mixtures are known to the person skilled in the art and are described in the literature, for example mixtures in VA displays in EP 1 378 557 A1 and mixtures for OCB displays in EP 1 306 418 A1 and DE 102 24 046 A1.

The polymerizable compounds of formula I are especially suitable for use in an LC host mixture that comprises one or more compounds comprising an alkenyl group, ("alkenyl compound"), where this alkenyl group is stable to a polymerization reaction under the conditions used for the polymerization of the polymerizable compounds of formula I or of the other polymerizable compounds contained in the LC medium. Compared to reactive mesogens known from prior art the polymerizable compounds of formula I in such an LC host mixture shows improved properties, like solubility, reactivity or capability of generating a tilt angle.

The LC host mixture is preferably a nematic LC mixture.

The alkenyl groups in the alkenyl compounds are preferably selected from straight-chain, branched or cyclic alkenyl, in particular having 2 to 25 C atoms, particularly preferably having 2 to 12 C atoms, in which, in addition, one or more non-adjacent CH$_2$ groups may each be replaced by —O—, —S—, —CO—, —CO—O—, —O—CO—, or —O—CO—O— in such a way that O and/or S atoms are not linked directly to one another, and in which, in addition, one or more H atoms may each be replaced by F or Cl.

Preferred alkenyl groups are straight-chain alkenyl having 2 to 7 C atoms and cyclohexenyl, in particular ethenyl, propenyl, butenyl, pentenyl, hexenyl, heptenyl, 1,4-cyclohexen-1-yl and 1,4-cyclohexen-3-yl.

The concentration of compounds containing an alkenyl group in the LC host mixture (i.e. without any polymerizable compounds) is preferably from 5% to 100%, very preferably from 20% to 60%.

Especially preferred are LC mixtures containing 1 to 5, preferably 1, 2 or 3 compounds having an alkenyl group.

The compounds containing an alkenyl group are preferably selected from the following formulae:

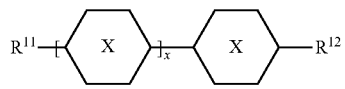

AN

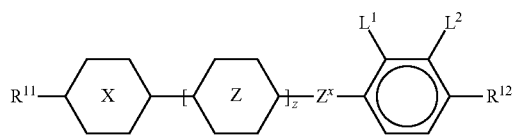

AY in which the individual radicals, on each occurrence identically or differently, each, independently of one another, have the following meaning:

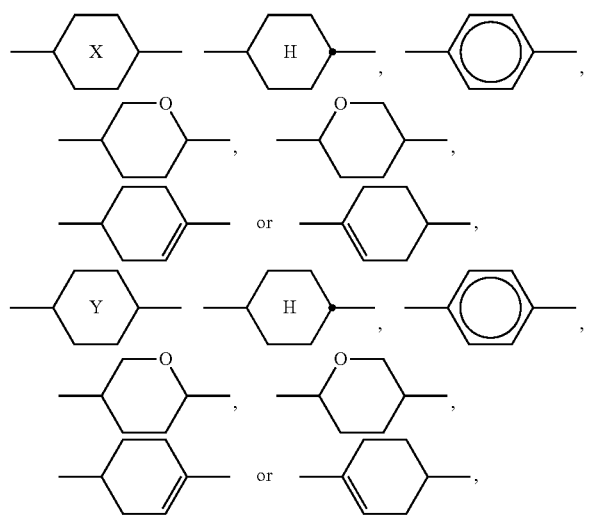

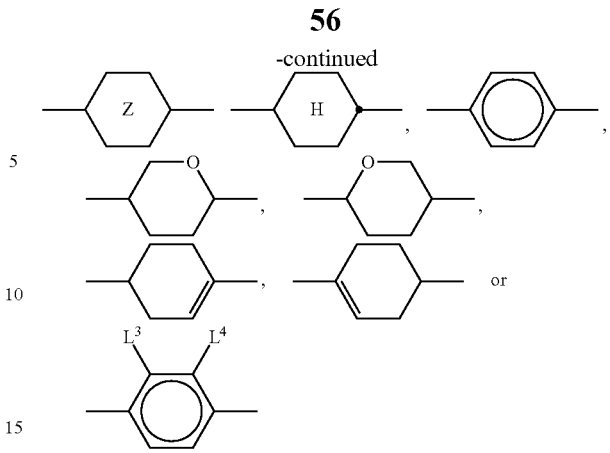

R$^{11}$ alkenyl having 2 to 9 C atoms or, if at least one of the rings X, Y and Z denotes cyclohexenyl, also one of the meanings of R$^{12}$, R$^{12}$ alkyl having 1 to 12 C atoms, in which, in addition, one or two non-adjacent CH$_2$ groups may each be replaced by —O—, —CH═CH—, —CO—, —OCO— or —COO— in such a way that O atoms are not linked directly to one another, Z$^x$ —CH$_2$CH$_2$—, —CH═CH—, —CF$_2$O—, —OCF$_2$—, —CH$_2$O—, —OCH$_2$—, —CO—O—, —O—CO—, —C$_2$F$_4$—, —CF═CF—, —CH═CH—CH$_2$O—, or a single bond, preferably a single bond, L$^{1-4}$ each, independently of one another, H, F, Cl, OCF$_3$, CF$_3$, CH$_3$, CH$_2$F or CHF$_2$H, preferably H, F or Cl, x 1 or 2, z 0 or 1.

R$^{12}$ is preferably straight-chain alkyl or alkoxy having 1 to 8 C atoms or straight-chain alkenyl having 2 to 7 C atoms.

The LC medium preferably comprises no compounds containing a terminal vinyloxy group (—O—CH═CH$_2$), in particular no compounds of formulae AN and AY in which R$^{11}$ or R$^{12}$ denotes or contains a terminal vinyloxy group (—O—CH═CH$_2$).

Preferably, L$^1$ and L$^2$ denote F, or one of L$^1$ and L$^2$ denotes F and the other denotes Cl, and L$^3$ and L$^4$ denote F, or one of L$^3$ and L$^4$ denotes F and the other denotes Cl.

The compounds of the formula AN are preferably selected from the following sub-formulae:

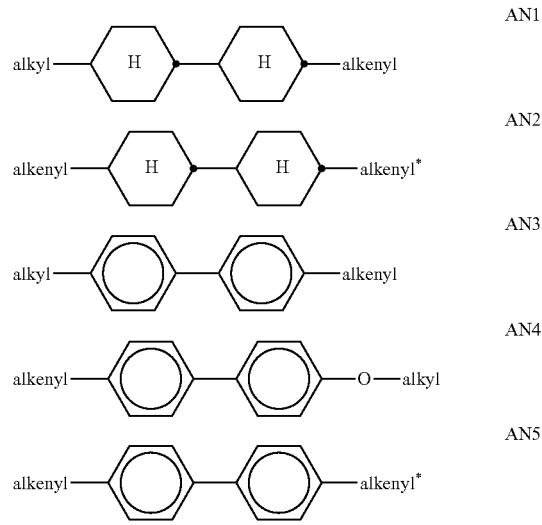

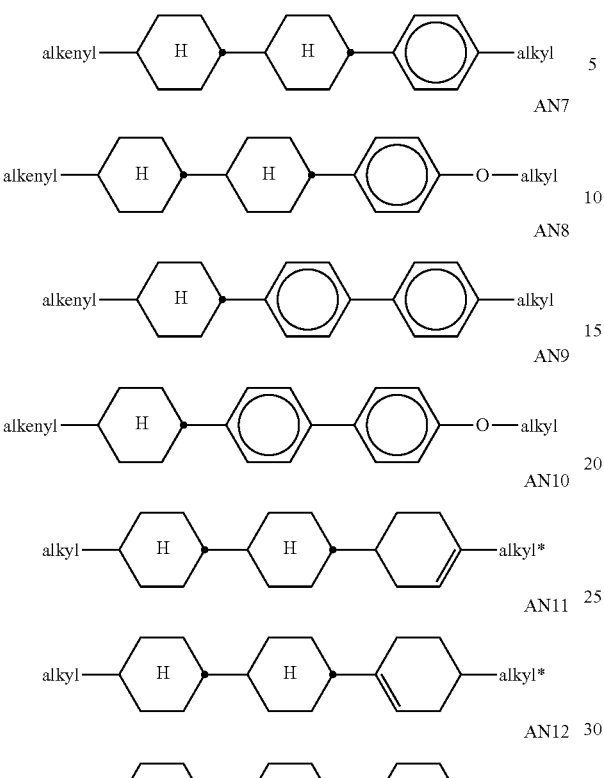

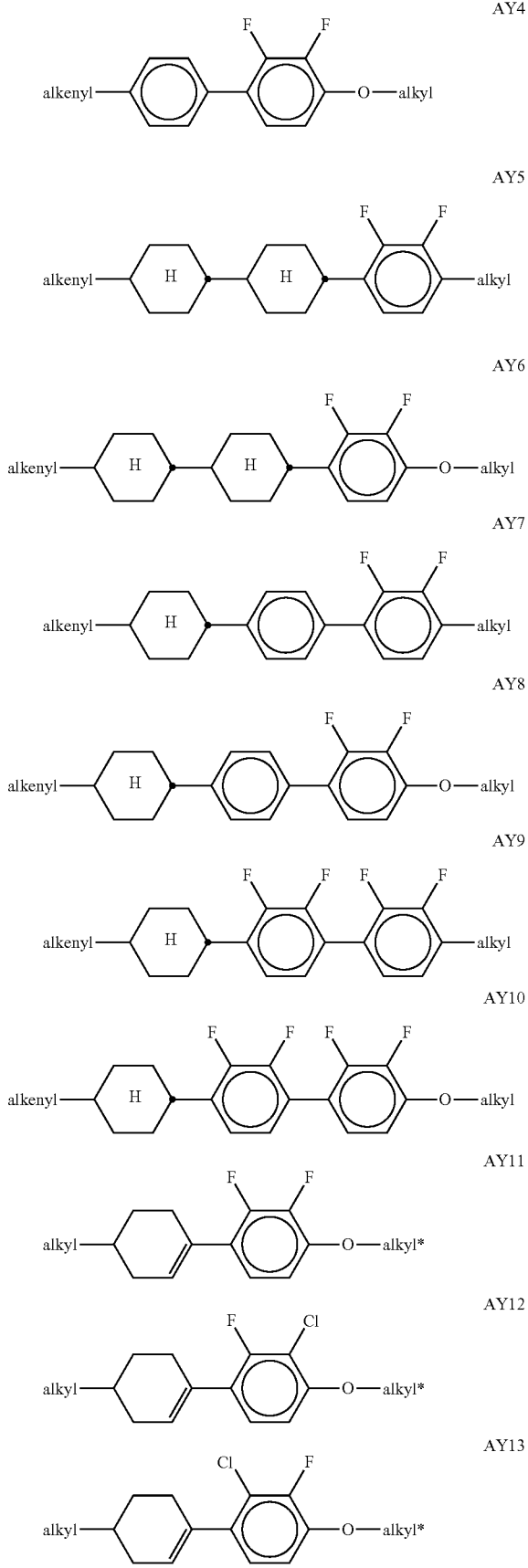

in which alkyl and alkyl* each, independently of one another, denote a straight-chain alkyl radical having 1-6 C atoms, and alkenyl and alkenyl* each, independently of one another, denote a straight-chain alkenyl radical having 2-7 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

The compounds of the formula AY are preferably selected from the following sub-formulae:

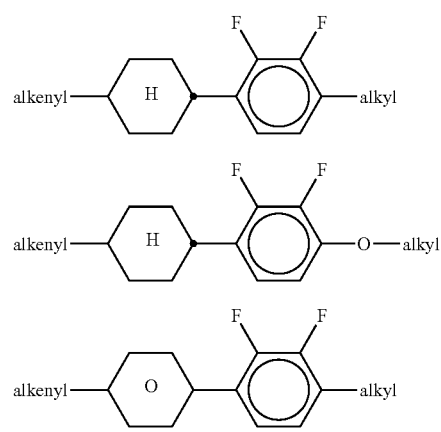

AY14
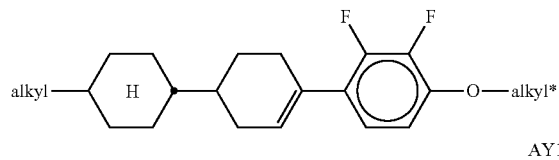
AY15
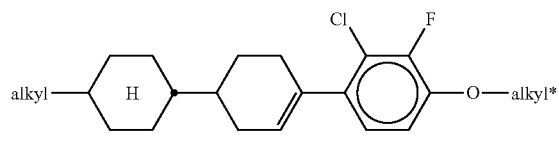
AY16
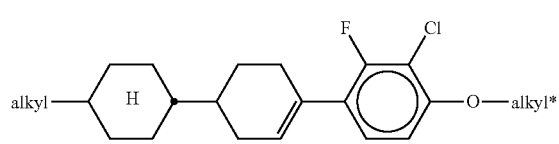
AY17
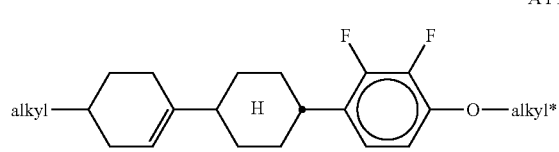
AY18
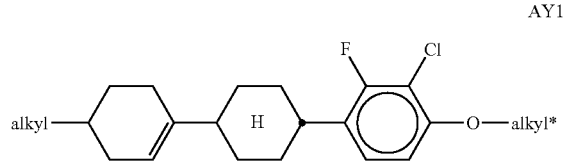
AY19
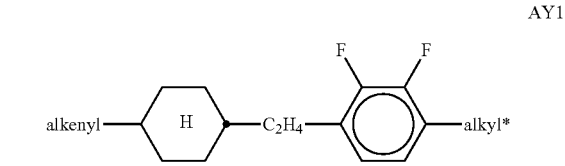
AY20
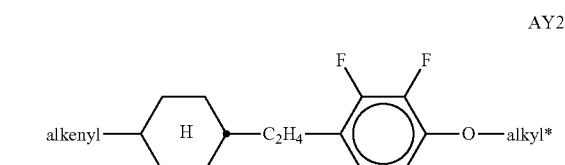
AY21
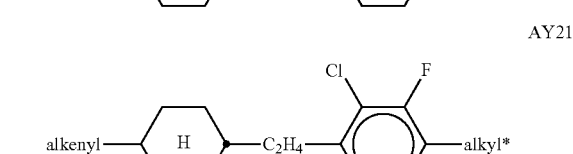
AY22
AY23

AY24
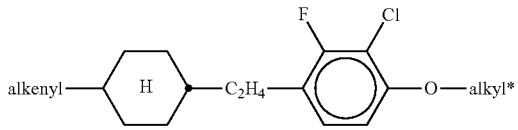
AY25
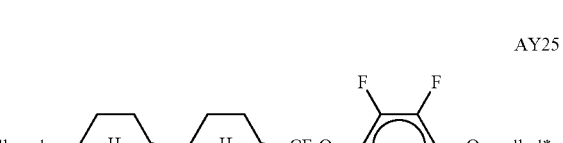
AY25
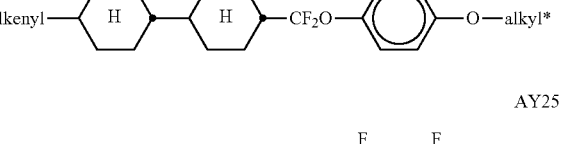
AY26
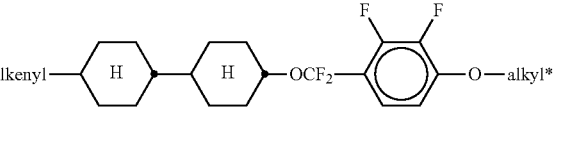
AY27
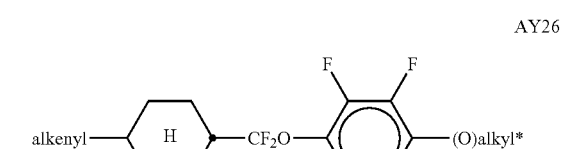
AY28
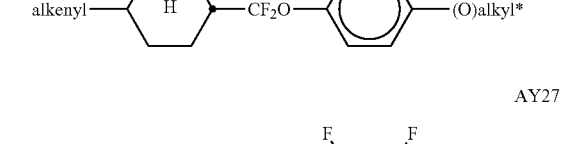
AY29
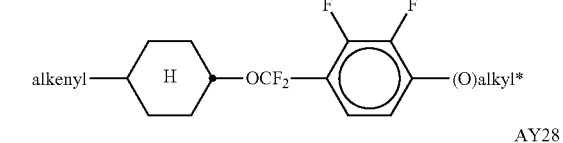
AY30
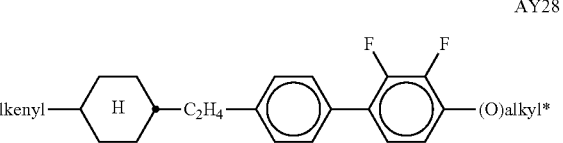

in which alkyl and alkyl* each, independently of one another, denote a straight-chain alkyl radical having 1-6 C atoms, and alkenyl and alkenyl* each, independently of one another, denote a straight-chain alkenyl radical having 2-7 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Very particularly preferred compounds of the formula AN are selected from the following sub-formulae:

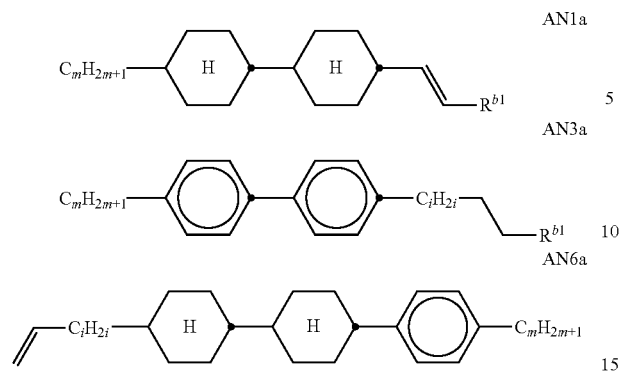

in which m denotes 1, 2, 3, 4, 5 or 6, i denotes 0, 1, 2 or 3, and $R^{b1}$ denotes H, $CH_3$ or $C_2H_5$, Especially preferred are the following compounds:

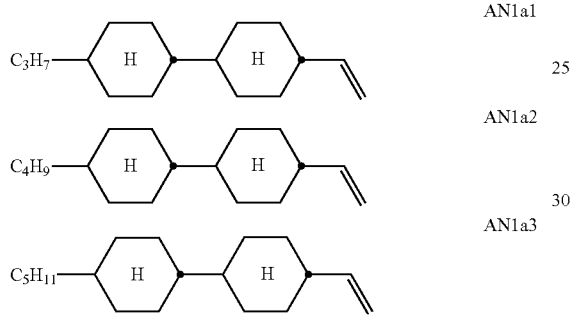

Most preferred is the compound of formula AN1a1.

Very particularly preferred compounds of the formula AY are selected from the following sub-formulae:

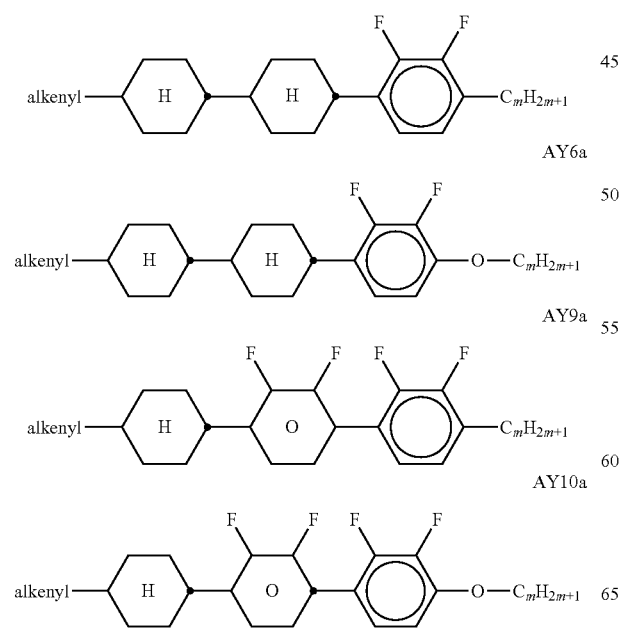

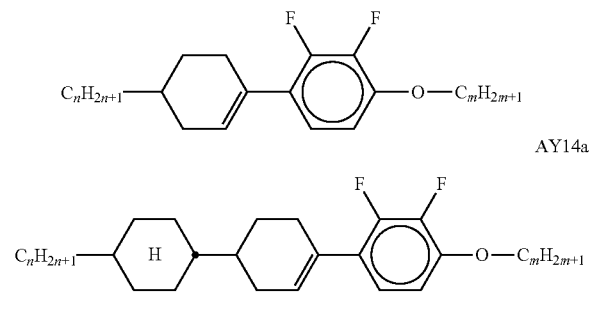

in which m and n each, independently of one another, denote 1, 2, 3, 4, 5 or 6, and alkenyl denotes $CH_2$=CH—, $CH_2$=$CHCH_2CH_2$—, $CH_3$—CH=CH—, $CH_3$—$CH_2$—CH=CH—, $CH_3$—$(CH_2)_2$—CH=CH—, $CH_3$—$(CH_2)_3$—CH=CH— or $CH_3$—CH=CH—$(CH_2)_2$—.

In a first preferred embodiment the LC medium contains an LC host mixture based on compounds with negative dielectric anisotropy. Such LC media are especially suitable for use in PSA-VA displays. Particularly preferred embodiments of such an LC medium are those of sections a)-y) below:

a) LC medium which comprises one or more compounds of the formulae CY and/or PY:

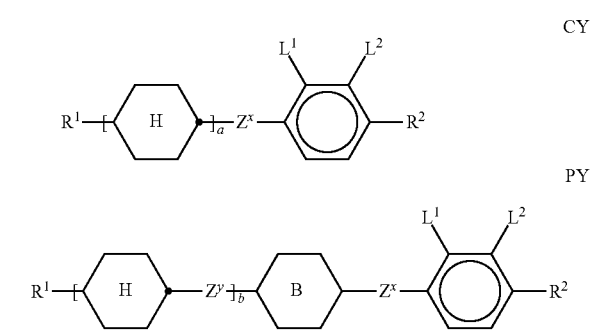

wherein
a denotes 1 or 2,
b denotes 0 or 1,

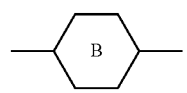

denotes

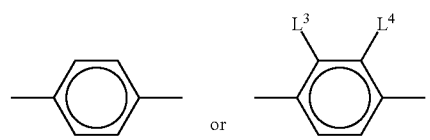

$R^1$ and $R^2$ each, independently of one another, denote alkyl having 1 to 12 C atoms, where, in addition, one or two non-adjacent $CH_2$ groups may each be replaced by —O—, —CH=CH—, —CO—, —OCO— or —COO— in such a way that O atoms are not linked directly to one another, preferably alkyl or alkoxy having 1 to 6 C atoms, $Z^x$ and $Z^y$ each, independently of one another, denote —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond, $L^{1-4}$ each, independently of one another, denote F, Cl, OCF$_3$, CF$_3$, CH$_3$, CH$_2$F, CHF$_2$.

Preferably, both $L^1$ and $L^2$ denote F or one of $L^1$ and $L^2$ denotes F and the other denotes Cl, or both $L^3$ and $L^4$ denote F or one of $L^3$ and $L^4$ denotes F and the other denotes Cl.

The compounds of the formula CY are preferably selected from the group consisting of the following sub-formulae:

CY1
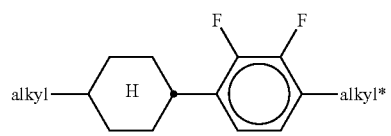

CY2
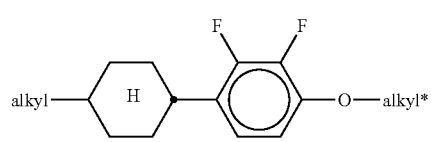

CY3
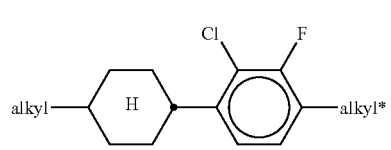

CY4
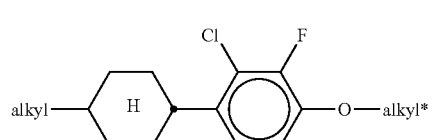

CY5
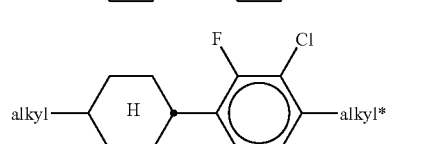

CY6
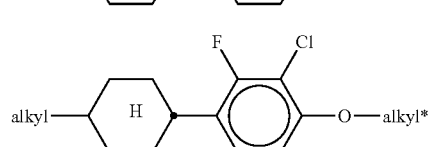

CY7
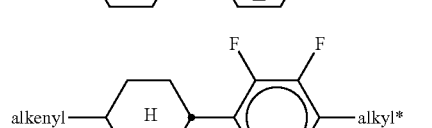

CY8
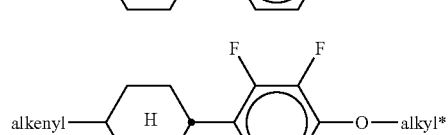

-continued

CY9
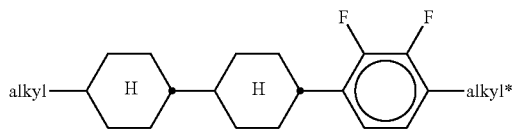

CY10
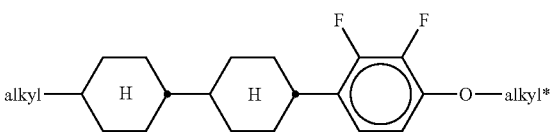

CY11
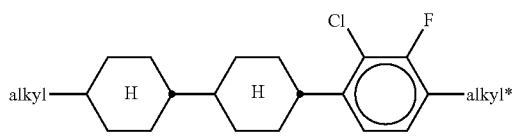

CY12
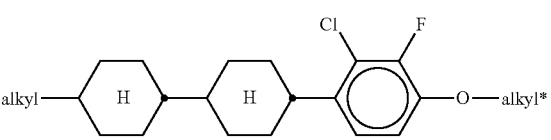

CY13
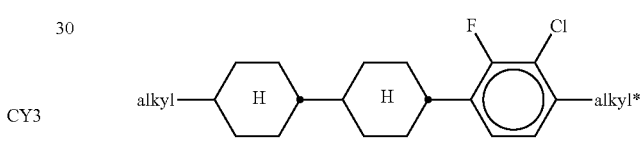

CY14

CY15
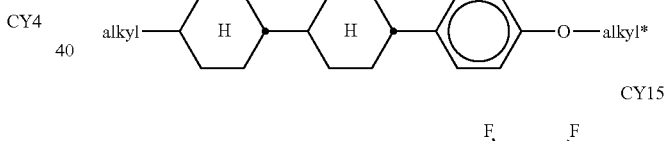

CY16
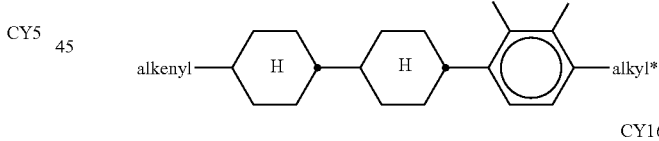

CY17
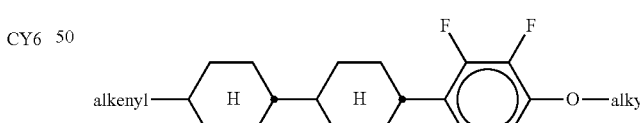

CY18
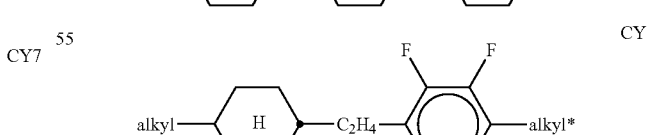

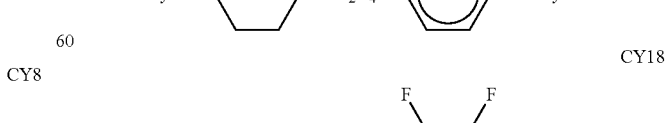

CY19
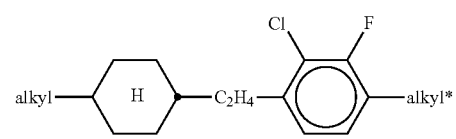

CY20
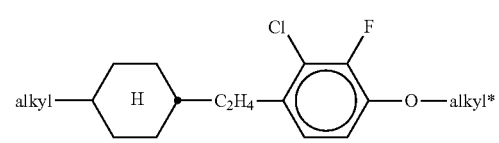

CY21
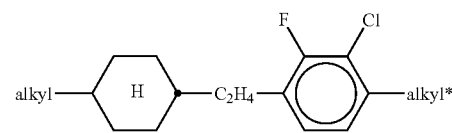

CY22
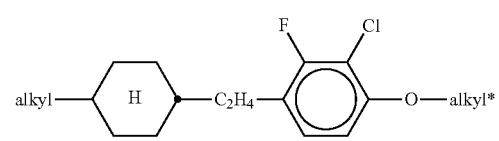

CY23
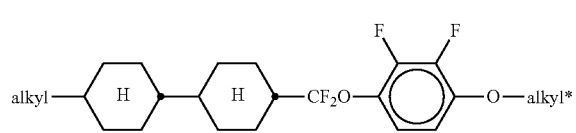

CY24
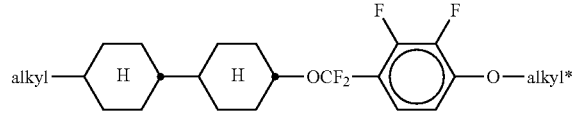

CY25
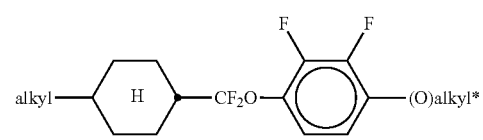

CY25
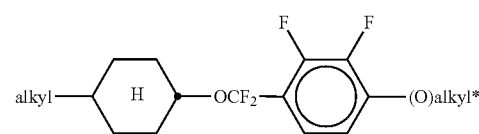

CY26
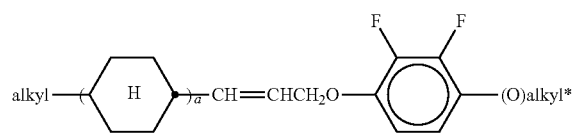

CY27
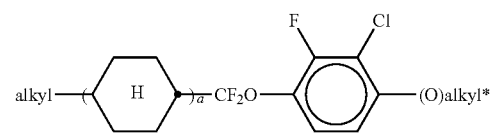

CY28
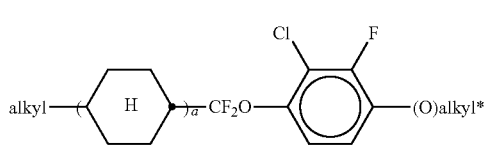

CY29
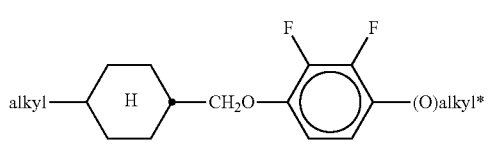

CY30
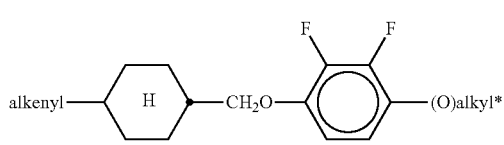

CY31
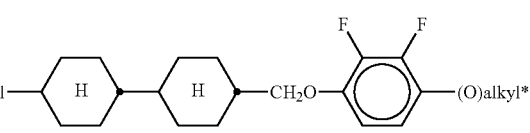

CY32 in which a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula PY are preferably selected from the group consisting of the following sub-formulae:

PY1
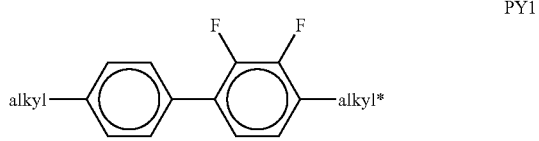

PY2
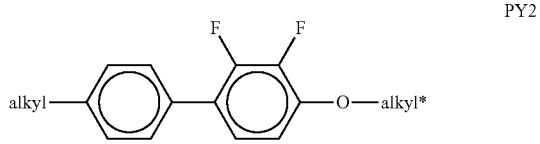

PY3
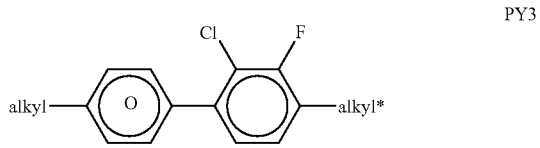

PY4 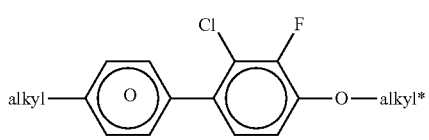

PY5 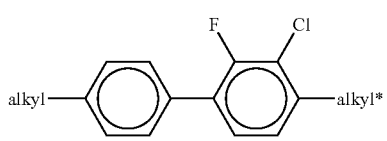

PY6 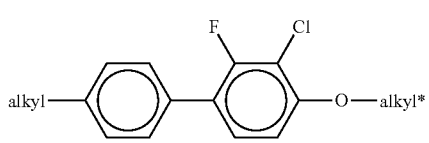

PY7 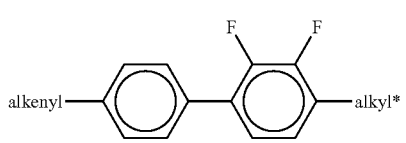

PY8 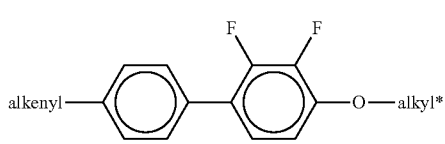

PY9 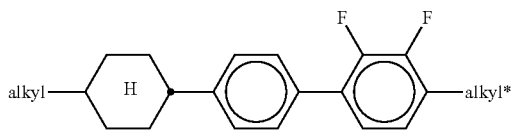

PY10 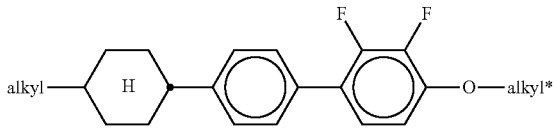

PY11 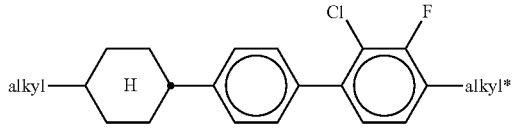

PY12 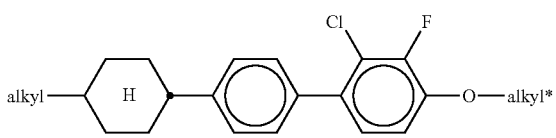

PY13 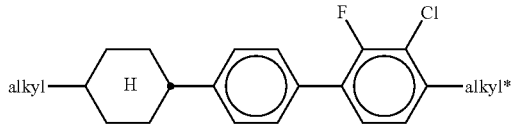

PY14 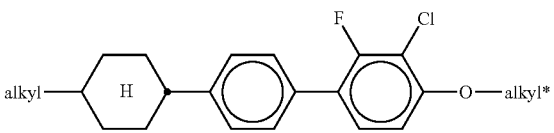

PY15 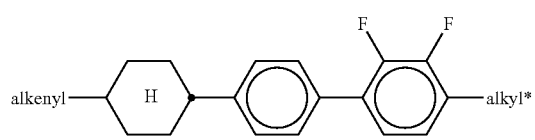

PY16 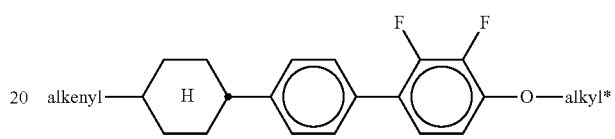

PY17 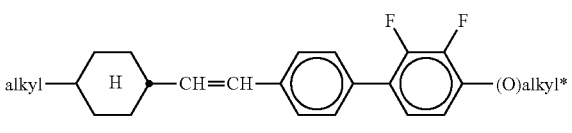

PY18 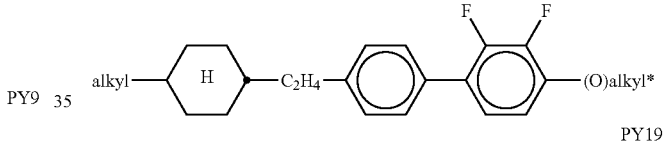

PY19 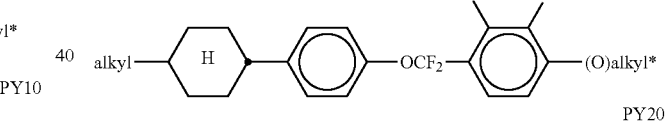

PY20 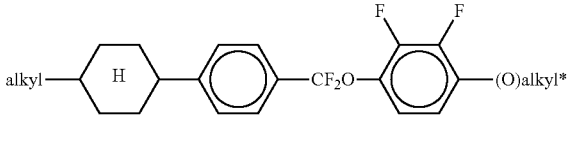

in which alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

b) LC medium which additionally comprises one or more compounds of the following formula:

ZK 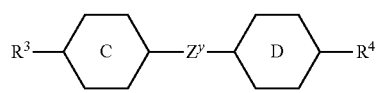

in which the individual radicals have the following meanings:

denotes

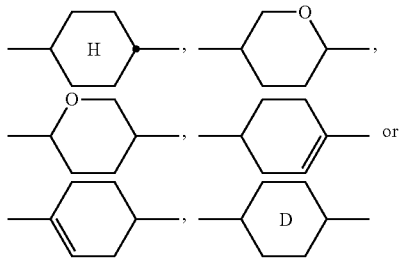

denotes

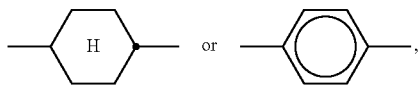

R³ and R⁴ each, independently of one another, denote alkyl having 1 to 12 C atoms, in which, in addition, one or two non-adjacent CH₂ groups may each be replaced by —O—, —CH=CH—, —CO—, —O—CO— or —CO—O— in such a way that O atoms are not linked directly to one another, $Z^y$ denotes —CH₂CH₂—, —CH=CH—, —CF₂O—, —OCF₂—, —CH₂O—, —OCH₂—, —CO—O—, —O—CO—, —C₂F₄—, —CF=CF—, —CH=CH—CH₂O— or a single bond, preferably a single bond.

The compounds of the formula ZK are preferably selected from the group consisting of the following sub-formulae:

ZK1

ZK2
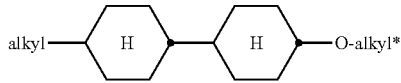

ZK3
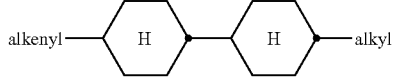

ZK4

ZK5
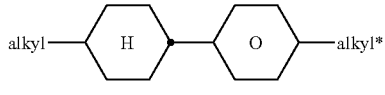

ZK6
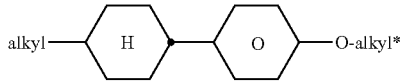

ZK7
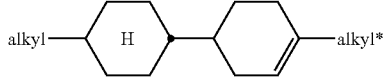

ZK8
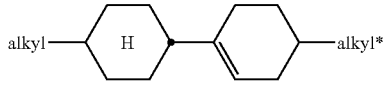

ZK9
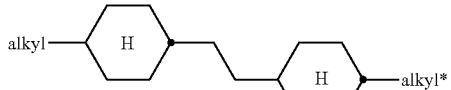

ZK10
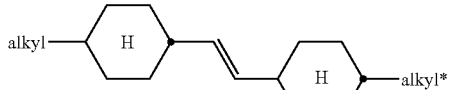

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl preferably denotes CH₂=CH—, CH₂=CHCH₂CH₂—, CH₃—CH=CH—, CH₃—CH₂—CH=CH—, CH₃—(CH₂)₂—CH=CH—, CH₃—(CH₂)₃—CH=CH— or CH₃—CH=CH—(CH₂)₂—.

c) LC medium which additionally comprises one or more compounds of the following formula:

DK
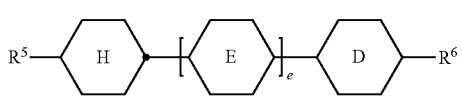

in which the individual radicals on each occurrence, identically or differently, have the following meanings:

R⁵ and R⁶ each, independently of one another, have one of the meanings indicated above for R¹,

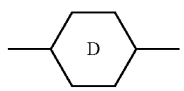

denotes

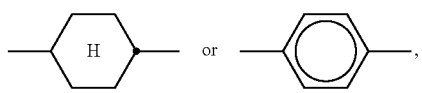

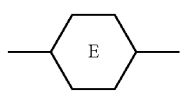

denotes

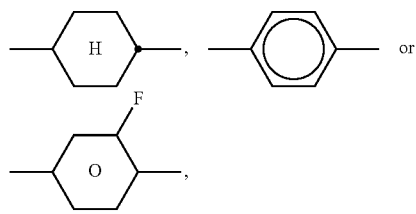

and e denotes 1 or 2.

The compounds of the formula DK are preferably selected from the group consisting of the following sub-formulae:

DK1
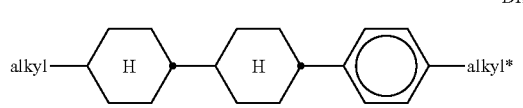

DK2
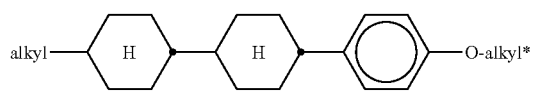

DK3

DK4
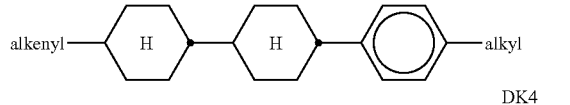

DK5
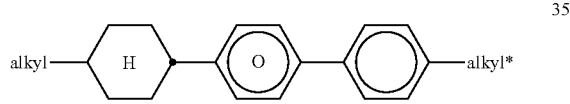

DK6
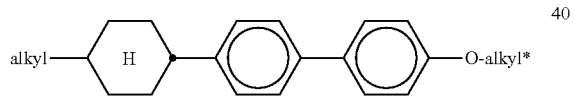

DK7
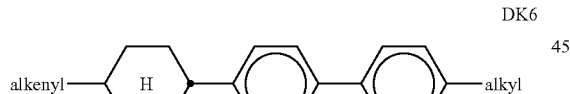

DK8
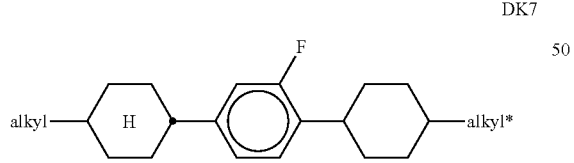

DK9
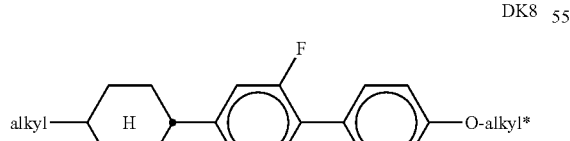

DK10
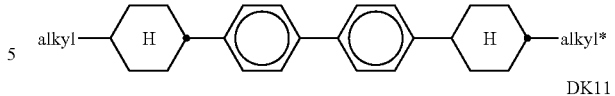

DK11
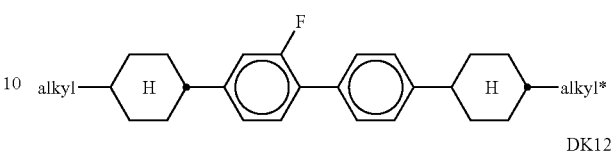

DK12
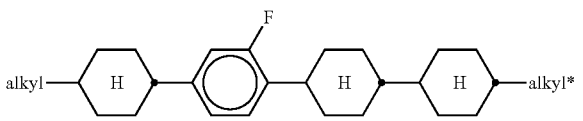

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

d) LC medium which additionally comprises one or more compounds of the following formula:

LY
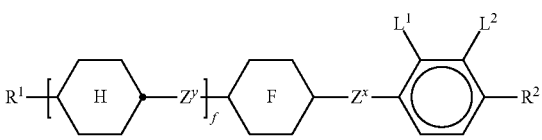

in which the individual radicals have the following meanings:

denotes

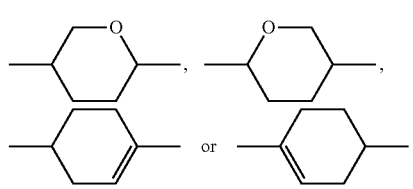

f denotes 0 or 1, $R^1$ and $R^2$ each, independently of one another, denote alkyl having 1 to 12 C atoms, where, in addition, one or two non-adjacent $CH_2$ groups may each be replaced by —O—, —CH=CH—, —CO—, —OCO— or —COO— in such a way that O atoms are not linked directly to one another, $Z^x$ and $Z^y$ each, independently of one another, denote —$CH_2CH_2$—, —CH=CH—, —$CF_2O$—, —$OCF_2$—, —CH₂O—, —OCH₂—, —CO—O—, —O—CO—, —C₂F₄—, —CF=CF—, —CH=CH—CH₂O— or a single bond, preferably a single bond, L¹ and L² each, independently of one another, denote F, Cl, OCF₃, CF₃, CH₃, CH₂F, CHF₂.

Preferably, both radicals L¹ and L² denote F or one of the radicals L¹ and L² denotes F and the other denotes Cl.

The compounds of the formula LY are preferably selected from the group consisting of the following sub-formulae:

LY1
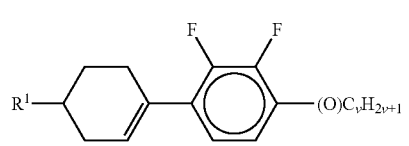

LY2
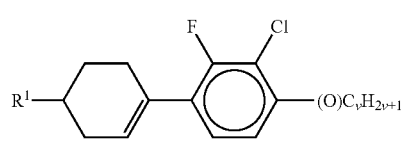

LY3
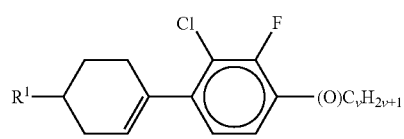

LY4
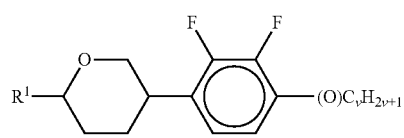

LY5
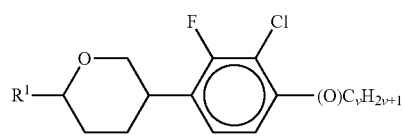

LY6
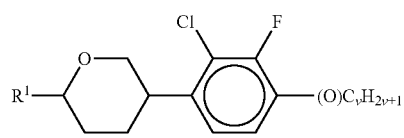

LY7
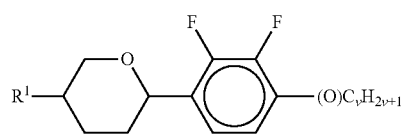

LY8
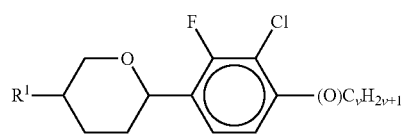

LY9
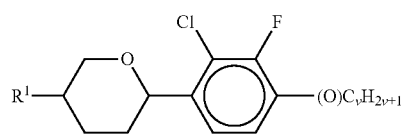

-continued

LY10
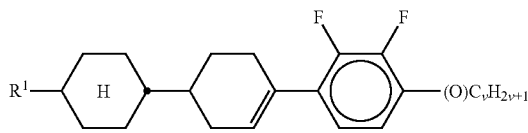

LY11
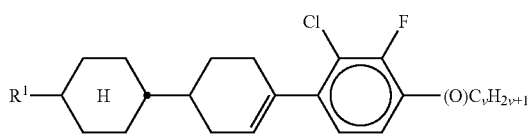

LY12
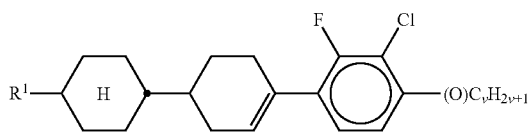

LY15
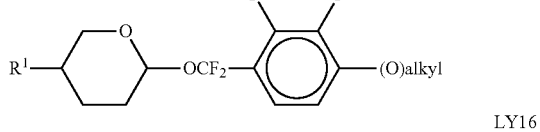

LY16
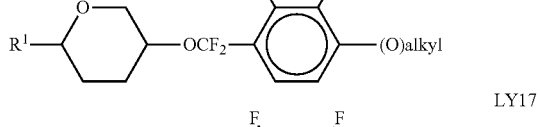

LY17
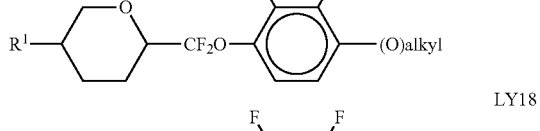

LY18
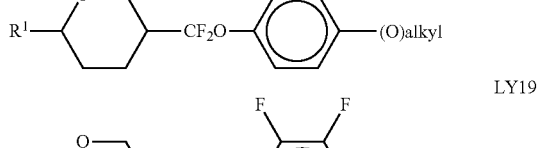

LY19
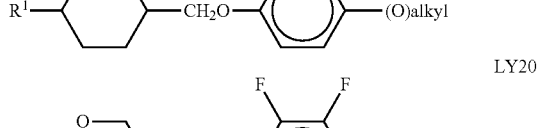

LY20
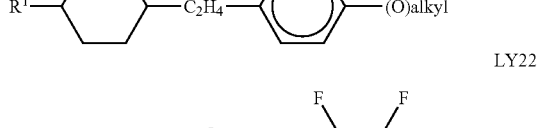

LY22
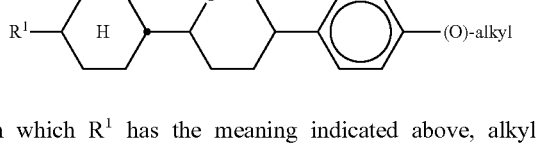

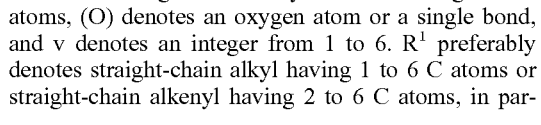

in which R¹ has the meaning indicated above, alkyl denotes a straight-chain alkyl radical having 1-6 C atoms, (O) denotes an oxygen atom or a single bond, and v denotes an integer from 1 to 6. R¹ preferably denotes straight-chain alkyl having 1 to 6 C atoms or straight-chain alkenyl having 2 to 6 C atoms, in particular CH₃, C₂H₅, n-C₃H₇, n-C₄H₉, n-C₅H₁₁, CH₂=CH—, CH₂=CHCH₂CH₂—, CH₃—CH=CH—, CH₃—CH₂—CH=CH—, CH₃—(CH₂)₂—CH=CH—, CH₃—(CH₂)₃—CH=CH— or CH₃—CH=CH—(CH₂)₂—.

e) LC medium which additionally comprises one or more compounds selected from the group consisting of the following formulae:

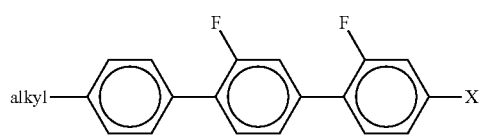

G1

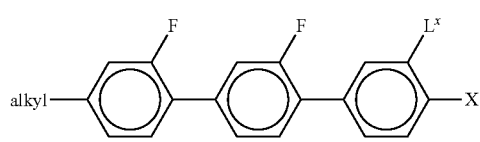

G2

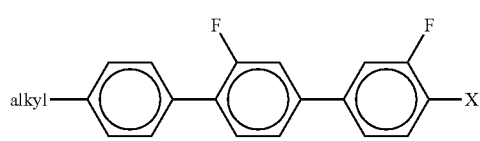

G3

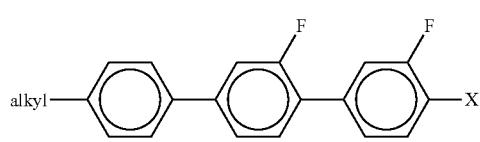

G4 in which alkyl denotes $C_{1-6}$-alkyl, $L^x$ denotes H or F, and X denotes F, Cl, OCF₃, OCHF₂ or OCH=CF₂. Particular preference is given to compounds of the formula G1 in which X denotes F.

f) LC medium which additionally comprises one or more compounds selected from the group consisting of the following formulae:

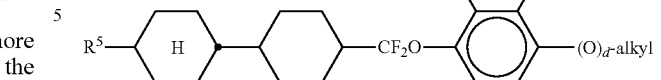

Y1

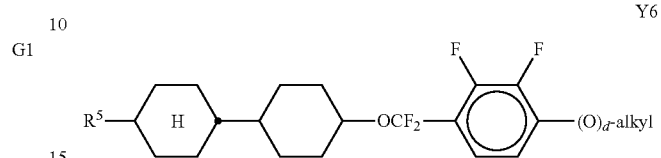

Y2

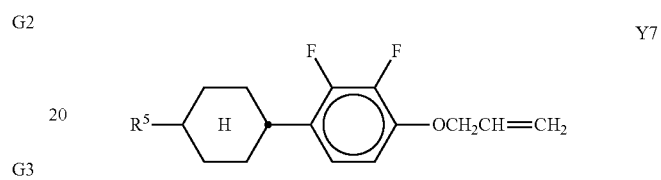

Y3

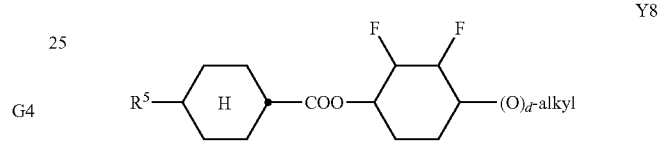

Y4

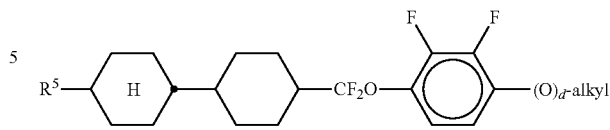

Y5

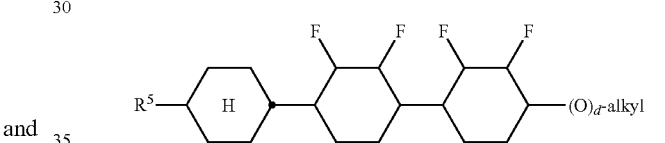

Y6

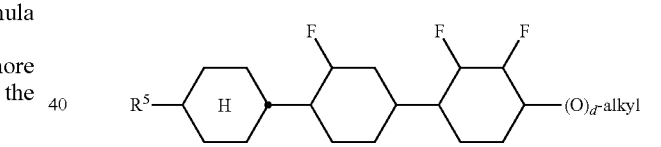

Y7

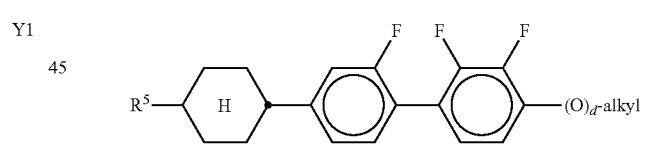

Y8

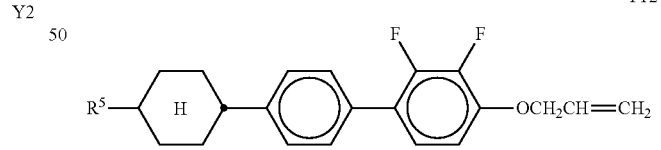

Y9

Y10

Y11

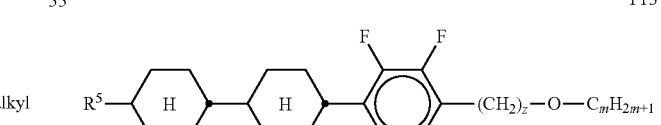

Y12

Y13

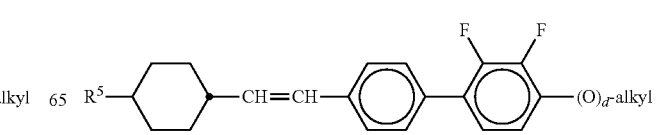

Y14

-continued

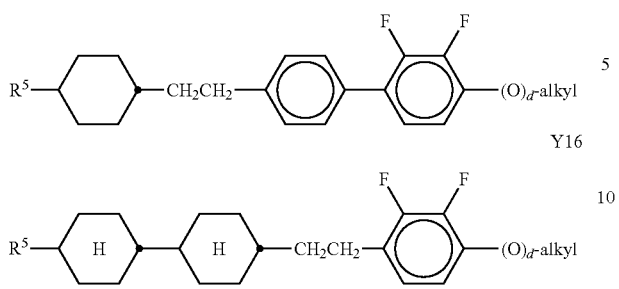

Y15

Y16 in which R⁵ has one of the meanings indicated above for R¹, alkyl denotes $C_{1-6}$-alkyl, d denotes 0 or 1, and z and m each, independently of one another, denote an integer from 1 to 6. R⁵ in these compounds is particularly preferably $C_{1-6}$-alkyl or -alkoxy or $C_{2-6}$-alkenyl, d is preferably 1. The LC medium according to the invention preferably comprises one or more compounds of the above-mentioned formulae in amounts of 5% by weight.

g) LC medium which additionally comprises one or more biphenyl compounds selected from the group consisting of the following formulae:

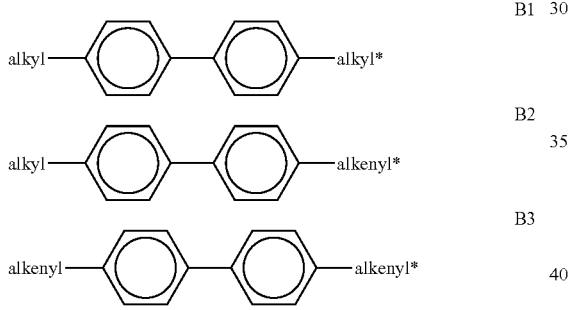

B1

B2

B3 in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2$=CH—, $CH_2$=CHCH$_2$CH$_2$—, $CH_3$—CH=CH—, $CH_3$—CH$_2$—CH=CH—, $CH_3$—(CH$_2$)$_2$—CH=CH—, $CH_3$—(CH$_2$)$_3$—CH=CH— or $CH_3$—CH=CH—(CH$_2$)$_2$—.

The proportion of the biphenyls of the formulae B1 to B3 in the LC mixture is preferably at least 3% by weight, in particular 5% by weight.

The compounds of the formula B2 are particularly preferred.

The compounds of the formulae B1 to B3 are preferably selected from the group consisting of the following sub-formulae:

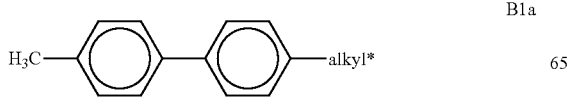

B1a

-continued

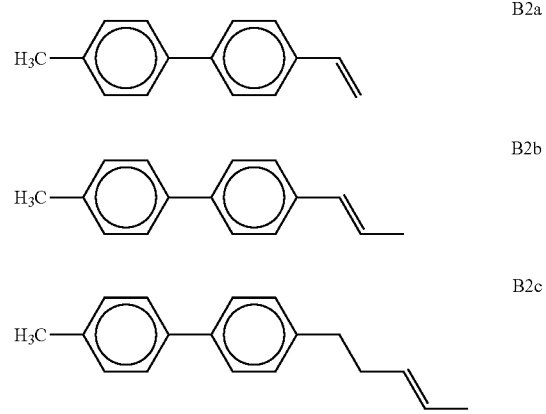

B2a

B2b

B2c in which alkyl* denotes an alkyl radical having 1-6 C atoms. The medium according to the invention particularly preferably comprises one or more compounds of the formulae B1a and/or B2c.

h) LC medium which additionally comprises one or more terphenyl compounds of the following formula:

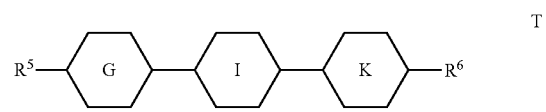

T in which R⁵ and R⁶ each, independently of one another, have one of the meanings indicated above for R¹, and

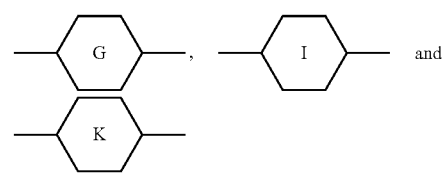

each, independently of one another, denote

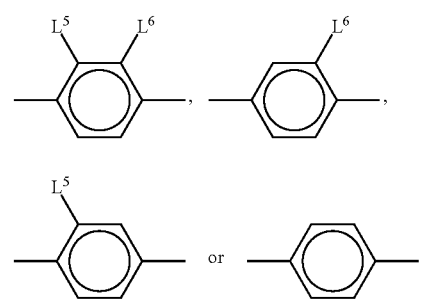

in which L⁵ denotes F or Cl, preferably F, and L⁶ denotes F, Cl, OCF$_3$, CF$_3$, CH$_3$, CH$_2$F or CHF$_2$, preferably F.

The compounds of the formula T are preferably selected from the group consisting of the following sub-formulae:

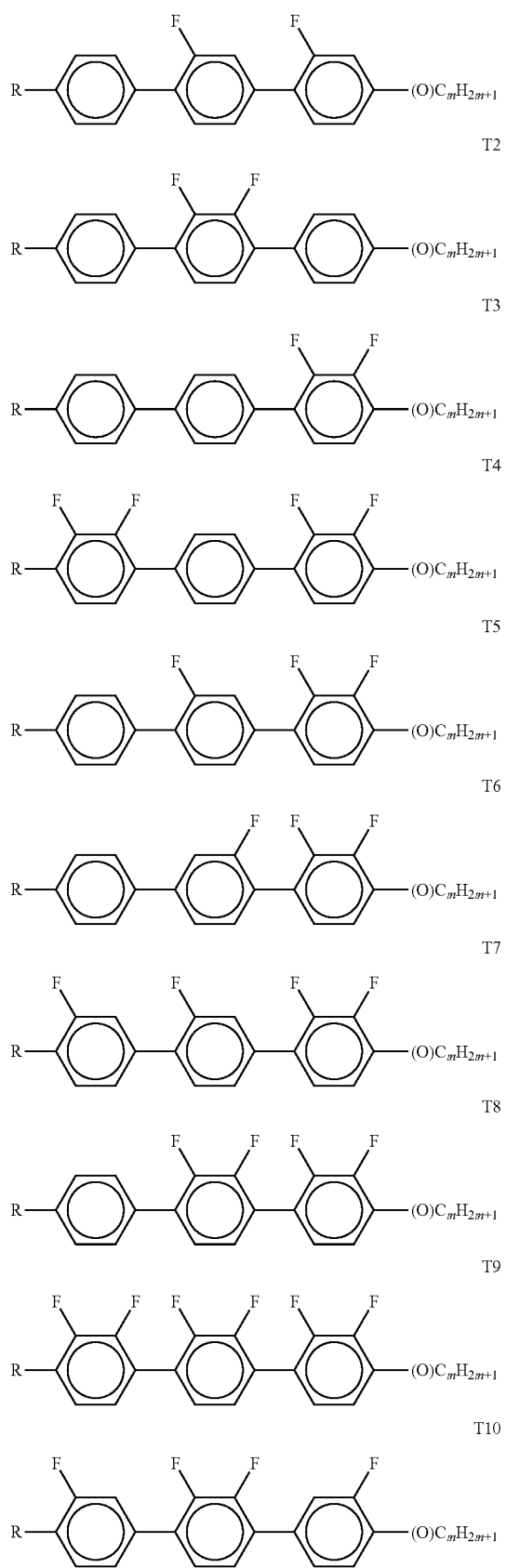
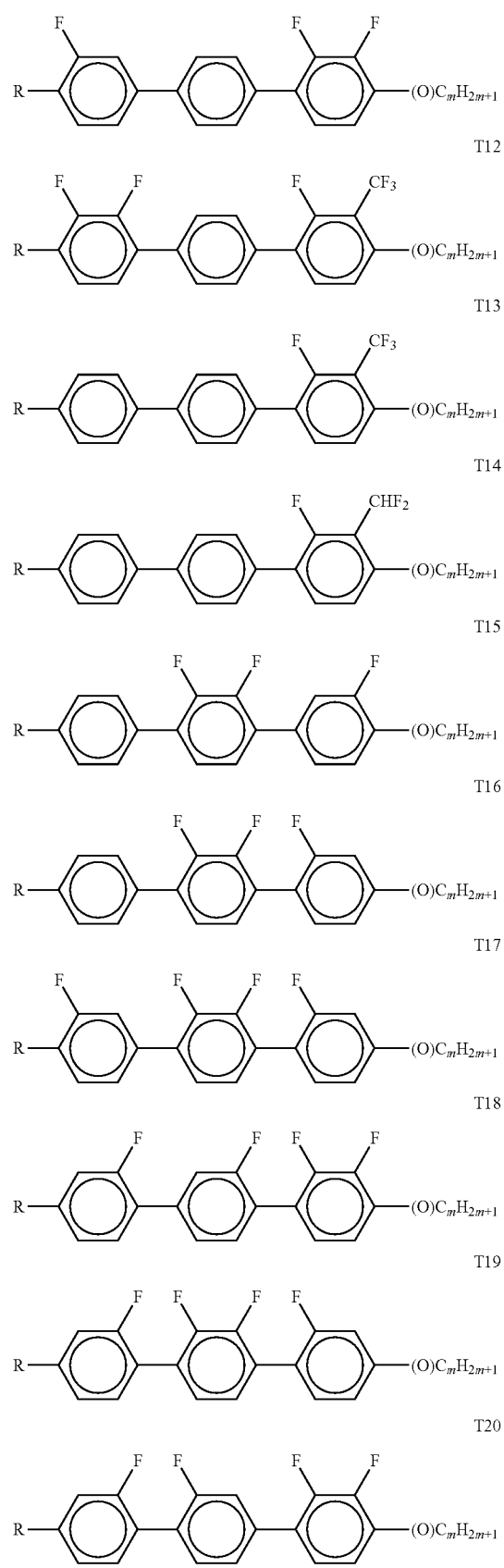

-continued

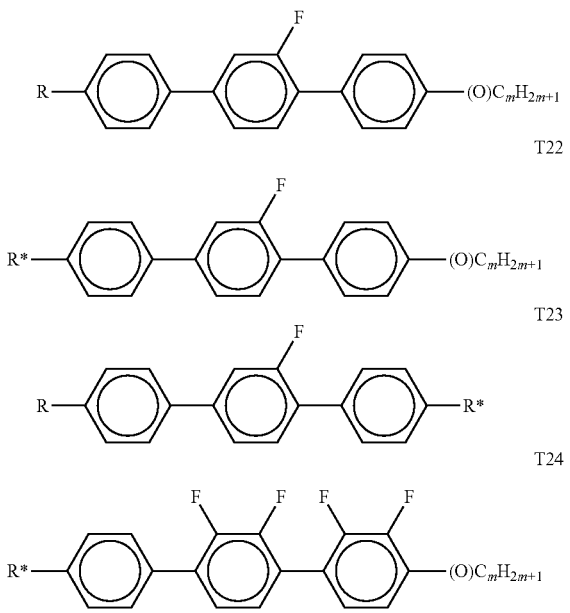

T21

T22

T23

T24 in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

R preferably denotes methyl, ethyl, propyl, butyl, pentyl, hexyl, methoxy, ethoxy, propoxy, butoxy or pentoxy.

The LC medium according to the invention preferably comprises the terphenyls of the formula T and the preferred sub-formulae thereof in an amount of 0.5-30% by weight, in particular 1-20% by weight.

Particular preference is given to compounds of the formulae T1, T2, T3 and T21. In these compounds, R preferably denotes alkyl, furthermore alkoxy, each having 1-5 C atoms.

The terphenyls are preferably employed in mixtures according to the invention if the Δn value of the mixture is to be ≥0.1. Preferred mixtures comprise 2-20% by weight of one or more terphenyl compounds of the formula T, preferably selected from the group of compounds T1 to T22.

i) LC medium which additionally comprises one or more compounds selected from the group consisting of the following formulae:

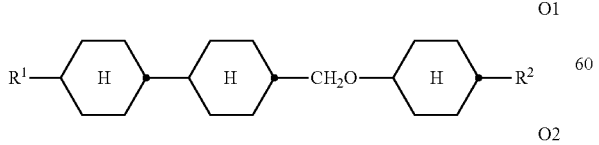

O1

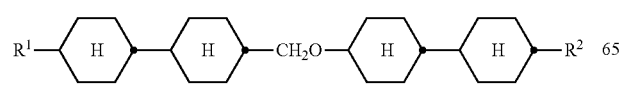

O2

-continued

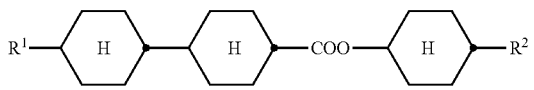

O3

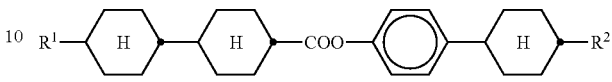

O4

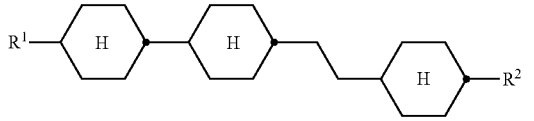

O5

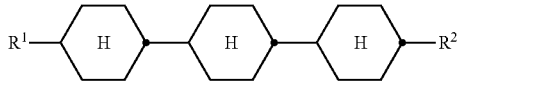

O6

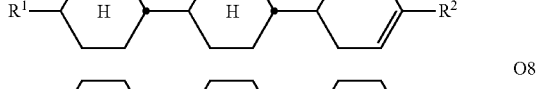

O7

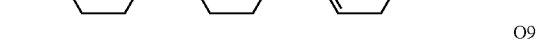

O8

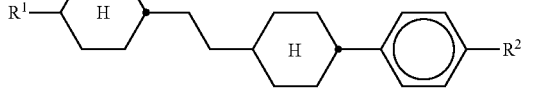

O9

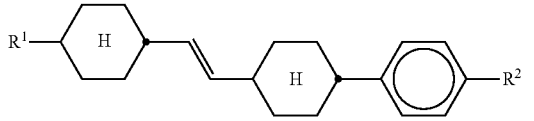

O10

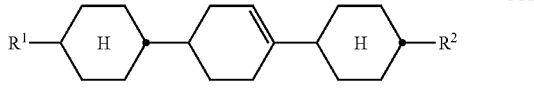

O11 in which $R^1$ and $R^2$ have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae O1, O3 and O4.

k) LC medium which additionally comprises one or more compounds of the following formula:

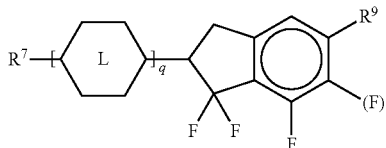

FI

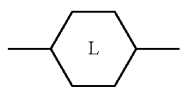

in which denotes

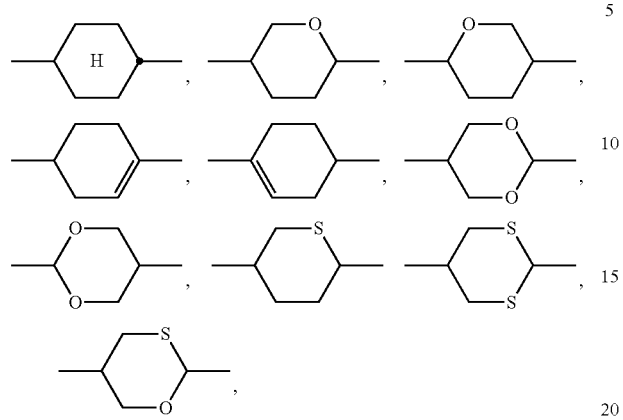

$R^9$ denotes H, $CH_3$, $C_2H_5$ or n-$C_3H_7$, (F) denotes an optional fluorine substituent, q denotes 1, 2 or 3, and $R^7$ has one of the meanings indicated for $R^1$, preferably in amounts of >3% by weight, in particular ≥5% by weight and very particularly preferably 5-30% by weight.

Particularly preferred compounds of the formula FI are selected from the group consisting of the following sub-formulae:

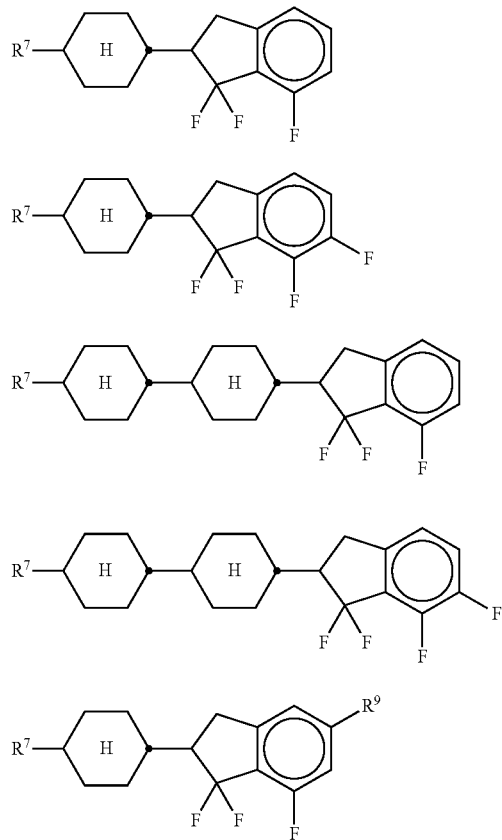

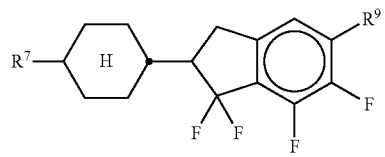

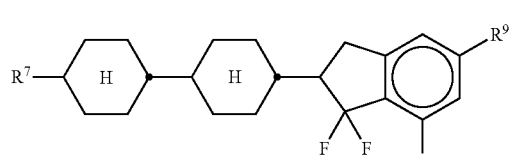

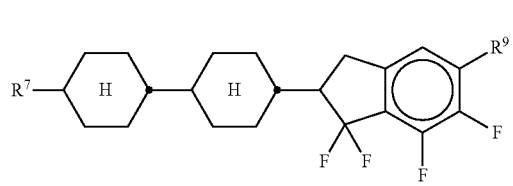

in which $R^7$ preferably denotes straight-chain alkyl, and $R^9$ denotes $CH_3$, $C_2H_5$ or n-$C_3H_7$. Particular preference is given to the compounds of the formulae FI1, FI2 and FI3.

l) LC medium which additionally comprises one or more compounds selected from the group consisting of the following formulae:

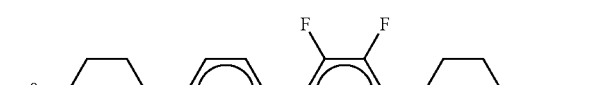

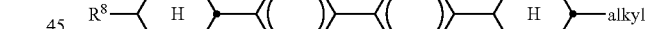

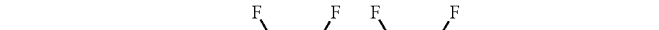

in which $R^8$ has the meaning indicated for $R^1$, and alkyl denotes a straight-chain alkyl radical having 1-6 C atoms.

m) LC medium which additionally comprises one or more compounds which contain a tetrahydronaphthyl or naphthyl unit, such as, for example, the compounds selected from the group consisting of the following formulae:

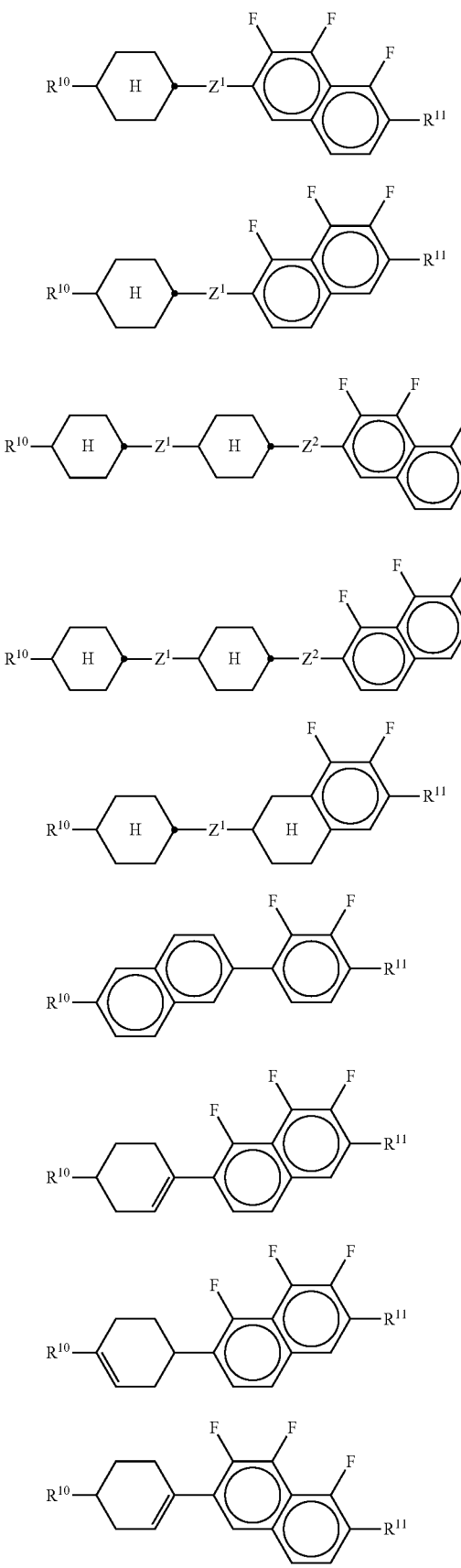

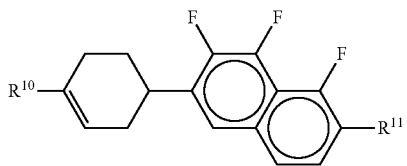

in which $R^{10}$ and $R^{11}$ each, independently of one another, have one of the meanings indicated for $R^1$, preferably denote straight-chain alkyl or alkoxy having 1 to 6 C atoms or straight-chain alkenyl having 2 to 6 C atoms, and $Z^1$ and $Z^2$ each, independently of one another, denote —C$_2$H$_4$—, —CH=CH—, —(CH$_2$)$_4$—, —(CH$_2$)$_3$O—, —O(CH$_2$)$_3$—, —CH=CH—CH$_2$CH$_2$—, —CH$_2$CH$_2$CH=CH—, —CH$_2$O—, —OCH$_2$—, —CO—O—, —O—CO—, —C$_2$F$_4$—, —CF=CF—, —CF=CH—, —CH=CF—, —CH$_2$— or a single bond.

n) LC medium which additionally comprises one or more difluorodibenzochromans and/or chromans of the following formulae:

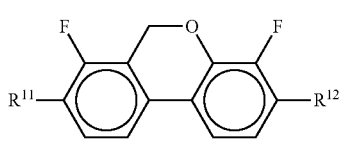

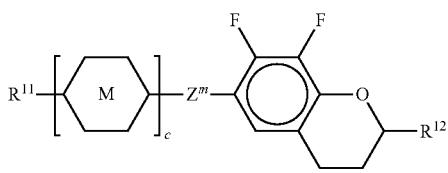

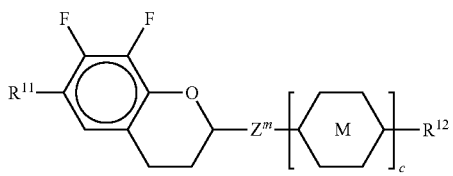

in which
$R^{11}$ and $R^{12}$ each, independently of one another, have the meanings indicated above,
ring M is trans-1,4-cyclohexylene or 1,4-phenylene,
$Z^m$ —C$_2$H$_4$—, —CH$_2$O—, —OCH$_2$—, —CO—O— or —O—CO—,
c is 0 or 1,
preferably in amounts of 3 to 20% by weight, in particular in amounts of 3 to 15% by weight.
Particularly preferred compounds of the formulae BC, CR and RC are selected from the group consisting of the following sub-formulae:

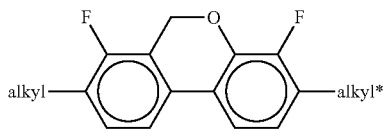

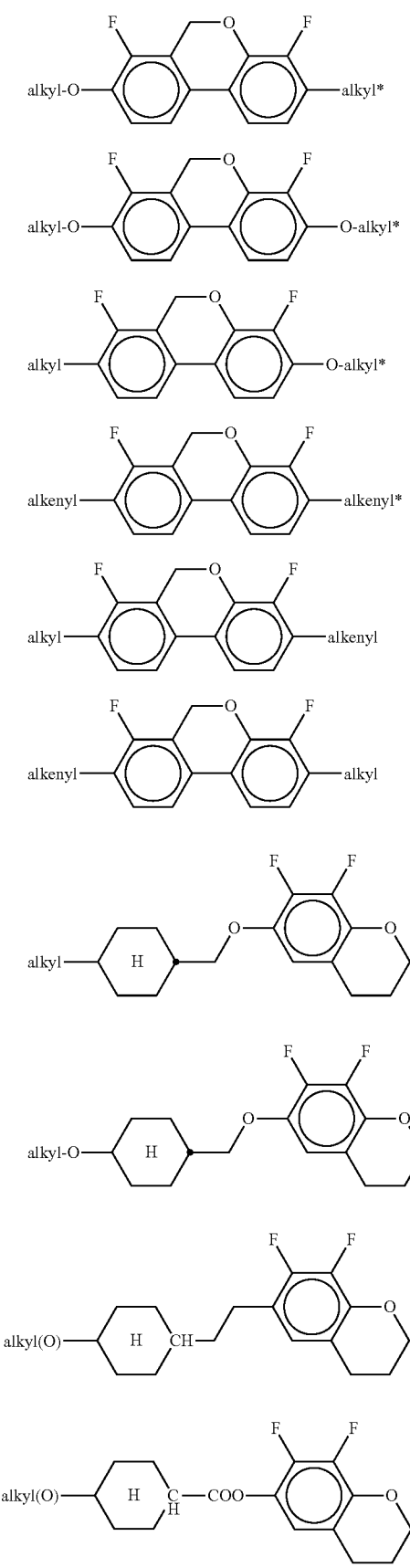

BC2
BC3
BC4
BC5
BC6
BC7
CR1
CR2
CR3
CR4

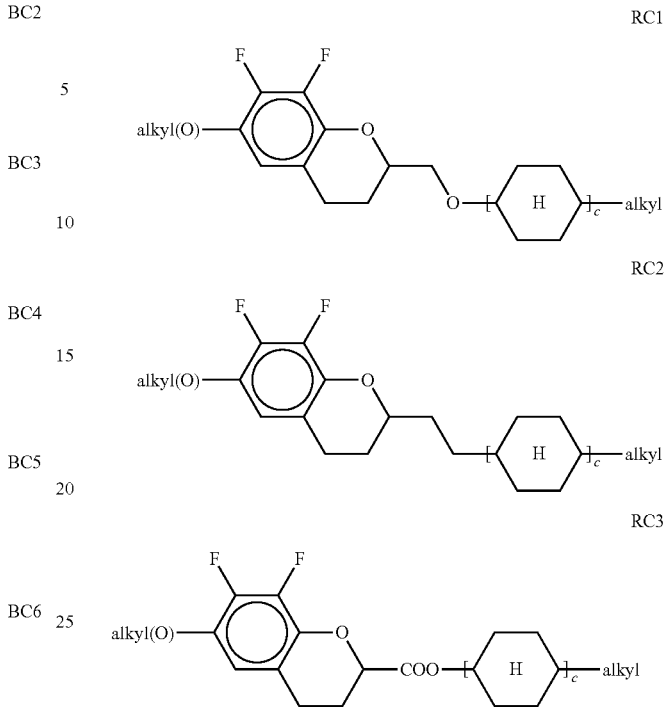

RC1
RC2
RC3 in which alkyl and alkyl* each, independently of one another, denote a straight-chain alkyl radical having 1-6 C atoms, (O) denotes an oxygen atom or a single bond, c is 1 or 2, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Very particular preference is given to mixtures comprising one, two or three compounds of the formula BC-2.

o) LC medium which additionally comprises one or more fluorinated phenanthrenes and/or dibenzofurans of the following formulae:

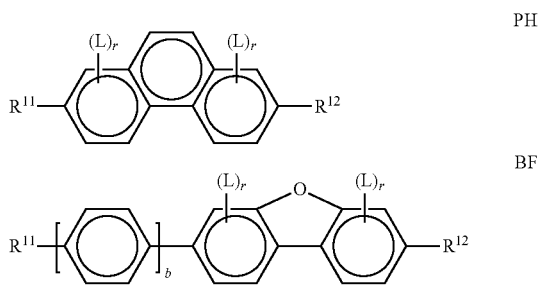

PH
BF in which $R^{11}$ and $R^{12}$ each, independently of one another, have the meanings indicated above, b denotes 0 or 1, L denotes F, and r denotes 1, 2 or 3.

Particularly preferred compounds of the formulae PH and BF are selected from the group consisting of the following sub-formulae:

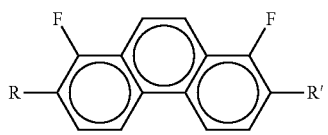

PH1

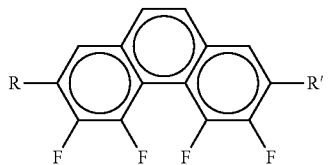

PH2

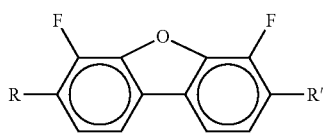

BF1

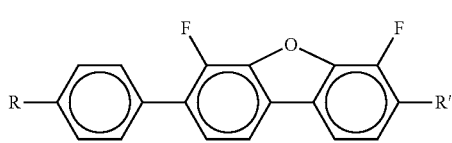

BF2 in which R and R' each, independently of one another, denote a straight-chain alkyl or alkoxy radical having 1-7 C atoms.

p) LC medium which additionally comprises one or more monocyclic compounds of the following formula

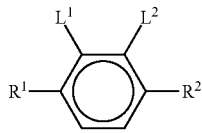

Y wherein $R^1$ and $R^2$ each, independently of one another, denote alkyl having 1 to 12 C atoms, where, in addition, one or two non-adjacent $CH_2$ groups may each be replaced by —O—, —CH=CH—, —CO—, —OCO— or —COO— in such a way that O atoms are not linked directly to one another, preferably alkyl or alkoxy having 1 to 6 C atoms, $L^1$ and $L^2$ each, independently of one another, denote F, Cl, $OCF_3$, $CF_3$, $CH_3$, $CH_2F$, $CHF_2$.

Preferably, both $L^1$ and $L^2$ denote F or one of $L^1$ and $L^2$ denotes F and the other denotes Cl, The compounds of the formula Y are preferably selected from the group consisting of the following sub-formulae:

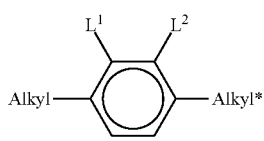

Y1

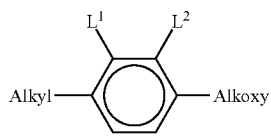

Y2

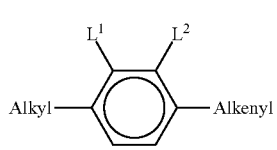

Y3

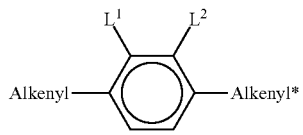

Y4

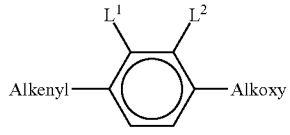

Y5

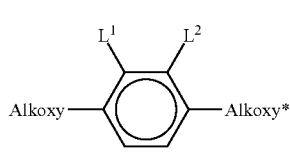

Y6

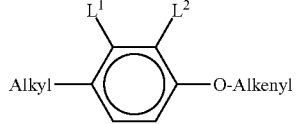

Y7

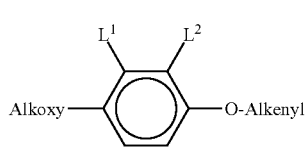

Y8

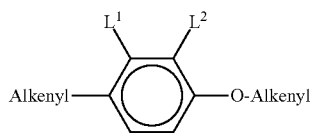

Y9

Y10 in which, Alkyl and Alkyl* each, independently of one another, denote a straight-chain alkyl radical having 1-6 C atoms, Alkoxy denotes a straight-chain alkoxy radical having 1-6 C atoms, Alkenyl and Alkenyl* each, independently of one another, denote a straight-chain alkenyl radical having 2-6 C atoms, and O denotes an oxygen atom or a single bond. Alkenyl and Alkenyl* preferably denote $CH_2$=CH—, $CH_2$=CHCH$_2$CH$_2$—, $CH_3$—CH=CH—, $CH_3$—CH$_2$—CH=CH—, $CH_3$—(CH$_2$)$_2$—CH=CH—, $CH_3$—(CH$_2$)$_3$—CH=CH— or $CH_3$—CH=CH—(CH$_2$)$_2$—.

Particularly preferred compounds of the formula Y are selected from the group consisting of the following sub-formulae:

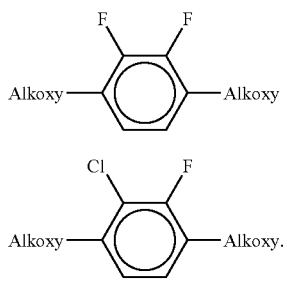

wherein Alkoxy preferably denotes straight-chain alkoxy with 3, 4, or 5 C atoms.

q) LC medium which, apart from the polymerizable compounds according to the invention, in particular of the formula I or sub-formulae thereof and the comonomers, comprises no compounds which contain a terminal vinyloxy group (—O—CH=CH$_2$).

r) LC medium which comprises 1 to 5, preferably 1, 2 or 3, polymerizable compounds, preferably selected from polymerizable compounds according to the invention, in particular of the formula I or sub-formulae thereof.

s) LC medium in which the proportion of polymerizable compounds, in particular of the formula I or sub-formulae thereof, in the mixture as a whole is 0.05 to 5%, preferably 0.1 to 1%.

t) LC medium which comprises 1 to 8, preferably 1 to 5, compounds of the formulae CY1, CY2, PY1 and/or PY2. The proportion of these compounds in the mixture as a whole is preferably 5 to 60%, particularly preferably 10 to 35%. The content of these individual compounds is preferably in each case 2 to 20%.

u) LC medium which comprises 1 to 8, preferably 1 to 5, compounds of the formulae CY9, CY10, PY9 and/or PY10. The proportion of these compounds in the mixture as a whole is preferably 5 to 60%, particularly preferably 10 to 35%. The content of these individual compounds is preferably in each case 2 to 20%.

v) LC medium which comprises 1 to 10, preferably 1 to 8, compounds of the formula ZK, in particular compounds of the formulae ZK1, ZK2 and/or ZK6. The proportion of these compounds in the mixture as a whole is preferably 3 to 25%, particularly preferably 5 to 45%. The content of these individual compounds is preferably in each case 2 to 20%.

w) LC medium in which the proportion of compounds of the formulae CY, PY and ZK in the mixture as a whole is greater than 70%, preferably greater than 80%.

x) LC medium in which the LC host mixture contains one or more compounds containing an alkenyl group, preferably selected from the group consisting of formula CY, PY and LY, wherein one or both of $R^1$ and $R^2$ denote straight-chain alkenyl having 2-6 C atoms, formula ZK and DK, wherein one or both of $R^3$ and $R^4$ or one or both of $R^5$ and $R^6$ denote straight-chain alkenyl having 2-6 C atoms, and formula B2 and B3, very preferably selected from formulae CY15, CY16, CY34, CY32, PY15, PY16, ZK3, ZK4, DK3, DK6, B2 and B3, most preferably selected from formulae ZK3, ZK4, B2 and B3. The concentration of these compounds in the LC host mixture is preferably from 2 to 70%, very preferably from 3 to 55%.

y) LC medium which contains one or more, preferably 1 to 5, compounds selected of formula PY1—PY8, very preferably of formula PY2. The proportion of these compounds in the mixture as a whole is preferably 1 to 30%, particularly preferably 2 to 20%. The content of these individual compounds is preferably in each case 1 to 20%.

z) LC medium which contains one or more, preferably 1, 2 or 3, compounds of formula T2. The content of these compounds in the mixture as a whole is preferably 1 to 20%.

In a second preferred embodiment the LC medium contains an LC host mixture based on compounds with positive dielectric anisotropy. Such LC media are especially suitable for use in PSA-OCB-, PSA-TN-, PSA—Posi-VA-, PSA-IPS- or PSA-FFS-displays.

Particularly preferred is an LC medium of this second preferred embodiment, which contains one or more compounds selected from the group consisting of compounds of formula AA and BB

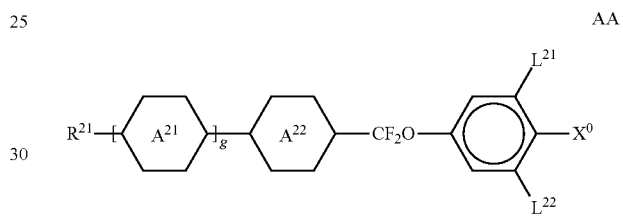

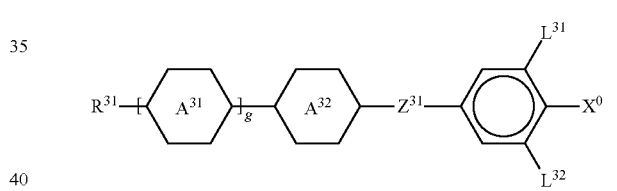

and optionally contains, in addition to the compounds of formula AA and/or BB, one or more compounds of formula CC

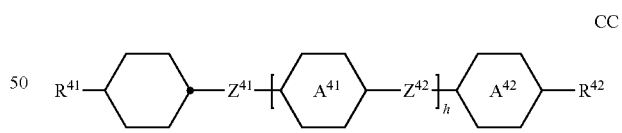

in which the individual radicals have the following meanings:

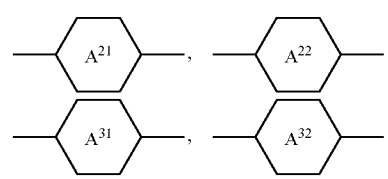

each, independently of one another, and on each occurrence, identically or differently

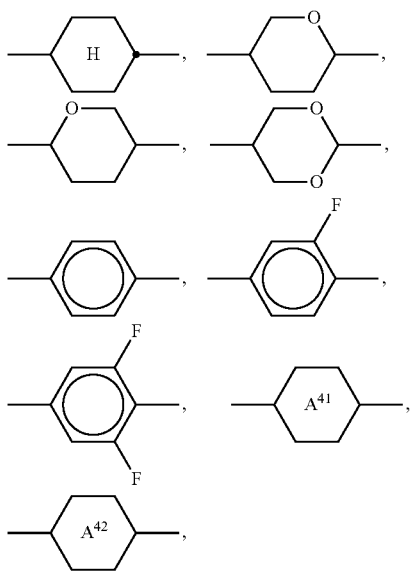

each, independently of one another, and on each occurrence, identically or differently

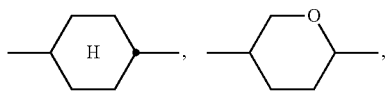

-continued

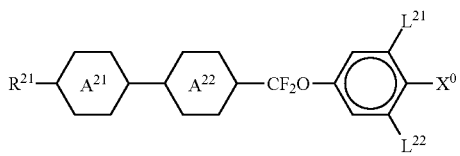

$R^{21}$, $R^{31}$, $R^{41}$, $R^{42}$ each, independently of one another, alkyl, alkoxy, oxaalkyl or fluoroalkyl having 1 to 9 C atoms or alkenyl having 2 to 9 C atoms, $X^0$ F, Cl, halogenated alkyl or alkoxy having 1 to 6 C atoms or halogenated alkenyl or alkenyloxy having 2 to 6 C atoms, $Z^{31}$ —CH$_2$CH$_2$—, —CF$_2$CF$_2$—, —COO—, trans-CH=CH—, trans-CF=CF—, —CH$_2$O— or a single bond, preferably —CH$_2$CH$_2$—, —COO—, trans-CH=CH— or a single bond, particularly preferably —COO—, trans-CH=CH— or a single bond, $Z^{41}$, $Z^{42}$ —CH$_2$CH$_2$—, —COO—, trans-CH=CH—, trans-CF=CF—, —CH$_2$O—, —CF$_2$O—, —C≡C— or a single bond, preferably a single bond, $L^{21}$, $L^{22}$, $L^{31}$, $L^{32}$ H or F, g 0, 1, 2 or 3, e.g., 1, 2, or 3 h 0, 1, 2 or 3.

$X^0$ is preferably F, Cl, CF$_3$, CHF$_2$, OCF$_3$, OCHF$_2$, OCFHCF$_3$, OCFHCHF$_2$, OCFHCHF$_2$, OCF$_2$CH$_3$, OCF$_2$CHF$_2$, OCF$_2$CHF$_2$, OCF$_2$CF$_2$CHF$_2$, OCF$_2$CF$_2$CHF$_2$, OCFHCF$_2$CF$_3$, OCFHCF$_2$CHF$_2$, OCF$_2$CF$_2$CF$_3$, OCF$_2$CF$_2$CClF$_2$, OCClFCF$_2$CF$_3$ or CH=CF$_2$, very preferably F or OCF$_3$ The compounds of formula AA are preferably selected from the group consisting of the following formulae:

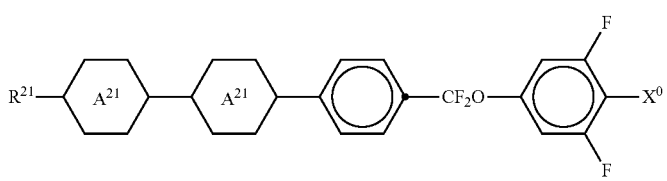

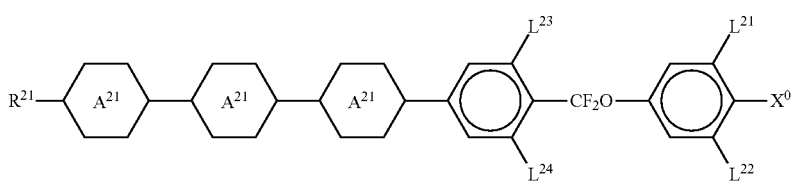

in which $A^{21}$, $R^{21}$, $X^0$, $L^{21}$ and $L^{22}$ have the meanings given in formula AA, $L^{23}$ and $L^{24}$ each, independently of one another, are H or F, and $X^0$ is preferably F. Particularly preferred are compounds of formulae AA1 and AA2.

Particularly preferred compounds of formula AA1 are selected from the group consisting of the following subformulae:

AA1a
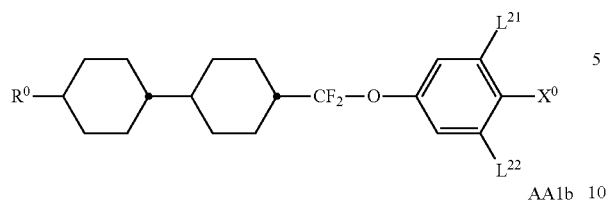

AA1b
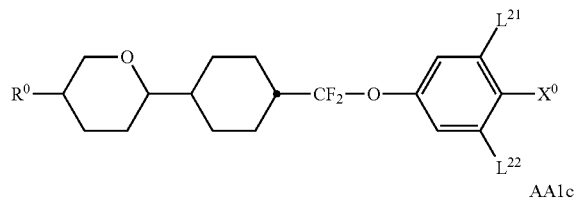

AA1c
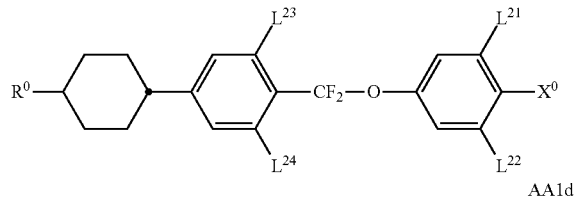

AA1d
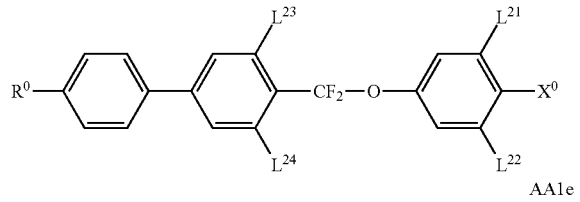

AA1e
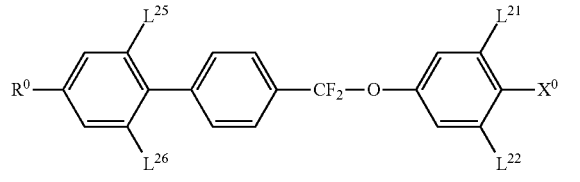

in which $R^0$ has one of the meanings given for $R^{21}$ in formula AA1, $X^0$, $L^{21}$ and $L^{22}$ have the meaning given in formula AA1, $L^{23}$, $L^{24}$, $L^{25}$ and $L^{26}$ are each, independently of one another, H or F, and $X^0$ is preferably F.

Very particularly preferred compounds of formula AA1 are selected from the group consisting of the following subformulae:

AA1a1
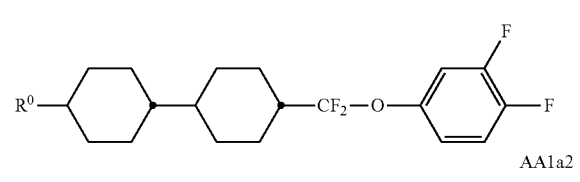

AA1a2
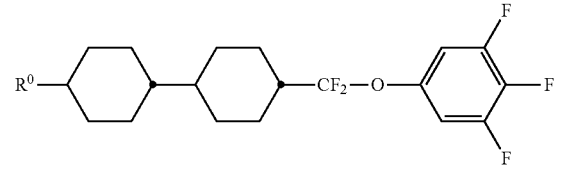

AA1b1
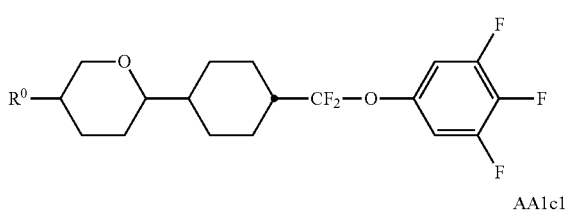

AA1c1
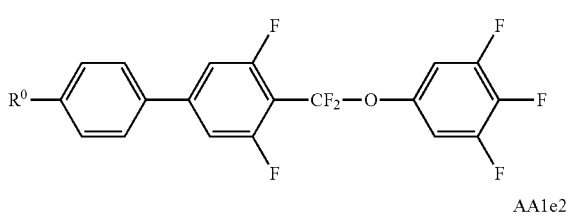

AA1e2
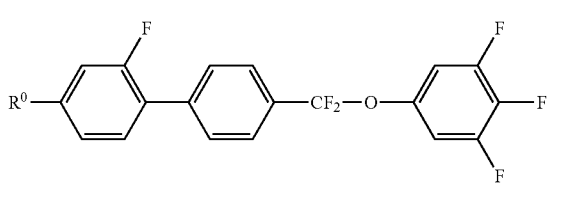

In which $R^0$ has the meaning given for $R^{21}$ in formula AA1.

Very preferred compounds of formula AA2 are selected from the group consisting of the following subformulae:

AA2a
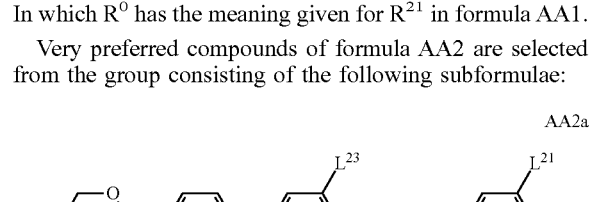

AA2b
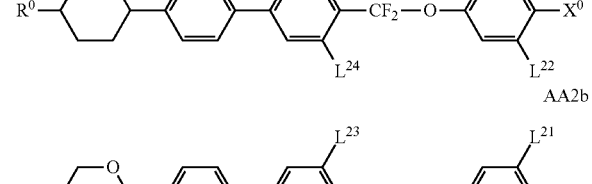

AA2c
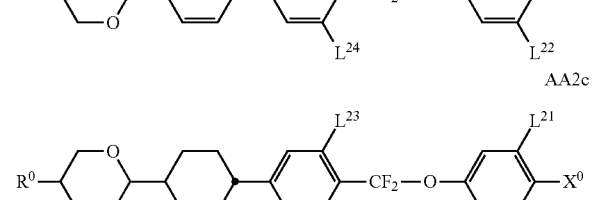

AA2f
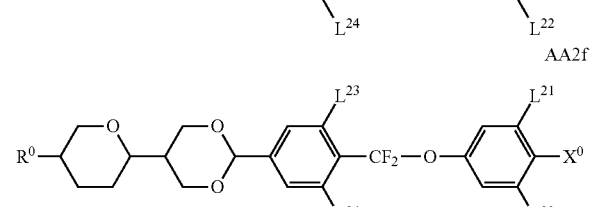

AA2g
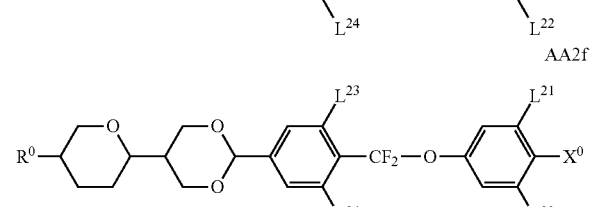

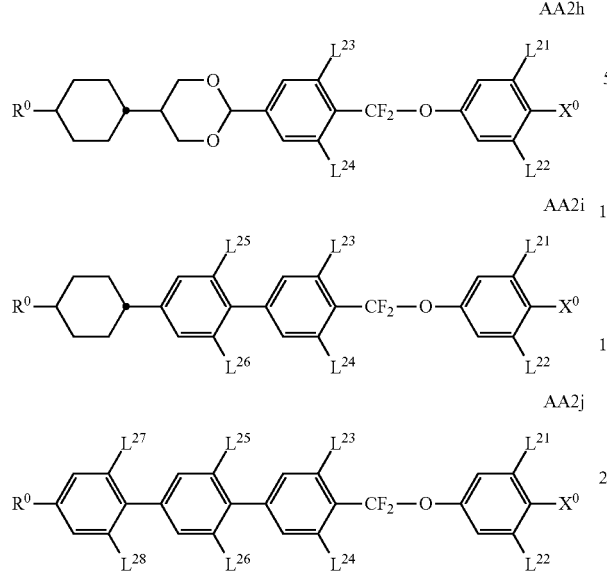

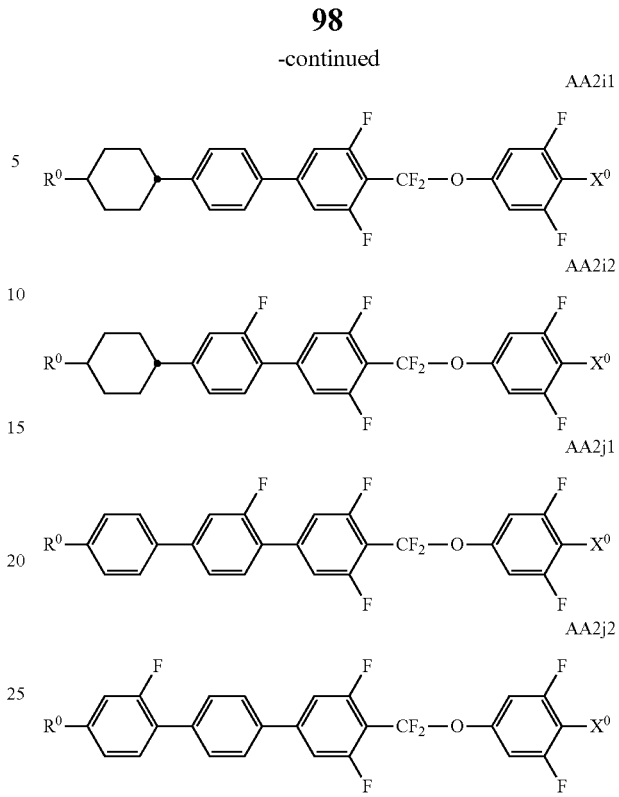

in which $R^0$ has the meaning given for $R^{21}$ in formula AA2, $X^0$, $L^{21}$ and $L^{22}$ have the meaning given in formula AA2, $L^{23}$, $L^{24}$, $L^{25}$, $L^{26}$, $L^{27}$ and $L^{28}$ each, independently of one another, are H or F, and $X^0$ is preferably F.

Very particularly preferred compounds of formula AA2 are selected from the group consisting of the following subformulae:

in which $R^0$ has the meaning given for $R^{21}$ in formula AA2.

Particularly preferred compounds of formula AA3 are selected from the group consisting of the following subformulae:

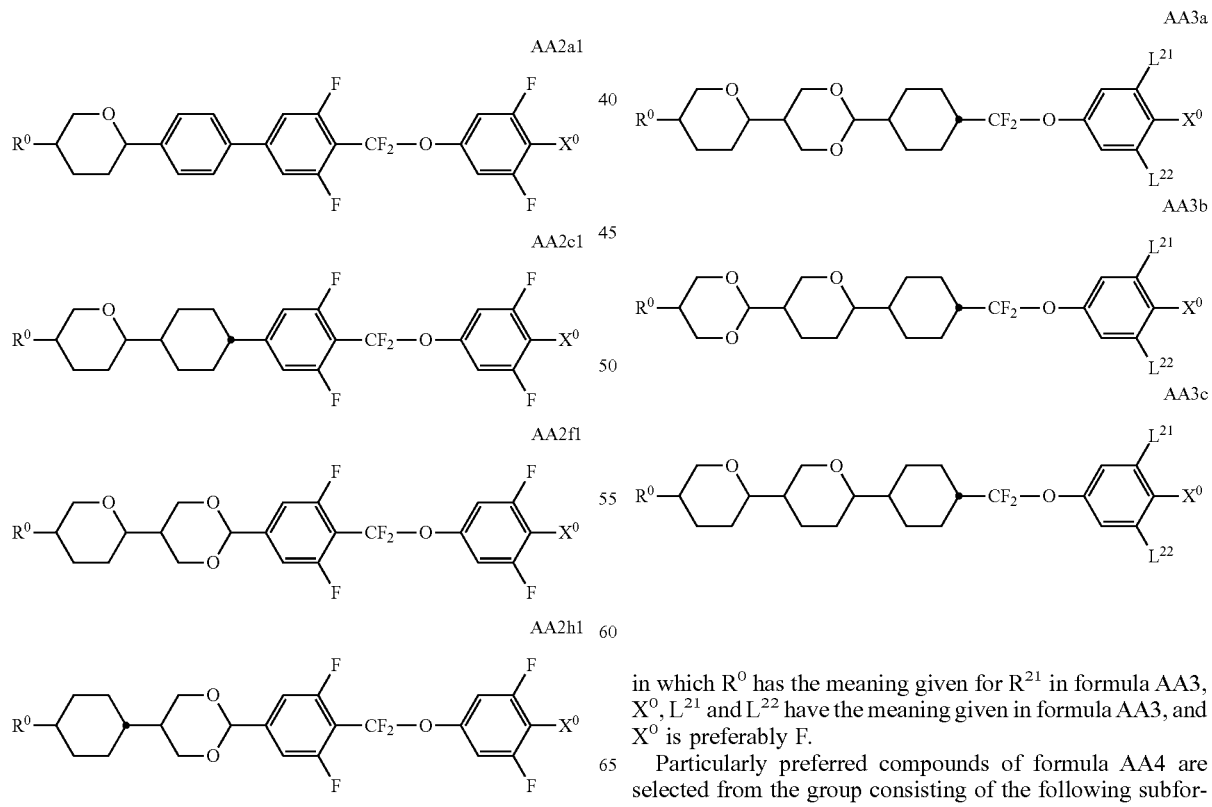

in which $R^0$ has the meaning given for $R^{21}$ in formula AA3, $X^0$, $L^{21}$ and $L^{22}$ have the meaning given in formula AA3, and $X^0$ is preferably F.

Particularly preferred compounds of formula AA4 are selected from the group consisting of the following subformulae:

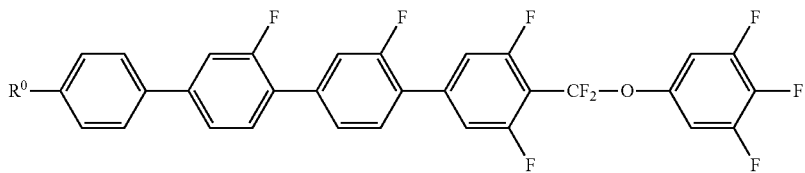
AA4a in which R⁰ has the meaning given for R²¹ in formula AA3.

The compounds of formula BB are preferably selected from the group consisting of the following formulae:

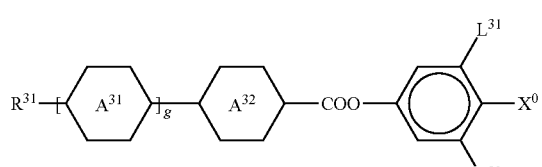
BB1

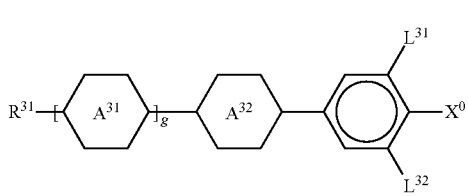
BB2

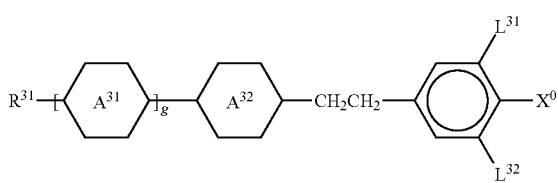
BB3 in which $A^{31}$, $A^{32}$, $R^{31}$, g, $X^0$, $L^{31}$ and $L^{32}$ have the meanings given in formula BB, and $X^0$ is preferably F. Particularly preferred are compounds of formulae BB1 and BB2.

Particularly preferred compounds of formula BB1 are selected from the group consisting of the following subformulae:

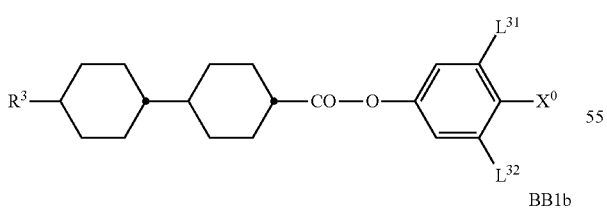
BB1a

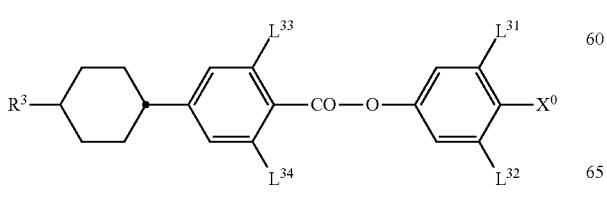
BB1b in which $R^3$ has the meaning given for $R^{31}$ in formula BB1, $X^0$, $L^{31}$ and $L^{32}$ have the meaning given in formula BB1, $L^{33}$ and $L^{34}$ each, independently of one another, are H or F, and $X^0$ is preferably F.

Very particularly preferred compounds of formula BB1a are selected from the group consisting of the following subformulae:

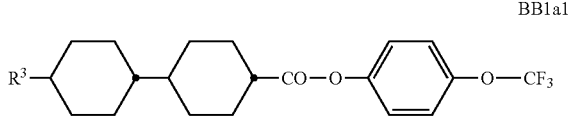
BB1a1

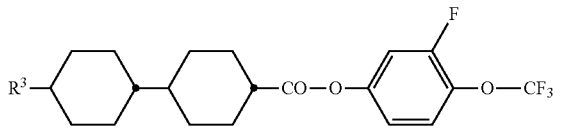
BB1a2

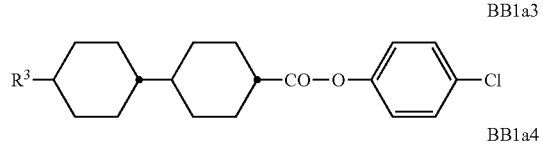
BB1a3

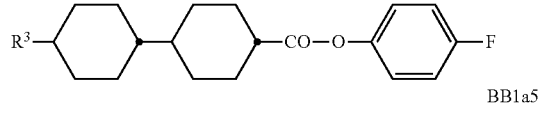
BB1a4

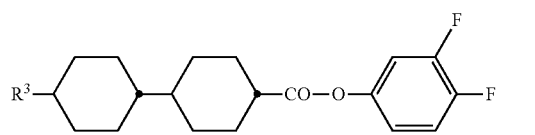
BB1a5

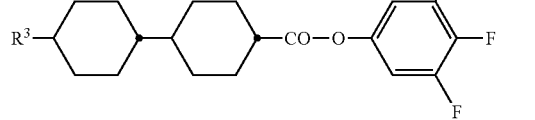
BB1a6 in which $R^3$ has the meaning given for $R^{31}$ in formula BB1.

Very particularly preferred compounds of formula BB1b are selected from the group consisting of the following subformulae:

BB1b1

-continued

BB1b2
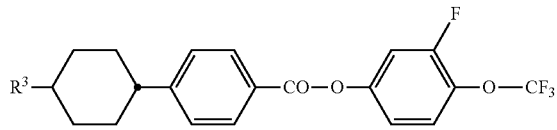

BB1b3
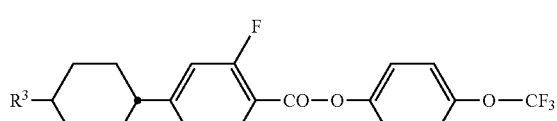

BB1b4
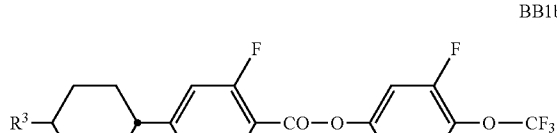

in which R³ has the meaning given for R³¹ in formula BB1.

Particularly preferred compounds of formula BB2 are selected from the group consisting of the following subformulae:

BB2a
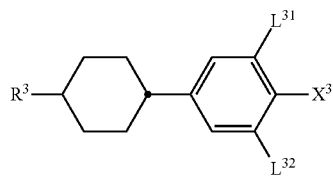

BB2b
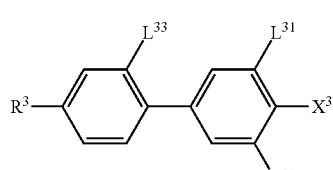

BB2c
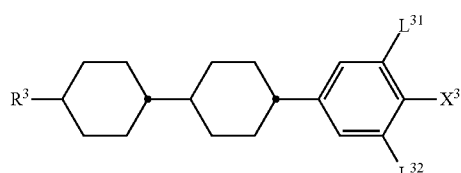

BB2d
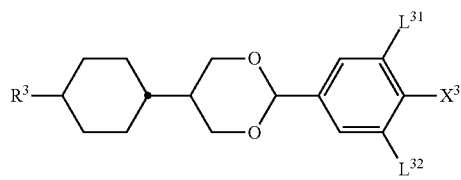

BB2e
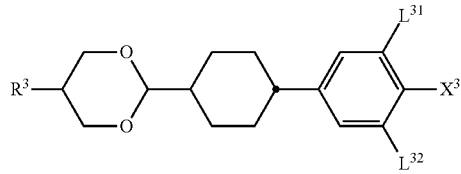

-continued

BB2f, BB2g, BB2h, BB2i, BB2k
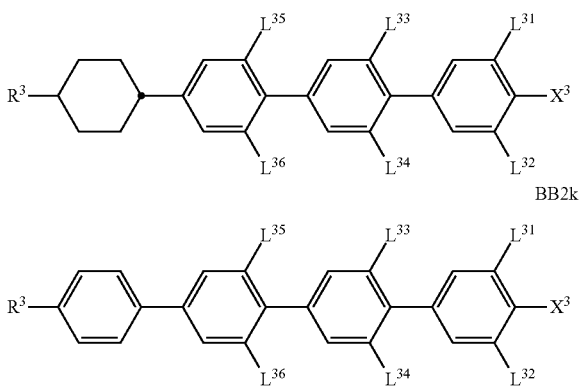

in which $R^3$ has one of the meanings given for $R^{21}$ in formula BB2, $X^3$ has one of the meanings given for $X^0$ in formula BB2, $X^0$, $L^{31}$ and $L^{32}$ have the meaning given in formula BB2, $L^{33}$, $L^{34}$, $L^{35}$ and $L^{36}$ are each, independently of one another, H or F, and $X^3$ is preferably F.

Very particularly preferred compounds of formula BB2 are selected from the group consisting of the following subformulae:

BB2a1
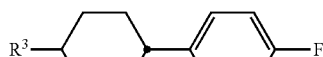

BB2a2

BB2a3
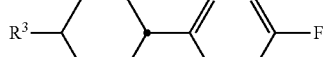

-continued

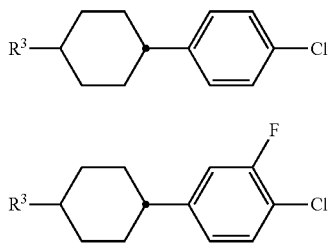

BB2a4

BB2a5 in which $R^3$ has the meaning given for $R^{31}$ in formula BB2.

Very particularly preferred compounds of formula BB2b are selected from the group consisting of the following subformulae

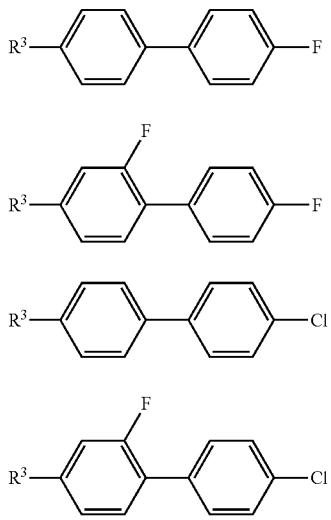

BB2b1

BB2b2

BB2b3

BB2b4 in which $R^3$ has the meaning given for $R^{31}$ in formula BB2.

Very particularly preferred compounds of formula BB2c are selected from the group consisting of the following subformulae:

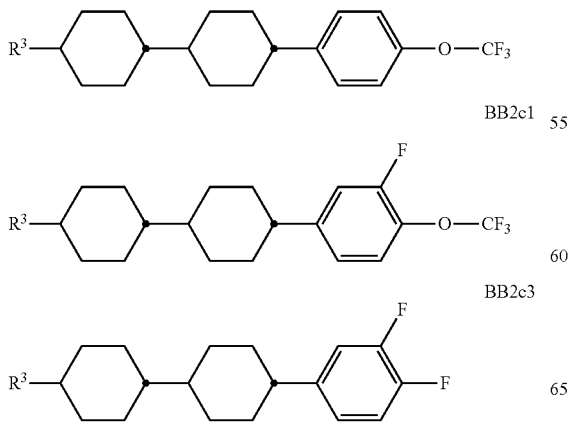

BB2c1

BB2c1

BB2c3

-continued

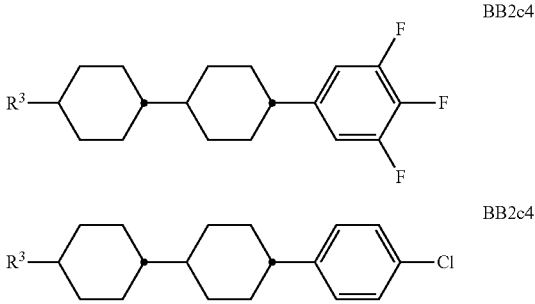

BB2c4

BB2c4 in which $R^3$ has the meaning given for $R^{31}$ in formula BB2.

Very particularly preferred compounds of formula BB2d and BB2e are selected from the group consisting of the following subformulae:

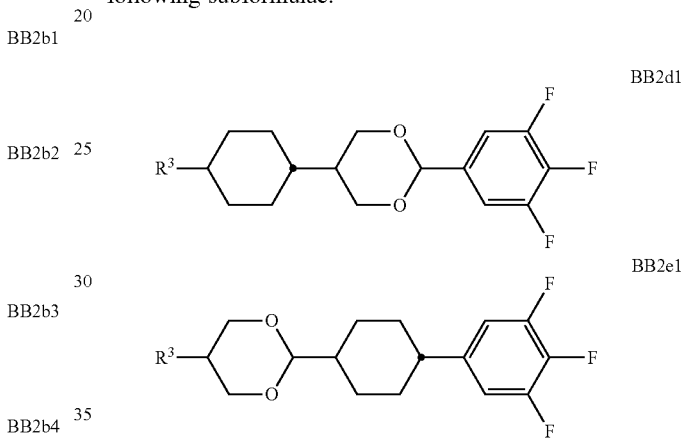

BB2d1

BB2e1 in which $R^3$ has the meaning given for $R^{31}$ in formula BB2.

Very particularly preferred compounds of formula BB2f are selected from the group consisting of the following subformulae:

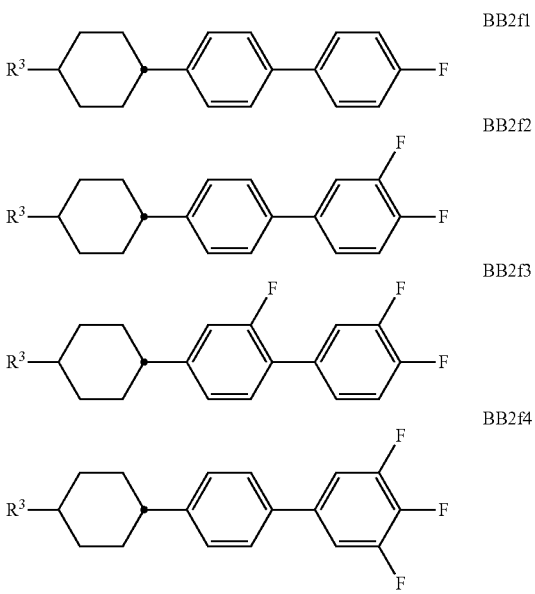

BB2f1

BB2f2

BB2f3

BB2f4

BB2f4

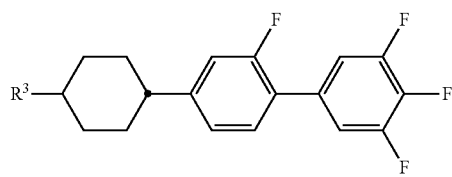

in which R³ has the meaning given for R³¹ in formula BB2.

Very particularly preferred compounds of formula BB2g are selected from the group consisting of the following subformulae:

BB2g1

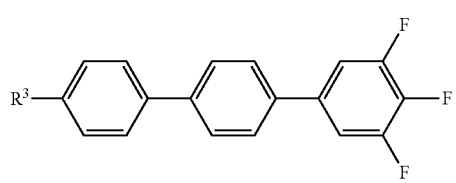

BB2g2

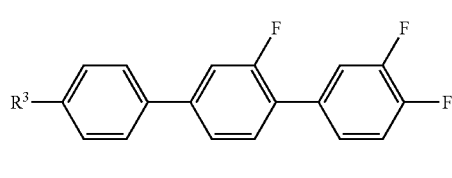

BB2g3

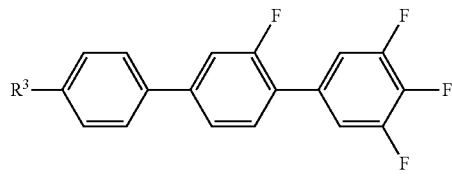

BB2g4

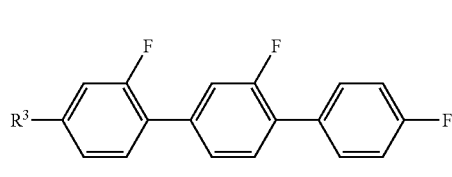

BB2g5

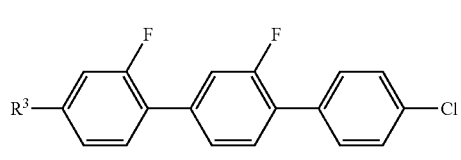

in which R³ has the meaning given for R³¹ in formula BB2.

Very particularly preferred compounds of formula BB2h are selected from the group consisting of the following subformulae:

BB2h1

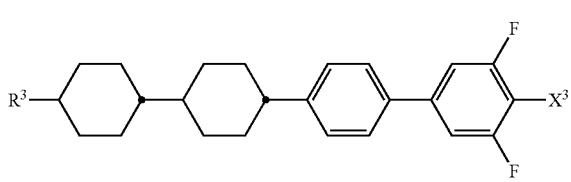

BB2h2

(structure)

BB2h3

(structure)

in which R³ has the meaning given for R³¹ in formula BB2, and X³ has one of the meanings given for X⁰ in formula BB2.

Very particularly preferred compounds of formula BB2l are selected from the group consisting of the following subformulae:

BB2i1

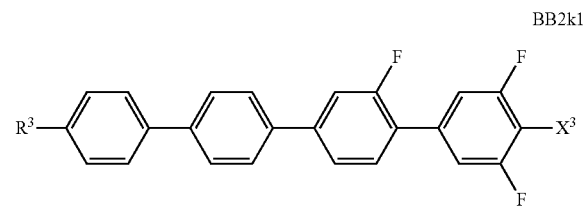

BB2i2

(structure)

in which R³ has the meaning given for R³¹ in formula BB2, and X³ has one of the meanings given for X⁰ in formula BB2.

Very particularly preferred compounds of formula BB2k are selected from the group consisting of the following subformulae:

BB2k1

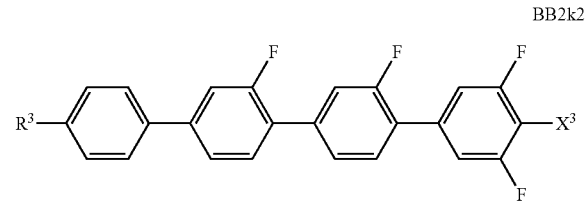

BB2k2

(structure)

in which R³ has the meaning given for R³¹ in formula BB2, and X³ has one of the meanings given for X⁰ in formula BB2.

Alternatively to, or in addition to, the compounds of formula BB1 and/or BB2 the LC media may also comprise one or more compounds of formula BB3 as defined above.

Particularly preferred compounds of formula BB3 are selected from the group consisting of the following subformulae:

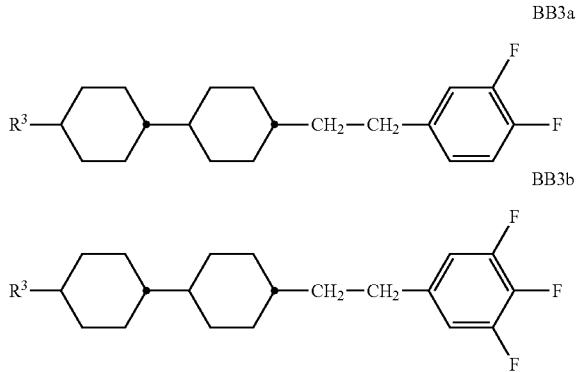

in which R³ has the meaning given for R³¹ in formula BB3.

Preferably the LC media according to this second preferred embodiment comprise, in addition to the compounds of formula AA and/or BB, one or more dielectrically neutral compounds having a dielectric anisotropy in the range from −1.5 to +3, preferably selected from the group of compounds of formula CC as defined above.

Particularly preferred compounds of formula CC are selected from the group consisting of the following subformulae:

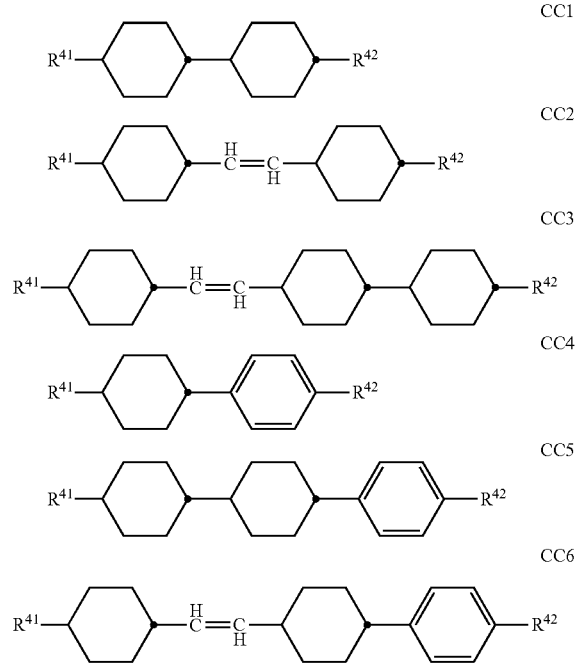

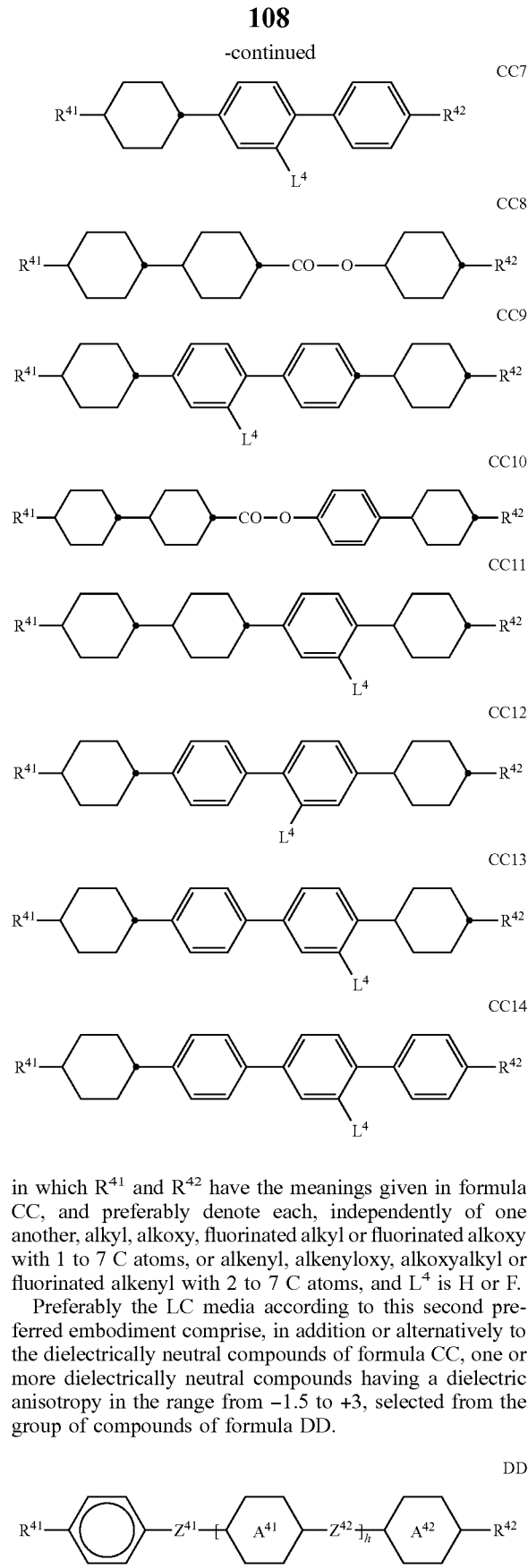

in which $R^{41}$ and $R^{42}$ have the meanings given in formula CC, and preferably denote each, independently of one another, alkyl, alkoxy, fluorinated alkyl or fluorinated alkoxy with 1 to 7 C atoms, or alkenyl, alkenyloxy, alkoxyalkyl or fluorinated alkenyl with 2 to 7 C atoms, and $L^4$ is H or F.

Preferably the LC media according to this second preferred embodiment comprise, in addition or alternatively to the dielectrically neutral compounds of formula CC, one or more dielectrically neutral compounds having a dielectric anisotropy in the range from −1.5 to +3, selected from the group of compounds of formula DD.

In which $A^{41}$, $A^{42}$, $Z^{41}$, $Z^{42}$, $R^{41}$, $R^{42}$ and h have the meanings given in formula CC.

Particularly preferred compounds of formula DD are selected from the group consisting of the following subformulae:

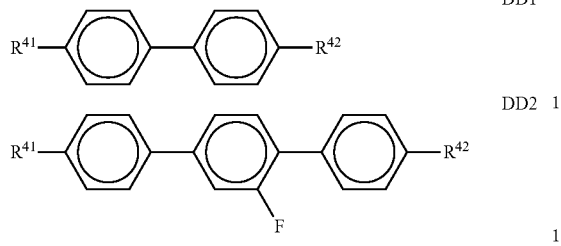

DD1

DD2 in which $R^{41}$ and $R^{42}$ have the meanings given in formula DD and $R^{41}$ preferably denotes alkyl, and in formula DD1 $R^{42}$ preferably denotes alkenyl, particularly preferably —$(CH_2)_2$—CH=CH—$CH_3$, and in formula DD2 $R^{42}$ preferably denotes alkyl, —$(CH_2)_2$—CH=$CH_2$ or —$(CH_2)_2$—CH=CH—$CH_3$.

The compounds of formula AA and BB are preferably used in the LC medium according to the invention in a concentration from 2% to 60%, more preferably from 3% to 35%, and very particularly preferably from 4% to 30% in the mixture as a whole.

The compounds of formula CC and DD are preferably used in the LC medium according to the invention in a concentration from 2% to 70%, more preferably from 5% to 65%, even more preferably from 10% to 60%, and very particularly preferably from 10%, preferably 15%, to 55% in the mixture as a whole.

The combination of compounds of the preferred embodiments mentioned above with the polymerized compounds described above causes low threshold voltages, low rotational viscosities and very good low-temperature stabilities in the LC media according to the invention at the same time as constantly high clearing points and high HR values, and allows the rapid establishment of a particularly low pretilt angle in PSA displays. In particular, the LC media exhibit significantly shortened response times, in particular also the grey-shade response times, in PSA displays compared with the media from the prior art.

The liquid-crystal mixture preferably has a nematic phase range of at least 80 K, particularly preferably at least 100 K, and a rotational viscosity of not greater than 250 mPa·s, preferably not greater than 200 mPa·s, at 20° C.

In the VA-type displays according to the invention, the molecules in the layer of the LC medium in the switched-off state are aligned perpendicular to the electrode surfaces (homeotropically) or have a tilted homeotropic alignment. On application of an electrical voltage to the electrodes, a realignment of the LC molecules takes place with the longitudinal molecular axes parallel to the electrode surfaces.

LC media according to the invention based on compounds with negative dielectric anisotropy according to the first preferred embodiment, in particular for use in displays of the PSA-VA type, have a negative dielectric anisotropy $\Delta\in$, preferably from −0.5 to −10, in particular from −2.5 to −7.5, at 20° C. and 1 kHz.

The birefringence $\Delta n$ in LC media according to the invention for use in displays of the PSA-VA type is preferably below 0.16, particularly preferably from 0.06 to 0.14, very particularly preferably from 0.07 to 0.12.

In the OCB-type displays according to the invention, the molecules in the layer of the LC medium have a "bend" alignment. On application of an electrical voltage, a realignment of the LC molecules takes place with the longitudinal molecular axes perpendicular to the electrode surfaces.

LC media according to the invention for use in displays of the PSA-OCB type are preferably those based on compounds with positive dielectric anisotropy according to the second preferred embodiment, and preferably have a positive dielectric anisotropy $\Delta\in$ from +4 to +17 at 20° C. and 1 kHz.

The birefringence $\Delta n$ in LC media according to the invention for use in displays of the PSA-OCB type is preferably from 0.14 to 0.22, particularly preferably from 0.16 to 0.22.

LC media according to the invention, based on compounds with positive dielectric anisotropy according to the second preferred embodiment, for use in displays of the PSA-TN-, PSA-posi-VA-, PSA-IPS- or PSA-FFS-type, preferably have a positive dielectric anisotropy $\Delta\in$ from +2 to +30, particularly preferably from +3 to +20, at 20° C. and 1 kHz.

The birefringence $\Delta n$ in LC media according to the invention for use in displays of the PSA-TN-, PSA-posi-VA-, PSA-IPS- or PSA-FFS-type is preferably from 0.07 to 0.15, particularly preferably from 0.08 to 0.13.

The LC media according to the invention may also comprise further additives which are known to the person skilled in the art and are described in the literature, such as, for example, polymerization initiators, inhibitors, stabilizers, surface-active substances or chiral dopants. These may be polymerizable or non-polymerizable. Polymerizable additives are accordingly ascribed to the polymerizable component or component A). Non-polymerizable additives are accordingly ascribed to the non-polymerizable component or component B).

In a preferred embodiment the LC media contain one or more chiral dopants, preferably in a concentration from 0.01 to 1%, very preferably from 0.05 to 0.5%. The chiral dopants are preferably selected from the group consisting of compounds from Table B below, very preferably from the group consisting of R- or S-1011, R- or S-2011, R- or S-3011, R- or S-4011, and R- or S-5011.

In another preferred embodiment the LC media contain a racemate of one or more chiral dopants, which are preferably selected from the chiral dopants mentioned in the previous paragraph.

Furthermore, it is possible to add to the LC media, for example, 0 to 15% by weight of pleochroic dyes, furthermore nanoparticles, conductive salts, preferably ethyldimethyldodecylammonium 4-hexoxybenzoate, tetrabutylammonium tetraphenylborate or complex salts of crown ethers (cf., for example, Haller et al., Mol. Cryst. Liq. Cryst. 24, 249-258 (1973)), for improving the conductivity, or substances for modifying the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

The individual components of the preferred embodiments a)-z) of the LC media according to the invention are either known or methods for the preparation thereof can readily be derived from the prior art by the person skilled in the relevant art, since they are based on standard methods described in the literature. Corresponding compounds of the formula CY are described, for example, in EP-A-0 364 538.

Corresponding compounds of the formula ZK are described, for example, in DE-A-26 36 684 and DE-A-33 21 373.

The LC media which can be used in accordance with the invention are prepared in a manner conventional per se, for example by mixing one or more of the above-mentioned compounds with one or more polymerizable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

It goes without saying to the person skilled in the art that the LC media according to the invention may also comprise compounds in which, for example, H, N, O, Cl, F have been replaced by the corresponding isotopes.

The structure of the LC displays according to the invention corresponds to the usual geometry for PSA displays, as described in the prior art cited at the outset. Geometries without protrusions are preferred, in particular those in which, in addition, the electrode on the color filter side is unstructured and only the electrode on the TFT side has slots. Particularly suitable and preferred electrode structures for PSA-VA displays are described, for example, in US 2006/0066793 A1.

The following examples explain the present invention without restricting it. However, they show the person skilled in the art preferred mixture concepts with compounds preferably to be employed and the respective concentrations thereof and combinations thereof with one another. In addition, the examples illustrate which properties and property combinations are accessible.

The following abbreviations are used:
(m, m, z: in each case, independently of one another, 1, 2, 3, 4, 5 or 6)

TABLE A

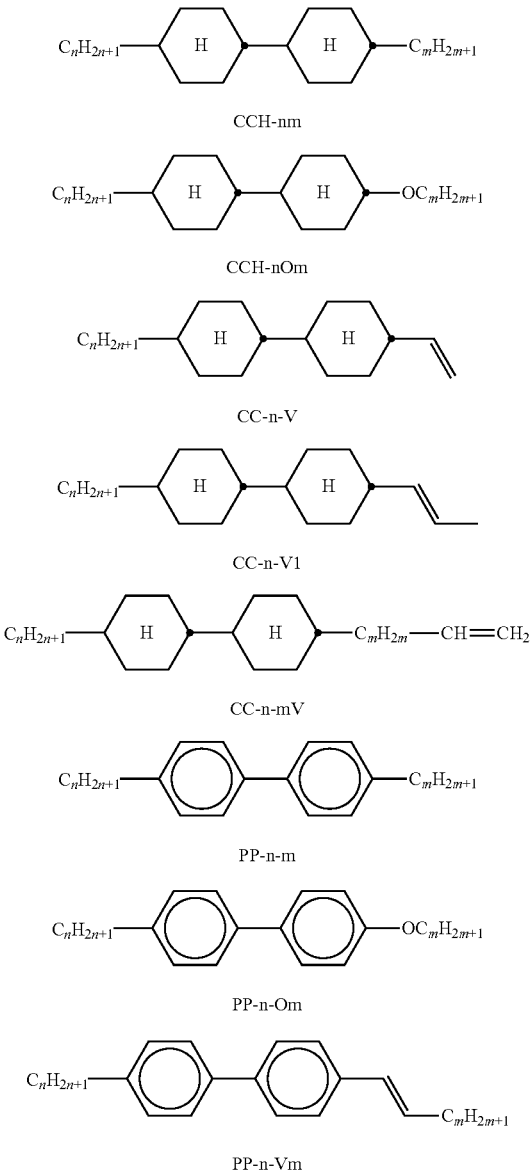

TABLE A-continued
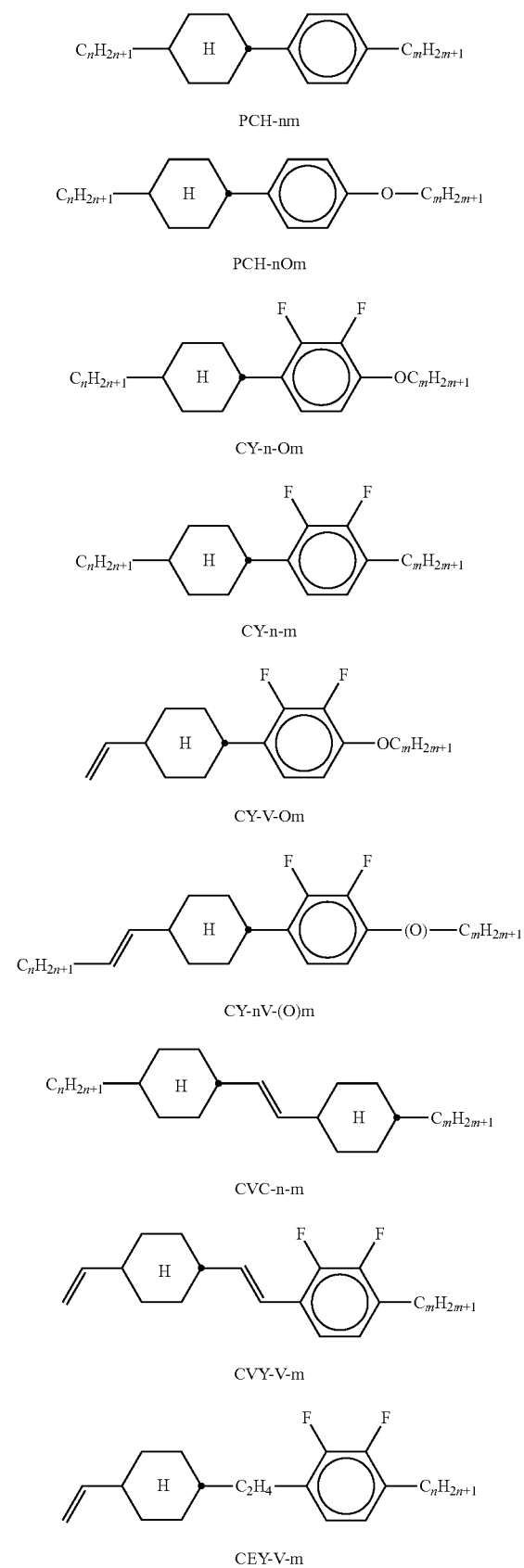

TABLE A-continued
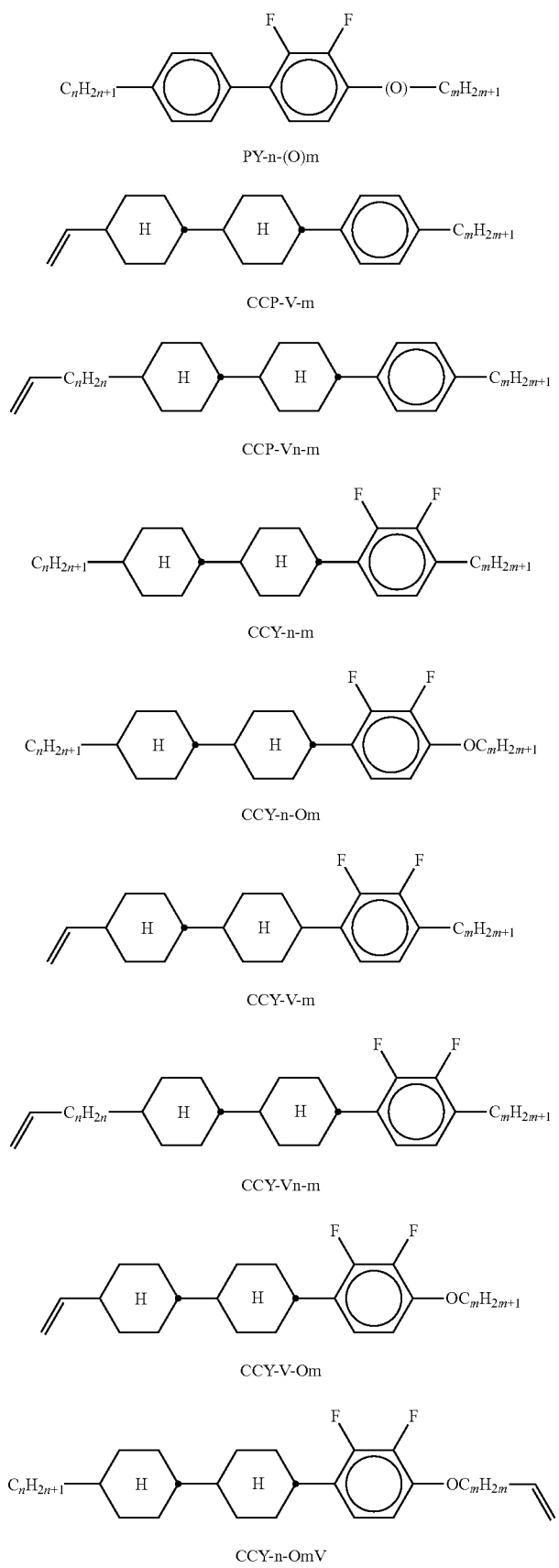

TABLE A-continued
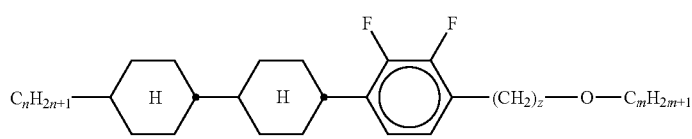
CCY-n-zOm
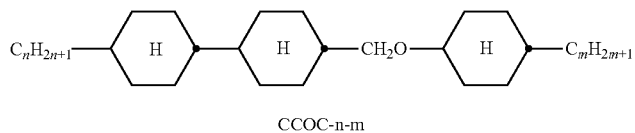
CCOC-n-m
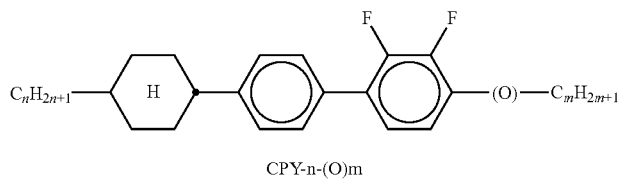
CPY-n-(O)m
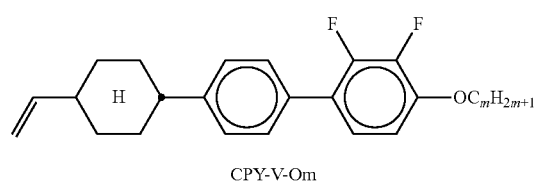
CPY-V-Om
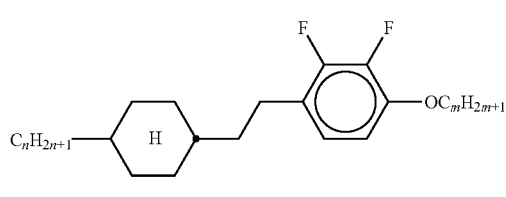
CEY-n-Om
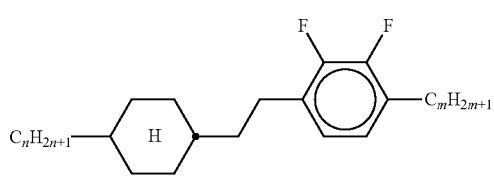
CEY-n-m
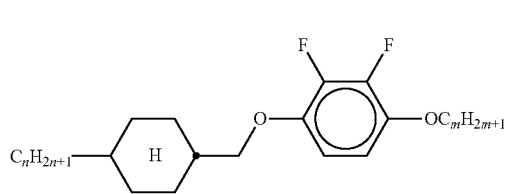
COY-n-Om
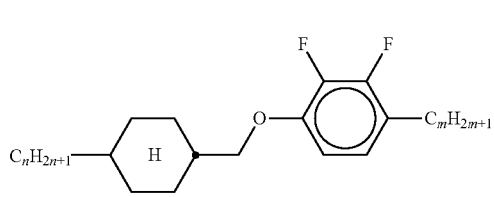
COY-n-m TABLE A-continued
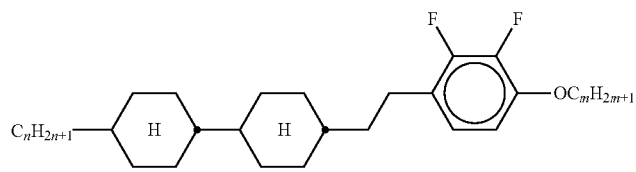
CCEY-n-Om
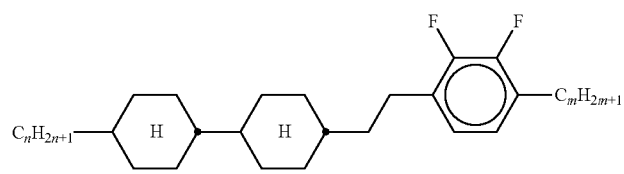
CCEY-n-m
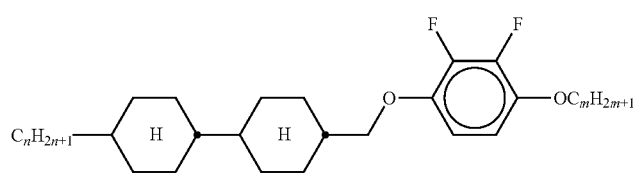
CCOY-n-Om
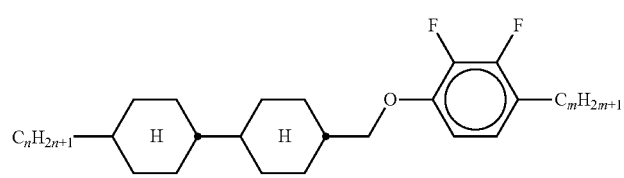
CCOY-n-m
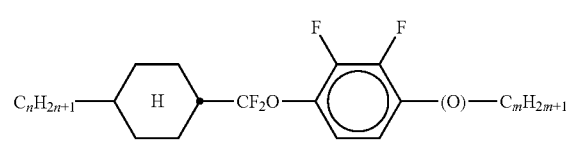
CQY-n-(O)m
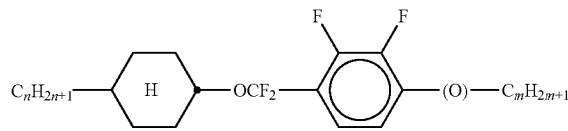
CQIY-n-(O)m
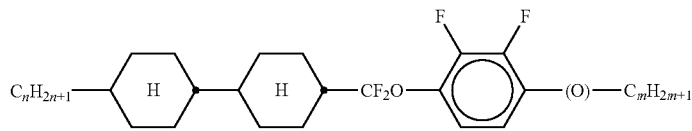
CCQY-n-(O)m
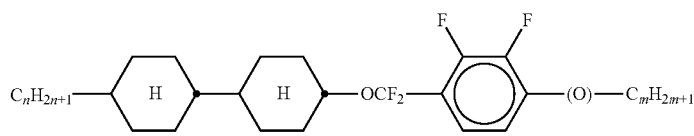
CCQIY-n-(O)m TABLE A-continued
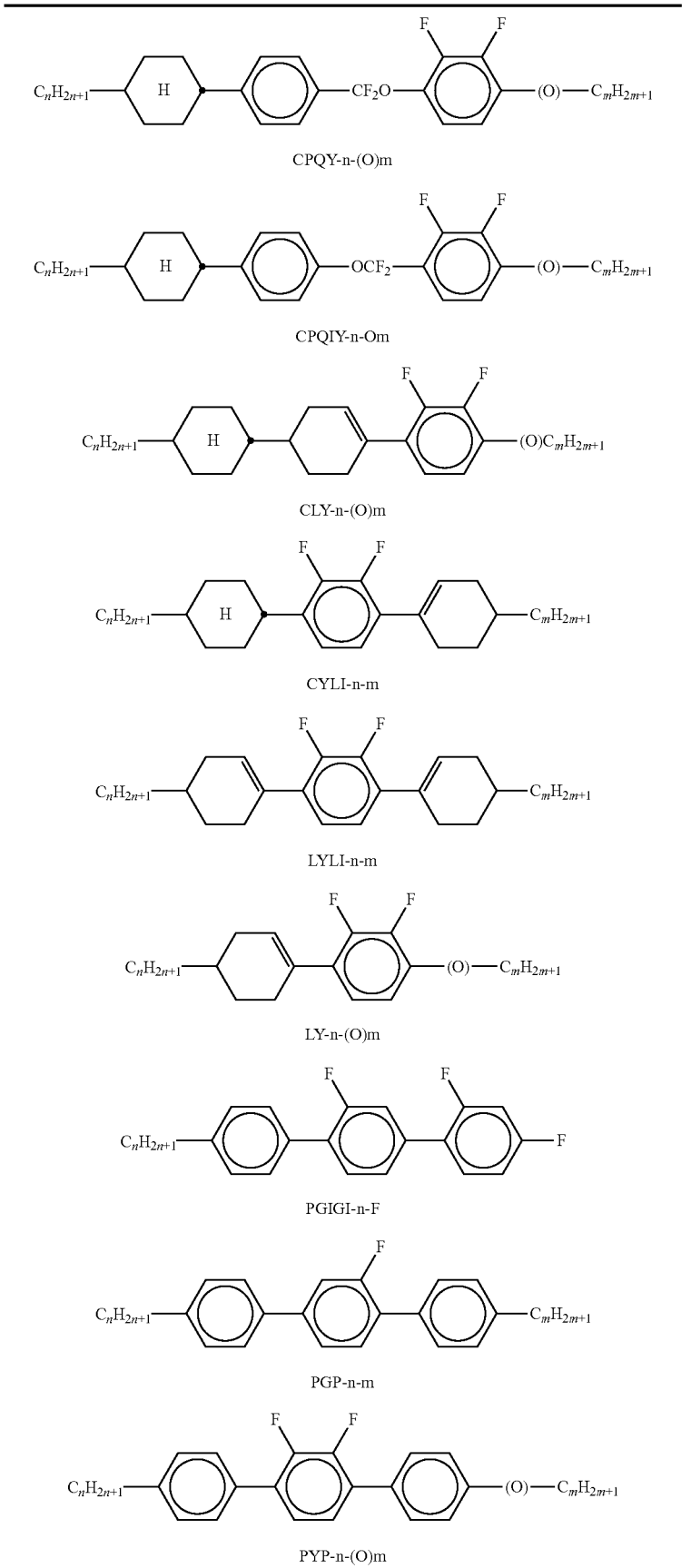

TABLE A-continued
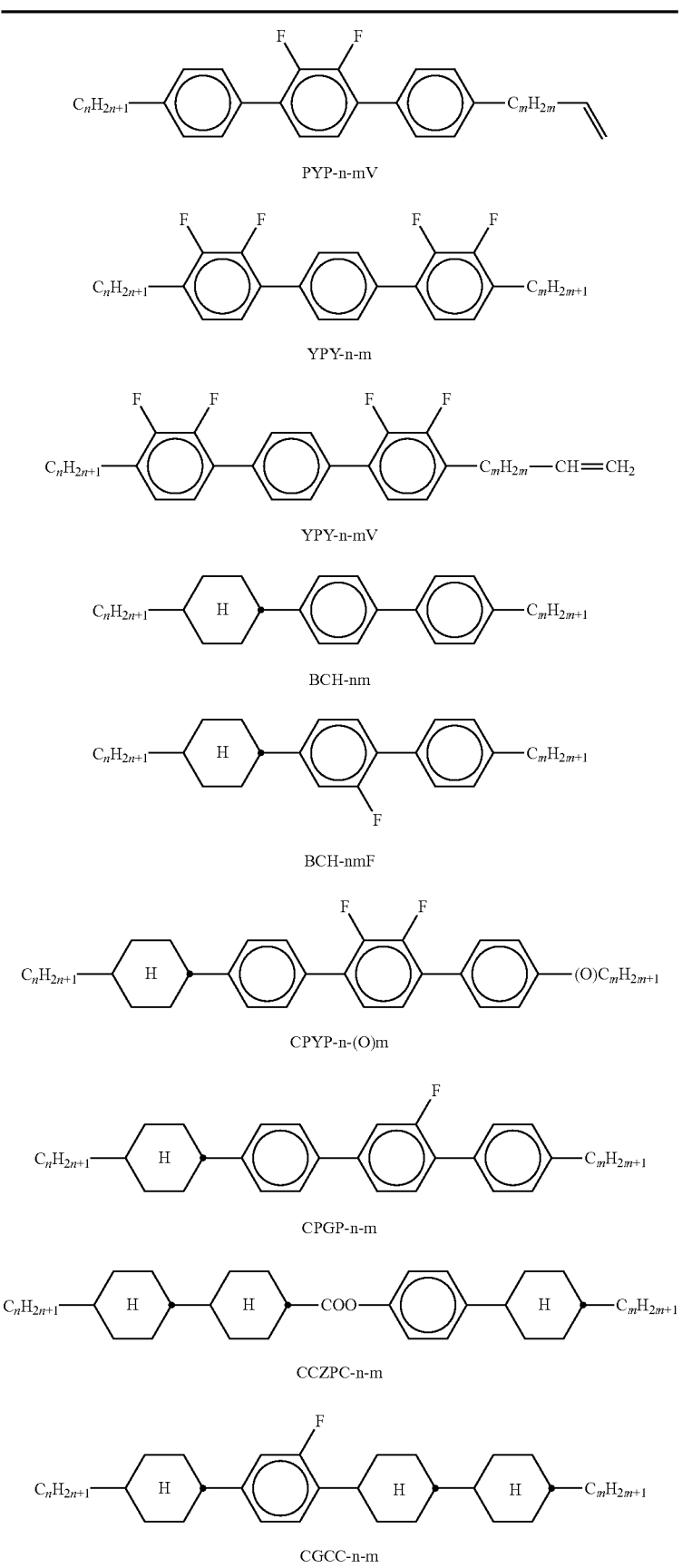

TABLE A-continued
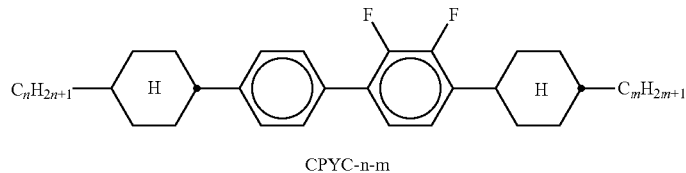
CPYC-n-m
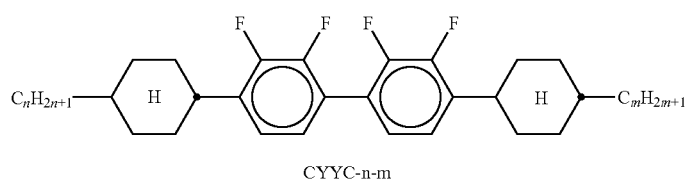
CYYC-n-m
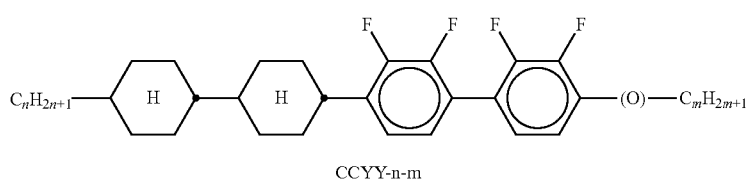
CCYY-n-m
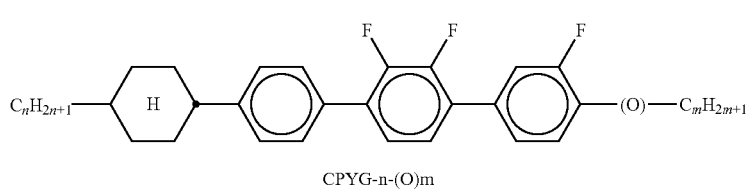
CPYG-n-(O)m
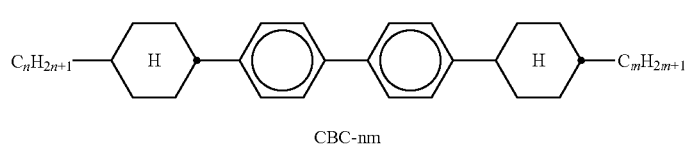
CBC-nm
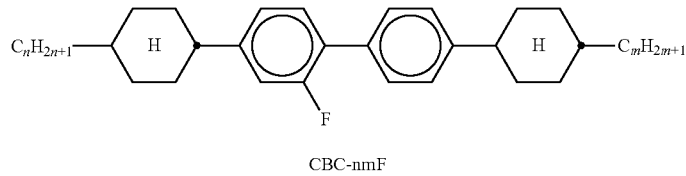
CBC-nmF
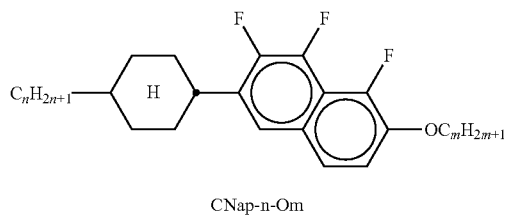
CNap-n-Om
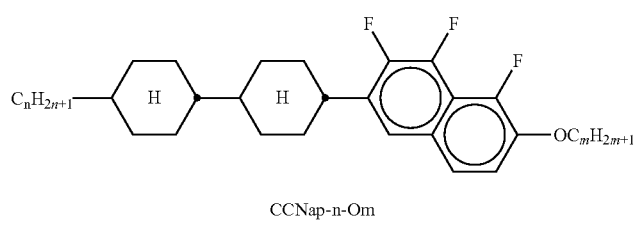
CCNap-n-Om TABLE A-continued

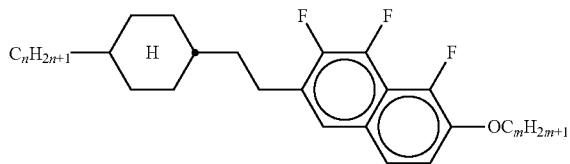

CENap-n-Om

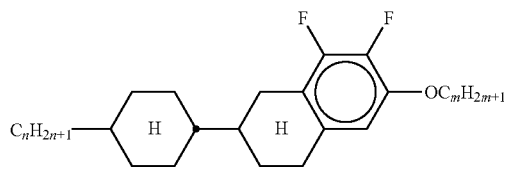

CTNap-n-Om

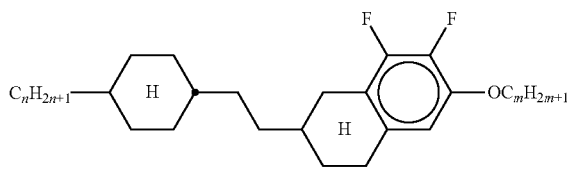

CETNap-n-Om

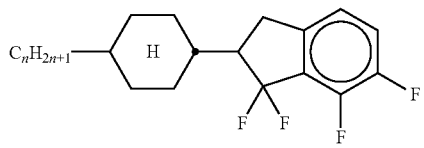

CK-n-F

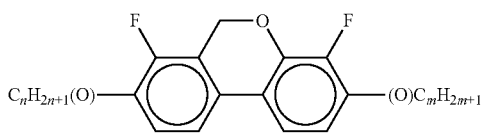

DFDBC-n(O)-(O)m

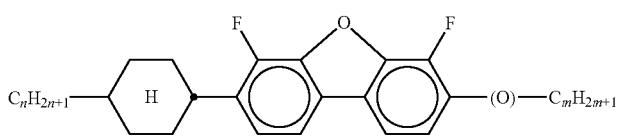

C-DFDBF-n-(O)m

In a preferred embodiment of the present invention, the LC media according to the invention comprise one or more compounds selected from the group consisting of compounds from Table A.

TABLE B

Table B shows possible chiral dopants which can be added to the LC media according to the invention.

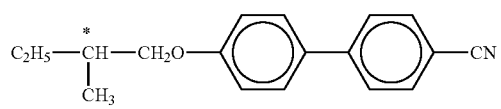

C 15

TABLE B-continued
Table B shows possible chiral dopants which can be added to the LC media according to the invention.
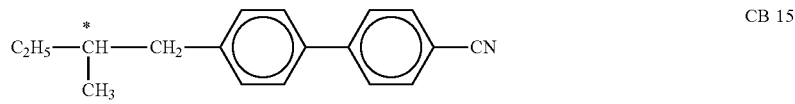
CB 15
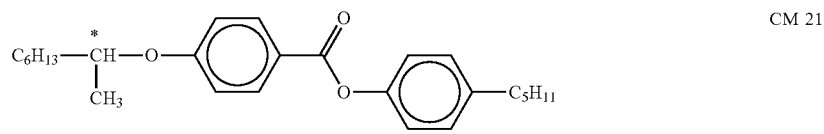
CM 21
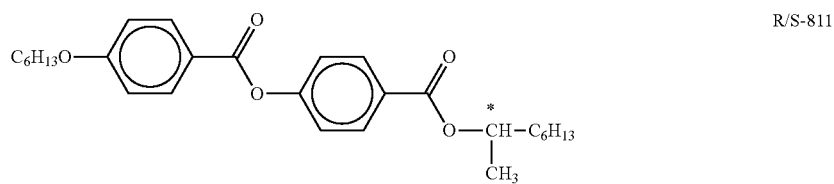
R/S-811
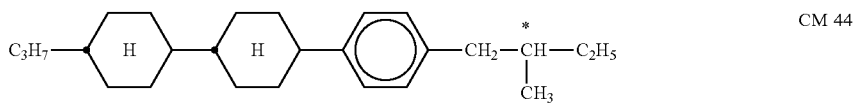
CM 44
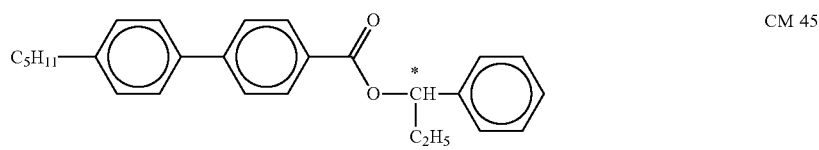
CM 45
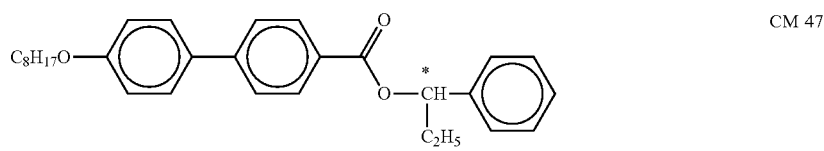
CM 47
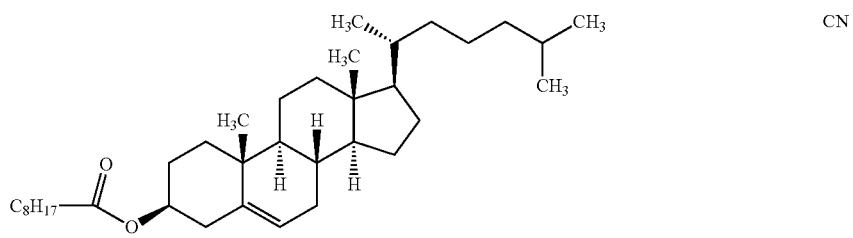
CN
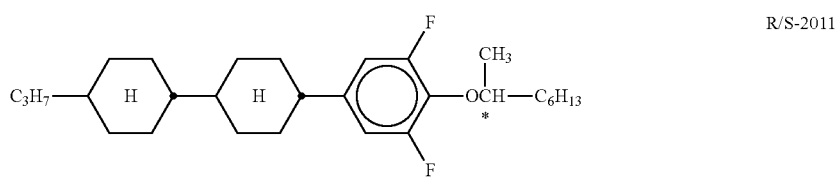
R/S-2011
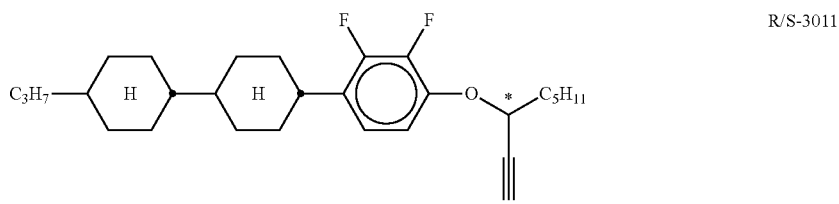
R/S-3011

TABLE B-continued

Table B shows possible chiral dopants which can be added to the LC media according to the invention.

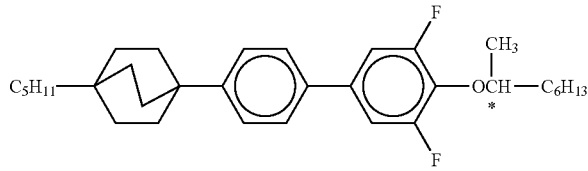

R/S-4011

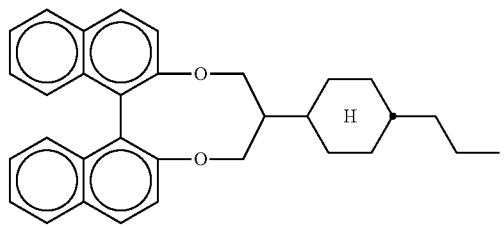

R/S-5011

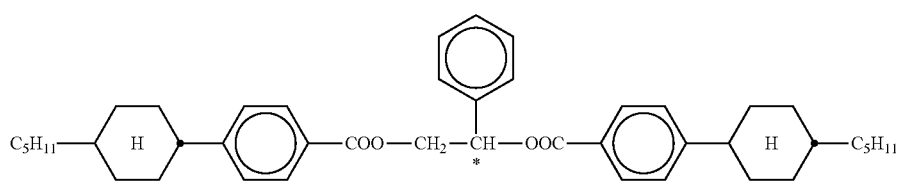

R/S-1011

The LC media preferably comprise 0 to 10% by weight, in particular 0.01 to 5% by weight, particularly preferably 0.1 to 3% by weight, of dopants. The LC media preferably comprise one or more dopants selected from the group consisting of compounds from Table B.

TABLE C

Table C shows possible stabilizers which can be added to the LC media according to the invention.

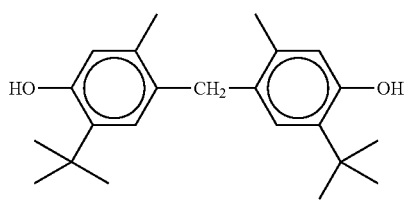

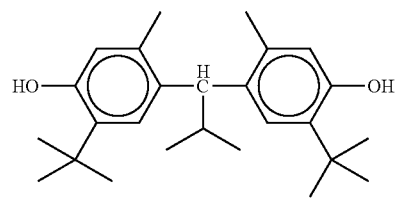

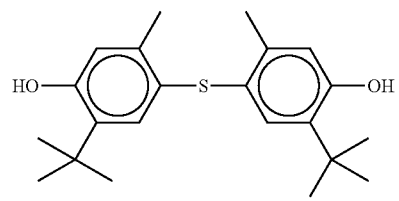

TABLE C-continued
Table C shows possible stabilizers which can be added to the LC media according to the invention.
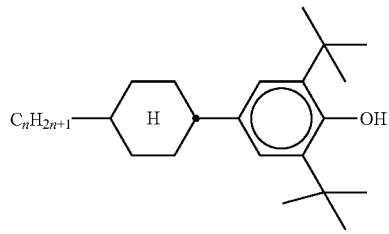
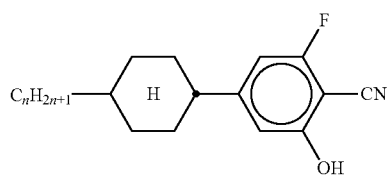
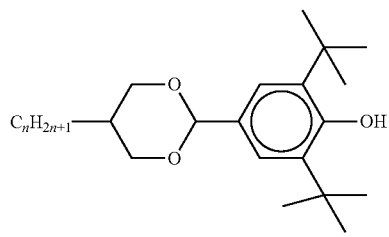
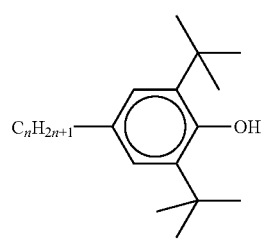
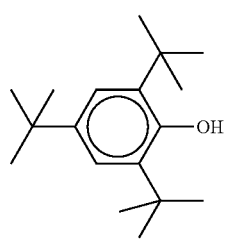
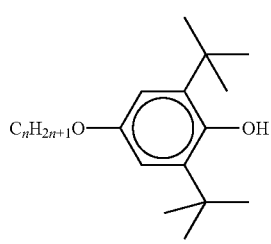

TABLE C-continued
Table C shows possible stabilizers which can be added to the LC media according to the invention.
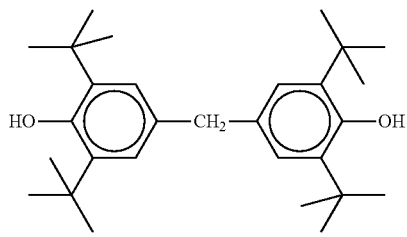
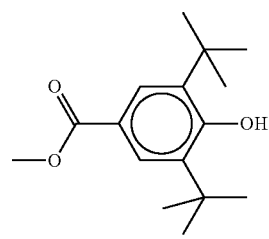
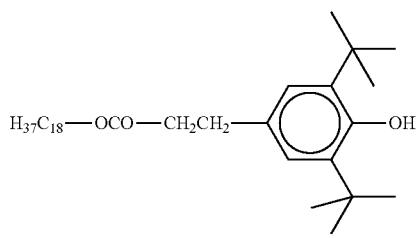
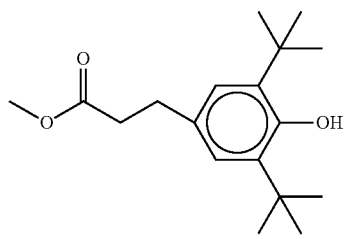
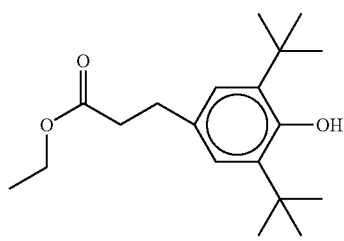
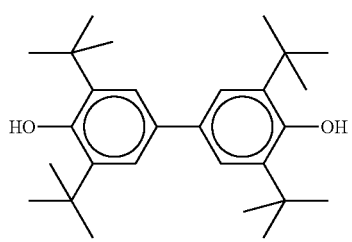

TABLE C-continued
Table C shows possible stabilizers which can be added to the LC media according to the invention.
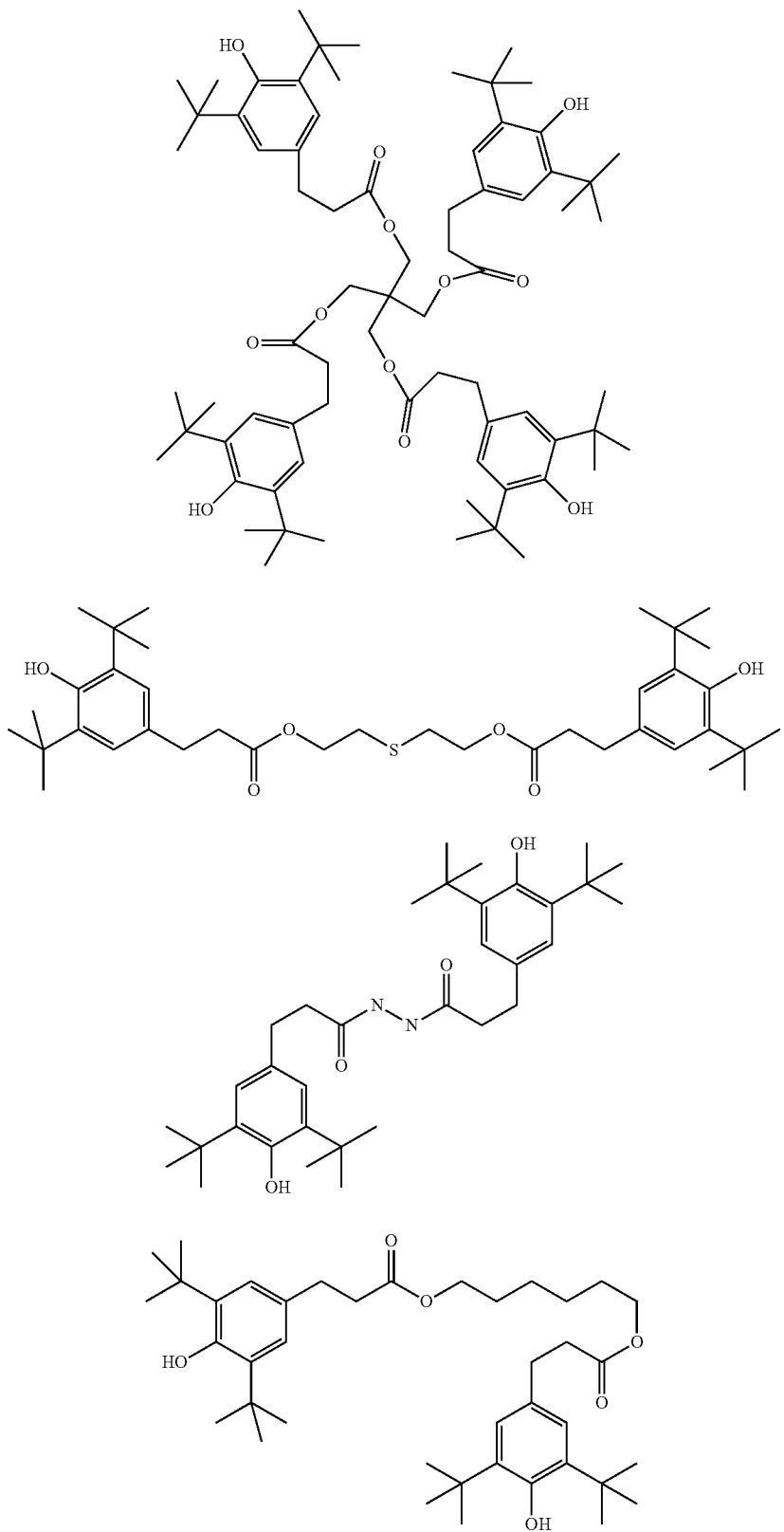

TABLE C-continued
Table C shows possible stabilizers which can be added to the LC media according to the invention.
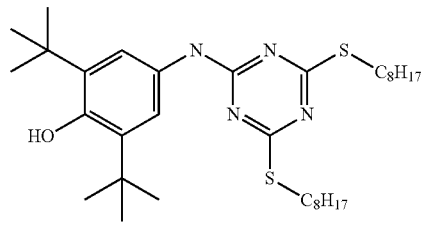
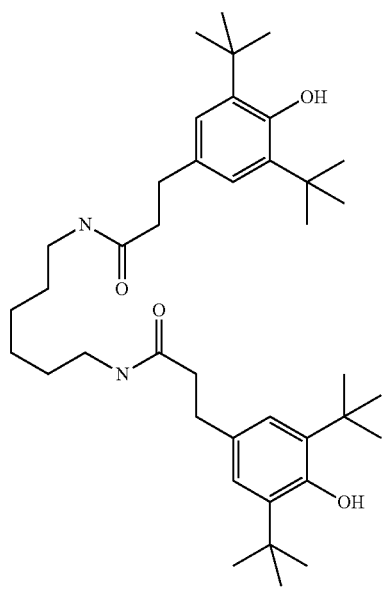 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
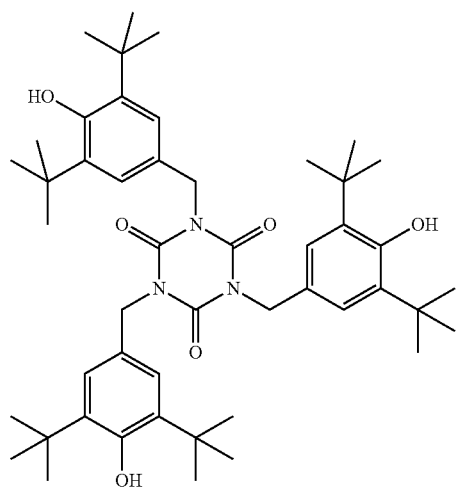 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]

141
TABLE C-continued
Table C shows possible stabilizers which can be added to the LC media according to the invention.
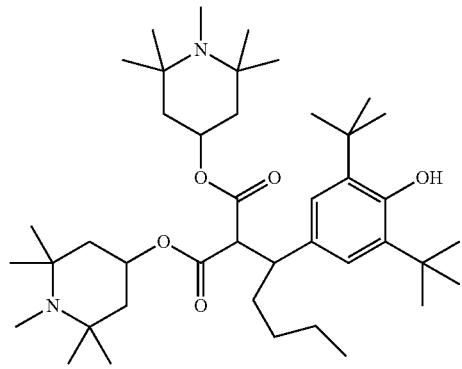 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]
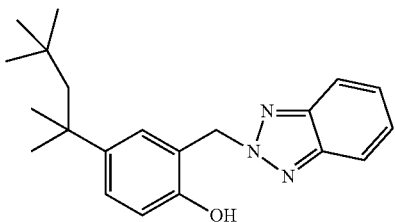 [SMILES: CC(C)(C)CC(C)(C)c1ccc(O)c(Cn2nc3ccccc3n2)c1]
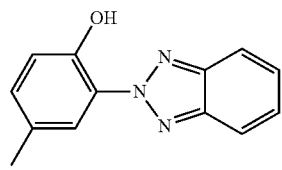 [SMILES: Cc1ccc(O)c(-n2nc3ccccc3n2)c1]
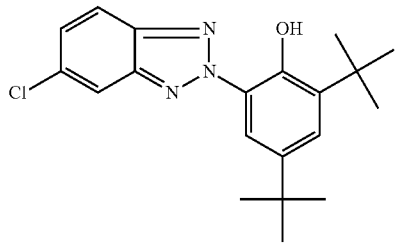 [SMILES: CC(C)(C)c1cc(-n2nc3ccc(Cl)cc3n2)c(O)c(C(C)(C)C)c1]
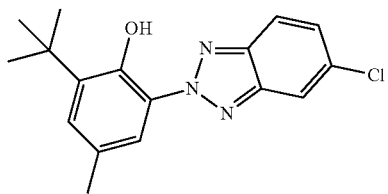 [SMILES: Cc1cc(-n2nc3ccc(Cl)cc3n2)c(O)c(C(C)(C)C)c1]

TABLE C-continued
Table C shows possible stabilizers which can be added to the LC media according to the invention.
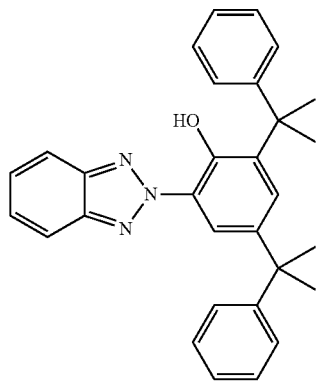 [SMILES: CC(C)(c1ccccc1)c1cc(-n2nc3ccccc3n2)c(O)c(C(C)(C)c2ccccc2)c1]
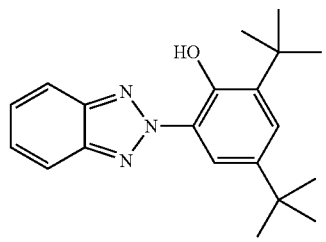 [SMILES: CC(C)(C)c1cc(-n2nc3ccccc3n2)c(O)c(C(C)(C)C)c1]
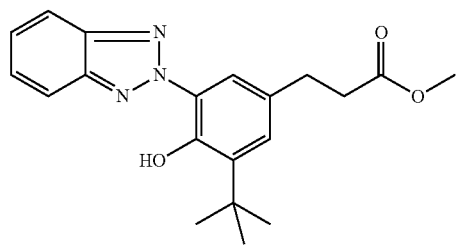 [SMILES: COC(=O)CCc1cc(-n2nc3ccccc3n2)c(O)c(C(C)(C)C)c1]
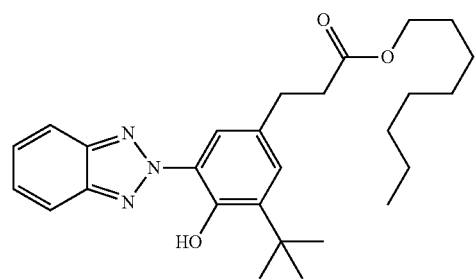 [SMILES: CCCCCCCCOC(=O)CCc1cc(-n2nc3ccccc3n2)c(O)c(C(C)(C)C)c1]

TABLE C-continued
Table C shows possible stabilizers which can be added to the LC media according to the invention.
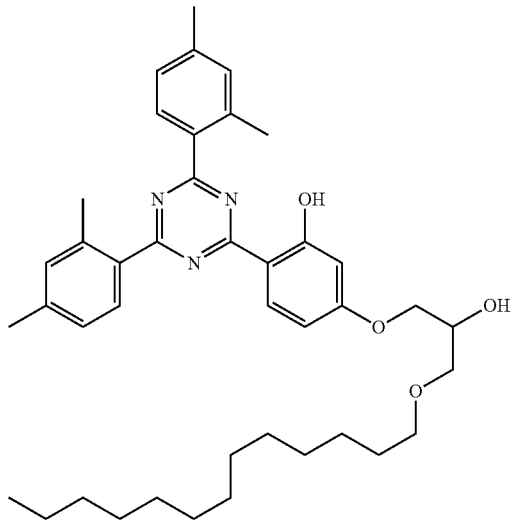 [SMILES: CCCCCCCCCCCCCOCC(O)COc1ccc(-c2nc(-c3ccc(C)cc3C)nc(-c3ccc(C)cc3C)n2)c(O)c1]
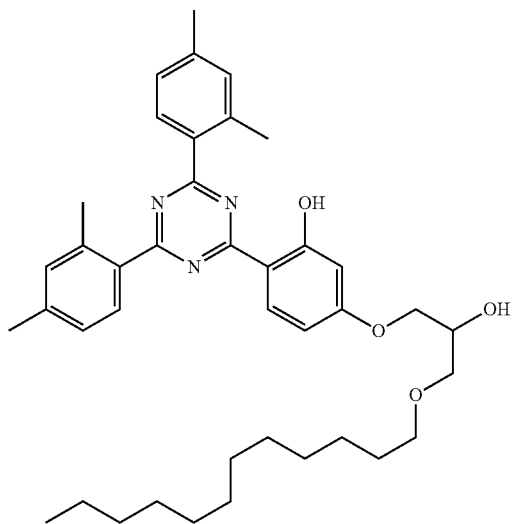 [SMILES: CCCCCCCCCCCCOCC(O)COc1ccc(-c2nc(-c3ccc(C)cc3C)nc(-c3ccc(C)cc3C)n2)c(O)c1]
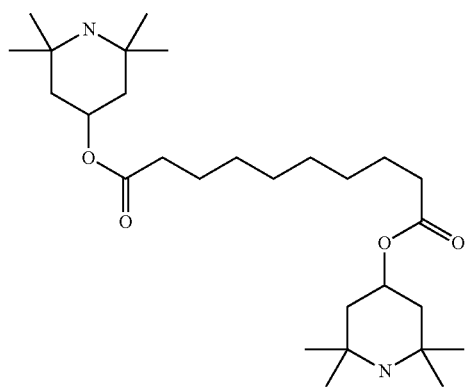

TABLE C-continued

Table C shows possible stabilizers which can be added to the LC media according to the invention.

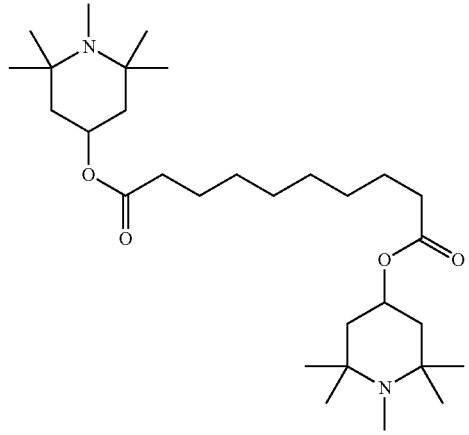

(n here denotes an integer from 1 to 12, preferably 1, 2, 3, 4, 5, 6, 7 or 8, terminal methyl groups are not shown).

The LC media preferably comprise 0 to 10% by weight, in particular 1 ppm to 5% by weight, particularly preferably 1 ppm to 1% by weight, of stabilizers. The LC media preferably comprise one or more stabilizers selected from the group consisting of compounds from Table C.

TABLE D

Table D shows illustrative compounds which can be used in the LC media in accordance with the present invention, preferably as reactive mesogenic compounds.

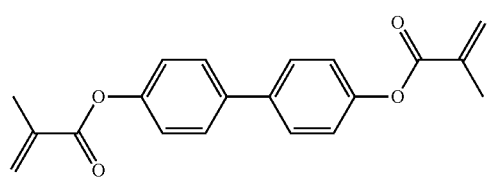 [SMILES: C=C(C)C(=O)Oc1ccc(-c2ccc(OC(=O)C(=C)C)cc2)cc1]
RM-1

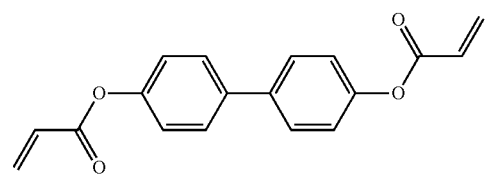 [SMILES: C=CC(=O)Oc1ccc(-c2ccc(OC(=O)C=C)cc2)cc1]
RM-2

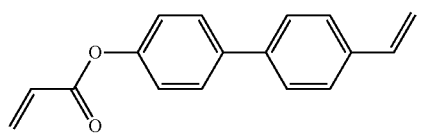 [SMILES: C=CC(=O)Oc1ccc(-c2ccc(C=C)cc2)cc1]
RM-3

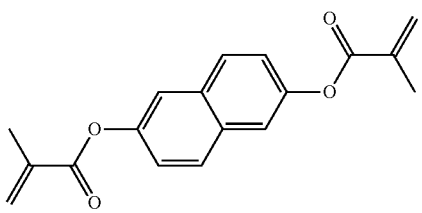 [SMILES: C=C(C)C(=O)Oc1ccc2cc(OC(=O)C(=C)C)ccc2c1]
RM-4

TABLE D-continued
Table D shows illustrative compounds which can be used in the LC media in accordance with the present invention, preferably as reactive mesogenic compounds.
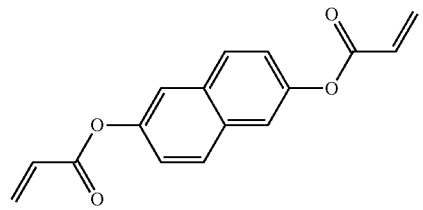 [SMILES: C=CC(=O)Oc1ccc2cc(OC(=O)C=C)ccc2c1]
RM-5
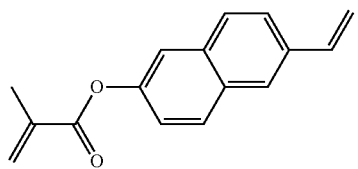 [SMILES: C=Cc1ccc2cc(OC(=O)C(=C)C)ccc2c1]
RM-6
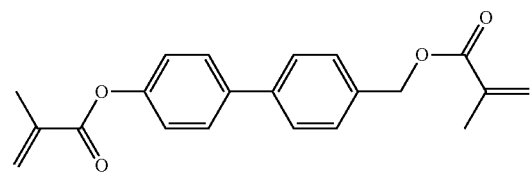 [SMILES: C=C(C)C(=O)OCc1ccc(-c2ccc(OC(=O)C(=C)C)cc2)cc1]
RM-7
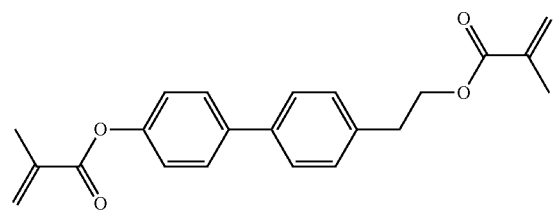 [SMILES: C=C(C)C(=O)OCCc1ccc(-c2ccc(OC(=O)C(=C)C)cc2)cc1]
RM-8
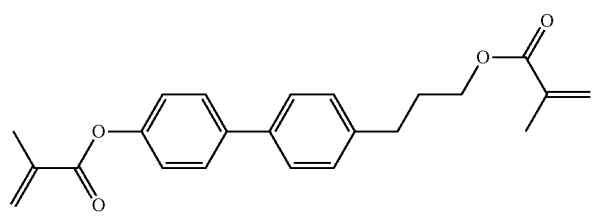 [SMILES: C=C(C)C(=O)OCCCc1ccc(-c2ccc(OC(=O)C(=C)C)cc2)cc1]
RM-9
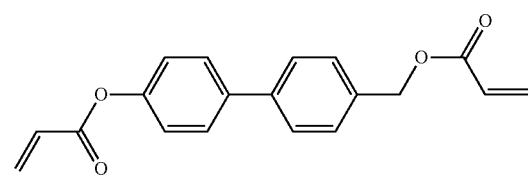 [SMILES: C=CC(=O)OCc1ccc(-c2ccc(OC(=O)C=C)cc2)cc1]
RM-10
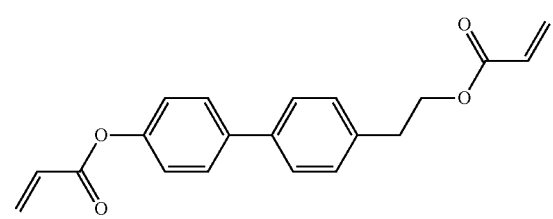 [SMILES: C=CC(=O)OCCc1ccc(-c2ccc(OC(=O)C=C)cc2)cc1]
RM-11

TABLE D-continued
Table D shows illustrative compounds which can be used in the LC media in accordance with the present invention, preferably as reactive mesogenic compounds.
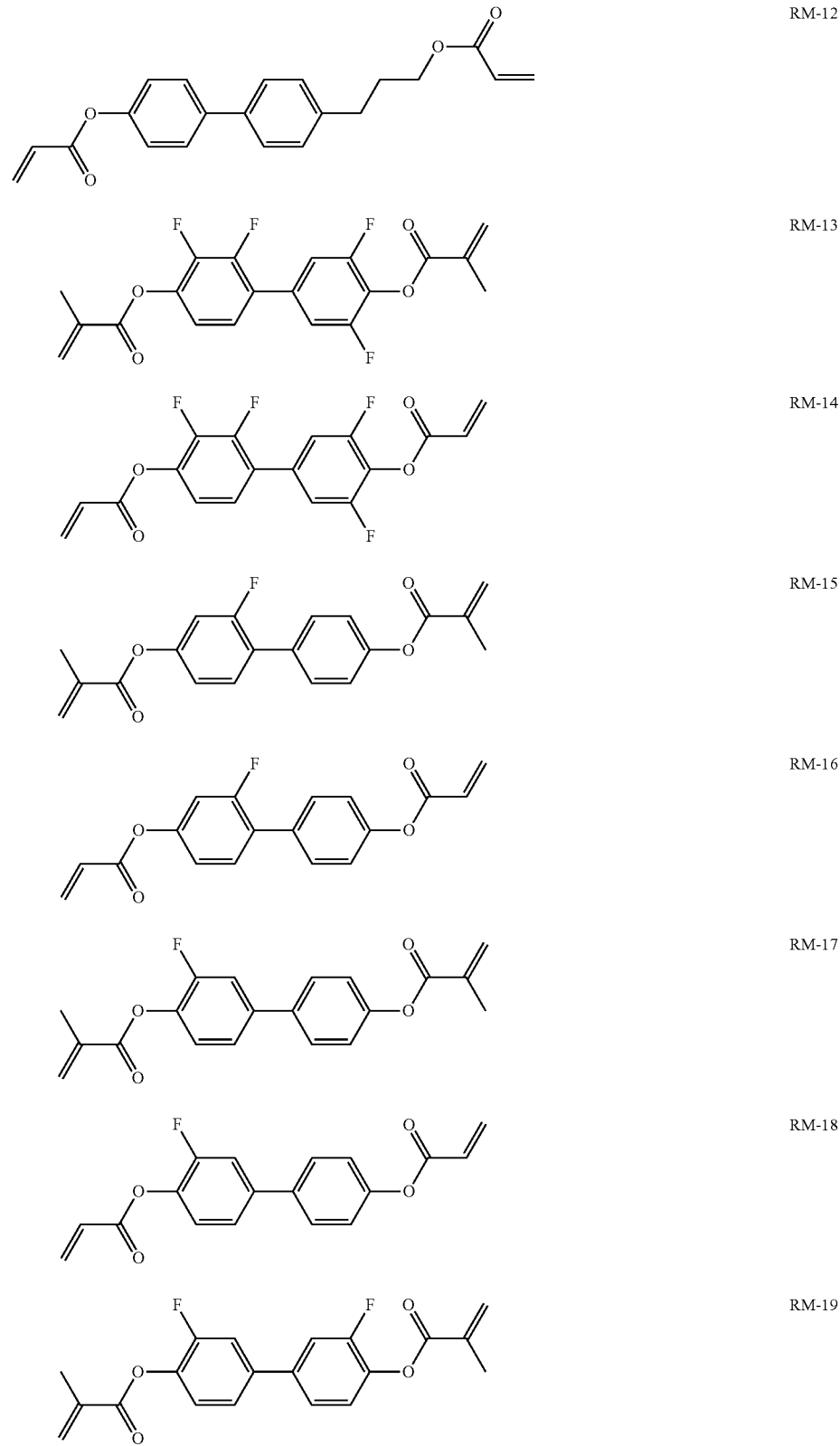

TABLE D-continued
Table D shows illustrative compounds which can be used in the LC media in accordance with the present invention, preferably as reactive mesogenic compounds.
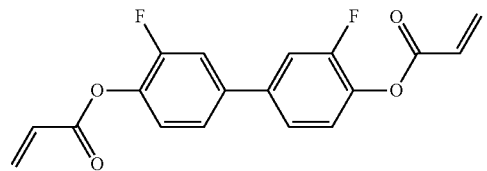 [SMILES: C=CC(=O)Oc1ccc(-c2ccc(OC(=O)C=C)c(F)c2)cc1F]
RM-20
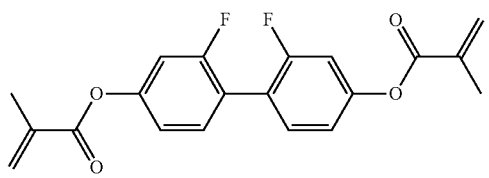 [SMILES: C=C(C)C(=O)Oc1ccc(-c2ccc(OC(=O)C(=C)C)cc2F)c(F)c1]
RM-21
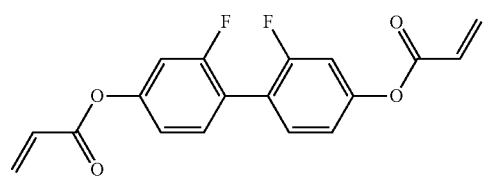 [SMILES: C=CC(=O)Oc1ccc(-c2ccc(OC(=O)C=C)cc2F)c(F)c1]
RM-22
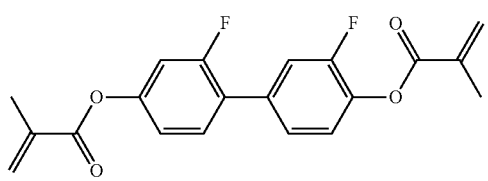 [SMILES: C=C(C)C(=O)Oc1ccc(-c2ccc(OC(=O)C(=C)C)c(F)c2)c(F)c1]
RM-23
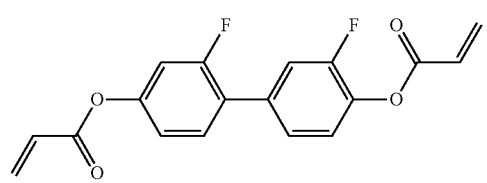 [SMILES: C=CC(=O)Oc1ccc(-c2ccc(OC(=O)C=C)c(F)c2)c(F)c1]
RM-24
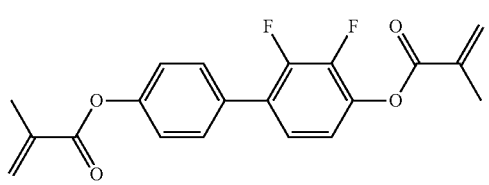 [SMILES: C=C(C)C(=O)Oc1ccc(-c2ccc(OC(=O)C(=C)C)c(F)c2F)cc1]
RM-25
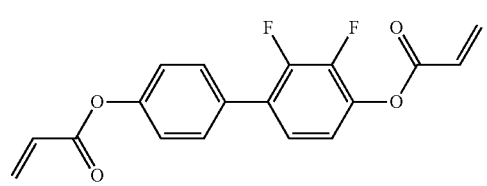
RM-26
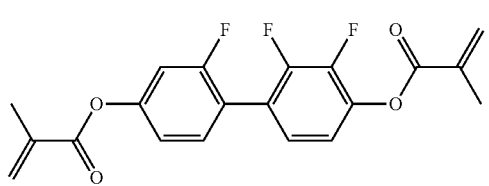 [SMILES: C=C(C)C(=O)Oc1ccc(-c2ccc(OC(=O)C(=C)C)c(F)c2F)c(F)c1]
RM-27

TABLE D-continued
Table D shows illustrative compounds which can be used in the LC media in accordance with the present invention, preferably as reactive mesogenic compounds.
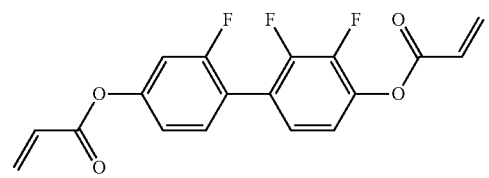 [SMILES: C=CC(=O)Oc1ccc(-c2ccc(OC(=O)C=C)c(F)c2F)c(F)c1]
RM-28
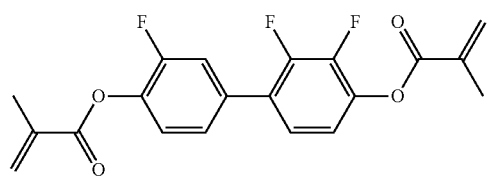 [SMILES: C=C(C)C(=O)Oc1ccc(-c2ccc(OC(=O)C(=C)C)c(F)c2F)cc1F]
RM-29
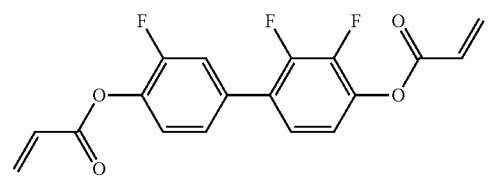 [SMILES: C=CC(=O)Oc1ccc(-c2ccc(OC(=O)C=C)c(F)c2F)cc1F]
RM-30
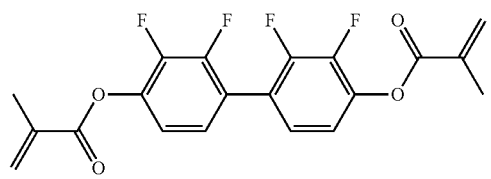 [SMILES: C=C(C)C(=O)Oc1ccc(-c2ccc(OC(=O)C(=C)C)c(F)c2F)c(F)c1F]
RM-31
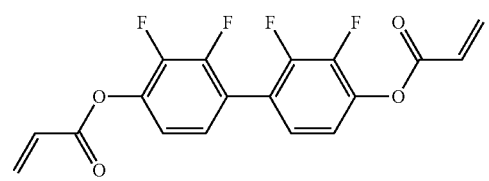 [SMILES: C=CC(=O)Oc1ccc(-c2ccc(OC(=O)C=C)c(F)c2F)c(F)c1F]
RM-32
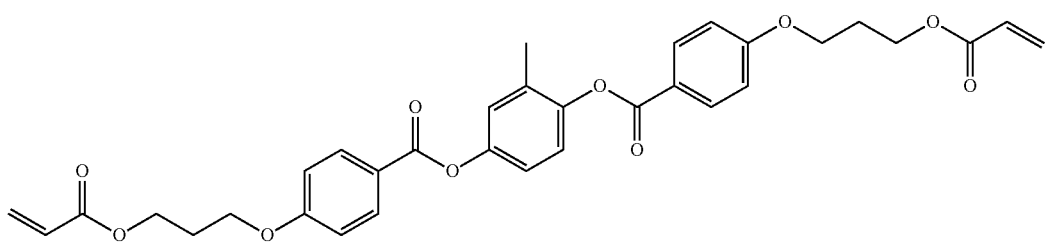 [SMILES: C=CC(=O)OCCCOc1ccc(C(=O)Oc2ccc(OC(=O)c3ccc(OCCCOC(=O)C=C)cc3)c(C)c2)cc1]
RM-33
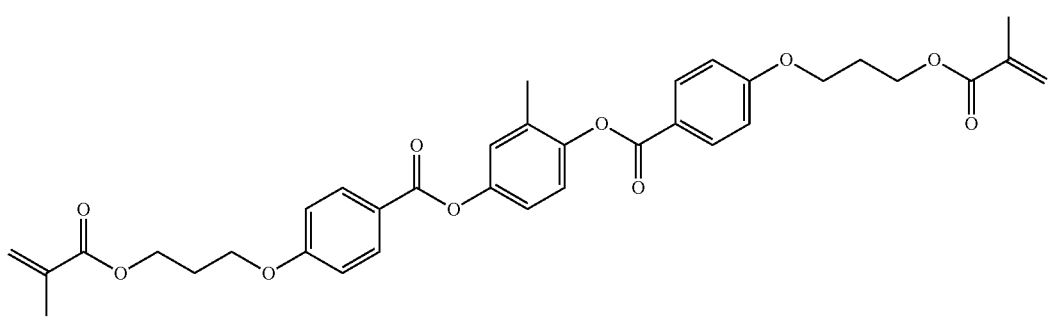 [SMILES: C=C(C)C(=O)OCCCOc1ccc(C(=O)Oc2ccc(OC(=O)c3ccc(OCCCOC(=O)C(=C)C)cc3)c(C)c2)cc1]
RM-34

TABLE D-continued
Table D shows illustrative compounds which can be used in the LC media in accordance with the present invention, preferably as reactive mesogenic compounds.
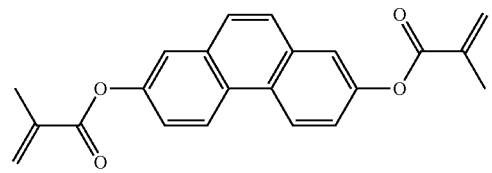 [SMILES: C=C(C)C(=O)Oc1ccc2c(ccc3cc(OC(=O)C(=C)C)ccc32)c1]
RM-35
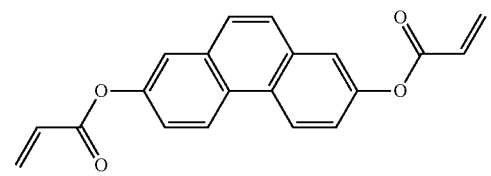
RM-36
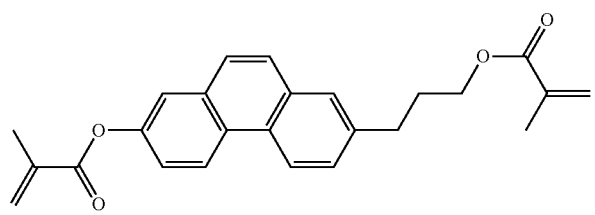 [SMILES: C=C(C)C(=O)OCCCc1ccc2c(ccc3cc(OC(=O)C(=C)C)ccc32)c1]
RM-37
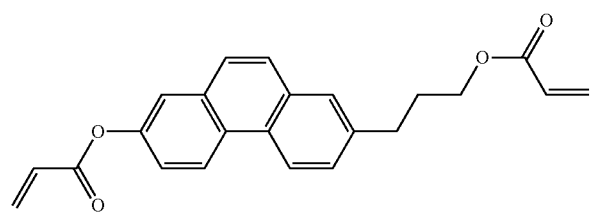 [SMILES: C=CC(=O)OCCCc1ccc2c(ccc3cc(OC(=O)C=C)ccc32)c1]
RM-38
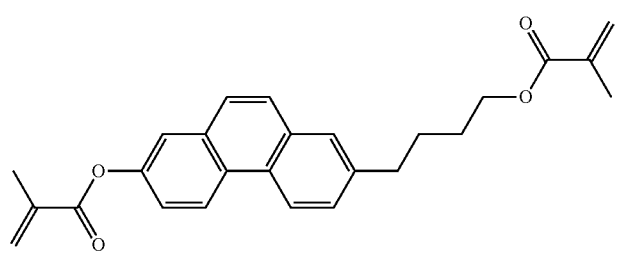 [SMILES: C=C(C)C(=O)OCCCCc1ccc2c(ccc3cc(OC(=O)C(=C)C)ccc32)c1]
RM-39
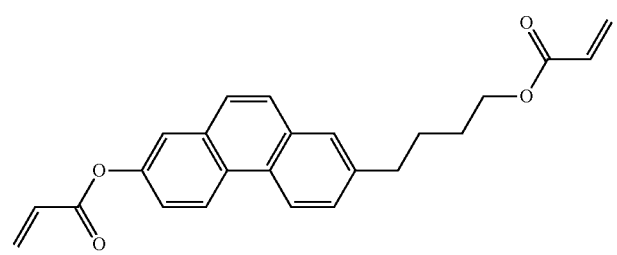 [SMILES: C=CC(=O)OCCCCc1ccc2c(ccc3cc(OC(=O)C=C)ccc32)c1]
RM-40
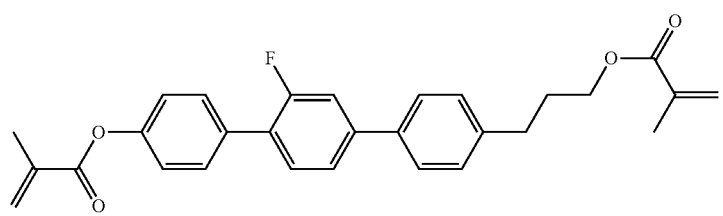 [SMILES: C=C(C)C(=O)OCCCc1ccc(-c2ccc(-c3ccc(OC(=O)C(=C)C)cc3)c(F)c2)cc1]
RM-41

TABLE D-continued
Table D shows illustrative compounds which can be used in the LC media in accordance with the present invention, preferably as reactive mesogenic compounds.
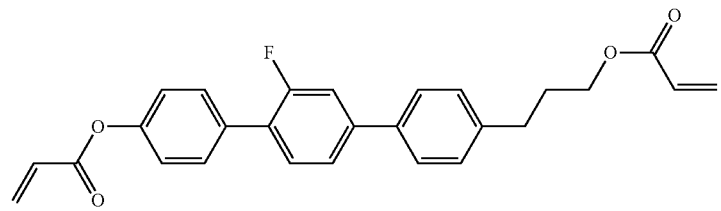 [SMILES: C=CC(=O)OCCCc1ccc(-c2ccc(-c3ccc(OC(=O)C=C)cc3)c(F)c2)cc1] RM-42
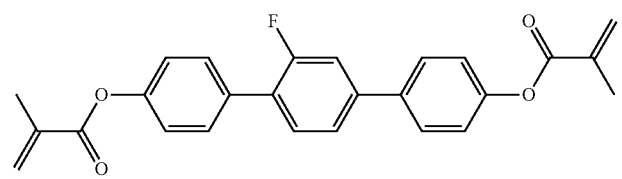 [SMILES: C=C(C)C(=O)Oc1ccc(-c2ccc(-c3ccc(OC(=O)C(=C)C)cc3)c(F)c2)cc1] RM-43
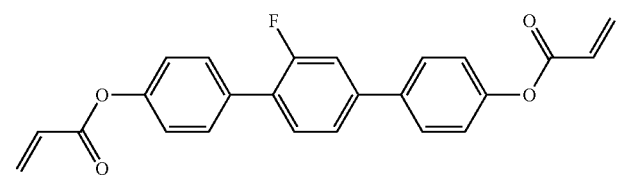 [SMILES: C=CC(=O)Oc1ccc(-c2ccc(-c3ccc(OC(=O)C=C)cc3)c(F)c2)cc1] RM-44
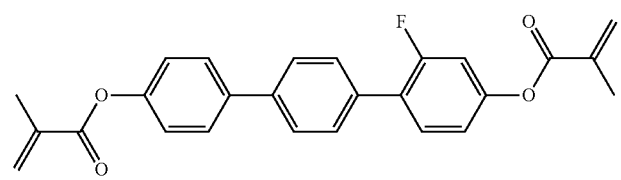 [SMILES: C=C(C)C(=O)Oc1ccc(-c2ccc(-c3ccc(OC(=O)C(=C)C)cc3F)cc2)cc1] RM-45
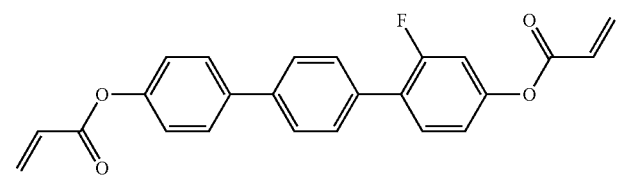 [SMILES: C=CC(=O)Oc1ccc(-c2ccc(-c3ccc(OC(=O)C=C)cc3F)cc2)cc1] RM-46
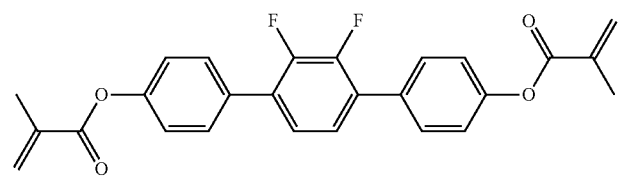 [SMILES: C=C(C)C(=O)Oc1ccc(-c2ccc(-c3ccc(OC(=O)C(=C)C)cc3)c(F)c2F)cc1] RM-47
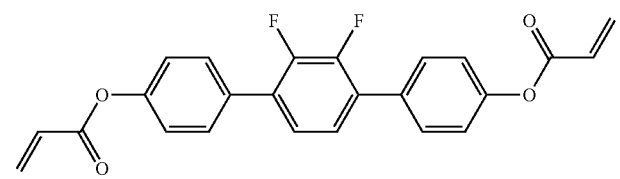 [SMILES: C=CC(=O)Oc1ccc(-c2ccc(-c3ccc(OC(=O)C=C)cc3)c(F)c2F)cc1] RM-48
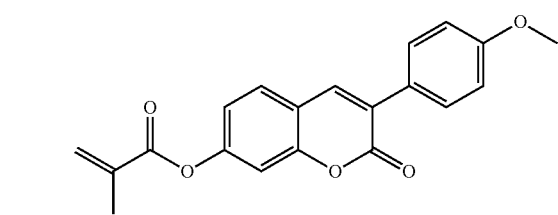 [SMILES: C=C(C)C(=O)Oc1ccc2cc(-c3ccc(OC)cc3)c(=O)oc2c1] RM-49

TABLE D-continued
Table D shows illustrative compounds which can be used in the LC media in accordance with the present invention, preferably as reactive mesogenic compounds.
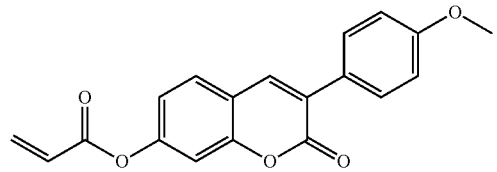 [SMILES: C=CC(=O)Oc1ccc2cc(-c3ccc(OC)cc3)c(=O)oc2c1]
RM-50
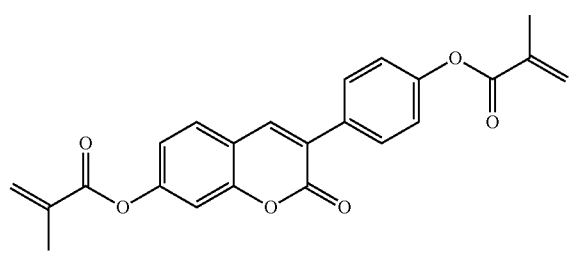 [SMILES: C=C(C)C(=O)Oc1ccc(-c2cc3ccc(OC(=O)C(=C)C)cc3oc2=O)cc1]
RM-51
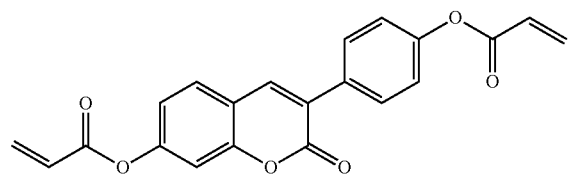 [SMILES: C=CC(=O)Oc1ccc(-c2cc3ccc(OC(=O)C=C)cc3oc2=O)cc1]
RM-52
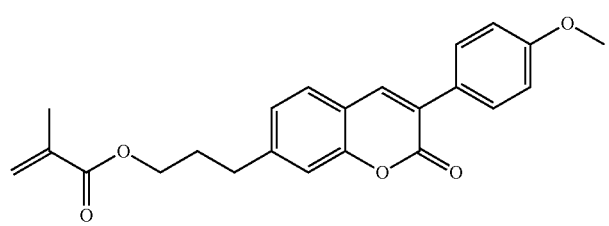 [SMILES: C=C(C)C(=O)OCCCc1ccc2cc(-c3ccc(OC)cc3)c(=O)oc2c1]
RM-53
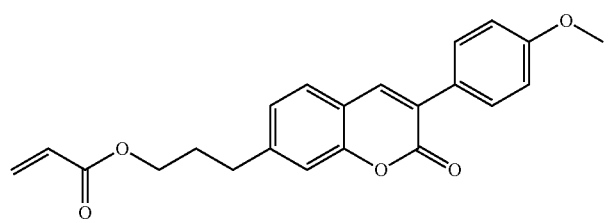 [SMILES: C=CC(=O)OCCCc1ccc2cc(-c3ccc(OC)cc3)c(=O)oc2c1]
RM-54
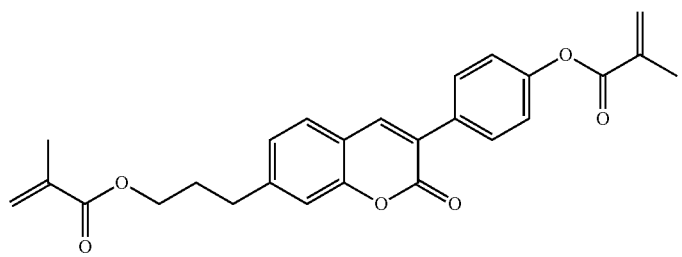 [SMILES: C=C(C)C(=O)OCCCc1ccc2cc(-c3ccc(OC(=O)C(=C)C)cc3)c(=O)oc2c1]
RM-55

TABLE D-continued
Table D shows illustrative compounds which can be used in the LC media in accordance with the present invention, preferably as reactive mesogenic compounds.
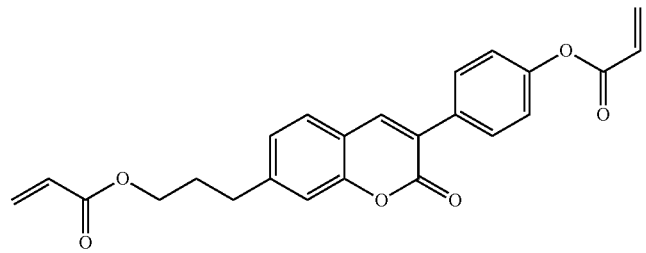 [SMILES: C=CC(=O)OCCCc1ccc2cc(-c3ccc(OC(=O)C=C)cc3)c(=O)oc2c1]
RM-56
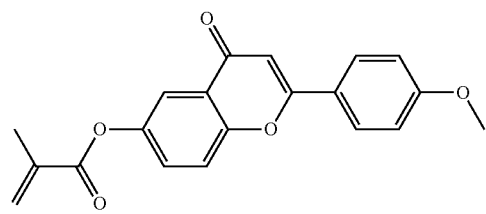 [SMILES: C=C(C)C(=O)Oc1ccc2oc(-c3ccc(OC)cc3)cc(=O)c2c1]
RM-57
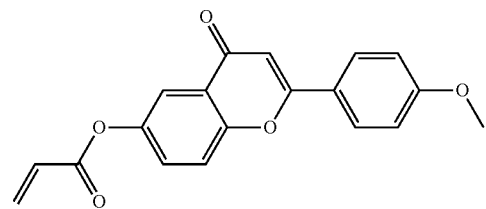 [SMILES: C=CC(=O)Oc1ccc2oc(-c3ccc(OC)cc3)cc(=O)c2c1]
RM-58
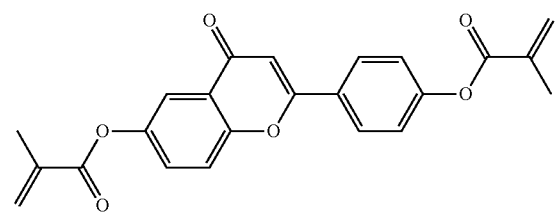 [SMILES: C=C(C)C(=O)Oc1ccc(-c2cc(=O)c3cc(OC(=O)C(=C)C)ccc3o2)cc1]
RM-59
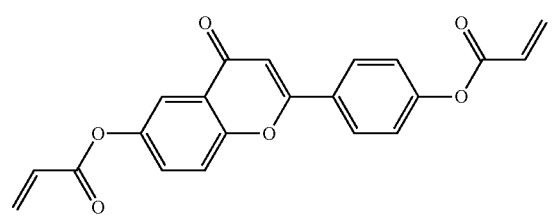 [SMILES: C=CC(=O)Oc1ccc(-c2cc(=O)c3cc(OC(=O)C=C)ccc3o2)cc1]
RM-60

TABLE D-continued
Table D shows illustrative compounds which can be used in the LC media in accordance with the present invention, preferably as reactive mesogenic compounds.
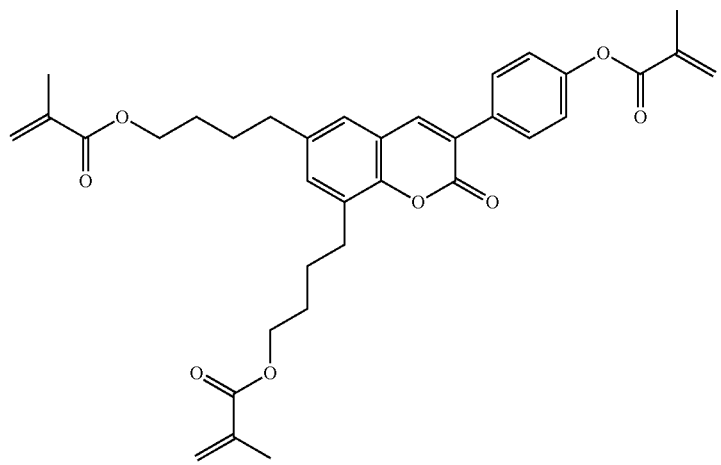 [SMILES: C=C(C)C(=O)OCCCCc1cc(CCCCOC(=O)C(=C)C)c2oc(=O)c(-c3ccc(OC(=O)C(=C)C)cc3)cc2c1]
RM-61
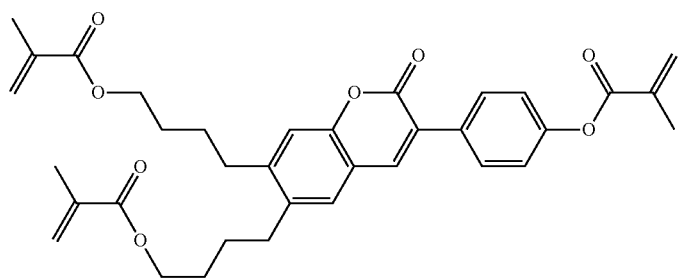 [SMILES: C=C(C)C(=O)OCCCCc1cc2cc(-c3ccc(OC(=O)C(=C)C)cc3)c(=O)oc2cc1CCCCOC(=O)C(=C)C]
RM-62
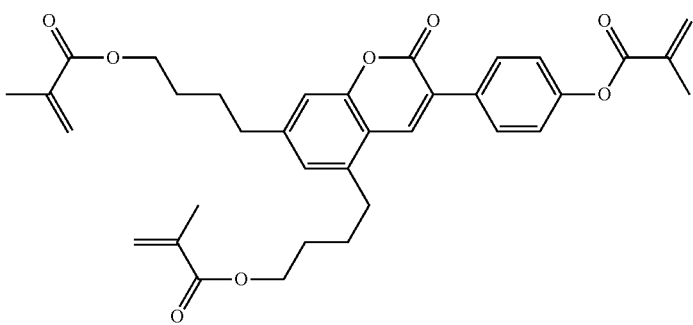 [SMILES: C=C(C)C(=O)OCCCCc1cc(CCCCOC(=O)C(=C)C)c2cc(-c3ccc(OC(=O)C(=C)C)cc3)c(=O)oc2c1]
RM-63
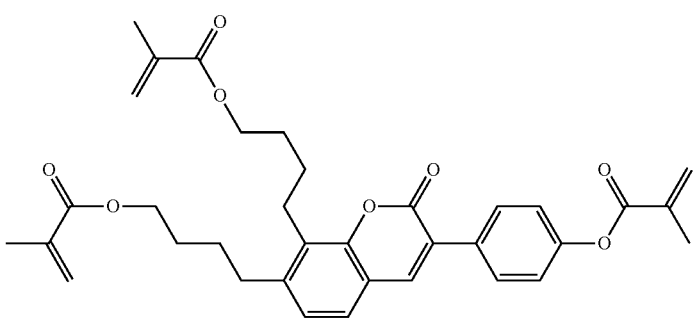 [SMILES: C=C(C)C(=O)OCCCCc1ccc2cc(-c3ccc(OC(=O)C(=C)C)cc3)c(=O)oc2c1CCCCOC(=O)C(=C)C]
RM-64

TABLE D-continued
Table D shows illustrative compounds which can be used in the LC media in accordance with the present invention, preferably as reactive mesogenic compounds.
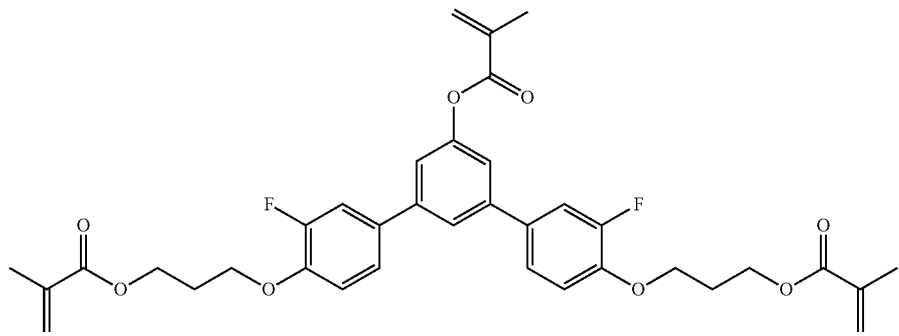 [SMILES: C=C(C)C(=O)OCCCOc1ccc(-c2cc(OC(=O)C(=C)C)cc(-c3ccc(OCCCOC(=O)C(=C)C)c(F)c3)c2)cc1F]
RM-65
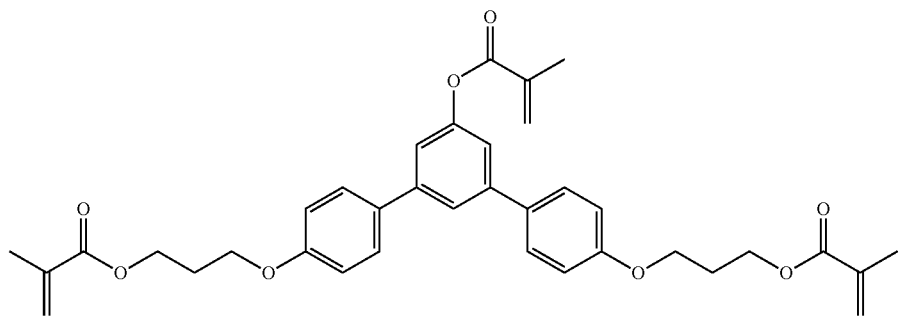 [SMILES: C=C(C)C(=O)OCCCOc1ccc(-c2cc(OC(=O)C(=C)C)cc(-c3ccc(OCCCOC(=O)C(=C)C)cc3)c2)cc1]
RM-66
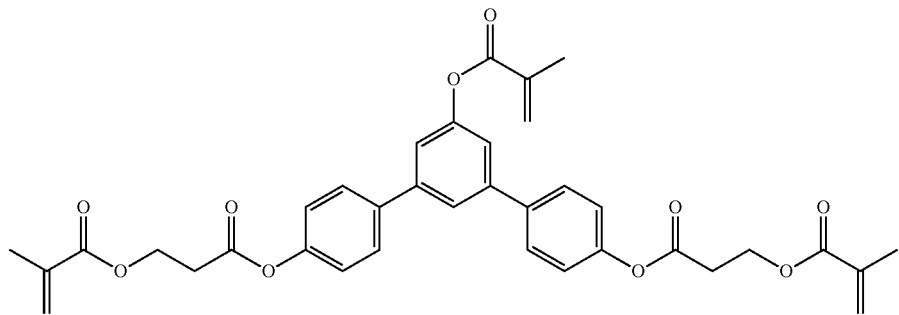 [SMILES: C=C(C)C(=O)OCCC(=O)Oc1ccc(-c2cc(OC(=O)C(=C)C)cc(-c3ccc(OC(=O)CCOC(=O)C(=C)C)cc3)c2)cc1]
RM-67
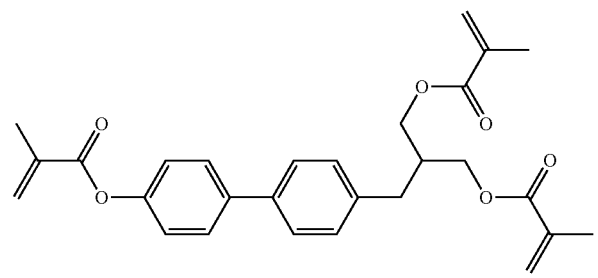 [SMILES: C=C(C)C(=O)OCC(COC(=O)C(=C)C)Cc1ccc(-c2ccc(OC(=O)C(=C)C)cc2)cc1]
RM-68

TABLE D-continued
Table D shows illustrative compounds which can be used in the LC media in accordance with the present invention, preferably as reactive mesogenic compounds.
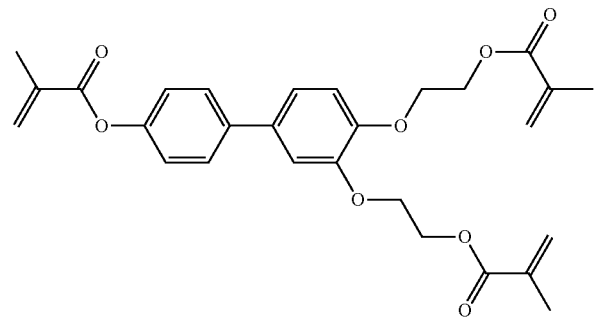 [SMILES: C=C(C)C(=O)OCCOc1ccc(-c2ccc(OC(=O)C(=C)C)cc2)cc1OCCOC(=O)C(=C)C]
RM-69
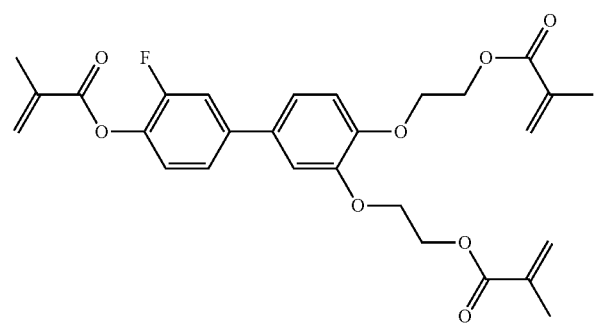 [SMILES: C=C(C)C(=O)OCCOc1ccc(-c2ccc(OC(=O)C(=C)C)c(F)c2)cc1OCCOC(=O)C(=C)C]
RM-70
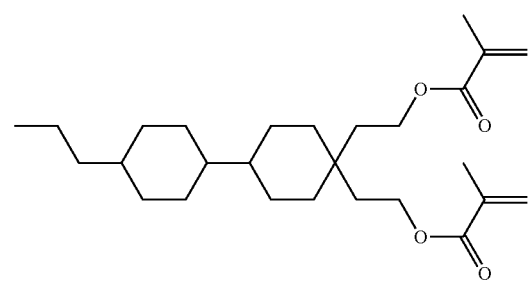 [SMILES: C=C(C)C(=O)OCCC1(CCOC(=O)C(=C)C)CCC(C2CCC(CCC)CC2)CC1]
RM-71
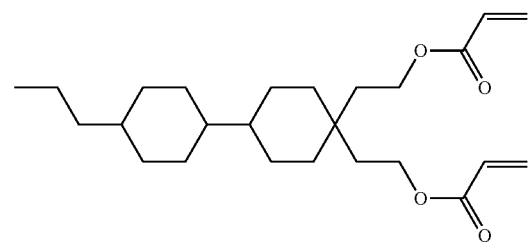 [SMILES: C=CC(=O)OCCC1(CCOC(=O)C=C)CCC(C2CCC(CCC)CC2)CC1]
RM-72
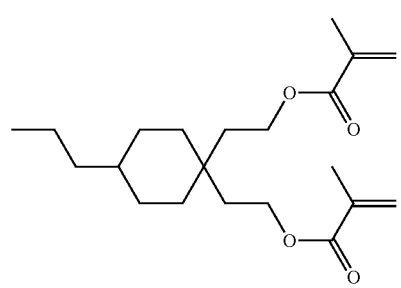 [SMILES: C=C(C)C(=O)OCCC1(CCOC(=O)C(=C)C)CCC(CCC)CC1]
RM-73

TABLE D-continued
Table D shows illustrative compounds which can be used in the LC media in accordance with the present invention, preferably as reactive mesogenic compounds.
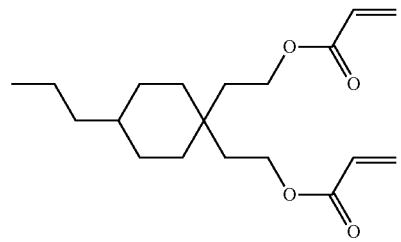 [SMILES: C=CC(=O)OCCC1(CCOC(=O)C=C)CCC(CCC)CC1] RM-74
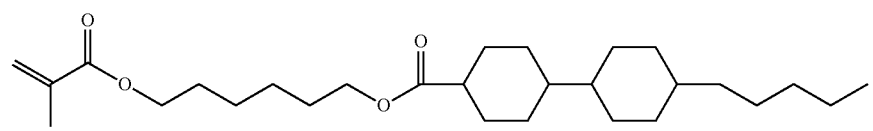 [SMILES: C=C(C)C(=O)OCCCCCCOC(=O)C1CCC(C2CCC(CCCCC)CC2)CC1] RM-75
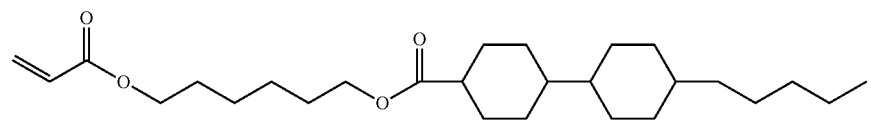 [SMILES: C=CC(=O)OCCCCCCOC(=O)C1CCC(C2CCC(CCCCC)CC2)CC1] RM-76
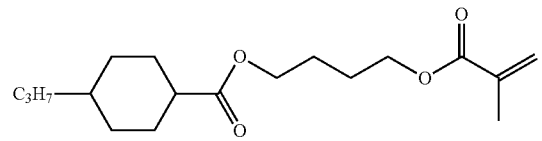 RM-77
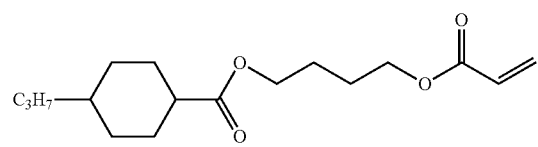 RM-78
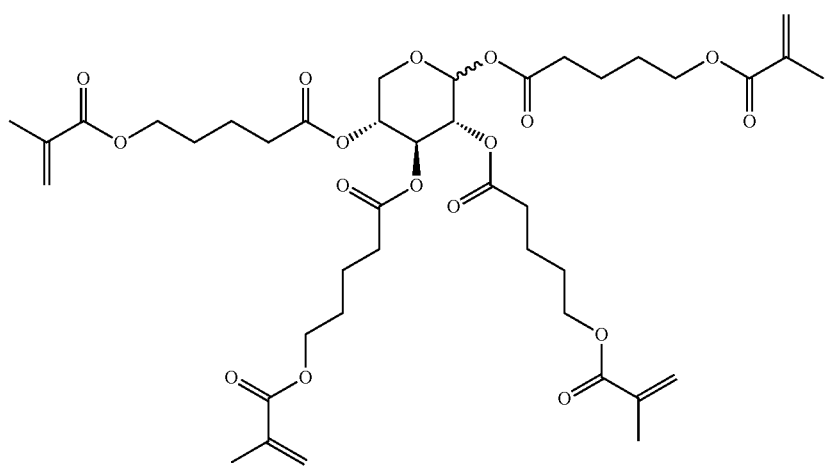 [SMILES: C=C(C)C(=O)OCCCCC(=O)OC1OC[C@@H](OC(=O)CCCCOC(=O)C(=C)C)[C@H](OC(=O)CCCCOC(=O)C(=C)C)[C@H]1OC(=O)CCCCOC(=O)C(=C)C] RM-79

TABLE D-continued
Table D shows illustrative compounds which can be used in the LC media in accordance with the present invention, preferably as reactive mesogenic compounds.
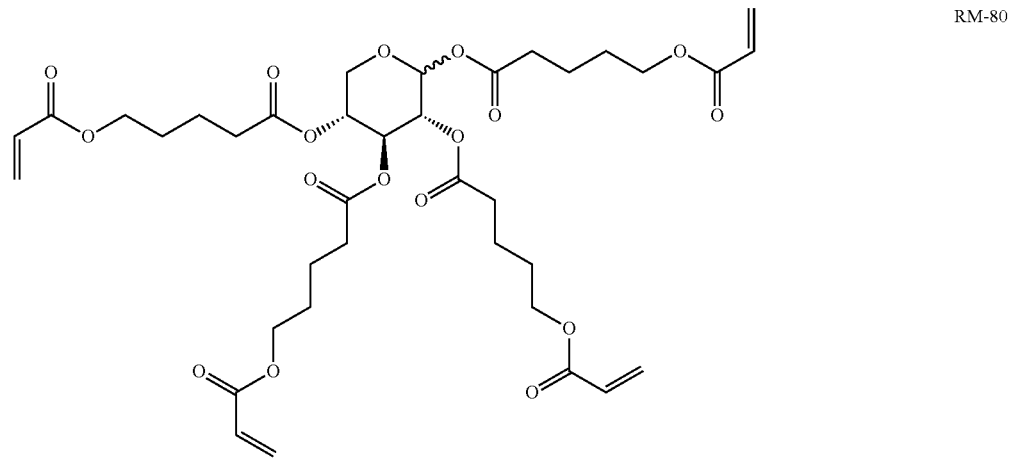
RM-80
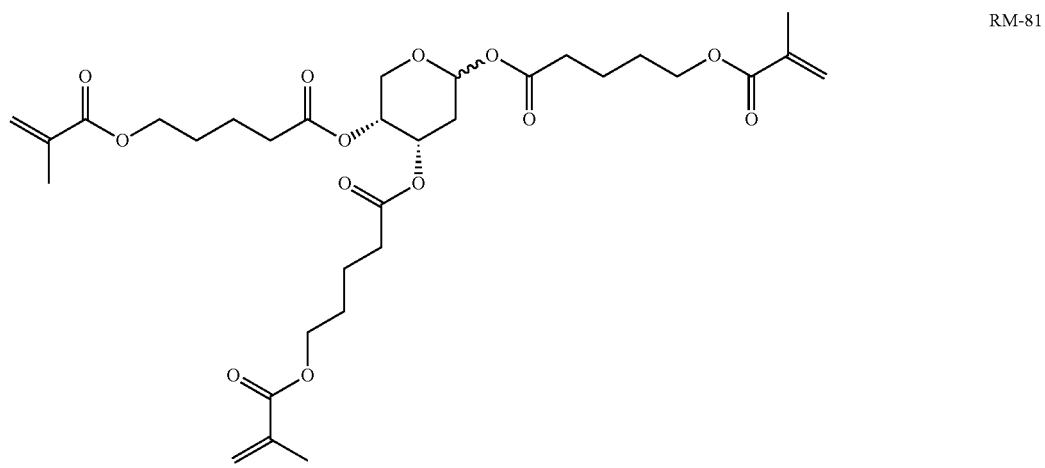
RM-81
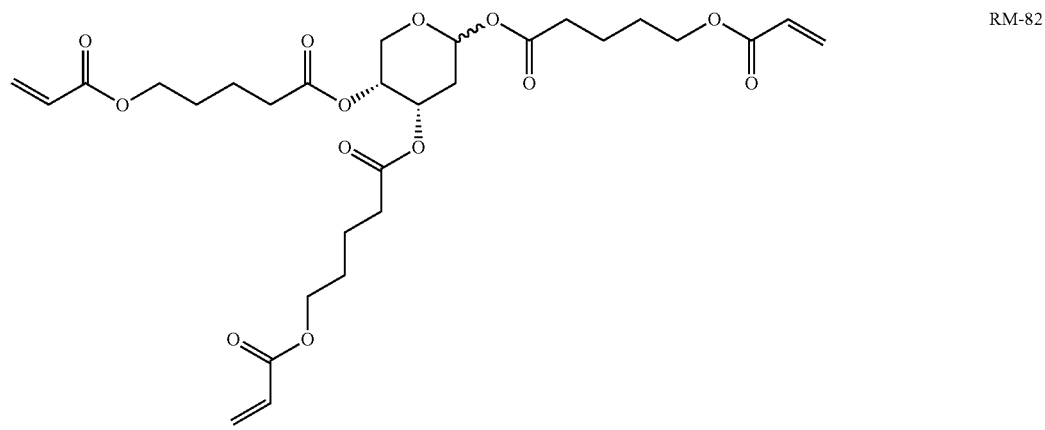
RM-82

TABLE D-continued

Table D shows illustrative compounds which can be used in the LC media in accordance with the present invention, preferably as reactive mesogenic compounds.

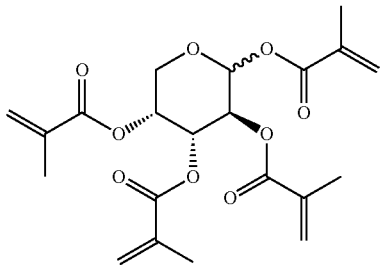 [SMILES: C=C(C)C(=O)OC1OC[C@@H](OC(=O)C(=C)C)[C@@H](OC(=O)C(=C)C)[C@@H]1OC(=O)C(=C)C]

RM-83

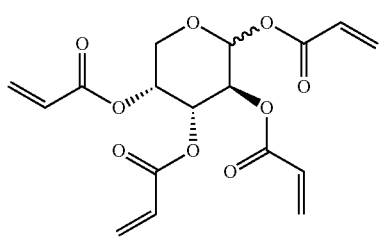 [SMILES: C=CC(=O)OC1OC[C@@H](OC(=O)C=C)[C@@H](OC(=O)C=C)[C@@H]1OC(=O)C=C]

RM-84

In a preferred embodiment of the present invention, the mesogenic media comprise one or more compounds selected from the group of the compounds from Table D.

In addition, the following abbreviations and symbols are used:

$V_0$ threshold voltage, capacitive [V] at 20° C.,
$n_e$ extraordinary refractive index at 20° C. and 589 nm,
$n_o$ ordinary refractive index at 20° C. and 589 nm,
Δn optical anisotropy at 20° C. and 589 nm,
$\in_\perp$ dielectric permittivity perpendicular to the director at 20° C. and 1 kHz,
$\in_\parallel$ dielectric permittivity parallel to the director at 20° C. and 1 kHz,
Δ∈ dielectric anisotropy at 20° C. and 1 kHz,
cl.p., T(N,I) clearing point [° C.],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN].

Unless explicitly noted otherwise, all concentrations in the present application are quoted in percent by weight and relate to the corresponding mixture as a whole, comprising all solid or liquid-crystalline components, without solvents.

Unless explicitly noted otherwise, all temperature values indicated in the present application, such as, for example, for the melting point T(C,N), the transition from the smectic (S) to the nematic (N) phase T(S,N) and the clearing point T(N,I), are quoted in degrees Celsius (° C.). M.p. denotes melting point, cl.p.=clearing point. Furthermore, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status November 1997, Merck KGaA, Germany, and apply for a temperature of 20° C., and Δn is determined at 589 nm and Δ∈ at 1 kHz, unless explicitly indicated otherwise in each case.

The term "threshold voltage" for the present invention relates to the capacitive threshold ($V_0$), also known as the Freedericks threshold, unless explicitly indicated otherwise. In the examples, the optical threshold may also, as generally usual, be quoted for 10% relative contrast ($V_{10}$).

Unless stated otherwise, the process of polymerizing the polymerizable compounds in the PSA displays as described above and below is carried out at a temperature where the LC medium exhibits a liquid crystal phase, preferably a nematic phase, and most preferably is carried out at room temperature.

Unless stated otherwise, methods of preparing test cells and measuring their electrooptical and other properties are carried out by the methods as described hereinafter or in analogy thereto.

The display used for measurement of the capacitive threshold voltage consists of two plane-parallel glass outer plates at a separation of 25 μm, each of which has on the inside an electrode layer and an unrubbed polyimide alignment layer on top, which effect a homeotropic edge alignment of the liquid-crystal molecules.

The display or test cell used for measurement of the tilt angles consists of two plane-parallel glass outer plates at a separation of 4 μm, each of which has on the inside an electrode layer and a polyimide alignment layer on top, where the two polyimide layers are rubbed antiparallel to one another and effect a homeotropic edge alignment of the liquid-crystal molecules.

The polymerizable compounds are polymerized in the display or test cell by irradiation with UVA light of defined intensity for a prespecified time, with a voltage simultaneously being applied to the display (usually 10 V to 30 V alternating current, 1 kHz). In the examples, unless indicated otherwise, a metal halide lamp and an intensity of 100 mW/cm² is used for polymerization. The intensity is measured using a standard UVA meter (Hoenle UV-meter high end with UVA sensor).

The tilt angle is determined by crystal rotation experiment (Autronic-Melchers TBA-105). A low value (i.e. a large deviation from the 90° angle) corresponds to a large tilt here.

The VHR value is measured as follows: 0.3% of a polymerizable monomeric compound is added to the LC host mixture, and the resultant mixture is introduced into VA-VHR test cells (not rubbed, VA-polyimide alignment layer, LC-layer thickness d≈6 μm). The HR value is determined after 5 min at 100° C. before and after UV exposure at 1 V, 60 Hz, 64 μs pulse (measuring instrument: Autronic-Melchers VHRM-105).

EXAMPLE 1

Polymerizable monomeric compound 1 of formula I2-1 is prepared as follows.

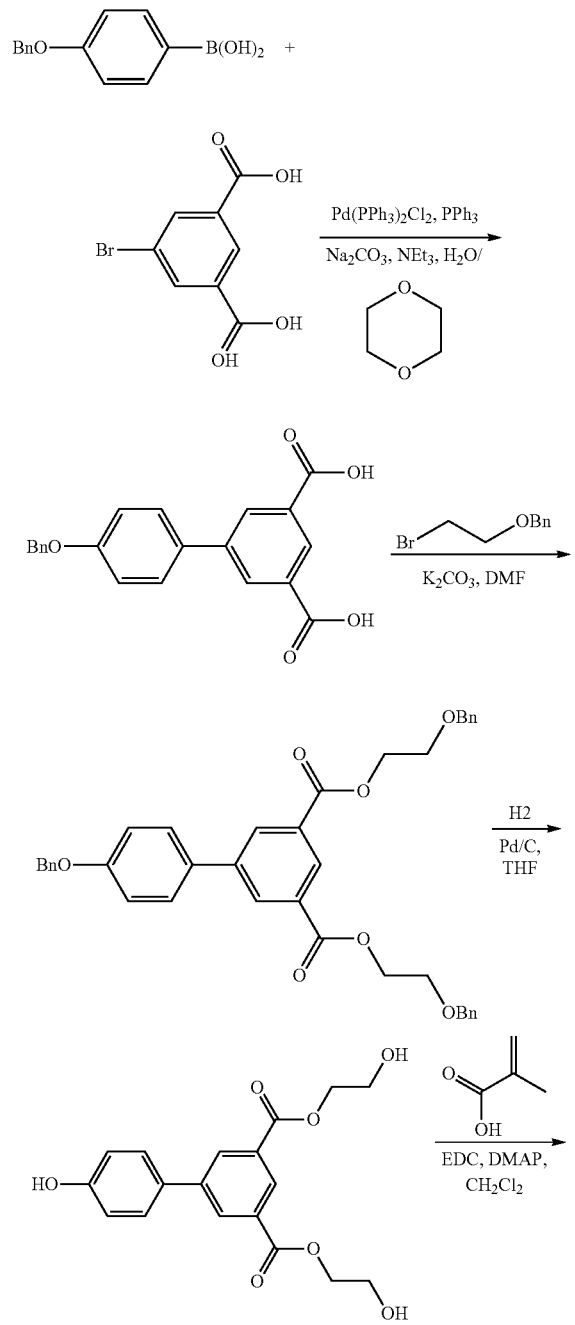

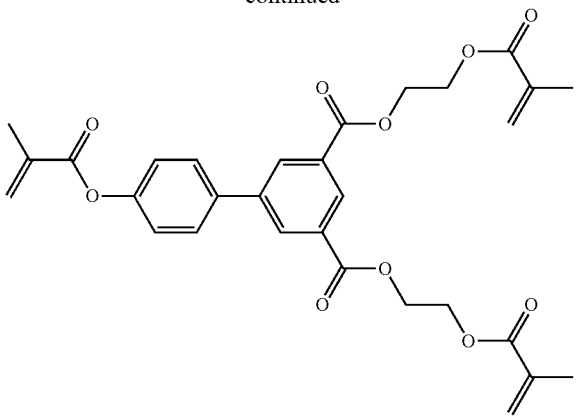

1

1.1 4'-Benzyloxy-biphenyl-3,5-dicarboxylic acid

4'-benzyloxy-biphenyl-3,5-dicarboxylic acid is prepared from commercially available [4-(benzyloxy)phenyl]-boronic acid and 5-bromo-isophthalic acid.

To a solution of sodium carbonate (31.26 g, 295.0 mol) in dist. water (135 ml) is added 1,4-dioxane (210 ml), 5-bromo-isophthalic acid (14.46 g, 59.0 mmol) and [4-(benzyloxy)phenyl]-boronic acid (14.82 g, 65.0 mol) followed by bis(triphenylphosphine)palladium(II) dichloride (0.83 g, 1.2 mmol), triphenylphosphine (0.31 g, 1.2 mmol) and triethylamine (0.12 g, 1.2 mmol) under nitrogen atmosphere. The reaction mixture is heated at reflux for 2 hs. After cooling to room temperature 400 ml dist. water is added, and the reaction mixture is neutralized with conc. HCl acid under cooling to pH~1. The precipitated crude product is filtrated, washed with dist. water, and further purified by recrystallization from acetonitrile to provide gray crystals of 4'-benzyloxy-biphenyl-3,5-dicarboxylic acid (17.4 g).

1.2 4'-Benzyloxy-biphenyl-3,5-dicarboxylic acid bis-(2-benzyloxy-ethyl)ester To a solution of 4'-benzyloxy-biphenyl-3,5-dicarboxylic acid (8.00 g, 105.64 mmol) in DMF (50 ml) is added potassium carbonate (7.62 g, 55.12 mmol). To the resulted suspension (2-bromo-ethoxymethyl)-benzene (10.87 g. 50.52 mmol) is added. The reaction mixture is stirred at 70° C. overnight. After cooling to room temperature, the reaction mixture is added into 100 ml water and extracted with 60 ml methyl-t-butyl ether (MTBE). The organic phase is washed with sat. aq. NaCl solution, dried over sodium sulfate. After removing solvent in vacuo, the oily residue is purified by silica gel chromatography with heptane/ethylacetate 7:3 to provide 4'-benzyloxy-biphenyl-3,5-dicarboxylic acid bis-(2-benzyloxy-ethyl)ester as white oil (8.0 g).

1.3 4'-Hydroxy-biphenyl-3,5-dicarboxylic acid bis-(2-hydroxy-ethyl)ester

A solution of 4'-benzyloxy-biphenyl-3,5-dicarboxylic acid bis-(2-benzyloxyethyl)ester (8.0 g, 13.0 mmol) in tetrahydrofuran (80 ml) is treated with palladium (5%) on activated charcoal (2.0 g) and submitted to hydrogenation for 15 hs. The catalyst is then filtered off, and the remaining solution is concentrated in vacuo. The residue is recrystallized from toluene/ethylacetate solvent mixture to afford 4'-hydroxy-biphenyl-3,5-dicarboxylic acid bis-(2-hydroxy-ethyl)ester as white solid (4.2 g).

1.4 4'-(2-Methyl-acryloyloxy)-biphenyl-3,5-dicarboxylic acid bis-[2-(2-methyl-acryloyloxy)-ethyl] ester Methacrylic acid (5.95 g, 69.1 mmol) and 4-(dimethylamino)pyridine (0.15 g, 1.2 mmol) is added to a suspension of 4'-hydroxy-biphenyl-3,5-dicarboxylic acid bis-(2-hydroxy-ethyl)ester (4.2 g, 12.1 mmol) in dichloromethane (110 ml). The reaction mixture is treated dropwise at 0° C. with a solution of N-(3-dimethylaminopropyl)-N'-ethylcarbodiimide (10.7 g, 69.1 mmol) in dichloromethane (50 ml) and stirred for 20 h at room temperature. After removing solvent in vacuo, the oily residue is purified by silica gel chromatography with heptane/ethyl acetate 8:2. The obtained product is recrystallized from ethanol/acetonitrile solvent mixture affords white crystals of 4'-(2-Methyl-acryloyloxy)-biphenyl-3,5-dicarboxylic acid bis-[2-(2-methyl-acryloyloxy)-ethyl]ester (2.6 g, m.p. 47° C.).

$^1$H-NMR (DMSO-$d_6$, 500 MHz): δ (ppm)=8.45 (m, 1 H, Ar—H), 8.42 (m, 2 H, Ar—H), 7.80 (d, J=8.5 Hz, 2 H, Ar—H), 7.35 (d, J=8.5 Hz, 2 H, Ar—H), 6.32 (m, 1 H, $H_{olefin}$), 6.04 (m, 2 H, $H_{olefin}$), 5.93 (m, 1 H, $H_{olefin}$), 5.68 (m, 2 H, $H_{olefin}$), 4.62-4.60 (m, 2 H, OCH$_2$), 4.51-4.49 (m, 2 H, OCH$_2$), 2.03 (br. s, 3 H, CH$_3$), 1.87 (m, 6H, 2×CH$_3$).

EXAMPLE 2

Polymerizable monomeric compound 2 of formula I2-4 is prepared as follows.

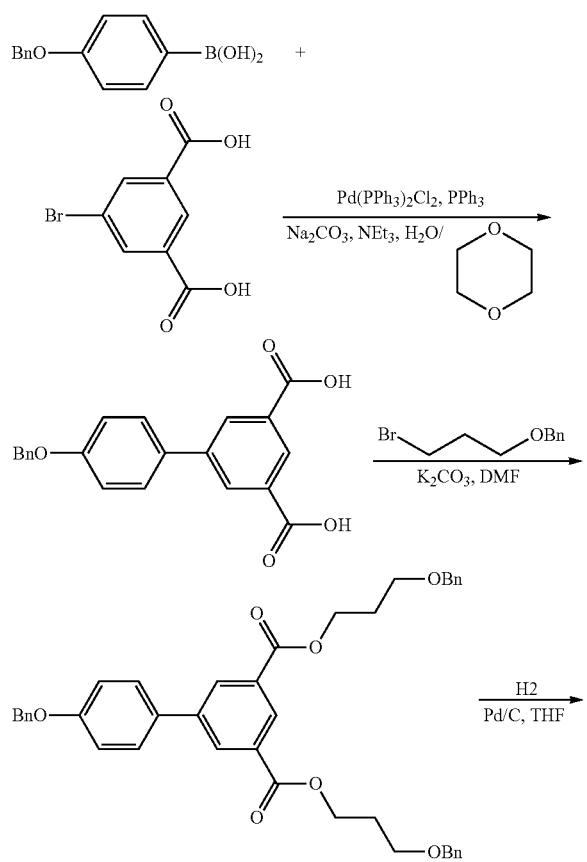

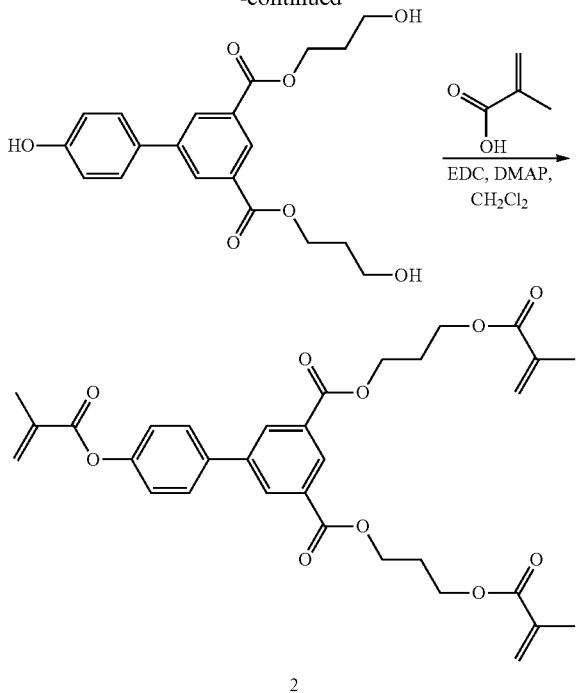

2.1 4'-Benzyloxy-biphenyl-3,5-dicarboxylic acid

4'-benzyloxy-biphenyl-3,5-dicarboxylic acid is prepared as described in Example 1.

2.2 4'-Benzyloxy-biphenyl-3,5-dicarboxylic acid bis-(3-benzyloxy-propyl)ester To a solution of 4'-benzyloxy-biphenyl-3,5-dicarboxylic acid (8.00 g, 22.96 mmol) in DMF (50 ml) is added potassium carbonate (7.62 g, 55.12 mmol). To the resulted suspension (2-bromo-propoxymethyl)-benzene (11.58 g. 50.52 mmol) is added. The reaction mixture is stirred at 70° C. for 3 hs. After cooling to room temperature, the reaction mixture is poured into 100 ml ice-water mixture and extracted with 60 ml MTBE. The organic phase is washed with sat. aq. NaCl solution and dried over sodium sulfate. After removing solvent in vacuo, the solid residue is recrystallization from isopropanol. 4'-benzyloxy-biphenyl-3,5-dicarboxylic acid bis-(3-benzyloxy-propyl)ester is obtained as white crystals (8.1 g).

2.3 4'-Hydroxy-biphenyl-3,5-dicarboxylic acid bis-(3-hydroxy-propyl)ester

A solution of 4'-benzyloxy-biphenyl-3,5-dicarboxylic acid bis-(3-benzyloxypropyl)ester (8.1 g, 12.6 mmol) in tetrahydrofuran (80 ml) is treated with palladium (5%) on activated charcoal (2.0 g) and submitted to hydrogenation for 15 hs. The catalyst is then filtered off, and the remaining solution is concentrated in vacuo. The residue is recrystallized from toluene/ethylacetate solvent mixture to give white crystals of 4'-hydroxy-biphenyl-3,5-dicarboxylic acid bis-(3-hydroxy-propyl)ester (4.5 g).

2.4 4'-(2-Methyl-acryloyloxy)-biphenyl-3,5-dicarboxylic acid bis-[3-(2-methyl-acryloyloxy)-propyl] ester Methacrylic acid (5.77 g, 67.0 mmol) and 4-(dimethylamino)pyridine (0.14 g, 1.2 mmol) is added to a suspension of 4'-hydroxy-biphenyl-3,5-dicarboxylic acid bis-(3-hydroxy-propyl)ester (4.40 g, 11.8 mmol) in dichloromethane (100 ml). The reaction mixture is treated dropwise at 0° C. with a solution of N-(3-dimethylaminopropyl)-N'-ethylcarbodiimide (10.4 g, 67.0 mmol) in dichloromethane (60 ml) and stirred for 20 hs at room temperature. The reaction mixture is concentrated in vacuo and filtrated through silica gel. After removing solvent, the crude product is recrystallization from ethanol/acetonitrile solvent mixture to afford white crystals of 4'-(2-methylacryloyloxy)-biphenyl-3,5-dicarboxylic acid bis-[3-(2-methyl-acryloyloxy)propyl]ester (2.5 g, m.p. 42° C.).

$^1$H-NMR (DMSO-$d_6$, 500 MHz): δ (ppm)=8.46 (m, 1 H, Ar—H), 8.41 (m, 2 H, Ar—H), 7.80 (d, J=8.5 Hz, 2 H, Ar—H), 7.35 (d, J=8.5 Hz, 2 H, Ar—H), 6.32 (m, 1 H, H$_{olefin}$), 6.02 (m, 2 H, H$_{olefin}$), 5.93 (m, 1 H, H$_{olefin}$), 5.61 (m, 2 H, H$_{olefin}$), 4.47-4.44 (m, 2 H, OCH$_2$), 4.30-4.28 (m, 2 H, OCH$_2$), 2.16-2.14 (m, 2 H, OCH$_2$CH$_2$CH$_2$O), 2.04 (br. s, 3 H, CH$_3$), 1.84 (m, 6H, 2×CH$_3$).

EXAMPLE 3

Polymerizable monomeric compound 3 of formula I3-4 is prepared as follows.

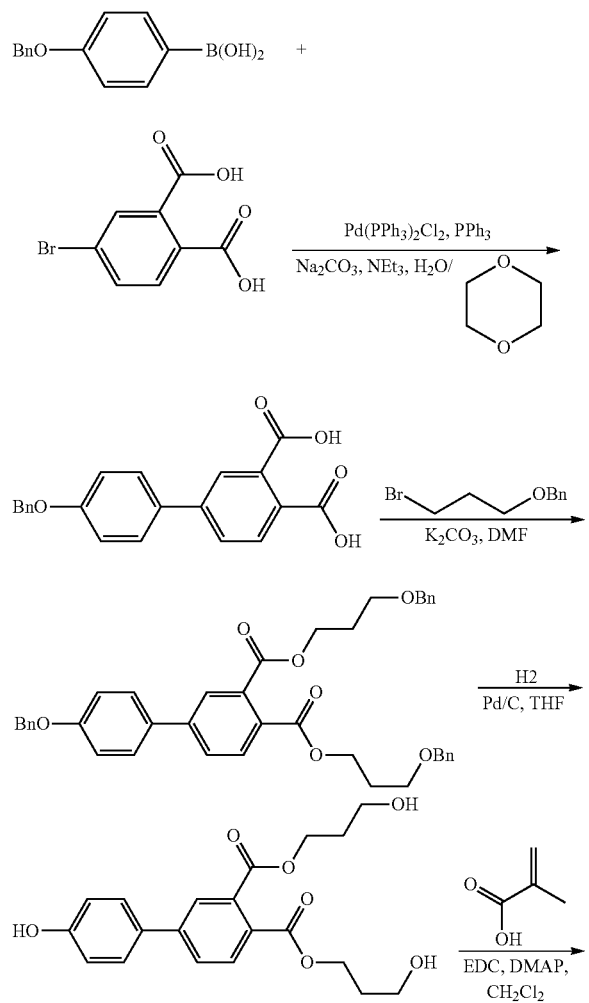

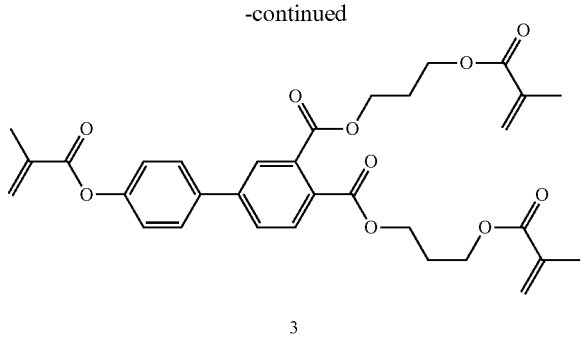

3

3.1 4'-Benzyloxy-biphenyl-3,4-dicarboxylic acid

4'-benzyloxy-biphenyl-3,4-dicarboxylic acid is prepared from commercially available [4-(benzyloxy)phenyl]-boronic acid and 5-bromo-phthalic acid.

To a solution of sodium carbonate (31.27 g, 295.1 mmol) in dist. water (135 ml) is added 1,4-dioxane (210 ml), 5-bromo-phthalic acid (14.46 g, 59.0 mmol) and [4-(benzyloxy)phenyl]-boronic acid (14.82 g, 65.0 mmol) followed by bis(triphenylphosphine)palladium(II) dichloride (0.83 g, 1.2 mmol), triphenylphosphine (0.31 g, 1.2 mmol) and triethylamine (0.12 g, 1.2 mmol) under nitrogen atmosphere. The reaction mixture is heated at reflux for 2 hs. After cooling to room temperature, 400 ml dist. water is added and the reaction mixture is neutralized with conc. HCl acid to pH~1 under cooling. The precipitated crude product is filtrated, washed with dist. water, and further purified by recrystallization from acetonitrile to provide gray crystals of 4'-benzyloxy-biphenyl-3,4-dicarboxylic acid (15.8 g.

3.2 4'-Benzyloxy-biphenyl-3,4-dicarboxylic acid bis-(3-benzyloxy-propyl)ester To a solution of 4'-benzyloxy-biphenyl-3,4-dicarboxylic acid (8.00 g, 22.96 mmol) in DMF (50 ml) is added potassium carbonate (7.62 g, 55.12 mmol). To the resulted suspension (2-bromo-propoxymethyl)-benzene (11.58 g. 50.52 mmol) is added. The reaction mixture is stirred at 70° C. for 3 hs. After cooling to room temperature, the reaction mixture is poured into 100 ml ice-water mixture and extracted with 60 ml MTBE. The organic phase is washed with sat. aq. NaCl solution and dried over sodium sulfate. After removing solvent in vacuo, the oily residue is purified by silica gel chromatography with elute heptane/ethylacetate 7:3. 4'-benzyloxy-biphenyl-3,4-dicarboxylic acid bis-(3-benzyloxy-propyl)ester is obtained as colorless solid (6.0 g).

3.2 4'-Hydroxy-biphenyl-3,4-dicarboxylic acid bis-(3-hydroxy-propyl)ester

A solution of 4'-benzyloxy-biphenyl-3,4-dicarboxylic acid bis-(3-benzyloxypropyl)ester (6.0 g, 9.3 mmol) in tetrahydrofuran (60 ml) is treated with palladium (5%) on activated charcoal (0.6 g) and submitted to hydrogenation for 20 hs. The catalyst is then filtered off, and the remaining solution is concentrated in vacuo. After further drying in high vacuo 4'-hydroxy-biphenyl-3,4-dicarboxylic acid bis-(3-hydroxy-propyl)ester is obtained as oil and used without further purification (3.4 g).

3.3 4'-(2-Methyl-acryloyloxy)-biphenyl-3,4-dicarboxylic acid bis-[3-(2-methyl-acryloyloxy)-propyl] ester Methacrylic acid (4.46 g, 51.8 mmol) and 4-(dimethylamino)pyridine (0.11 g, 0.9 mmol) is added to a suspension of 4'-hydroxy-biphenyl-3,4-dicarboxylic acid bis-(3-hydroxy-propyl)ester (3.40 g, 9.1 mmol) in dichloromethane (100 ml). The reaction mixture is treated dropwise at 0° C. with a solution of N-(3-dimethylaminopropyl)-N'-ethylcarbodiimide (8.04 g, 51.8 mmol) in dichloromethane (60 ml) and stirred for 20 hs at room temperature. The reaction mixture is concentrated in vacuo and filtrated through silica gel. After removing solvent, the crude product is purified by silica gel chromatography with elute heptane/ethylacetate 7:3. 4'-(2-Methyl-acryloyloxy)-biphenyl-3,4-dicarboxylic acid bis-[3-(2-methyl-acryloyloxy)-propyl]ester is obtained as colorless oil (1.7 g).

$^1$H-NMR (CDCl$_3$, 500 MHz): δ (ppm)=7.86 (d, $^4J_{H,H}$=1.5 Hz, 1 H, Ar—H), 7.82 (d, $^3J_{H,H}$=8.0 Hz, 1 H, Ar—H), 7.72 (dd, $^3J_{H,H}$=8.0 Hz, $^4J_{H,H}$=1.5 Hz 1 H, Ar—H), 7.62 (d, J=8.5 Hz, 2 H, Ar—H), 7.24 (d, J=8.5 Hz, 2 H, Ar—H), 6.37 (m, 1H, H$_{olefin}$), 6.10 (m, 2 H, H$_{olefin}$), 5.78 (m, 1 H, H$_{olefin}$), 5.56-5.53 (m, 2 H, H$_{olefin}$), 4.46-4.42 (m, 2 H, OCH$_2$), 4.31-4.27 (m, 2 H, OCH$_2$), 2.16-2.13 (m, 2 H, OCH$_2$CH$_2$CH$_2$O), 2.08 (br. s, 3 H, CH$_3$), 1.94 (br. s, 3H, CH$_3$), 1.92 (br. s, 3H, CH$_3$).

EXAMPLE 4

Polymerizable monomeric compound 4 of formula I4-1 is prepared as follows.

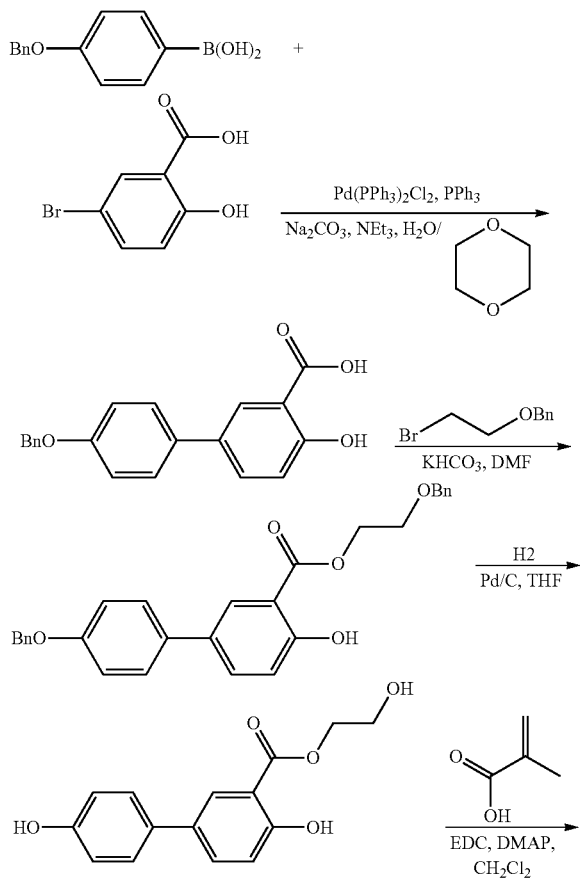

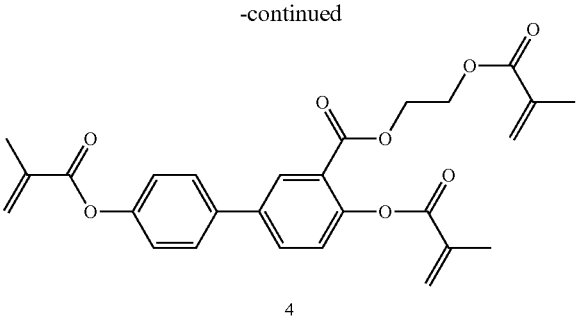

4

4.1 4'-Benzyloxy-4-hydroxy-biphenyl-3-carboxylic acid

4'-Benzyloxy-4-hydroxy-biphenyl-3-carboxylic acid is prepared from commercially available [4-(benzyloxy)phenyl]-boronic acid and 5-bromo-2-hydroxyl benzoic acid.

To a solution of sodium carbonate (36.63 g, 345.6 mmol) in dist. water (160 ml) is added 1,4-dioxane (245 ml), 5-bromo-2-hydroxyl benzoic acid (15.00 g, 69.1 mmol) and [4-(benzyloxy)phenyl]-boronic acid (15.76 g, 69.1 mmol) followed by bis(triphenylphosphine)palladium(II) dichloride (0.97 g, 1.4 mmol), triphenylphosphine (0.36 g, 1.4 mmol) and triethylamine (0.14 g, 1.4 mmol) under nitrogen atmosphere. The reaction mixture is heated at reflux for 2 hs. After cooling to room temperature, 200 ml dist. water is added and the reaction mixture is neutralized with conc. HCl acid to pH~1 under cooling. The precipitated crude product is filtrated, washed with dist. water. After drying in vacuo, the obtained gray crystals of 4'-benzyloxy-4-hydroxyl biphenyl-3-carboxylic acid (22 g) were used without further purification.

4.2 4'-Benzyloxy-4-hydroxy-biphenyl-3-carboxylic acid 2-benzyloxy-ethyl ester To a solution of 4'-benzyloxy-4-hydroxyl-biphenyl-3-carboxylic acid (18.00 g, 39.3 mmol) in DMF (50 ml) is added potassium bicarbonate (4.72 g, 47.2 mmol). To the resulted suspension (2-bromo-ethoxymethyl)-benzene (12.69 g. 59.0 mmol) is added. The reaction mixture is stirred at 40° C. for overnight. After cooling to room temperature, the reaction mixture is poured into 200 ml ice-water mixture and extracted with 120 ml MTBE. The organic phase is washed with sat. aq. NaCl solution and dried over sodium sulfate. After removing solvent in vacuo, the oily residue is purified by silica gel chromatography with elute heptane/ethylacetate 8:2 and recrystallized from acetonitrile to afford 4'-benzyloxy-4-hydroxyl biphenyl-3-carboxylic acid 2-benzyloxy-ethyl ester as white crystals (4.2 g).

4.3 4,4'-Dihydroxy-biphenyl-3-carboxylic acid 2-hydroxy-ethyl ester

A solution of 4'-benzyloxy-4-hydroxyl biphenyl-3-carboxylic acid 2-benzyloxyethyl ester (4.2 g, 9.2 mmol) in tetrahydrofuran (40 ml) is treated with palladium (5%) on activated charcoal (1.0 g) and submitted to hydrogenation for 21 hs. The catalyst is then filtered off, and the remaining solution is concentrated in vacuo. The solid residue is recrystallized from acetonitrile to provide white crystals of 4,4'-dihydroxy-biphenyl-3-carboxylic acid 2-hydroxyethyl ester (1.8 g).

4.4 4,4'-Bis-(2-methyl-acryloyloxy)-biphenyl-3-carboxylic acid 2-(2-methyl-acryloyloxy)-ethyl ester Methacrylic acid (3.22 g, 37.4 mmol) and 4-(dimethylamino)pyridine (0.08 g, 0.66 mmol) is added to a suspension of 4,4'-dihydroxy-biphenyl-3-carboxylic acid 2-hydroxyethyl ester (1.80 g, 6.6 mmol) in dichloromethane (80 ml). The reaction mixture is treated dropwise at 0° C. with a solution of N-(3-dimethylaminopropyl)-N'-ethylcarbodiimide (5.81 g, 37.4 mmol) in dichloromethane (30 ml) and stirred for 20 hs at room temperature. The reaction mixture is concentrated in vacuo and filtrated through silica gel. After removing solvent, the crude product is recrystallized from ethanol to afford white crystals of 4,4'-bis-(2-methylacryloyloxy)-biphenyl-3-carboxylic acid 2-(2-methyl-acryloyloxy)-ethyl ester (2.2 g, m.p. 84° C.).

$^1$H-NMR (DMSO-d$_6$, 500 MHz): δ (ppm)=8.17 (m, 1 H, Ar—H), 8.01 (m, 1 H, Ar—H), 7.76 (d, J=8.5 Hz, 2 H, Ar—H), 7.40 (m, 1 H, Ar—H), 7.32 (d, J=8.5 Hz, 2 H, Ar—H), 6.32 (m, 2 H, H$_{olefin}$), 6.28 (m, 1 H, H$_{olefin}$), 6.03 (m, 1 H, H$_{olefin}$), 5.93 (m, 2 H, H$_{olefin}$), 5.90 (m, 1 H, H$_{olefin}$), 5.68 (m, 1 H, H$_{olefin}$), 4.50-4.48 (m, 2 H, OCH$_2$), 4.39-4.37 (m, 2 H, OCH$_2$), 2.03 (br. s, 3 H, CH$_3$), 2.01 (br. s, 3 H, CH$_3$), 1.86 (br. s, 6H, CH$_3$).

EXAMPLE 5

Polymerizable monomeric compound 5 of formula I9-1 is prepared as follows.

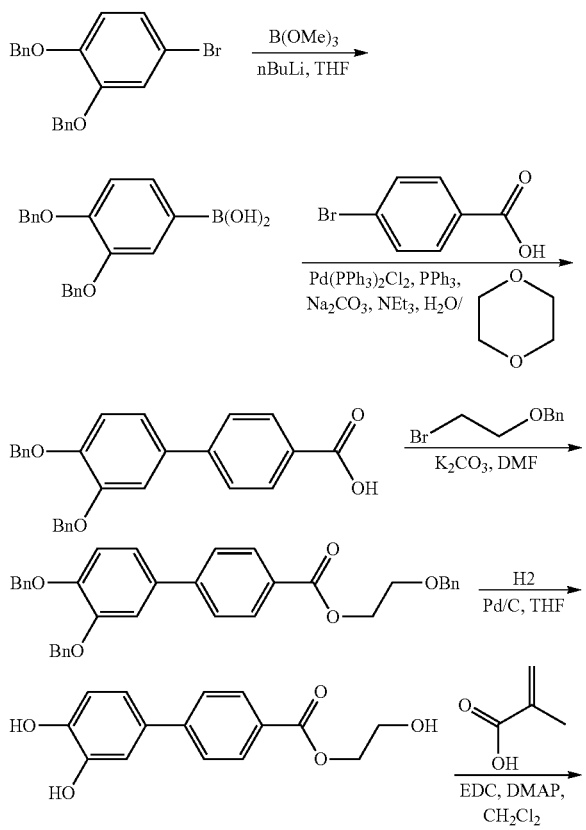

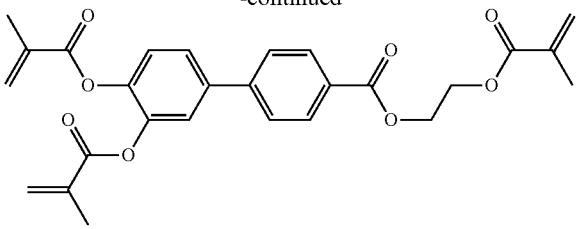

5

5.1 3,4-Bis-benzyloxy-phenyl-boronic acid 3,4-Bis-benzyloxy-phenyl-boronic acid is prepared from commercially available 1,2-bis-benzyloxy-4-bromo-benzene.

1,2-bis-benzyloxy-4-bromo-benzene (20.00 g, 54.2 mmol) is dissolved in dry THF (250 ml) under nitrogen atmosphere. The solution is cooled down in a dry ice bath to −70° C. 37 ml 15% solution of n-butyllithium in n-hexane is added dropwise with the temperature controlled below −60° C. The reaction mixture is continued stirring at this temperature for 1 h. The solution of trimethylborate (6.19 g, 59.6 mmol) in 6 ml dry THF is added dropwise. The reaction mixture is allowed slowly warming up to 0° C. under stirring, and then hydrolyzed carefully by dropwise addition of water. The reaction mixture is acidified with conc. HCl acid to pH~1 under cooling. The organic phase is separated. The aqueous is extracted with MTBE. The combined organic phase is dried over sodium sulfate. After removing solvent in vacuo, the crude product is recrystallized from heptane to provide pinkish crystals of 3,4-bis-benzyloxy-phenyl-boronic acid (13.8 g).

5.2 3',4'-Bis-benzyloxy-biphenyl-4-carboxylic acid

To a solution of sodium carbonate (21.88 g, 206.5 mmol) in dist. water (95 ml) is added 1,4-dioxane (150 ml), 4-bromobenzoic acid (8.38 g, 41.3 mmol) and 3,4-bis-benzyloxy-phenyl-boronic acid (13.80 g, 41.3 mmol) followed by bis(triphenylphosphine)palladium(II) dichloride (0.58 g, 0.8 mmol), triphenylphosphine (0.22 g, 0.8 mmol) and triethylamine (0.08 g, 0.8 mmol) under nitrogen atmosphere. The reaction mixture is heated at reflux for 2 hs. After cooling to room temperature, 200 ml dist. water is added and the reaction mixture is neutralized with conc. HCl acid to pH~1 under cooling. The precipitated crude product is filtrated, washed with dist. water. After drying in vacuo, the obtained gray crystals of 3',4'-bis-benzyloxy-biphenyl-4-carboxylic acid (14.6 g) were used without further purification.

5.3 3',4'-Bis-benzyloxy-biphenyl-4-carboxylic acid 2-benzyloxy-ethyl ester

To a solution of 3',4'-bis-benzyloxy-biphenyl-4-carboxylic acid (8.00 g, 19.5 mmol) in DMF (30 ml) is added potassium carbonate (3.23 g, 23.4 mmol). To the resulted suspension (2-bromo-ethoxymethyl)-benzene (4.61 g. 21.4 mmol) is added. The reaction mixture is stirred at 70° C. for 3 hs. After cooling to room temperature, the reaction mixture is poured into 100 ml ice-water mixture and extracted with 60 ml MTBE. The organic phase is washed with sat. aq. NaCl solution and dried over sodium sulfate. After removing solvent in vacuo, the crude product is purified by recrystallization from isopropanol/acetonitrile to afford 3',4'-bisbenzyloxy-biphenyl-4-carboxylic acid 2-benzyloxy-ethyl ester as off-white crystals (7.2 g).

5.4 3',4'-Dihydroxy-biphenyl-4-carboxylic acid 2-hydroxy-ethyl ester

A solution of 3',4'-bis-benzyloxy-biphenyl-4-carboxylic acid 2-benzyloxy-ethyl ester (7.2 g, 12.0 mmol) in tetrahydrofuran (70 ml) is treated with palladium (5%) on activated charcoal (2.0 g) and submitted to hydrogenation for 18 hs. The catalyst is then filtered off, and the remaining solution is concentrated in vacuo. The solid residue is recrystallized from acetonitrile to provide gray crystals of 3',4'-dihydroxy-biphenyl-4-carboxylic acid 2-hydroxy-ethyl ester (2.7 g).

5.5 3',4'-Bis-(2-methyl-acryloyloxy)-biphenyl-4-carboxylic acid 2-(2-methyl-acryloyloxy)-ethyl ester Methacrylic acid (4.83 g, 56.1 mmol) and 4-(dimethylamino)pyridine (0.12 g, 0.98 mmol) is added to a suspension of 3',4'-dihydroxy-biphenyl-4-carboxylic acid 2-hydroxyethyl ester (2.7 g, 9.8 mmol) in dichloromethane (100 ml). The reaction mixture is treated dropwise at 0° C. with a solution of N-(3-dimethylaminopropyl)-N'-ethylcarbodiimide (8.71 g, 56.1 mmol) in dichloromethane (40 ml) and stirred for 20 hs at room temperature. The reaction mixture is concentrated in vacuo and filtrated through silica gel. After removing solvent, the crude product is recrystallized from ethanol/acetonitrile to afford white crystals of 3',4'-bis-(2-methyl-acryloyloxy)-biphenyl-4-carboxylic acid 2-(2-methyl-acryloyloxy)-ethyl ester (1.7 g, m.p. 63° C.).

$^1$H-NMR (DMSO-$d_6$, 500 MHz): δ (ppm)=8.04 (d, J=8.5 Hz, 2 H, Ar—H), 7.89 (d, J=8.5 Hz, 2 H, Ar—H), 7.79 (m, 1 H, Ar—H), 7.75 (m, 1 H, Ar—H), 7.50 (m, 1H, Ar—H), 6.22 (m, 2 H, $H_{olefin}$), 6.05 (m, 1 H, $H_{olefin}$), 5.91 (m, 2 H, $H_{olefin}$), 5.69 (m, 1 H, $H_{olefin}$), 4.57-4.55 (m, 2 H, OCH$_2$), 4.49-4.47 (m, 2 H, OCH$_2$), 1.96 (br. s, 6 H, 2×CH$_3$), 1.88 (br. s, 3H, CH$_3$).

EXAMPLE 6

Polymerizable monomeric compound 6 of formula I9-2 is prepared as follows.

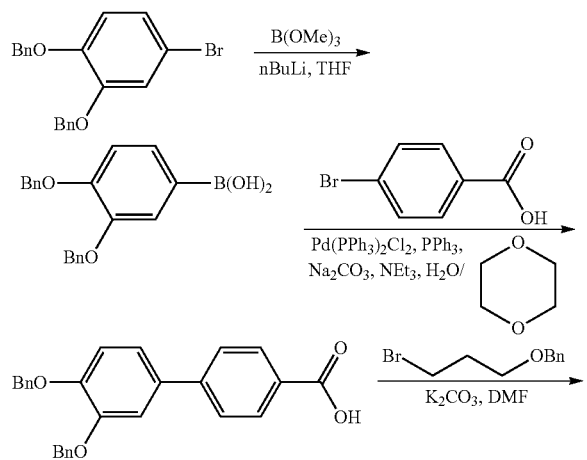

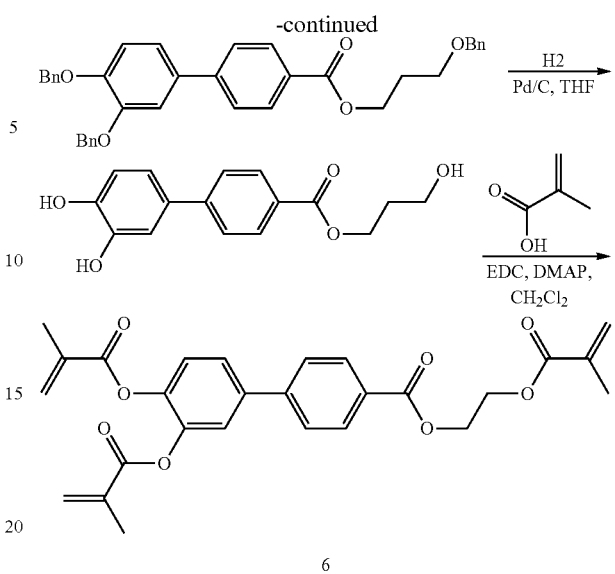

3,4-Bis-benzyloxy-phenyl-boronic acid and 3',4'-bis-benzyloxy-biphenyl-4-carboxylic acid are prepared as described in Example 5.

6.1 3',4'-Bis-benzyloxy-biphenyl-4-carboxylic acid 3-benzyloxy-propyl ester

To a solution of 3',4'-bis-benzyloxy-biphenyl-4-carboxylic acid (8.00 g, 19.5 mmol) in DMF (30 ml) is added potassium carbonate (3.23 g, 23.4 mmol). To the resulted suspension (3-bromo-propoxymethyl)-benzene (4.91 g. 21.4 mmol) is added. The reaction mixture is stirred at 70° C. for 3 hs. After cooling to room temperature, the reaction mixture is poured into 100 ml ice-water mixture and extracted with 60 ml MTBE. The organic phase is washed with sat. aq. NaCl solution and dried over sodium sulfate. After removing solvent in vacuo, the crude product is purified by recrystallization from isopropanol/acetonitrile to afford 3',4'-bis-benzyloxy-biphenyl-4-carboxylic acid 3-benzyloxy-propyl ester as white crystals (7.5 g).

6.2 3',4'-Dihydroxy-biphenyl-4-carboxylic acid 3-hydroxy-propyl ester

A solution of 3',4'-bis-benzyloxy-biphenyl-4-carboxylic acid 3-benzyloxypropyl ester (7.5 g, 13.4 mmol) in tetrahydrofuran (80 ml) is treated with palladium (5%) on activated charcoal (2.0 g) and submitted to hydrogenation for 19 hs. The catalyst is then filtered off, and the remaining solution is concentrated in vacuo. The solid residue is recrystallized from acetonitrile to provide white crystals of 3',4'-dihydroxy-biphenyl-4-carboxylic acid 3-hydroxypropyl ester (3.3 g).

6.3 3',4'-Bis-(2-methyl-acryloyloxy)-biphenyl-4-carboxylic acid 3-(2-methyl-acryloyloxy)-propyl ester Methacrylic acid (5.45 g, 63.3 mmol) and 4-(dimethylamino)pyridine (0.14 g, 1.11 mmol) is added to a suspension of 3',4'-dihydroxy-biphenyl-4-carboxylic acid 3-hydroxypropyl ester (3.2 g, 11.1 mmol) in dichloromethane (100 ml). The reaction mixture is treated dropwise at 0° C. with a solution of N-(3-dimethylaminopropyl)-N'-ethylcarbodiimide (9.82 g, 63.2 mmol) in dichloromethane (40 ml) and stirred for 20 hs at room temperature. The reaction mixture is concentrated in vacuo and the oily residue is purified by silica gel chromatography with dichloromethane to provide 3',4'-bis-(2-methylacryloyloxy)-biphenyl-4-carboxylic acid 3-(2-methyl-acryloyloxy)-propyl ester colorless oil (2.3 g).

¹H-NMR (DMSO-d₆, 500 MHz): δ (ppm)=8.05 (d, J=8.5 Hz, 2 H, Ar—H), 7.87 (d, J=8.5 Hz, 2 H, Ar—H), 7.78 (m, 1 H, Ar—H), 7.74 (m, 1 H, Ar—H), 7.50 (m, 1 H, Ar—H), 6.22 (m, 2 H, H$_{olefin}$), 6.04 (m, 1 H, H$_{olefin}$), 5.92 (m, 2 H, H$_{olefin}$), 5.66 (m, 1 H, H$_{olefin}$), 4.41-4.39 (m, 2 H, OCH₂), 4.30-4.27 (m, 2 H, OCH₂), 2.12 (m, 2 H, OCH₂CH₂CH₂O), 1.97 (br. s, 6 H, 2×CH₃), 1.87 (br. s, 3H, CH₃).

EXAMPLE 7

Polymerizable monomeric compound 7 of formula I8-1 is prepared as follows.

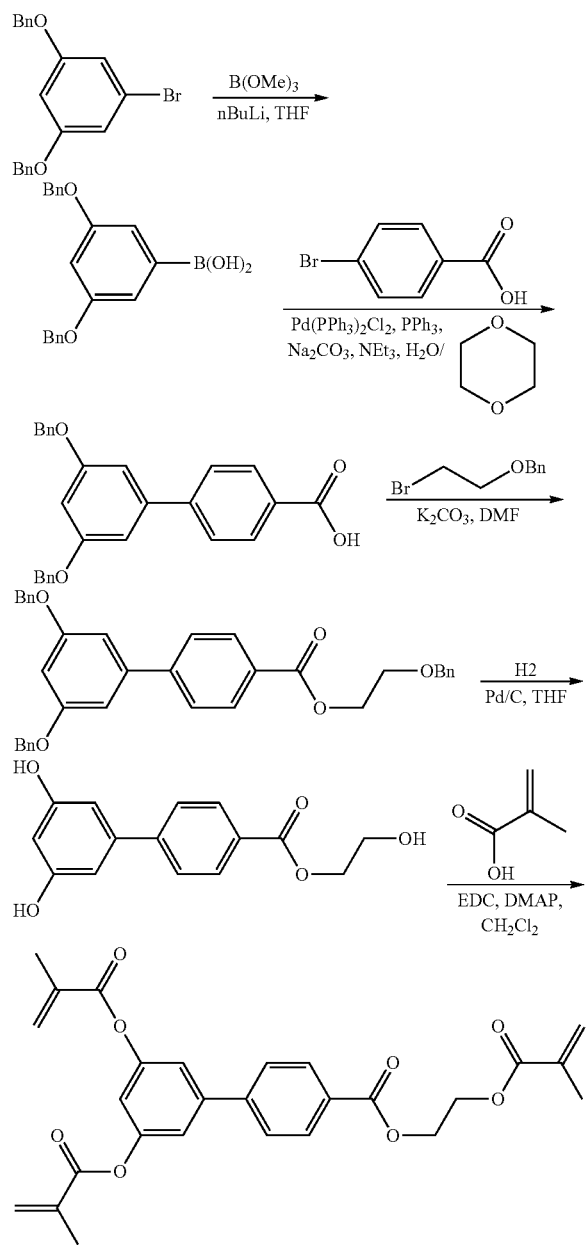

7

7.1 3,5-Bis-benzyloxy-phenyl-boronic acid 3,5-Bis-benzyloxy-phenyl-boronic acid is prepared from commercially available 1,3-bis-benzyloxy-5-bromo-benzene.

1,3-bis-benzyloxy-5-bromo-benzene (20.00 g, 54.16 mmol) is dissolved in dry THF (250 ml) under nitrogen atmosphere. The solution is cooled down in a dry ice bath to −70° C. 37 ml 15% solution of n-butyllithium in n-hexane is added dropwise with the temperature controlled below −60° C. The reaction mixture is continued stirring at this temperature for 1 h. The solution of trimethylborate (6.19 g, 59.6 mmol) in 6 ml dry THF is added dropwise. The reaction mixture is allowed slowly warming up to 0° C. under stirring, and then hydrolyzed carefully by dropwise addition of water. The reaction mixture is acidified with conc. HCl acid to pH~1 under cooling. The organic phase is separated. The aqueous is extracted with MTBE. The combined organic phase is dried over sodium sulfate. After removing solvent in vacuo, the crude product is recrystallized from heptane to provide pinkish crystals of 3,5-bis-benzyloxy-phenyl-boronic acid (13.8 g).

7.2 3',5'-Bis-benzyloxy-biphenyl-4-carboxylic acid

To a solution of sodium carbonate (21.88 g, 206.5 mmol) in dist. water (95 ml) is added 1,4-dioxane (150 ml), 4-bromobenzoic acid (8.38 g, 41.3 mmol) and 3,5-bis-benzyloxy-phenyl-boronic acid (13.80 g, 41.3 mmol) followed by bis(triphenylphosphine)palladium(II) dichloride (0.58 g, 0.8 mmol), triphenylphosphine (0.22 g, 0.8 mmol) and triethylamine (0.08 g, 0.8 mmol) under nitrogen atmosphere. The reaction mixture is heated at reflux for 2 hs. After cooling to room temperature, 200 ml dist. water is added and the reaction mixture is neutralized with conc. HCl acid to pH~1 under cooling. The precipitated crude product is filtrated, washed with dist. water. After drying in vacuo, the crude product is recrystallized in acetonitrile to provide gray crystals of 3',5'-bis-benzyloxy-biphenyl-4-carboxylic acid (6.0 g).

7.3 3',5'-Bis-benzyloxy-biphenyl-4-carboxylic acid 2-benzyloxy-ethyl ester

To a solution of 3',5'-bis-benzyloxy-biphenyl-4-carboxylic acid (6.00 g, 14.6 mmol) in DMF (30 ml) is added potassium carbonate (2.42 g, 17.5 mmol). To the resulted suspension (2-bromo-ethoxymethyl)-benzene (3.46 g. 16.1 mmol) is added. The reaction mixture is stirred at 70° C. for 3 hs. After cooling to room temperature, the reaction mixture is poured into 100 ml ice-water mixture and extracted with 60 ml MTBE. The organic phase is washed with sat. aq. NaCl solution and dried over sodium sulfate. After removing solvent in vacuo, 3',5'-bis-benzyloxy-biphenyl-4-carboxylic acid 2-benzyloxy-ethyl ester is obtained (8.0 g) and used for the next step without further purification.

7.4 3',5'-Dihydroxy-biphenyl-4-carboxylic acid 2-hydroxy-ethyl ester

A solution of 3',5'-bis-benzyloxy-biphenyl-4-carboxylic acid 2-benzyloxy-ethyl ester (8.0 g, 14.6 mmol) in tetrahydrofuran (100 ml) is treated with palladium (5%) on activated charcoal (1.0 g) and submitted to hydrogenation for 20 hs. The catalyst is then filtered off, and the remaining solution is concentrated in vacuo. The solid residue is recrystallized from acetonitrile to provide white crystals of 3',5'-dihydroxy-biphenyl-4-carboxylic acid 2-hydroxy-ethyl ester (2.3 g).

7.5 3',5'-Bis-(2-methyl-acryloyloxy)-biphenyl-4-carboxylic acid 2-(2-methyl-acryloyloxy)-ethyl ester Methacrylic acid (4.12 g, 47.8 mmol) and 4-(dimethylamino)pyridine (0.10 g, 0.84 mmol) is added to a suspension of 3',5'-dihydroxy-biphenyl-4-carboxylic acid 2-hydroxy-ethyl ester (2.30 g, 8.4 mmol) in dichloromethane (100 ml). The reaction mixture is treated dropwise at 0° C. with a solution of N-(3-dimethylaminopropyl)-N'-ethylcarbodiimide (7.42 g, 47.8 mmol) in dichloromethane (40 ml) and stirred for 20 hs at room temperature. The reaction mixture is concentrated in vacuo and filtrated through silica gel. After removing solvent, the crude product is recrystallized from ethanol to afford white crystals of 3',5'-bis-(2-methyl-acryloyloxy)-biphenyl-4-carboxylic acid 2-(2-methyl-acryloyloxy)-ethyl ester (2.5 g, m.p. 66° C.).

$^1$H-NMR (CDCl$_3$, 500 MHz): δ (ppm)=8.10 (d, J=8.5 Hz, 2 H, Ar—H), 7.65 (d, J=8.5 Hz, 2 H, Ar—H), 7.29 (m, 2 H, Ar—H), 7.05 (t, J=2.0 Hz, 1 H, Ar—H), 6.37 (m, 2 H, H$_{olefin}$), 6.15 (m, 1 H, H$_{olefin}$), 5.79 (m, 2 H, H$_{olefin}$), 5.60 (m, 1 H, H$_{olefin}$), 4.60-4.58 (m, 2 H, OCH$_2$), 4.52-4.50 (m, 2 H, OCH$_2$), 2.07 (br. s, 6 H, 2×CH$_3$), 1.96 (m, 3H, CH$_3$).

EXAMPLE 8

Polymerizable monomeric compound 8 of formula I1-1 is prepared as follows.

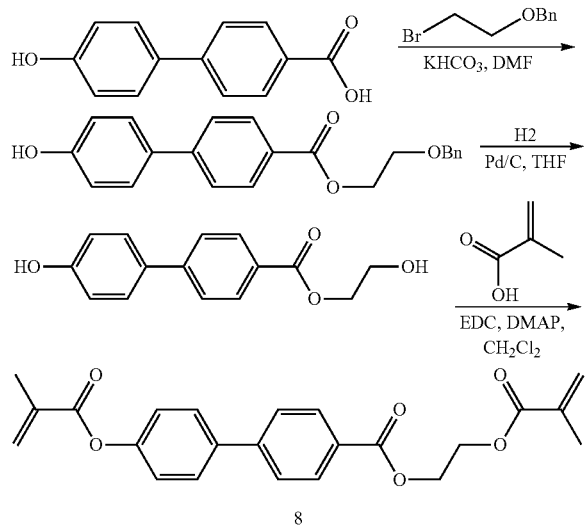

8

8.1 4'-Hydroxy-biphenyl-4-carboxylic acid 2-benzyloxy-ethyl ester

4'-Hydroxy-biphenyl-4-carboxylic acid 2-benzyloxy-ethyl ester is prepared from commercially available 4'-hydroxy-biphenyl-4-carboxylic acid.

To a solution of 4'-hydroxy-biphenyl-4-carboxylic acid (4.28 g, 20 mmol) in DMF (30 ml) is added potassium bicarbonate (2.40 g, 24.0 mmol). To the resulted suspension (2-bromo-ethoxymethyl)-benzene (6.45 g. 30.0 mmol) is added. The reaction mixture is stirred at 40° C. overnight. After cooling to room temperature, the reaction mixture is poured into 100 ml ice-water mixture and extracted with 60 ml MTBE. The organic phase is washed with sat. aq. NaCl solution and dried over sodium sulfate. After removing solvent in vacuo, the crude product is purified by recrystallization from heptane to afford 4'-hydroxybiphenyl-4-carboxylic acid 2-benzyloxy-ethyl ester as white crystals (3.0 g).

8.2 4'-Hydroxy-biphenyl-4-carboxylic acid 2-hydroxy-ethyl ester

A solution of 4'-hydroxy-biphenyl-4-carboxylic acid 2-benzyloxy-ethyl ester (3.0 g, 8.0 mmol) in tetrahydrofuran (30 ml) is treated with palladium (5%) on activated charcoal (1.0 g) and submitted to hydrogenation for 15 hs. The catalyst is then filtered off, and the solvent of the remaining solution is removed in vacuo. 4'-Hydroxy-biphenyl-4-carboxylic acid 2-hydroxy-ethyl ester is obtained as white crystals and used for the next step without further purification (2.1 g).

8.3 4'-(2-Methyl-acryloyloxy)-biphenyl-4-carboxylic acid 2-(2-methylacryloyloxy)-ethyl ester Methacrylic acid (2.05 g, 23.0 mmol) and 4-(dimethylamino)pyridine (0.1 g, 0.8 mmol) is added to a suspension of 4'-hydroxy-biphenyl-4-carboxylic acid 2-hydroxy-ethyl ester (2.10 g, 7.9 mmol) in dichloromethane (90 ml). The reaction mixture is treated dropwise at 0° C. with a solution of N-(3-dimethylaminopropyl)-N'-ethylcarbodiimide (3.70 g, 23.8 mmol) in dichloromethane (30 ml) and stirred for 20 hs at room temperature. The reaction mixture is concentrated in vacuo and filtrated through silica gel. After removing solvent, the crude product is recrystallized from ethanol to afford white crystals of 4'-(2-Methyl-acryloyloxy)-biphenyl-4-carboxylic acid 2-(2-methyl-acryloyloxy)-ethyl ester (1.7 g, m.p. 79° C.).

$^1$H-NMR (DMSO-d$_6$, 500 MHz): δ (ppm)=8.04 (d, J=8.5 Hz, 2 H, Ar—H), 7.86 (d, J=8.5 Hz, 2 H, Ar—H), 7.81 (d, J=8.5 Hz, 2 H, Ar—H), 7.32 (d, J=8.5 Hz, 2 H, Ar—H), 6.31 (br. s, 1 H, H$_{olefin}$), 6.05 (m, 1 H, H$_{olefin}$), 5.92 (m, 1 H, H$_{olefin}$), 5.69 (m, 1 H, H$_{olefin}$), 4.58-4.56 (m, 2 H, OCH$_2$), 4.49-4.47 (m, 2 H, OCH$_2$), 2.03 (br. s, 3 H, CH$_3$), 1.88 (br. s, 3 H, CH$_3$).

EXAMPLE 9

Applying the same synthetic strategy as in Example 4, polymerizable monomeric compound 9 is prepared analogically as follows, starting from commercially available [4-(benzyloxy)phenyl]-boronic acid and 3-bromo-5-hydroxyl benzoic acid.

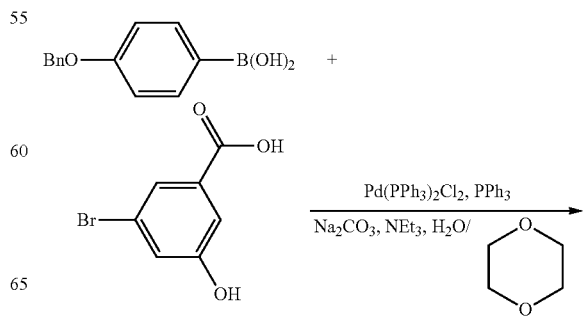

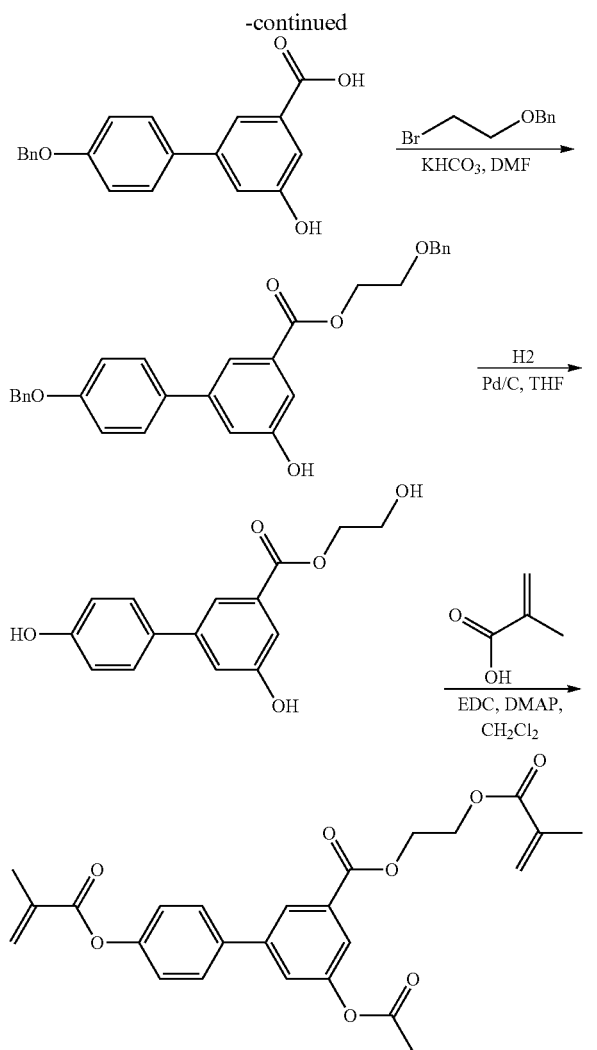

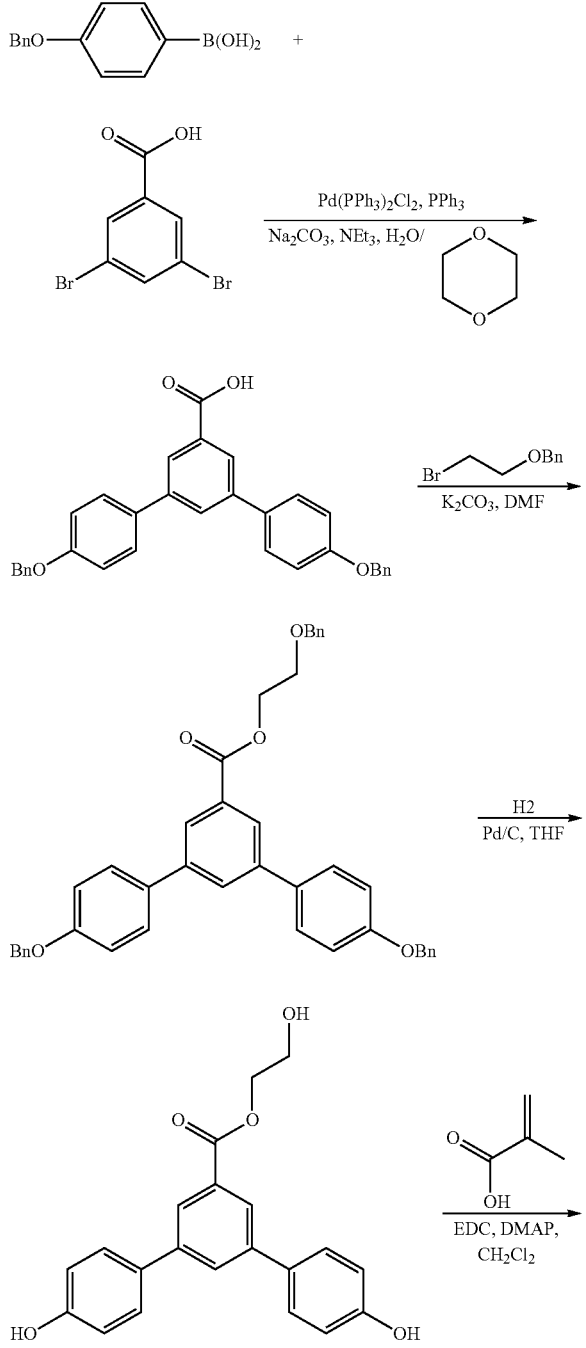

2 H, OCH$_2$), 4.50 (m, 2 H, OCH$_2$), 2.09 (m, 3 H, CH$_3$), 2.08 (m, 3 H, CH$_3$), 1.95 (m, 3 H, CH$_3$).

EXAMPLE 10

Applying the same synthetic strategy as in Example 1, polymerizable monomeric compound 10 is prepared analogically as follows, starting from commercially available [4-(benzyloxy)phenyl]-boronic acid and 3,5-dibromobenzoic acid.

For the last step the prepared 5,4'-dihydroxy-biphenyl-3-carboxylic acid 2-hydroxy-ethyl ester (5.30 g, 19.3 mmol) is dissolved in 50 ml dichloromethane. To this solution is added methacrylic acid (6.56 ml, 77.3 mmol) and 4-(dimethylamino)pyridine (0.24 g, 1.93 mmol) at room temperature. The reaction mixture is then cooled down to 0° C. and treated with a solution of N-(3-dimethylaminopropyl)-N'-ethylcarbodiimide (13.56 ml, 77.3 mmol) in dichloromethane (10 ml). After allowed to warm up to room temperature, the reaction mixture is stirred further for 20 hs. After removing solvent, the crude product is purified by column chromatography on silica gel with dichloromethane/ethylacetate 9:1 as eluent. Further recrystallization from ethanol afford white crystals of 5,4'-bis-(2-methyl-acryloyloxy)-biphenyl-3-carboxylic acid 2-(2-methyl-acryloyloxy)-ethyl ester (4.8 g, m.p. 62° C.).

$^1$H-NMR (CDCl$_3$, 500 MHz): δ (ppm)=8.15 (tr, J=2.0 Hz, 1 H, Ar—H), 7.77 (dd, J=2.0 Hz, 1 H, Ar—H), 7.63 (d, J=8.5 Hz, 2 H, Ar—H), 7.55 (tr, J=2.0 Hz, 1 H, Ar—H), 7.23 (d, J=8.5 Hz, 2 H, Ar—H), 6.40 (m, 2 H, H$_{olefin}$), 6.15 (m, 1 H, H$_{olefin}$), 5.81 (m, 2 H, H$_{olefin}$), 5.59 (m, 1 H, H$_{olefin}$), 4.60 (m,

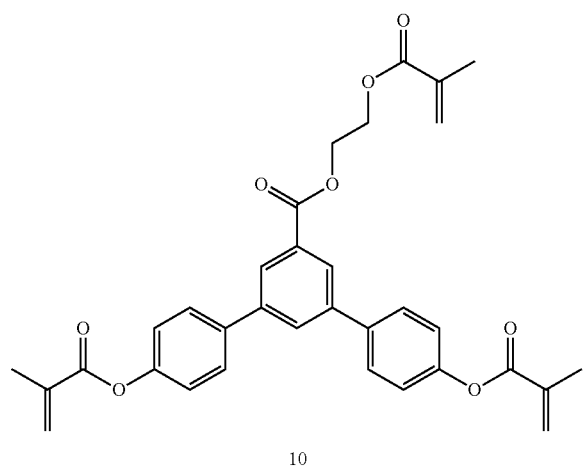

10

For the last step the prepared 4,4"-dihydroxy-[1,1';3',1"]terphenyl-5'-carboxylic acid 2-hydroxy-ethyl ester (7.00 g, 20.0 mmol) is dissolved in 80 ml dichloromethane. To this solution is added methacrylic acid (6.27 ml, 73.9 mmol) and 4-(dimethylamino)pyridine (0.25 g, 2.00 mmol) at room temperature. The reaction mixture is then cooled down to 0° C. and treated with a solution of N-(3-dimethylaminopropyl)-N'-ethylcarbodiimide (12.97 ml, 73.9 mmol) in dichloromethane (20 ml). After allowed to warm up to room temperature, the reaction mixture is stirred further for 20 hs. After removing solvent, the crude product is purified by column chromatography on silica gel with heptane/ethylacetate as eluent to afford white crystals of 4,4"-bis-(2-methylacryloyloxy)-[1,1';3',1"]terphenyl-5'-carboxylic acid 2-(2-methylacryloyloxy)-ethyl ester (7.0 g, m.p. 125° C.).

$^1$H-NMR (DMSO-d$_6$, 500 MHz): δ (ppm)=8.24 (tr, J=2.0 Hz, 1 H, Ar—H), 8.17 (d, J=2.0 Hz, 2 H, Ar—H), 7.89 (d, J=8.0 Hz, 4 H, Ar—H), 7.33 (d, J=8.0 Hz, 4 H, Ar—H), 6.32 (m, 2 H, H$_{olefin}$), 6.06 (m, 1 H, H$_{olefin}$), 5.93 (m, 2 H, H$_{olefin}$), 5.69 (m, 1 H, H$_{olefin}$), 4.60 (m, 2 H, OCH$_2$), 4.52 (m, 2 H, OCH$_2$), 2.03 (m, 6 H, CH$_3$), 1.87 (m, 3 H, CH$_3$).

EXAMPLE 11

Polymerizable monomeric compound 11 is prepared as follows.

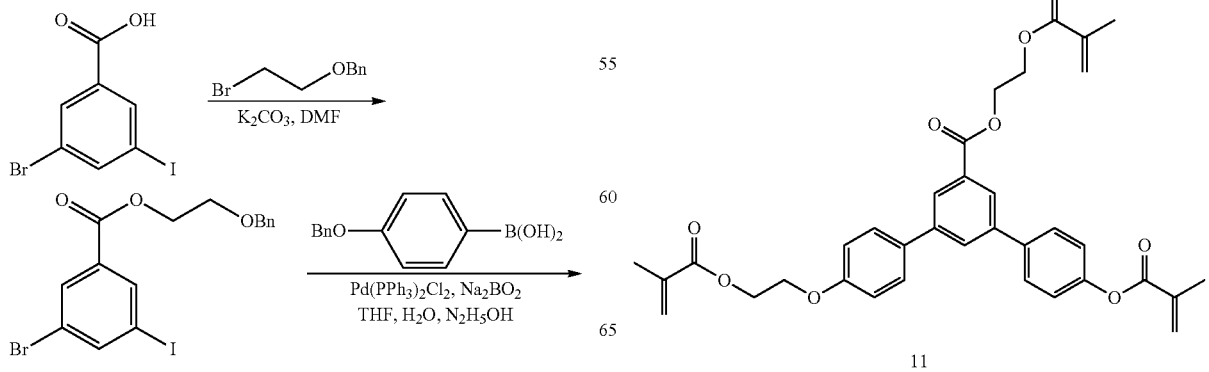

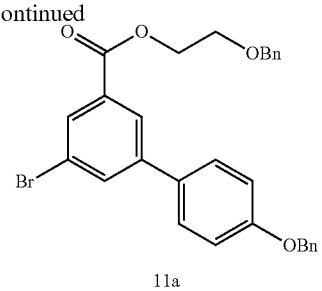

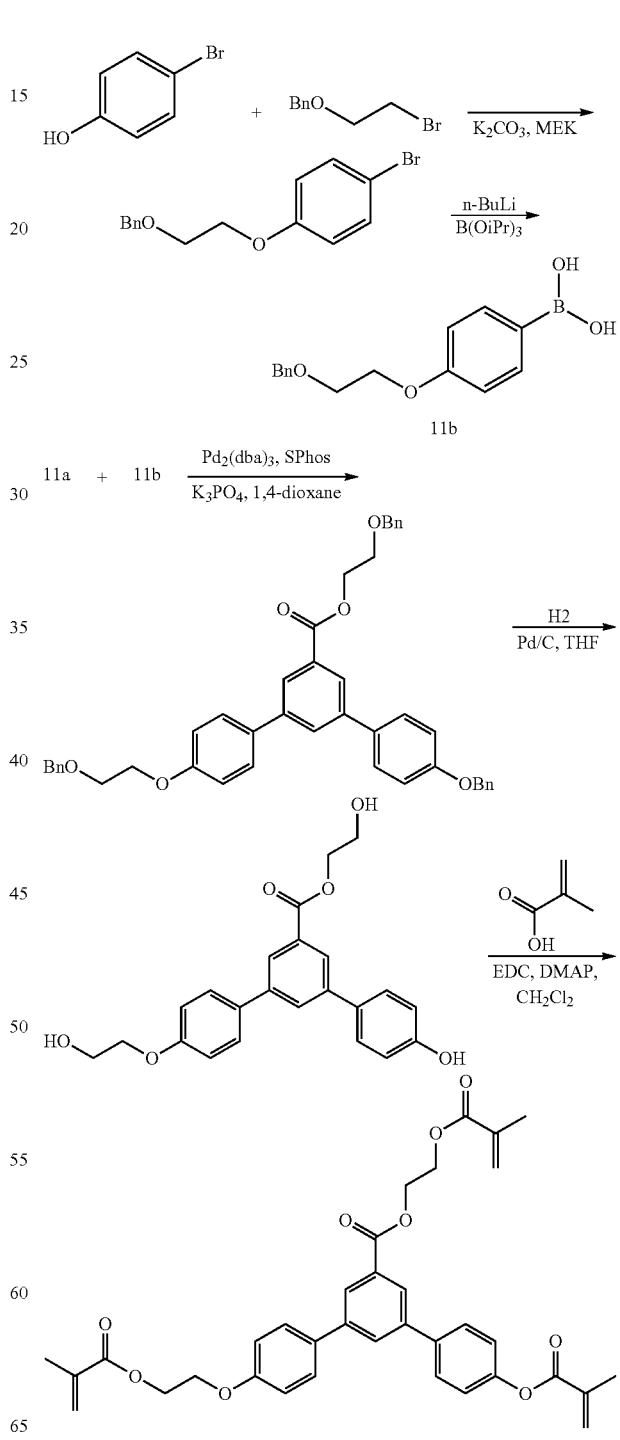

11

11.1 3-Bromo-5-iodo-benzoic acid 2-benzyloxy-ethyl ester

3-Bromo-5-iodo-benzoic acid 2-benzyloxy-ethyl ester is prepared from commercially available 3-bromo-5-iodo-benzoic acid and 2-bromoethoxymethyl-benzene.

To a solution of 3-bromo-5-iodo-benzoic acid (25.00 g, 76.5 mmol) in DMF (70 ml) is added potassium carbonate (12.68 g, 91.8 mmol). To the resulted suspension (2-bromoethoxymethyl)-benzene (13.30 ml, 84.12 mmol) is added. The reaction mixture is stirred at 70° C. for 3 hours. After cooling to room temperature, the reaction mixture is added into 1000 ml water and extracted with 3×300 ml methyl-t-butyl ether (MTBE). The organic phase is washed with sat. aq. NaCl solution, dried over sodium sulfate. After removing solvent in vacuo, 3-bromo-5-iodo-benzoic acid 2-benzyloxy-ethyl ester is obtained as brown oil (38.0 g).

11.2 4'-Benzyloxy-5-bromo-biphenyl-3-carboxylic acid 2-benzyloxy-ethyl ester (11a)

To a solution of sodium metaborate tetrahydrate (18.49 g, 132.7 mmol) in dist. water (70 ml) is added the solution of 3-bromo-5-iodo-benzoic acid 2-benzyloxy-ethyl ester (34.00 g, 73.7 mmol) and [4-(benzyloxy)phenyl]-boronic acid (16.82 g, 73.7 mmol) in 250 ml THF. After thoroughly degassing with argon, bis(triphenylphosphine)-palladium (II) chloride (2.95 g, 4.1 mmol) is added, followed by the addition of hydrazinium hydroxide (0.05 ml, 1 mmol). The reaction mixture is heated to reflux and stirred for 3 hours. After cooling to room temperature, the reaction mixture is carefully neutralized with HCl acid. The aqueous phase is separated and extracted with ethyl acetate. The organic phase is combined and dried over anhydrous sodium sulfate. After removing organic solvent, the oily residue is purified by column chromatography on silica gel with heptane/ethyl acetate as eluent. Further recrystallization from acetonitrile provide white crystals of 4'-benzyloxy-5-bromo-biphenyl-3-carboxylic acid 2-benzyloxy-ethyl ester 11a (14.3 g).

11.3 1-(2-Benzyloxy-ethoxy)-4-bromo-benzene 1-(2-Benzyloxy-ethoxy)-4-bromo-benzene is prepared from commercially available 2-bromo-ethoxymethyl-benzene and 4-bromo-phenol.

To a solution of 4-bromo-phenol (28.00 g, 157.0 mmol) in 300 ml methyl ethyl ketone is added potassium carbonate (26.03 g, 188.0 mmol). To the resulted suspension 2-bromo-ethoxymethyl-benzene (40.0 g, 186.0 mmol) is added. The reaction mixture is heated to 80° C. and stirred overnight. After cooling to room temperature, the reaction mixture is added into 500 ml water and extracted with 3×200 ml methyl-t-butyl ether (MTBE). The organic phase is washed with sat. aq. NaCl solution, dried over anhydrous sodium sulfate. After removing solvent in vacuo, the oily residue is purified by column chromatography on silica gel with 1-chlorobutane as eluent to afford 1-(2-benzyloxy-ethoxy)-4-bromobenzene as colorless oil (48.0 g).

11.4 4-(2-Benzyloxy-ethoxy)-phenyl-boric acid (11b)

To a solution of 1-(2-benzyloxy-ethoxy)-4-bromo-benzene (46.00 g, 150.0 mmol) and triisopropylborate (41.22 ml, 180.0 mmol) in 500 ml dry THF is added n-butyllithium solution (15% solution in n-hexane, 103.5 ml, 164.7 mmol) dropwise at −70° C. The reaction mixture is stirred at this temperature for 1 hour. After allowed slowly warming up to 0° C., the reaction mixture is added into 500 ml ice-water mixture and carefully neutralized to pH~1 with concentrated HCl acid. The aqueous phase is separated and extracted with 2×300 ml MTBE. The organic phase is combined and dried over anhydrous sodium sulfate. After removing solvent in vacuo, the solid residue is recrystallized with heptane/ethylacetate to afford 4-(2-benzyloxy-ethoxy)-phenyl-boric acid (11b) as white crystals (18.1 g).

11.5 4-Benzyloxy-4"-(2-benzyloxy-ethoxy)-[1,1';3',1"]terphenyl-5'-carboxylic acid 2-benzyloxy-ethyl ester To a solution of 4-(2-benzyloxy-ethoxy)-phenyl-boric acid (17.40 g, 64.0 mmol) and 4'-benzyloxy-5-bromo-biphenyl-3-carboxylic acid 2-benzyloxyethyl ester (33.09 g, 64.0 mmol) in 1000 ml dry 1,4-dioxane is added potassium phosphate (73.6 g, 320.0 mmol). After thoroughly degassing with argon, tris(dibenzylidene-acetone)dipalladium(0) (1.17 g, 1.3 mmol) and 2-dicyclohexylphosphino-2',6'-dimethoxybiphenyl (SPhos, 2.16 g, 5.1 mmol) is added to the resulted suspension. The reaction mixture is heated to reflux and stirred 3 hours. After cooling to room temperature, the reaction mixture is added into 1000 ml ice-water and carefully neutralized with conc. HCl acid. The aqueous phase is separated and extracted with 3×300 ml ethylacetate. The organic phase is combined and washed with sat. aq. NaCl solution, dried over anhydrous sodium sulfate. After removing solvent in vacuo, the oily residue is purified by column chromatography on silica gel with heptane/ethylacetate as eluent to afford 4-benzyloxy-4"-(2-benzyloxy-ethoxy)-[1,1';3',1"]terphenyl-5'-carboxylic acid 2-benzyloxy-ethyl ester as white crystal (19.2 g).

11.6 4-Hydroxy-4"-(2-hydroxy-ethoxy)-[1,1';3',1"]terphenyl-5'-carboxylic acid 2-hydroxy-ethyl ester A solution of 4-benzyloxy-4"-(2-benzyloxy-ethoxy)-[1,1';3',1"]terphenyl-5'-carboxylic acid 2-benzyloxy-ethyl ester (19.2 g, 28.9 mmol) in tetrahydrofuran (200 ml) is treated with palladium (5%) on activated charcoal (8.5 g) and submitted to hydrogenation for 20 hs. The catalyst is then filtered off, and the remaining solution is concentrated in vacuo. The solid residue is recrystallized from acetonitrile to afford 4-hydroxy-4"-(2-hydroxy-ethoxy)-[1,1';3',1"]terphenyl-5'-carboxylic acid 2-hydroxy-ethyl ester as white crystals (10.0 g).

11.7 4-(2-Methyl-acryloyloxy)-4"-[2-(2-methyl-acryloyloxy)-ethoxy]-[1,1';3',1"]terphenyl-5'-carboxylic acid 2-(2-methyl-acryloyloxy)-ethyl ester Methacrylic acid (12.44 g, 144.5 mmol) and 4-(dimethylamino)pyridine (0.31 g, 2.5 mmol) is added to a suspension of 4-hydroxy-4"-(2-hydroxyethoxy)-[1,1';3',1"]terphenyl-5'-carboxylic acid 2-hydroxy-ethyl ester (10.0 g, 25.3 mmol) in dichloromethane (240 ml). The reaction mixture is treated dropwise at 0° C. with a solution of N-(3-dimethylaminopropyl)-N' ethylcarbodiimide (22.4 g, 144.5 mmol) in dichloromethane (50 ml) and stirred for 20 h at room temperature. After removing solvent in vacuo, the oily residue is purified by silica gel chromatography with heptane/ethyl acetate. The obtained product is recrystallized from heptane/MTBE solvent mixture to afford white crystals of 4-(2-methyl-acryloyloxy)-4"-[2-(2-methyl-acryloyloxy)- ethoxy]-[1,1';3',1"]terphenyl-5'-carboxylic acid 2-(2-methyl-acryloyloxy)-ethyl ester (10.3 g, m.p. 73° C.).

$^1$H-NMR (DMSO-$d_6$, 500 MHz): δ (ppm)=8.16 (tr, J=2.0 Hz, 1 H, Ar—H), 8.11 (m, 2 H, Ar—H), 7.86 (d, J=7.0 Hz, 2 H, Ar—H), 7.76 (d, J=7.0 Hz, 2 H, Ar—H), 7.33 (d, J=7.0 Hz, 2 H, Ar—H), 7.11 (d, J=7.0 Hz, 2 H, Ar—H), 6.32 (m, 1 H, H$_{olefin}$), 6.06 (m, 2 H, H$_{olefin}$), 5.93 (m, 1 H, H$_{olefin}$), 5.70 (m, 2 H, H$_{olefin}$), 4.60 (m, 2 H, OCH$_2$), 4.53 (m, 2 H, OCH$_2$), 4.47 (m, 2 H, OCH$_2$), 4.33 (m, 2 H, OCH$_2$), 2.04 (br. s, 3 H, CH$_3$), 1.90 (br. s, 3H, CH$_3$), 1.88 (br. s, 3H, CH$_3$).

EXAMPLE 12

Applying the same synthetic strategy as in Example 11, polymerizable monomeric compound 12 is prepared analogically as follows, starting from commercially available 3-bromo-5-iodo-benzoic acid and 4-bromo-2-fluorophenol.

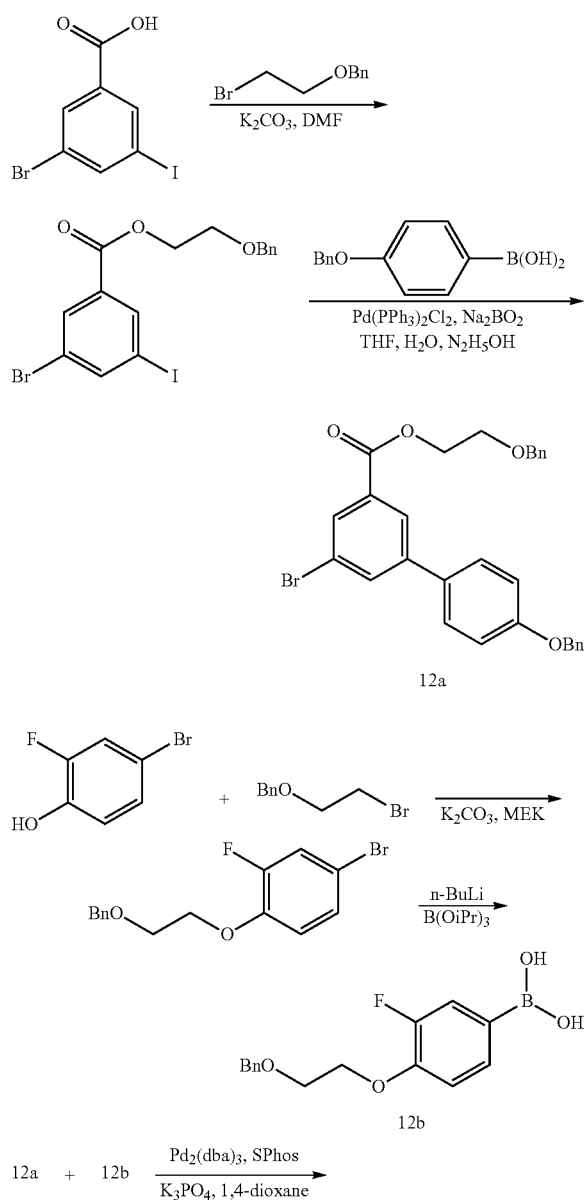

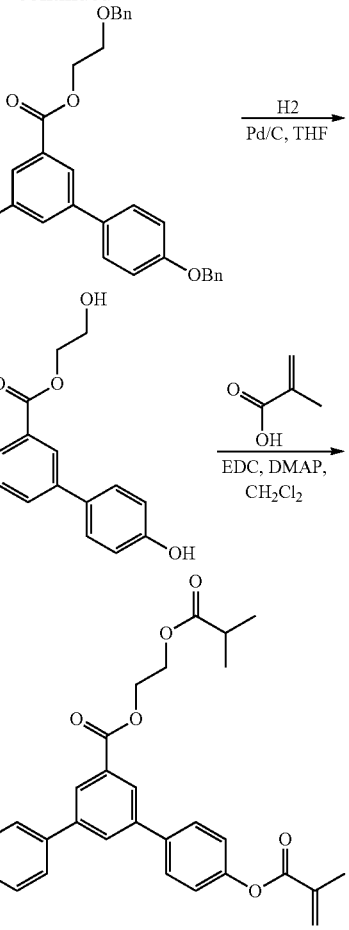

For the last step the prepared 3"-fluoro-4-hydroxy-4"-(2-hydroxy-ethoxy)-[1,1';3',1"]terphenyl-5'-carboxylic acid 2-hydroxy-ethyl ester (2.30 g, 5.7 mmol) is dissolved in 50 ml dichloromethane. To this solution is added methacrylic acid (2.74 ml, 31.8 mmol) and 4-(dimethylamino)pyridine (0.068 g, 0.56 mmol) at room temperature. The reaction mixture is then cooled down to 0° C. and treated with a solution of N-(3-dimethylaminopropyl)-N' ethylcarbodiimide (4.94 ml, 31.8 mmol) in dichloromethane (10 ml). After allowed to warm up to room temperature, the reaction mixture is stirred further for 20 hs. After removing solvent, the crude product is purified by column chromatography on silica gel with heptane/ethylacetate as eluent. Further recrystallization from heptane/MTBE solvent mixture afford white solid of 3"-fluoro-4-(2-methyl-acryloyloxy)-4"-[2-(2-methyl-acryloyloxy)-etho xy]-[1,1';3',1"]terphenyl-5'-carboxylic acid 2-(2-methyl-acryloyloxy)-ethyl ester (1.8 g, m.p. 72° C.).

$^1$H-NMR (DMSO-$d_6$, 500 MHz): δ(ppm)=8.20 (tr, J=2.0 Hz, 1 H, Ar—H), 8.13 (dd, J=2.0 Hz, 2 H, Ar—H), 7.88 (d, J=7.0 Hz, 2 H, Ar—H), 7.78 (dd, J=12.5 Hz, 1 H, Ar—H), 7.61 (d, J=8.5 Hz, 1 H, Ar—H), 7.34 (m, 3 H, Ar—H), 6.33 (m, 1 H, H$_{olefin}$), 6.05 (m, 2 H, H$_{olefin}$), 5.94 (m, 1 H, H$_{olefin}$), 5.70 (m, 2 H, H$_{olefin}$), 4.60 (m, 2 H, OCH$_2$), 4.53 (m, 2 H, OCH$_2$), 4.49 (m, 2 H, OCH$_2$), 4.43 (m, 2 H, OCH$_2$), 2.04 (m, 3 H, CH$_3$), 1.89 (m, 3 H, CH$_3$), 1.88 (m, 3 H, CH$_3$).

MIXTURE EXAMPLE 1

The nematic LC host mixture A is formulated as follows.

| | | | |
|---|---|---|---|
| CCH-501 | 9.00% | cl.p. | 70.0° C. |
| CCH-35 | 14.00% | Δn | 0.0825 |
| PCH-53 | 8.00% | Δε | −3.5 |
| PCH-304FF | 14.00% | $\varepsilon_\parallel$ | 3.5 |
| PCH-504FF | 13.00% | $K_3/K_1$ | 1.00 |
| CCP-302FF | 8.00% | $\gamma_1$ | 141 mPa s |
| CCP-502FF | 8.00% | $V_0$ | 2.10 V |
| CCP-21FF | 9.00% | | |
| CCP-31FF | 9.00% | | |
| CPY-2-O2 | 8.00% | | |

Polymerizable mixtures are prepared by adding monomer 1, 2, 5, 8, 9, 11 or 12 of Example 1, 2, 5, 8, 9, 11 and 12, respectively, to LC host mixture A at a concentration of 0.3% by weight.

MIXTURE EXAMPLE 2

The nematic LC host mixture B is formulated as follows.

| | | | |
|---|---|---|---|
| CY-3-O2 | 18.00% | cl.p. | +74.5° C. |
| CPY-2-O2 | 10.00% | Δn | 0.1021 |
| CPY-3-O2 | 10.00% | Δε | −3.1 |
| CCY-3-O2 | 9.00% | $\varepsilon_\parallel$ | 3.5 |
| CCY-4-O2 | 4.00% | $K_3/K_1$ | 1.16 |
| CC-3-V | 40.00% | $\gamma_1$ | 86 mPa s |
| PYP-2-3 | 9.00% | $V_0$ | 2.29 V |

Polymerizable mixtures are prepared by adding monomer 1 or 8 of Example 1 and 8, respectively, to LC host mixture B at a concentration of 0.3% by weight.

MIXTURE EXAMPLE 3

The nematic LC host mixture C is formulated as follows.

| | | | |
|---|---|---|---|
| CY-3-O2 | 15.00% | cl.p. | 74.5° C. |
| CY-5-O2 | 6.50% | Δn | 0.1082 |
| CCY-3-O2 | 11.00% | Δε | −3.0 |
| CPY-2-O2 | 5.50% | $\varepsilon_\parallel$ | 3.6 |
| CPY-3-O2 | 10.50% | $K_3/K_1$ | 1.21 |
| CC-3-V | 28.50% | $\gamma_1$ | 97 mPa s |
| CC-3-V1 | 10.00% | $V_0$ | 2.42 V |
| PYP-2-3 | 12.50% | | |
| PPGU-3-F | 0.50% | | |

Polymerizable mixtures are prepared by adding monomer 1, 2, 5, 8, 9, 11 or 12 of Example 1, 2, 5, 8, 9, 11 or 12, respectively, to LC host mixture C at a concentration of 0.3% by weight.

MIXTURE EXAMPLE 4

The nematic LC host mixture D is formulated as follows.

| | | | |
|---|---|---|---|
| CC-3-V | 20.00% | cl.p. | 74.5° C. |
| CC-3-V1 | 10.00% | Δn | 0.1084 |
| CCH-34 | 8.00% | Δε | −3.2 |
| CCH-35 | 4.00% | | |
| CCY-3-O1 | 5.50% | $K_3/K_1$ | 1.04 |
| CCY-3-O2 | 12.00% | $\gamma_1$ | 94 mPa s |
| CPY-2-O2 | 2.00% | $V_0$ | 2.33 V |
| CPY-3-O2 | 12.00% | | |
| PY-3-O2 | 15.00% | | |
| PY-4-O2 | 8.50% | | |
| PYP-2-3 | 3.00% | | |

Polymerizable mixtures are prepared by adding Monomer 2, 5, 9, 11 or 12 of Example 2, 5, 9, 11 or 12, respectively, to LC host mixture D at a concentration of 0.3% by weight.

MIXTURE EXAMPLE 5

The nematic LC host mixture E is formulated as follows.

| | | | |
|---|---|---|---|
| CC-3-V | 20.00% | cl.p. | 74.6° C. |
| CC-3-V1 | 10.00% | Δn | 0.1042 |
| CCH-35 | 9.00% | Δε | −3.1 |
| CCP-3-1 | 7.00% | | |
| CCY-3-O2 | 13.00% | $K_3/K_1$ | 1.13 |
| CPY-3-O2 | 13.00% | $\gamma_1$ | 94 mPa s |
| CY-3-O2 | 8.00% | $V_0$ | 2.48 V |
| PY-3-O2 | 15.00% | | |
| PY-4-O2 | 5.00% | | |

Polymerizable mixtures are prepared by adding Monomer 2, 5, 9, 11 or 12 of Example 2, 5, 9, 11 or 12, respectively, to LC host mixture E at a concentration of 0.3% by weight.

COMPARISON EXAMPLES

For comparison purposes, further polymerizable mixture were prepared from the nematic LC host mixtures A, B and C and
- trireactive polymerizable monomer C1 which is similar to monomer 1 but wherein the ester groups between spacer and aromatic ring are replaced by ether groups,
- trireactive polymerizable monomer C8 which is similar to monomer 8 but wherein the ester groups between spacer and aromatic ring are reversed,
- direactive monomer C-D1 having an alkyl spacer without an ester group,
- direactive monomer C-D2 having no spacer group.

Further comparison mixtures were prepared from the nematic LC host mixtures D and E and direactive monomer C-D2.

In all polymerizable mixtures the concentration of the respective monomer in the nematic LC host mixture was 0.3% by weight.

The structures of monomers 1, 2, 5, 8, 9, 11 and 12 according to the present invention and of monomers C1, C8, C-D1 and C-D2 of the comparison examples are shown below.

1

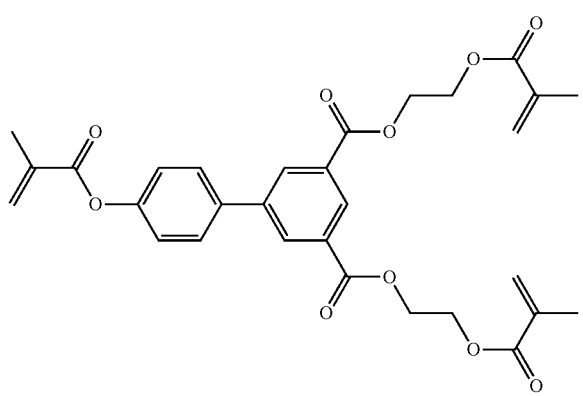

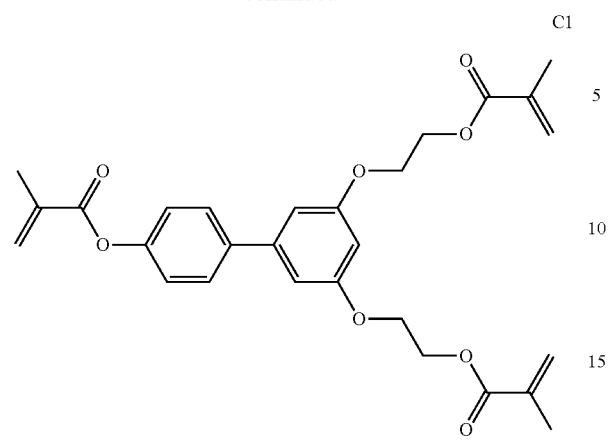
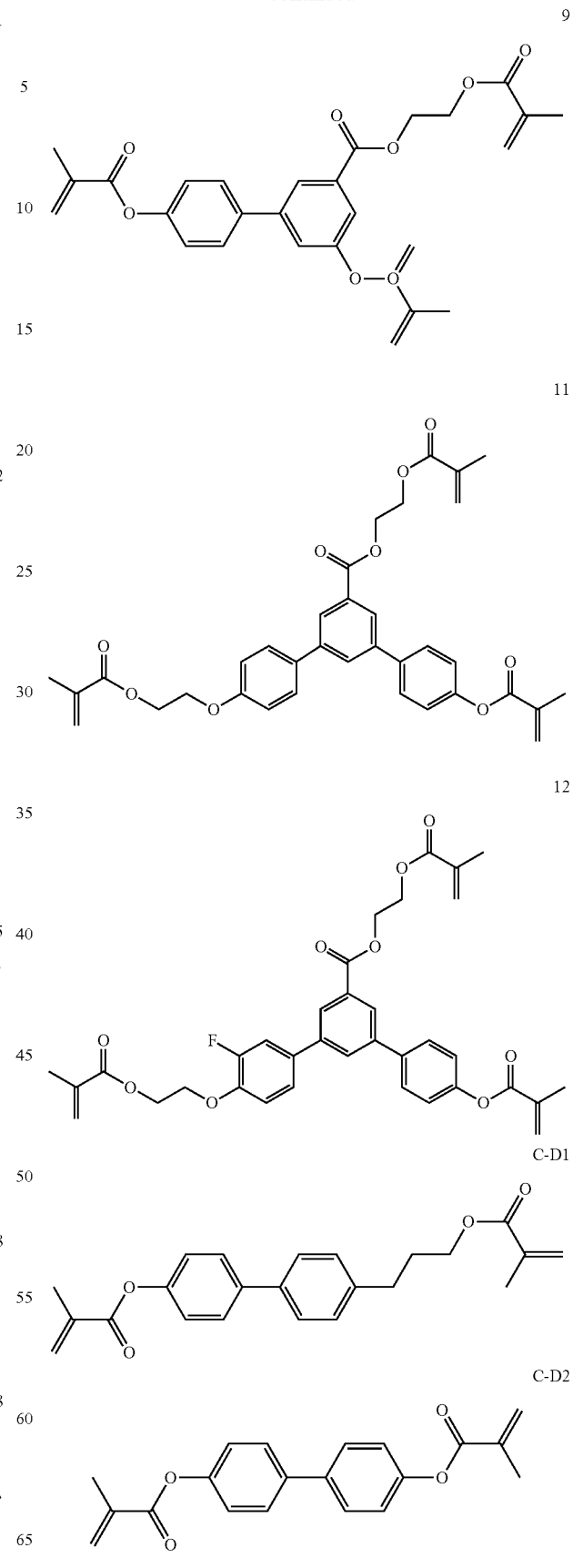

USE EXAMPLES

The polymerizable mixtures according to the invention and the polymerizable comparison mixtures are each inserted into a VA e/o test cell. The test cells comprise a VA-polyimide alignment layer (JALS-2096-R1) which is rubbed antiparallel (for the test cells with host mixture D and E the polyimide AL64101 was used). The LC-layer thickness d is approx. 4 μm.

Each test cell is irradiated with UV light having an intensity of 100 mW/cm$^2$ for the time indicated with application of a voltage of 24 $V_{rms}$ (alternating current), causing polymerization of the polymerizable monomeric compound.

The VHR values of the polymerizable mixtures before and after UV exposure are measured as described above. The VHR values of the mixtures are shown in Table 1.

TABLE 1

VHR values

| | Host B + C-D2 | Host B + 8 | Host B + 1 |
|---|---|---|---|
| | | VHR/% | |
| 0 min UV | 99.0 | 99.0 | 98.6 |
| 10 min UV | 86.4 | 90.8 | 94.8 |
| 2 h Suntest | 89.8 | 93.5 | 95.6 |

* "Suntest" means a second irradiation step with lower UV intensity but longer exposure time than the first step.

As can be seen from Table 1, the VHR values of the polymerizable mixture comprising monomer 1 or 8 according to the invention after UV exposure are significantly higher than the VHR values of polymerizable mixture comprising monomer C-D2.

In order to determine the polymerization rate, the residual content of unpolymerized RM (in % by weight) in the test cells is measured by HPLC after various exposure times. For this purpose each mixture is polymerized in the test cell under the stated conditions. The mixture is then rinsed out of the test cell using MEK (methyl ethyl ketone) and measured.

The residual concentrations of the respective monomer in the mixture after different exposure times are shown in Table 2.

The tilt angle is determined before and after UV irradiation by a crystal rotation experiment (Autronic-Melchers TBA-105).

The tilt angles are shown in Table 3.

TABLE 3

Tilt angles

| UV-Time/sec | Host A + C-D1 | Host A + C8 | Host A + 8 |
|---|---|---|---|
| | | Pretilt Angle/° | |
| 0 | 89.1 | 89.0 | 88.8 |
| 30 | 89.0 | 89.0 | 88.6 |
| 60 | 88.7 | 87.3 | 88.1 |
| 120 | 87.4 | 84.5 | 83.5 |
| 240 | 84.2 | 80.0 | 75.9 |
| 360 | 81.3 | 78.7 | 73.8 |

| UV-Time/sec | Host B + C-D1 | Host B + C8 | Host B + 8 |
|---|---|---|---|
| | | Pretilt Angle/° | |
| 0 | 89.1 | 88.9 | 88.8 |
| 30 | — | — | — |
| 60 | — | — | — |
| 120 | 85.3 | 81.8 | 80.2 |
| 240 | — | — | — |
| 360 | 79.5 | 77.9 | 76.1 |

| UV-Time/sec | Host A + C1 | Host A + 1 |
|---|---|---|
| | Pretilt Angle/° | |
| 0 | 88.9 | 88.4 |
| 30 | 88.5 | 85.4 |
| 60 | 86.8 | 82.0 |
| 120 | 82.7 | 77.3 |
| 240 | 74.2 | 72.3 |

As can be seen from Table 3, a small tilt angle after polymerization is achieved quickly in PSA displays containing a polymerizable mixture with monomer 1 or 8 according to the invention, which is smaller than in a PSA display containing a polymerizable mixture with monomer C-D1, C1 or C8.

The above measurements of the VHR, the residual monomer content and the pretilt angle were also carried out for

TABLE 2

Residual monomer content

| Time/min | Host A + C-D1 | Host A + C8 | Host A + 8 | Host B + C-D1 | Host B + C8 | Host B + 8 | Host A + C1 | Host A + 1 | Host B + C1 | Host B + 1 |
|---|---|---|---|---|---|---|---|---|---|---|
| | | | | | Residual RM/% | | | | | |
| 0 | 0.300 | 0.300 | 0.300 | 0.300 | 0.300 | 0.300 | 0.300 | 0.300 | 0.300 | 0.300 |
| 2 | 0.278 | 0.286 | 0.243 | 0.244 | 0.229 | 0.212 | 0.265 | 0.197 | 0.176 | 0.092 |
| 4 | 0.256 | 0.264 | 0.192 | — | — | — | 0.160 | 0.091 | 0.101 | — |
| 6 | 0.235 | 0.230 | 0.138 | 0.145 | 0.134 | 0.100 | 0.091 | 0.052 | 0.055 | 0.026 |

| Time/min | Host C + C1 | Host C + 1 |
|---|---|---|
| | Residual RM/% | |
| 0 | 0.300 | 0.300 |
| 0.5 | 0.269 | 0.236 |
| 1 | 0.189 | 0.155 |
| 3 | 0.100 | 0.064 |

As can be seen from Table 2, significantly more rapid and complete polymerization is achieved in PSA displays containing a polymerizable mixture with monomer 1 or 8 according to the invention, compared to PSA displays containing a polymerizable mixture with monomer C-D1, C1 or C8.

polymerizable mixtures comprising monomer 2, 5, 9, 11 or 12 in one of the LC host mixtures A, B, D and E, respectively, in comparison with polymerizable mixtures comprising monomer C-D2 in one of the LC host mixtures A, B, D and E, respectively. The results are shown below.

TABLE 4

| | | | VHR values | | | |
|---|---|---|---|---|---|---|
| | Host A + C-D2 | Host A + 5 | Host A + 2 | Host A + 12 | Host A + 11 | Host A + 9 |
| | | | VHR/% | | | |
| 0 min UV | 98.2 | 97.7 | 98.9 | 98.2 | 98.4 | 98.2 |
| 2 h Suntest | 97.6 | 98.6 | 98.2 | 98.5 | 98.9 | 98.3 |
| | Host B + C-D2 | Host B + 5 | Host B + 2 | Host B + 12 | Host B + 11 | Host B + 9 |
| | | | VHR/% | | | |
| 0 min UV | 98.5 | 98.5 | 98.2 | 98.6 | 96.9 | 96.8 |
| 2 h Suntest | 85.6 | 93.2 | 91.0 | 94.0 | 94.4 | 95.3 |
| 10 min UV | 83.5 | 91.2 | 90.6 | 90.0 | 93.8 | 93.2 |

| | Host D + C-D2 | Host D + 5 | Host D + 11 | Host E + C-D2 | Host E + 5 |
|---|---|---|---|---|---|
| | | | VHR/% | | |
| 0 min UV | 98.3 | 98.3 | 97.9 | 98.3 | 97.0 |
| 2 min UV | 94.8 | 96.4 | 97.5 | 94.8 | 96.8 |
| 15 min UV | 93.6 | 94.0 | 96.2 | 93.6 | 95.1 |
| 2 min UV + 2 h suntest | 95.5 | 96.6 | 97.7 | 95.5 | 96.8 |

In the host mixture A without an alkenyl compound, the monomers 2, 5, 9, 11 and 12 according to the present invention lead to higher VHR values after suntest, compared to the monomer C-D2. In addition, the monomers of the present invention do either show only a very small decrease or even an increase of the VHR after 2 h suntest compared to the initial VHR value.

In the host mixtures B, D and E containing an alkenyl compound (CC-3-V) the monomers 2, 5, 9, 11 and 12 according to the present invention show also higher VHR values after suntest compared to the monomer C-D2.

TABLE 5

| | | | Residual monomer content | | | |
|---|---|---|---|---|---|---|
| Time/ min | Host A + C-D2 | Host A + 5 | Host A + 2 | Host A + 12 | Host A + 11 | Host A + 9 |
| | | | Residual RM/% | | | |
| 0 | 0.3 | 0.3 | 0.3 | 0.3 | 0.3 | 0.3 |
| 2 | 0.264 | 0.256 | 0.193 | 0.062 | 0.174 | 0.250 |
| 4 | 0.203 | 0.182 | 0.102 | 0.023 | 0.059 | 0.126 |
| 6 | 0.173 | 0.128 | 0.044 | 0.008 | 0.022 | 0.065 |
| Time/ min | Host B + C-D2 | Host B + 5 | Host B + 2 | Host B + 12 | Host B + 11 | Host B + 9 |
| | | | Residual RM/% | | | |
| 0 | 0.3 | 0.3 | 0.3 | 0.3 | 0.3 | 0.3 |
| 2 | 0.185 | 0.182 | 0.134 | 0.048 | 0.072 | 0.152 |
| 6 | 0.067 | 0.074 | 0.041 | 0.006 | 0.01 | 0.048 |

| Time/ min | Host D + C-D2 | Host D + 5 | Host D + 11 |
|---|---|---|---|
| | | Residual RM/% | |
| 0 | 0.3 | 0.3 | 0.3 |
| 0.5 | 0.256 | 0.232 | 0.207 |
| 1 | 0.199 | 0.163 | 0.111 |
| 2 | 0.142 | 0.092 | 0.030 |
| 5 | 0.05 | 0.025 | 0.001 |

| Time/ min | Host E + C-D2 | Host E + 5 |
|---|---|---|
| | Residual RM/% | |
| 0 | 0.3 | 0.3 |
| 0.5 | 0.256 | 0.255 |
| 1 | 0.199 | 0.167 |
| 2 | 0.142 | 0.115 |

In all host mixtures A, B, D and E the monomers 2, 5, 9, 11 and 12 according to the present invention show faster polymerization with a lower residual RM content, compared to the monomer C-D2 of prior art.

TABLE 6

Pretilt angles

| UV-Time/ sec | Host A + C-D2 | Host A + 5 | Host A + 2 | Host A + 12 | Host A + 11 | Host A + 9 |
|---|---|---|---|---|---|---|
| | | | Pretilt Angle/° | | | |
| 0 | 89.6 | 88.4 | 88.4 | 88.7 | 89.0 | 89.5 |
| 30 | 89.0 | 87.2 | 86.1 | 83.4 | 86.2 | 88.0 |
| 60 | 88.2 | 86.6 | 83.1 | 75.2 | 78.7 | 83.9 |
| 120 | 84.9 | 81.9 | 77.1 | 69.6 | 71.9 | 77.0 |

| UV-Time/ sec | Host B + C-D2 | Host B + 5 | Host B + 2 | Host B + 12 | Host B + 11 | Host B + 9 |
|---|---|---|---|---|---|---|
| | | | Pretilt Angle/° | | | |
| 0 | 88.8 | 88.9 | 88.7 | 88.7 | 88.7 | 89.2 |
| 120 | 77.2 | 77.4 | 78.5 | 69.3 | 72.0 | 77.5 |

| UV-Time/ sec | Host D + C-D2 | Host D + 5 | Host D + 11 | Host E + C-D2 | Host E + 5 | Host E + 11 |
|---|---|---|---|---|---|---|
| | | | Pretilt Angle/° | | | |
| 0 | 89.1 | 89.1 | 89.6 | 89.9 | 89.7 | 90.0 |
| 60 | 86.4 | 85.5 | 72.5 | 89.6 | 89.8 | 86.3 |
| 120 | 78.0 | 75.0 | 67.6 | 89.6 | 86.7 | 67.2 |
| 180 | 76.1 | 72.2 | 65.4 | 85.1 | 79.8 | 63.2 |
| 300 | 73.5 | 70.2 | 65.2 | 79.6 | 70.6 | 56.9 |

The tilt angle measurements confirm the results of the residual monomer content measurements. Thus, in all host mixtures A, B, D and E the monomers 2, 5, 9, 11 and 12 according to the present invention show faster generation of a higher tilt, angle compared to the monomer C-D2 of prior art.

For measuring the solubility, monomers 1, 5, 8 and 9 of Example 1, 5, 8, 9 and 11, respectively, and monomer C-D2 of prior art are each dissolved at various concentrations from 0.3 to 3.0% by weight in the commercially available nematic LC mixture MJ011412 (Merck Japan Ltd.). The samples are stored for 1000 h at room temperature and checked if they remain a homogeneous solution. Afterwards the samples are centrifuged and filtrated, and the residual monomer concentration in the supernatant liquid is determined.

Maximum residual monomer concentration after 1000 h at RT:
Monomer C-D2: 0.46%
Monomer 8: 1.66%
Monomer 1: 1.00%
Monomer 5: 1.00%
Monomer 9: 1.00%
Monomer 11: 0.60%

It can be seen that the monomers according to the invention exhibit significantly better solubility than monomer C-D2 of prior art.

It can be seen that even monomer 11 shows a residual concentration of 0.6%, which is 100% higher than the RM concentration of 0.3% as typically used in PSA displays, whereas monomer C-D2 has residual concentration 0.46% which is only 50% higher than the typically used RM concentration of 0.3%.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents and publications, cited herein and of corresponding European patent application no. 13003221.2, filed Jun. 25, 2013, are incorporated by reference herein.

The invention claimed is:

1. A polymerizable compound according to the following formula

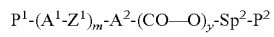
$$P^1\text{-}(A^1\text{-}Z^1)_m\text{-}A^2\text{-}(CO\text{---}O)_y\text{-}Sp^2\text{-}P^2 \qquad I$$

wherein
  $Sp^2$ is a spacer group which is optionally substituted by $P^1$—Sp'-,
  Sp' is alkylene with 1 to 12 C atoms,
  $P^1$ and $P^2$ independently of each other are each a polymerizable group,
  $A^1$, $A^2$ independently of each other, and on each occurrence identically or differently, are each an aryl, heteroaryl alicyclic or heterocyclic group having 4 to 25 C atoms, optionally containing fused rings, and which is unsubstituted or mono- or polysubstituted by L,
  $Z^1$ is, on each occurrence identically or differently, —O—, —S—, —CO—, —CO—O—, —O—CO—O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_n$—, —CF$_2$CH$_2$—, —CH$_2$CF$_2$—, —(CF$_2$)$_n$—, —CH=CH—, —CF=CF—, —CH=CF—, —CF=CH—, —C≡C—, —CH=CH—CO—O—, —O—CO—CH=CH—, —CH$_2$—CH$_2$—CO—O—, —O—CO—CH$_2$—CH$_2$—, —CR$^{00}$R$^{000}$—, or a single bond, L is P¹-, P¹-Sp¹-(O—CO)$_x$—F, Cl, Br, I,—CN,—NO$_2$,—NCO,—NCS, —OCN, —SCN, —C(=O )N(R$^x$)$_2$, —C(=O)Y¹, —C(=O)R$^x$, —N(R$^x$)$_2$, optionally substituted silyl, optionally substituted aryl or heteroaryl having 5 to 20 ring atoms, or straight-chain or branched alkyl having 1 to 25 C atoms, in which, in addition, one or more non-adjacent CH$_2$ groups are each optionally replaced, independently of one another, by —C(R$^{00}$)=C(R$^{000}$)—, —C≡C—, —N(R$^{00}$)—, —O—, —S—, —CO—, —CO—O—, —O—CO—, or —O—CO—O— in such a way that O and/or S atoms are not linked directly to one another, and in which, in addition, one or more H atoms are each optionally replaced by F, Cl, CN, P¹, P¹-Sp¹- or P¹-Sp¹(O—CO)$_x$—, Sp¹ is a spacer group which is optionally substituted by P¹-Sp'- or is a single bond, R$^{00}$ and R$^{000}$ are each, independently of one another, H or alkyl having 1 to 12 C atoms, Y¹ is halogen, R$^x$ is P¹, P¹-Sp¹-, P¹-(Sp¹—O—CO)$_x$—, H, halogen, straight chain, branched or cyclic alkyl having 1 to 25 C atoms, wherein one or more non-adjacent CH$_2$-groups are each optionally replaced by —O—, —S—, —CO—, —CO—O—, —CO—, or —O—CO—O— in such a manner that O- and/or S-atoms are not directly connected with each other, and wherein one or more H atoms are each optionally replaced by F, Cl, P¹-, P¹-Sp¹- or P¹-(Sp¹—O—CO)$_x$—, optionally substituted aryl, aryloxy, heteroaryl or heteroaryloxy having 5 to 20 ring atoms, m is 1, 2, 3 or 4, n is 1, 2, 3 or 4, x is 0 or 1, and y is 1;

with at least one of the following provisos:
(a) at least one of A¹ and A² is substituted by a group L denoting P¹-Sp¹—(O—CO)$_x$—,
(b) Sp² is substituted by P¹-Sp¹-,
(c) m is 2, 3, or 4, and/or
(d) P¹ and P² are selected from acrylate and methacrylate.

2. A polymerizable compound according to claim 1, wherein A¹ and A² are each, independently of one another, 1,4-phenylene, 1,3-phenylene, or 1,2-phenylene, which in each case is unsubstituted or mono- or polysubstituted by L.

3. A polymerizable compound according to claim 1, wherein

Sp¹ is selected from —(CH$_2$)$_{p1}$—, —(CH$_2$)$_{p2}$—O—(CH$_2$ $_{p3}$—, —(CH$_2$)$_{p1}$—O—, —O—(CH$_2$)$_{p1}$—, and

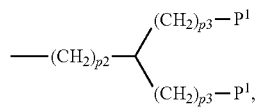

and

Sp² is selected from —(CH$_2$)$_{p1}$—,—(CH$_2$)$_{p2}$—O—(CH$_2$)$_{p3}$—, and

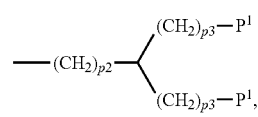

in which p1 is an integer from 1 to 6, and p2 and p3 are independently of each other 1, 2 or 3 provided that, in a group Sp¹—(O—CO)$_x$—, if x is 1 then Sp¹ is not —(CH$_2$)$_{p1}$—O— or —O—(CH$_2$)$_{p1}$—.

4. A polymerizable compound according to claim 1, wherein P¹ and P² are independently of each other selected from vinyloxy, acrylate, methacrylate, fluoroacrylate, chloroacrylate, oxetane and epoxide.

5. A polymerizable compound according to claim 1, wherein said compound is selected from the following sub-formulae:

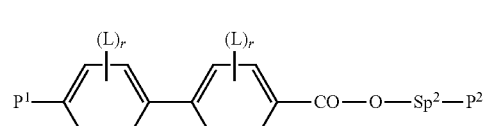
I1

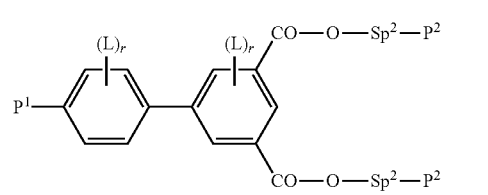
I2

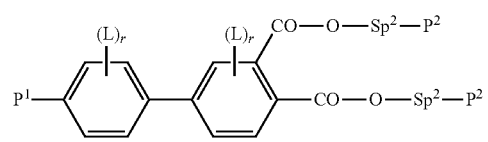
I3

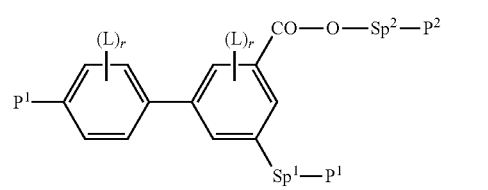
I4

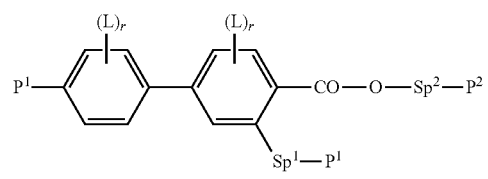
I5

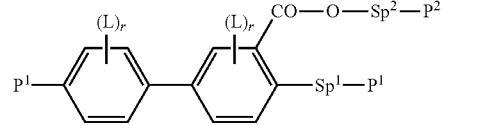
I6

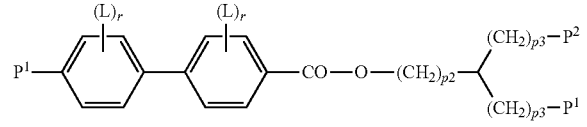
I7

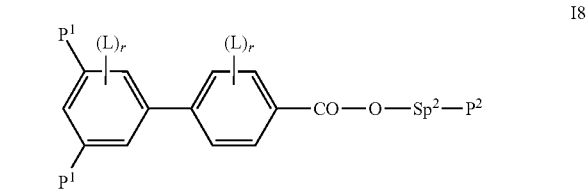
I8

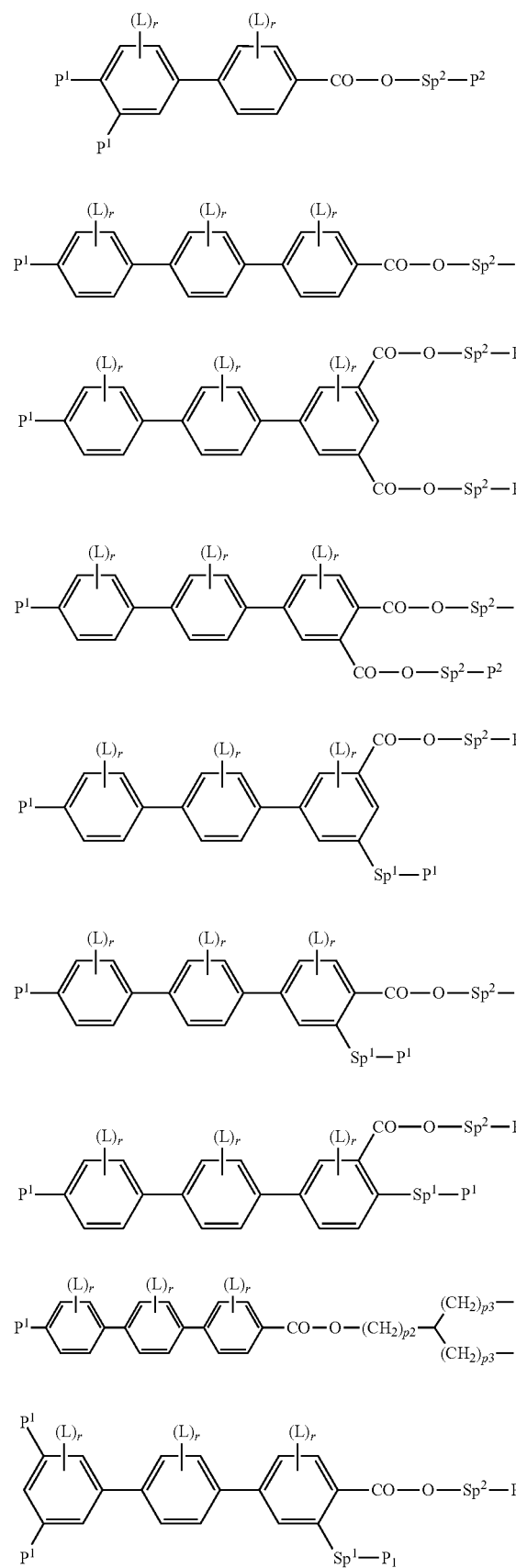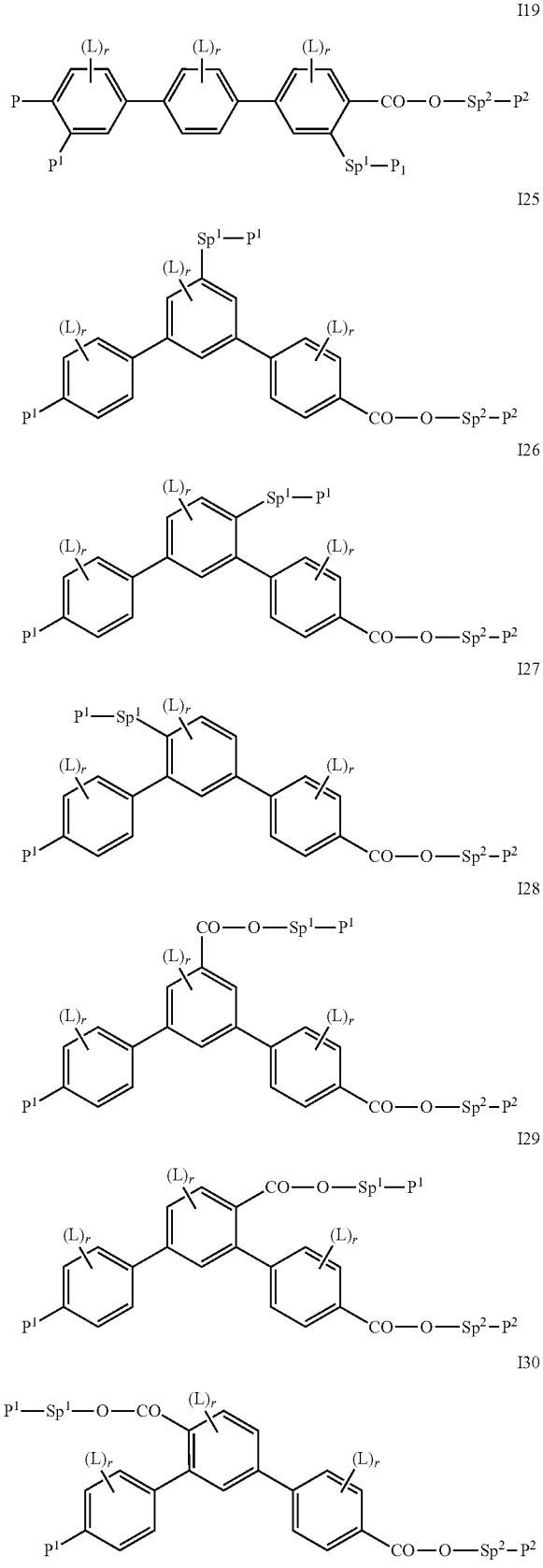
wherein r is 0, 1, 2, 3 or 4.

6. A liquid crystalline (LC) medium comprising
a polymerizable component A) comprising one or more polymerizable compounds according to claim 1, and
a liquid crystalline component B) comprising one or more compounds selected from mesogenic or liquid crystalline compounds.

7. The liquid crystalline medium according to claim 6, wherein component B comprises one or more compounds of formulae CY and/or PY:

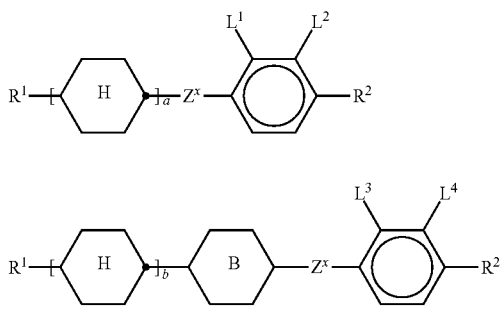

in which the individual radicals have the following meanings:
a denotes 1 or 2,
b denotes 0 or 1,

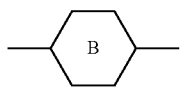

denotes

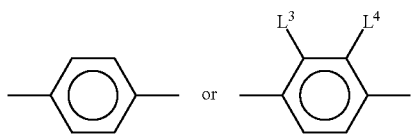

$R^1$ and $R^2$ each, independently of one another, denote alkyl having 1 to 12 C atoms,
where, in addition, one or two non-adjacent $CH_2$ groups are each optionally replaced by —O—, —CH=CH—, —CO—, —O—CO— or —CO—O— in such a way that O atoms are not linked directly to one another,
$Z^x$ denotes —CH=CH—, —CH$_2$O—, —OCH$_2$—, —CF$_2$O—, —OCF$_2$—, —O—, —CH$_2$—, —CH$_2$CH$_2$—or a single bond, and
$L^{1-4}$ each, independently of one another, denote F, Cl, OCF$_3$, CF$_3$, CH$_3$, CH$_2$F, or CHF$_2$.

8. The liquid crystalline medium according to claim 6, wherein component B comprises one or more compounds of the following formula:

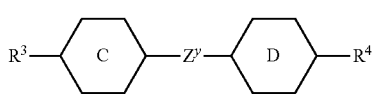

in which the individual radicals have the following meanings:

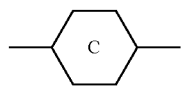

denotes

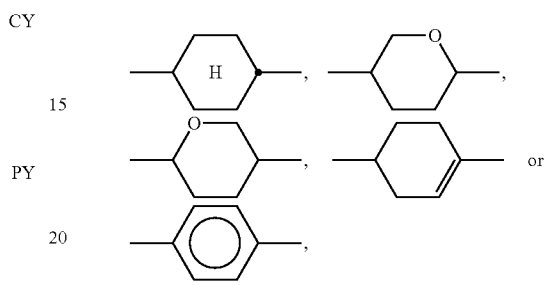

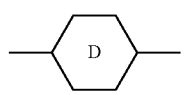

denotes

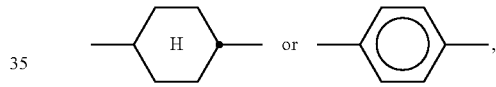

$R^3$ and $R^4$ each, independently of one another, denote alkyl having 1 to 12 C atoms, in which, in addition, one or two non-adjacent CH$_2$ groups are each optionally replaced by —O—, —CH=CH—, —CO—, —O—CO—or —CO—O—in such a way that O atoms are not linked directly to one another, and
$Z^y$ denotes —CH$_2$CH$_2$—, —CH=CH—, —CF$_2$O—, —OCF$_2$—, —CH$_2$O—, —OCH$_2$—, —COO—, —OCO—, —C$_2$F$_4$—, —CF=CF—or a single bond.

9. The liquid crystalline medium according to claim 6, wherein component B comprises one or more compounds comprising an alkenyl group, which is stable to a polymerization reaction under the conditions used for the polymerization of the polymerizable compounds.

10. The liquid crystalline medium according to claim 6, wherein the polymerizable compounds are polymerized.

11. A method of generating an electro-optical effect comprising applying a voltage to a liquid crystalline medium containing a polymerizable compound according to claim 1, in a liquid crystalline display.

12. A method of generating an electro-optical effect comprising applying a voltage to a liquid crystalline medium according to claim 6, in a liquid crystalline display.

13. A liquid crystalline display comprising one or more polymerizable compounds according to claim 1.

14. A liquid crystalline display comprising a liquid crystalline medium according to claim 6.

15. The liquid crystalline display according to claim 13, which is a PSA type display.

16. The liquid crystalline display according to claim 15, which is a PSA-VA, PSA-OCB, PSA-IPS, PS-FFS, PSA-posi-VA or PSA-TN display.

17. The liquid crystalline display according to claim 13, wherein said display contains a liquid crystalline cell having two substrates and two electrodes, where at least one substrate is transparent to light and at least one substrate has one or two elec-trodes, and a layer, located between the substrates, of said liquid crystalline medium comprising a polymerized component and a low—molecular—weight component, where the polymerized component is obtainable by polymerization of one or more polymerizable compounds between the substrates of the liquid crystalline cell in the liquid crystalline medium.

18. A process for the production of a liquid crystalline display according to claim 13, comprising the steps of filling the liquid crystalline medium into a liquid crystalline cell having two substrates and two electrodes, and polymerizing the polymerizable compounds.

19. A process of preparing an LC medium according to claim 6, comprising the steps of mixing one or more unpolymerizable liquid—crystalline compounds, or a liquid-crystalline component B) as defined in claim 6, with one or more of said polymerizable compounds, and optionally with further liquid—crystalline compounds and/or additives.

20. A polymerizable compound according to claim 3, wherein $P^l$ and $P^2$ are independently of each other selected from vinyloxy, acrylate, methacrylate, fluoroacrylate, chloroacrylate, oxetane and epoxide.

21. The method according to claim 11, wherein said liquid crystalline display is a display of the polymer sustained alignment type.

22. The method according to claim 12, wherein said liquid crystalline display is a display of the polymer sustained alignment type.

23. A polymerizable compound according to claim 1, wherein spacer groups $Sp^1$ and $Sp^2$ are of the formula Sp"-X", wherein Sp" is linked to the polymerizable group, Sp" is straight-chain or branched alkylene having 1 to 20 C atoms, which is optionally mono- or polysubstituted by F, Cl, Br, I, CN or $P^1$-Sp'-, and in which, in addition, one or more non-adjacent $CH_2$ groups may each be replaced, independently of one another, by —O—, —S—, -NH- ,) —N($R^0$) —, —Si($R^{00}R^{000}$)—, —CO—, —CO—O—, —O—CO—, —O—CO—O—, —S—CO—, —CO—S—,)—N($R^{00}$)—CO—O—, —O—CO—N($R^{00}$—),—N($R^{00}$),—CO—N($R^{00}$—, —CH=CH—or —C≡C—in such a way that O and/or S atoms are not linked directly to one another, X"is —O—, —S—, —CO—, —CO—O—CO—, —O—CO—O—,)—CO—N($R^{00}$—,)—N($R^{00}$)—CO—, —N($R^{00}$)—CO—N($R^{00}$)—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N —, —N=CH —N=N—, —CH=$CR^0$—, —$CY^2$=$CY^3$—, —C≡C—, —CH=CH—CO—O—, —O—CO—CH=CH—or a single bond, wherein X" denotes a single bond if it is adjacent to an ester group (O—CO or CO—O), $R^0$, $R^{00}$and $R^{000}$each, independently of one another, are H or alkyl having 1 to 12 C atoms, and $Y^2$ and $Y^3$ each, independently of one another, are H, F, Cl or CN.

* * * * *